OTHER PUBLICATIONS

US005545565A
United States Patent [19]
De Greve et al.
[11] Patent Number: 5,545,565
[45] Date of Patent: Aug. 13, 1996
[54] **TRANSFORMATION VECTORS ALLOWING EXPRESSION OF FOREIGN POLYPEPTIDE ENDOXINS FROM *BACILLUS THURINGIENSIS* IN PLANTS**
[75] Inventors: Henri M. J. De Greve, Brussels, Belgium; Maria B. L. F. Salgado, Guerrero, Mexico; **Mar

*Cell*, "Integration and Organization of Ti Plasmid Sequences in Crown Gall Tumors", vol. 19, pp. 729–739, Mar. 1980.

*The EMBO Journal*, "Cloning and Expression of the Crystal Protein Genes from *Bacillus thuringiensis* Strain Berliner 1715", vol. 1, No. 7, pp. 791–799, 1982.

*The EMBO Journal*, "Expression of Foreign Genes in Regenerated Plants and in Their Progeny", vol. 3, No. 8, pp. 1681–1689, 1984.

*Plant Physiol.*, "Transformation Zea Mays L. Using *Agrobacterium Tumefaciens* and the Shoot Apex", vol. 95, pp. 426–434, 1991.

"Fifth Annual Meeting of the International Program on Rice Biotechnology", Oct. 2–5, 1991.

"Research Papers /Agrobacteruim–Mediated Transformation of Rice (Oryza Sativa L.)", University of Washington.

*Genetics in Relation to Insect Management*, "Genetic Manipulation of Pathogens: Selection of Different Strains", Dulmage, H. T., The Rockefeller Foundation, pp. 116–127 (1979).

*Microbial Control of Pests and Plant Diseases 1970–1980*, "Insecticidal Activity of Isolates of *Bacillus thuringiensis* and Their Potential for Pest Control", Dulmage, H. T., pp. 193–222 (1981).

*Microbial Control of Insects and Mites*, "Determination and Significance of the Host Spectrum of *Bacillus thuringiensis*", Burgerjon, A. et al., pp. 305–325 (1971).

*Nucleic Acids Research*, "Efficient Octopine Ti Plasmid–Derived Vectors for Agrobacterium–Mediated Gene Transfer to Plants", vol. 13, pp. 4777–4788, 1985.

*Agric. Biol. Chem.*, "A Toxic Fragment from the Entomocidal Crystal Protein of *Bacillus thuringiensis*", vol. 48, No. 3, pp. 611–619, 1984.

*Journal of Molecular and Applied Genetics*, "A Cauliflower Mosaic Virus Promoter Directs Expression of Kanamycin Resistance in Morphogenic Transformed Plant Cells", vol. 2, No. 6, pp. 549–562, 1984.

*Journal of Molecular and Applied Genetics*, "Site–Specfic Mutagenesis of Agrobacterium Ti Plasmids and Transfer of Genes to Plant Cells", vol. 1, No. 2, pp. 149–164, 1981.

*Journal of Molecular and Applied Genetics*, "Nucleotide Sequence and Transcript Map of the *Agrobacterium tumefaciens* Ti Plasmid–Encoded Octopine Synthase Gene", vol. 1, No. 6. pp. 499–511, 1982.

*Journal of Bacteriology*, "Comparative Biochemistry of Entomocidal Parasporal Crystals of Selected *Bacillus thuringiensis* Strains", vol. 145, No. 2, pp. 1052–1062, Feb. 1981.

*Proc. R. Soc. Lond.*, "Interactions and DNA Transfer Between *Agrobacterium tumefaciens*, the Ti–Plasmid and the Plant Host", vol. 204, pp. 251–266, 1979.

*Proc. Natl. Acad. Sci.*, "Cloning and Localization of the Lepidopteran Protoxin Gene of *Bacillus thuringiensis* Subsp. kurstaki", vol. 70, pp. 6065–6069, 1982.

*Microbial Control of Pests and Plant Diseases 1970–1980*, "Susceptibility of Arthropod Species to *Bacillus thuringiensis* ", Appendix 1, 1981, pp. 837–896.

*CRC Critical Reviews in Microbiology*, "Ultrastructure, Physiology, and Biochemistry of *Bacillus thuringiensis* ", Oct. 1980, pp. 147–204.

*Proc. Natl. Acad. Sci.*, "Cloning and Expression of the *Bacillus thuringiensis* Crystal Protein Gene in *Escherichia coli*", vol. 78, No. 5, May 1981, pp. 2893–2897.

*Genetics and Biotechnology of Bacilli*, "Structural and Regulatory Analysis of a Cloned *Bacillus thuringiensis* Crystal Protein Gene", 1984, pp. 375–386.

*Applied and Environmental Microbiology*, "Bioassay for Homogeneous Parasporal Crystal of *Bacillus thuringiensis* Using the Tobacco Hornworm, *Manduca sexta*", vol. 33, No. 4, Apr. 1977, pp. 878–880.

*Archives of Biochemistry and Biophysics*, "Two Types of Entomodcidal Toxins in the Parasporal Crystals of *Bacillus thuringiensis* kurstaki", vol. 227, No. 1, 1983, pp. 233–241, 1983.

*The Embo Journal*, "Genetic Identification of Runctions of TL–DNA Transcripts in Octopine Crown Galls", vol. 1, No. 1, 1982, pp. 147–152.

*Cell*, "Stable Incorporation of Plasmid DNA into Higher Plant Cells: The Molecular Basis of Crown Gall Tumorigenesis", vol. 11, Jun. 1977, pp. 263–271.

*Biochimica et Biophsica Acta*, "Plant Tumors", vol. 516, 1978, pp. 167–191.

*Cell*, "Genetic Analysis of Grown Gall: Fine Structure Map of the T–DNA by Site–Directed Mutagenesis", vol. 27, Nov. 1981, pp. 143–153.

*The Journal of Biological Chemistry*, "Purification and Characterization of the Entomocidal Protoxin of *Bacillus thuringiensis*", vol. 256, No. 6, Mar. 25, 1981, pp. 3000–3004.

*Journal of Microbiological Methods 3*, "A Convenient Procedure for the Preparation of Highly Purifird Parasporal Crystals of *Bacillus thuringiensis* ", 1984, pp 69–76.

*Nature*, "Expression of Chimaeric Genes Transferred into Plant Cells Using a Ti–Plasmid–Derived Vector", vol. 303, May 19, 1983, pp. 209–213.

*Nature*, "A Binary Plant Vector Strategy Based on Separation of vir–and T–region of the *Agrobacterium tumefaciens* Ti–plasmid", vol. 303, May 12, 1983, pp. 179–180.

*Nucleic Acids Research*, "Binary Agrobacterium Vectors for Plant Transformation", vol. 12, 1984, pp. 8711–8721.

*Science*, "Introduction of Genetic Material into Plant Cells", vol. 222, Nov. 18, 1983, pp. 815–821.

*Current Bicrobiology*, "Mosquitocidal Protein of *Bacillus thuringiensis* subsp. *israelensis:* Identification and Partial Isolation of the Protein", vol. 9, 1983, pp. 279–284.

*Journal of General Microbiology* , "Purification of the Insecticidal Toxin in Crystals of *Bacillus thuringiensis*", vol. 118, 1980, pp. 1–11.

*Gene*, "Crown Gall Plant Tumors of Abnormal Morphology, Induced by *Agrobacterium tumefaciens* Carrying Mutated Octopine Ti Plasmids; Analysis of T–DNA Functions", vol. 14, 1981, pp. 33–50.

*Plasmid*, "The Functional Organization of the Octopine *Agrobacterium tumefaciens* Plasmid pTiB6S3", vol. 6, 1981, pp. 235–248.

*The Embo Journal*, "Enhanced Expression of Cro–β–Galactosidase Fusion Proteins Under the Control of the $P_R$ Promoter of Bacteriophage λ", vol. 1, No. 10, 1982, pp. 1217–1224.

*Mol Gen Genet*, "Plasmid ColE1 Conjugal Mobility: The Nature of bom, A Region Required in cis for Transfer", vol. 185, 1982, pp. 344–341.

The Embo Journal, "Chimeric Genes as Dominant Selectable Markers in Plant Cells", vol. 2, No. 6, Mar. 21, 1983, pp. 987–995.

*The Embo Journal*, "Intergeneric Transfer and Exchange Recombination of Restriction Fragments Cloned in pBR322: A Novel Strategy for the Reversed Genetics of the Ti Plasmids of *Agrobacterium tumefaciens*", vol. 2, No. 3, 1983, pp. 411–417.

*The Embo Journal*, "Ti Plasmid Vector for the Introduction of DNA into Plant Cells without Alteration of their Normal Regeneration Capacity", vol. 2, No. 12, 1983, pp. 2143–2150.

*Proc. Natl. Acad. Sci.*, "T–DNA from Agrobacterium Ti plasmid is in the Nuclear DNA Fraction of Crown Gall Tumor Cells", vol. 77, No. 7, Jul. 1980, pp. 4060–4064.

*Proc. Natl. Acad. Sci.*, "Expression of Bacterial Genes in Plant Cells", vol. 80, Aug. 1983, pp. 4803–4807.

*Proc. Natl. Acad. Sci.*, "Recombination Between Higher Plant DNA and the Ti Plasmid of *Agrobacterium tumefaciens*", vol. 77, No. 11, Nov. 1980, pp. 6448–6452.

*Nature*, "DNA from Ti Plasmid Present in Nucleus and Absent from Plastids of Crown Gall Plant Cells", vol. 287, Sep. 1980, pp. 359–361.

*Nature*, "A Chimaeric Antibiotic Resistance Gene as a Selectable Marker for Plant Cell Transformation", vol. 304, Jul. 14, 1983, pp. 184–187.

*Nature*, "T–DNA of a Crown Gall Teratoma is Covalently Joined to Host Plant DNA", vol. 287, Oct. 2, 1980, pp. 458–461.

*J. Mol. Biol.*, "Internal Organization, Boundaries and Integration of Ti–plasmid DNA in Nopaline Crown Gall Tumours", vol. 144, 1980, pp. 353–376.

*Gene*, "Plasmid pKC7: A Vector Containing Ten Restriction Endonuclease Sites Suitable for Cloning DNA Segments", vol. 7, 1979, pp. 79–82.

*Gene*, "The pUC Plasmids, an M13mp7–Derived System for Insertion Mutagenesis and Sequencing with Synthetic Universal Primers", vol. 19, 1982, pp. 259–268.

*Nature*, "Large Plasmid in *Agrobacterium tumefaciens* Essential for Crown Gall–Inducing Ability", vol. 252, Nov. 8, 1974, pp. 169–170.

*The Journal of Biological Chemistry*, "Transcriptional and Translational Start Sites for the *Bacillus thuringiensis* Crystal Protein Gene", vol. 258, No. 3, Feb. 10, 1983, pp. 1960–1967.

*Journal of Bacteriology*, "Positive–Selection Cloning Vehicle Useful for Overproduction of Hybrid Proteins", vol. 154, No. 2, May 1983, pp. 1005–1008.

*Nature*, "Light–Inducible and Chloroplast–Associated Expression of a Chimaeric Gene Introduced into *Nicotiana tabacum* using a Ti Plasmid Vector", vol. 310, Jul. 12, 1984, pp. 115–120.

*Journal of Bacteriology*, "Diversity of Locations for *Bacillus thuringiensis* Crystal Protein Genes", vol. 154, No. 1, pp. 419–428.

Thorne, et al. (1986) Journal of Bacteriology 166:801–811.

Hofte, et al. (Jun. 1989) Microbiological Reviews 53:242–255.

Vaeck, et al (1987) Nature 328:33–37.

Barton, et al. (1987) Plant Physiology 85:1103–1109.

Adang et al (1985) Gene 36: 289–300.

Schnepf, et al (1985) Journal of Biol. Chem. 260(10):6273–6280.

Barnes (Oct. 1985) Abstracts of the 1st International Congress on Plant Mol. Biology; Savannah, GA, USA, Abstract No. OR–21–10.

Klier, et al (1982) EMBO Journal 1(7): 791–799.

Fraley, et al (Aug. 1983) Proc. Natl. Acad. Sci. USA 80:4803–4807.

Reiss, et al (1984) EMBO Journal 3(13): 3317–3322.

de Block, et al. (1985) EMBO J. 4(6):1367–1372.

Comparison of N-terminal amino acid sequences of 130 Kd crystal proteins

1) Bt Whiteley: Met-Asp-Asn-Asn-Pro-Asn-Ile-Asn-Glu-Cys-Ile-Pro-Tyr-Asn-Cys-Leu-Ser-Asn-Pro 2) Bt2 : ? -Asp-Asn-Asn-Pro-Asn-Ile-Asn-Glu- ? -Ile-Pro-Tyr-Asn- ? -Leu- ? -Asn-Pro

FIG. 10

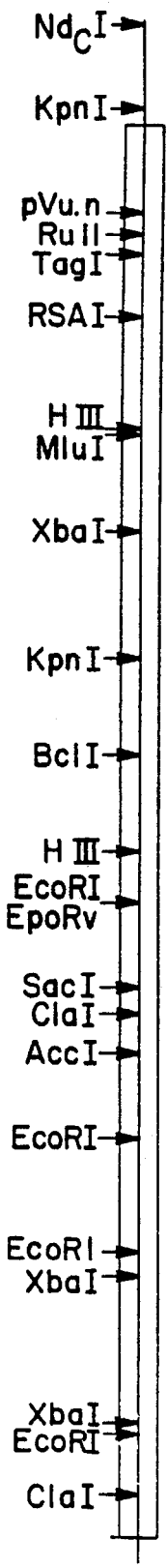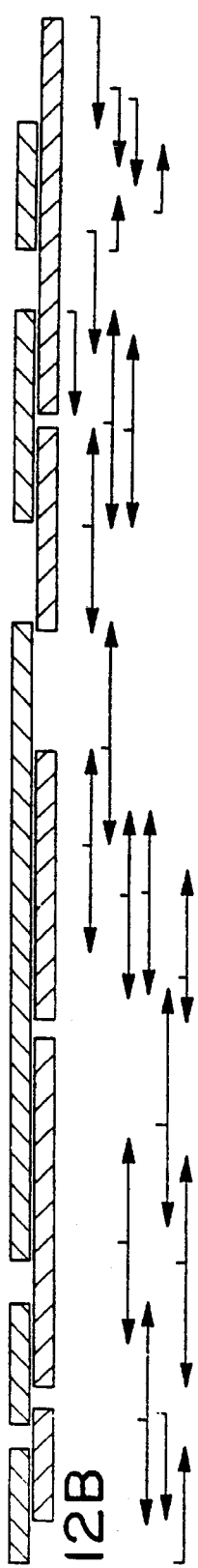
FIG.12A  FIG.12B  FIG.12C

AMINO ACID SEQUENCE COMPARISON OF FOUR BACILLUS THURINGIENSIS TOXINS

```
                     10         20         30         40         50
berliner      MDNNPNINEC IPYNCLSNPE VEVLGGERIE TGYTPIDISL SLTQFLLSEF
kur. HD73
kur. HD1
sotto 60         70         80         90        100
berliner      VPGAGFVLGL VDIIWGIFGP SQWDAFLVQI EQLINQRIEE FARNQAISRL
kur. HD73
kur. HD1                                P
sotto 110        120        130        140        150
berliner      EGLSNLYQIY AESFREWEAD PTNPALREEM RIQFNDMNSA LTTAIPLFAV
kur. HD73
kur. HD1                                                                L
sotto 160        170        180        190        200
berliner      QNYQVPLLSV YVQAANLHLS VLRDVSVFGQ RWGFDAATIN SRYNDLTRLI
kur. HD73
kur. HD1
sotto 210        220        230        240        250
berliner      GNYTDHAVRW YNTGLERVWG PDSRDWIRYN QFRRELTLTV LDIVSLFPNY
kur. HD73          Y                    V                         A
kur. HD1           Y                    V                         A  S
sotto              Y                    V                         A  S 260        270        280        290        300
berliner      DSRTYPIRTV SQLTREIYTN PVLENFDGSF RGSAQGIEGS IRSPHLMDIL
kur. HD73         R                                         R
kur. HD1          R                                      M  R  QN    Q
sotto             R           H                          M  R  QN    Q 310        320        330        340        350
berliner      NSITIYTDAH RGEYYWSGHQ IMASPVGFSG PEFTFPLYGT MGNAAPQQRI
kur. HD73                    Y
kur. HD1             V      FN         T        A   F N A     PV-L
sotto         R      V      FN         T        A  VF N A     PV-L 360        369        379        389        398
berliner      VAQLGQGVYR TLSSTLYRR- PFNIGINNQQ LSVLDGTEFA YGTSS-NLPS
kur. HD73
kur. HD1      SLT L  IF     P     I  ILGS P  E    F     S  FASLTT
sotto         SLT L  IF     P     I  ILGS P  E    F     S  FASLTT
```

FIG. 14A

```
                        408         418         428         438         448
berliner     AVYRKSGTVD SLDEIPPQNN NVPPRQGFSH RLSHVSMFRS GFSNSSVSII
kur. HD73    TI   QR        V          D  S        A          T LSQ   AAGAVYTL--
kur. HD1     TI   QR        V          D  S        A          T LSQ   AAGAVYTL--
sotto 458         468         478         488         498
berliner     RAPMFSWIHR SAEFNNIIPS SQITQIPLTK STNLGSGTSV VKGPGFTGGD
kur. HD73                    A     DS     AV  GNF FN  -  IS
kur. HD1          T    Q                                              H
sotto             T    Q 508    515              523         533         543
berliner     ILRRTSPGQI STLRVNI--- -TAPL-SQRY RVRIRYASTT NLQFHTSIDG
kur. HD73    LV  LN S NN IQN  GY  EVP  IHF ST  T          V     V   PIHLMVNWGN
kur. HD1
sotto 553         563         573         583         593
berliner     RPINQGNFSA TMSSGSNLQS GSFRTVGFTT PFNFSNGSSV FTLSAHVFNS
kur. HD73    SS FSNTVP      AT LD  SD---F YFE SA AFTS LG  NIVGVRN SG
kur. HD1
sotto
                        ↓
                        603         613         623         633         643
berliner     GNEVYIDRIE FVPAEVTFEA EYDLERAQKA VNELFTSSNQ IGLKTDVTDY
kur. HD73    TAG  I   F  I VTA L          N           A   T    L  M
kur. HD1
sotto                                                I 653         663         673         683         693
berliner     HIDQVSNLVE CLSDEFCLDE KKELSEKVKH AKRLSDERNL LQDPMFRGIN
kur. HD73              T Y              R                            S  KD
kur. HD1                                Q
sotto                                   Q 703         713         723         733         743
berliner     RQLDRGWRGS TDITIQGGDD VFKENYVTLL GTFDECYLTY LYQKIDESKL
kur. HD73       PE   G        G                    S          P
kur. HD1                                                       P
sotto                                                          P 753         763         773         783         793
berliner     KAYTRYQLRG YIEDSQDLEI YLIRYNAKHE TVNVPGTGSL WRLSAPSPIG
kur. HD73       F                                                  P    Q
kur. HD1                                                           P    Q
sotto                                                              P    Q
```

FIG.14B

```
                                                  797        807        817
berliner    ---------- ---------- ------KCAH HSHHFSLDID VGCTDLNEDL
kur. HD73   KCGEPNRCAP HLEWNPDLDC SCRDGE
kur. HD1    KCGEPNRCAP HLEWNPDLDC SCRDGE                         H
sotto       KCGEPNRCAP HLEWNPDLDC SCRDGE      R 827        837        847        857        867
berliner    GVWVIFKIKT QDGHARLGNL EFLEEKPLVG EALARVKRAE KKWRDKREKL
kur. HD73
kur. HD1                                                     -
sotto 877        887        897        907        917
berliner    EWETNIVYKE AKESVDALFV NSQYDRLQAD TNIAMIHAAD KRVHSIREAY
kur. HD73                                Q
kur. HD1                                 Q
sotto                           K                                ...

927        937        947        957        967
berliner    LPELSVIPGV MAAIFEELEG RIFTAFSLYD ARNVIKNGDF NNGLSCWNVK
kur. HD73
kur. HD1
sotto 977        987        997       1007       1017
berliner    GHVDVEEQNN HRSVLVVPEW EAEVSQEVRV CPGRGYILRV TAYKEGYGEG
kur. HD73             Q
kur. HD1              Q      L
sotto 1027       1037       1047       1057       1067
berliner    CVTIHEIENN TDELKFSNCV EEEVYPNNTV TCNDYTATQE EYEGTYTSRN
kur. HD73                              I               VN       G A
kur. HD1                               I               VN       G A
sotto 1077       1087       1097       1107       1117
berliner    RGYDGAYESN SSVPADYASA YEEKAYTDGR RDNPCESNRG YGDYTPLPAG
kur. HD73        NE PS-- --      V          S          E  F    R       V
kur. HD1         NE PS-- --      V          S          E  F    R       V
sotto 1127       1137       1147       1155
berliner    YVTKELEYFP ETDKVWIEIG ETEGTFIVDS VELLLMEE
kur. HD73
kur. HD1                               -
sotto
```

FIG. 14C

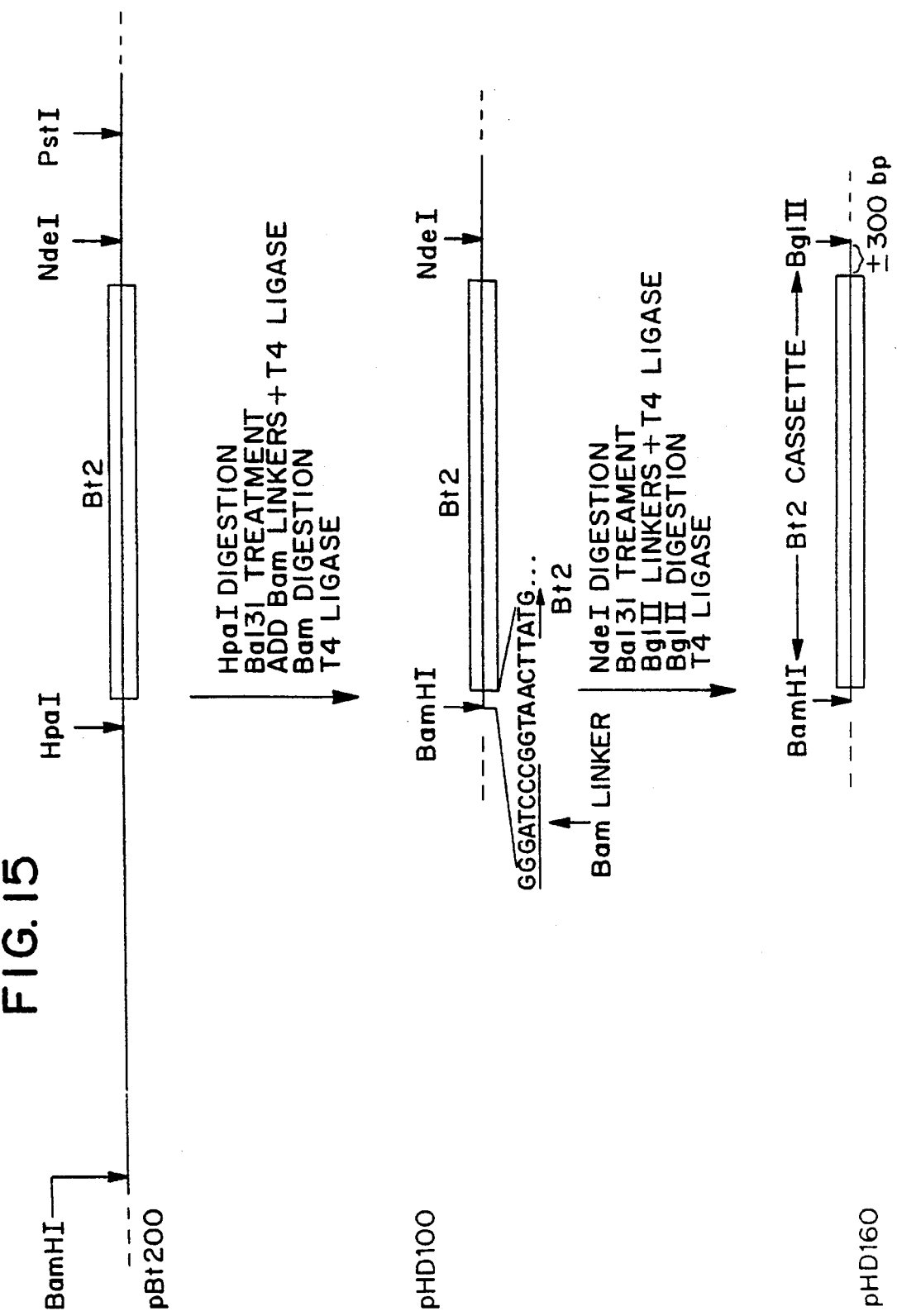

FIG. 16
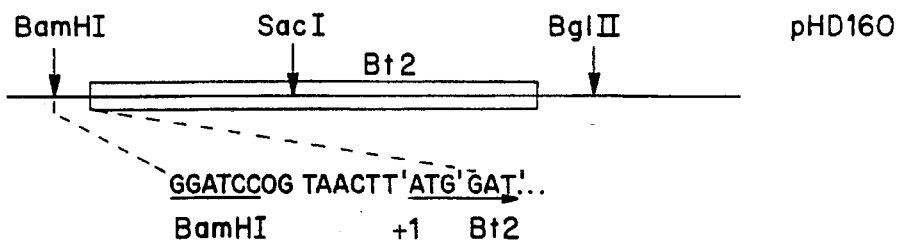
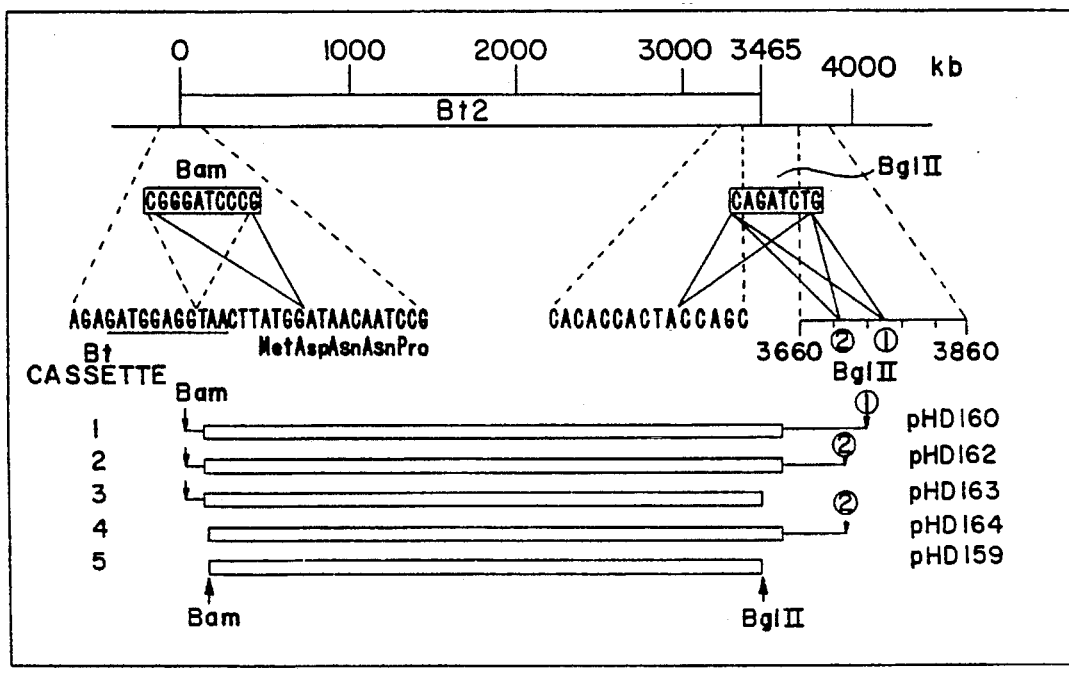
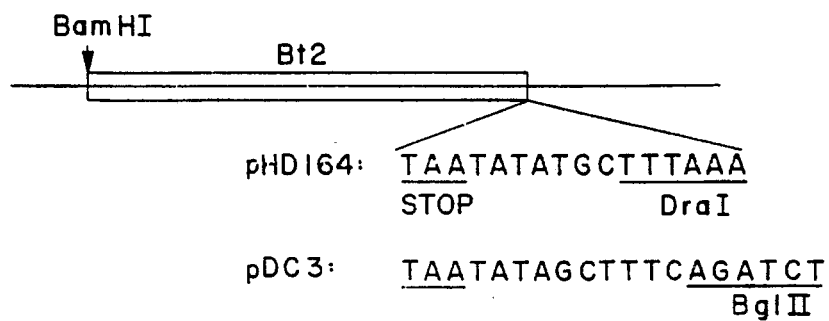

```
                    putative trypsin
                    cleavage site
         pBL 834           ↓              pLB879
           ↓     601                        ↓
Aa pos:  TyrIleAspArgIleGluPheValProAlaGluValThrPhe
         TATATAGATCGAATTGAATTTGTTCCGGCAGAAGTAACCTTT
Bp:           1800      1810      1820      1830
```

FIG. 22

Construction of Bt: NPTII Cassettes

| Plasmid | 5' ends of the Bt2 gene | Purpose |
|---|---|---|
| pLBKm13 | GGAT'CCC'GAT ... <br> +4  Bt2 | Fusion at initiator ATG |
| pLBKm23 | GGATCCCGTGGTATCTTAATTAAAAGAGATG <br> GAGGTAACTT'ATG'GAT ... <br> +1  Bt2 | Expression in E. coli |
| pLBKm33 | GGATCCCGTAACTT'ATG'GAT ... <br> BamHI        +1   Bt2 | Fusion to plant promotor |

23 = Bt·NPT2
860 = Bt·NPT860
865 = Bt·NPT865
NPT = NPT II intact
NF1 = control ext 1) pHD1050, pHD 1060, pGS1110: Pnos - Bt CATAAATTCCCCTCGGTATCCAATTAGAGTTCTGATCGACGGATCCCGTAACTT'ATG'GAT
                                                             BamHI          Bt2

2) pHD1076: Pssu pea - Bt

TAAAAACATTATATATAGCAAGTTTTAGCAGAAGCTTGGCTGCAGGTCGACGGATCCCGTAACTT'ATG'GAT
                                     HindIII          BamHI                    Bt2

3) pHD1080: Tp - Bt fusion

5'
   TAAAAACATTATATATAGCAAGTTTTAGCAGAAGCTTTGCAATTCATACAGAAGTGAGAAAA
                                     HindIII ATG'...'AGA'GTA'AAG 'TGC'ATG'GAT'CCC'GAT'AAC'AAT
                       TP                BamHI     +4 Bt2

4) pGS1151, pGS1152, pGS1153, pGS1161, pGS1162, pGS1163: PTR₂-Bt

ATACACCAAAATCGATGGAT'CCC'GAT
                  ClaI    BamHI +4 Bt2

5) pGS1171, pGS1181: Pssu 301 - Bt

AAGCAAAATTCTTCTAACC'ATG'GAT'CCC'GAT'
                      NcoI          +4 Bt2

6) pGS1251, pGS1252, pGS1261, pGS1262: P35S1 - Bt

CTGAAATCACCAGTCTCGGATCCCGTAACTT'ATG'GAT
                    BamHI          Bt2
                    pos 22 from RNA start 7) pGS1271, pGS1281: P35S2-Bt CAGTCTCTCTCTACAAATCGGATCCCGTAACTT'ATG'GAT
                    BamHI          Bt2
                     pos 36 from RNA start site

FIG. 28

-50 g callus material

-Homogenize at 0°C in 100 ml of the following buffer
 Na$_2$CO$_3$  pH 10   100mM PMFS  0.17 mg/ml EDTA  50 mM DTT  10 mM -sonicate 2 x 3 min at 400 Watt on ice -centrifuge 13,000 rpm; 30 min

↙    ↘ pellet I   supernatant I

-<u>Supernatant I</u>

-Acid precipitation: bring pH down slowly to 4.5 by adding
 dropwise 1 M HCl

-Incubate for 30 min at 0°C

-Centrifuge 10,000 rpm, 30 min

-Wash on ice with cold distilled H$_2$O

-Resuspend pellet in small volume of buffer: Na$_2$CO$_3$  pH 50 mM
 DTT 5 mM  PMSF  0.19 mg/ml -Incubate for 1 h at 0°C, while regularly resuspending -Centrifuge (in Eppendorf)

↙ supernatant = fraction I

-<u>Pellet I</u>

-Resuspend in 100 ml of the following buffer (0°C):

Na$_2$CO$_3$  pH 10  100 mM

DTT 10 mM

PMFS  0.17 mg/ml

EDTA 50 mM

1% Triton x 100

FIG. 37A

-Sonicate 2 x 3 min at 400 Watt on ice
-Centrifuge 13,000 rpm 30 min
       pellet II       Supernatant II Supernatant II:

-Acid precipitation: bring pH down slowly to 4.5 by adding dropwise 1 M HCl

-Incubate for 30 min at 0°C

-Centrifuge 10,000 rpm, 30 min

-Wash once with cold distilled $H_2O$

-Resuspend pellet in small volume of buffer: $Na_2CO_3$ Ph 10 50 mM Dtt 5 mM PMFS 0.17 mg/ml -Incubate for 1 h at 0°C, while regularly resuspending -Centrifuge (in Eppendorf)
       supernatant = fraction II Pellet II:

-Resuspend in 25 ml extraction buffer containing:

2% SDS $Na_2CO_3$ pH 10  100 mM

DTT 10 mM and agitate for 15 min

-Centrifuge 13,000 rpm, 30 min

-<u>Supernatant</u> ---> aceton precipitation:

mix with 9 volumes of aceton 1/40 vol 1 MHCl

-Incubate overnight at -20°C

-Centrifuge 13,000 rpm, 20 min

-Resuspend pellet in small volume of buffer
  containing { 2% SDS
                $Na_2CO_3$  pH 10  100 mM
                DTT  10 mM and boil for 10 min -Centrifuge ---> sup = fraction III

FIG. 37B

```
      6499      6509      6519      6529      6539      6549      6559      6569      6579
6489 AGATCTCCTTGCCCGGAGATCACCATGGACGACTTTCTCTATCTCTACGATCTAGGAAGAAAGTTCGACGGAGAAGGTGACGATAC
     001-BGLII           001-NCOI 6589      6599      6609      6619      6629      6639      6649      6659      6669      6679
CATGTTCACCACCGATAATGAGAAGATTAGCCTCTTCAATTTCAGAAAGAATGCTGACCCACAGATGGTTAGAGAGGCCTACGCGGCAGGTCTCATCAAG
                                                                      001-STUI
                                                                      001-BGLI 6689      6699      6709      6719      6729      6739      6749      6759      6769      6779
ACGATCTACCCGAGTAATAATCTCCAGGAGATCAAATACCTTCCAAGAAGGTTAAAGATGCAGTCAAAGATTCAGGACTAACTGCATCAAGAACACAG 6789      6799      6809      6819      6829      6839      6849      6859      6869      6879
AGAAAGATATATTTCTCAAGATCAGAAGTACTATTCCAGTATGGACGATTCAAGGCTTGCTTCATAAACCAAGGCAAGTAATAGAGATTGGAGTCTCTAA
                              001-SCAI 6889      6899      6909      6919      6929      6939      6949      6959      6969      6979
GAAAGTAGTTCCTACTGAATCAAAGGCCATGGAGTCAAAAATTCAGATCGAGGATCTAACACAGAACTCGCCGTGAAGACTGGGAACAGTTCATACAGAGT
                           002-NCOI 6989      6999      7009      7019      7029      7039      7049      7059      7069      7079
CTTTTACGACTCAATGACAAGAAGAAATCTTCGTCAACATGGTGGAGCACGACACTCTCGTCTACTCCAAGAATATCAAGATACAGTCTCAGAGACC
                           001-XMNI 7089      7099      7109      7119      7129      7139      7149      7159      7169      7179
AAAGGGCTATTGAGACTTTTCAACAAAGGGTAATATCGGGAAAACCTCCTCGGATTCCATTGCCCAGCTATCTGTCACTTCATCAAAAGGACAGTAGAAAA 7189      7199      7209      7219      7229      7239      7249      7259      7269      7279
GGAAGGTGGCACCTACACAAATGCCATCATTGCGATAAAGGAAAGGCTATCGTTCAAGATGCCTCTGCCGACAGTGGTCCCAAAGATGGACCCCCACCACG 7289      7299      7309      7319      7329      7339      7349      7359      7369      7379
AGGAGCATCGTGGAAAAGAAGACGTTCCAACCACGTCTTCAAAGCAAGTGGATTGATGTGATATCTCCACTGACGTAAGGGATGACGCACAATCCCACT
               002-XMNI                                            001-ECORV                ClaI→P35S-2
                                                                                         7469
      7389      7399      7409      7419      7429      7439      7449      7459
ATCCTTCGCAAGACCCTTCCTCTATATAAGGAAGTTCATTTGGAGAGGACACGCTGAAATCACCAGTCTCTCTACAAATCTATC
                                                                          ┌GGATCC←P35S-1
                                                                          └BamHI

NO MATCH FOR STRING
```

FIG. 40

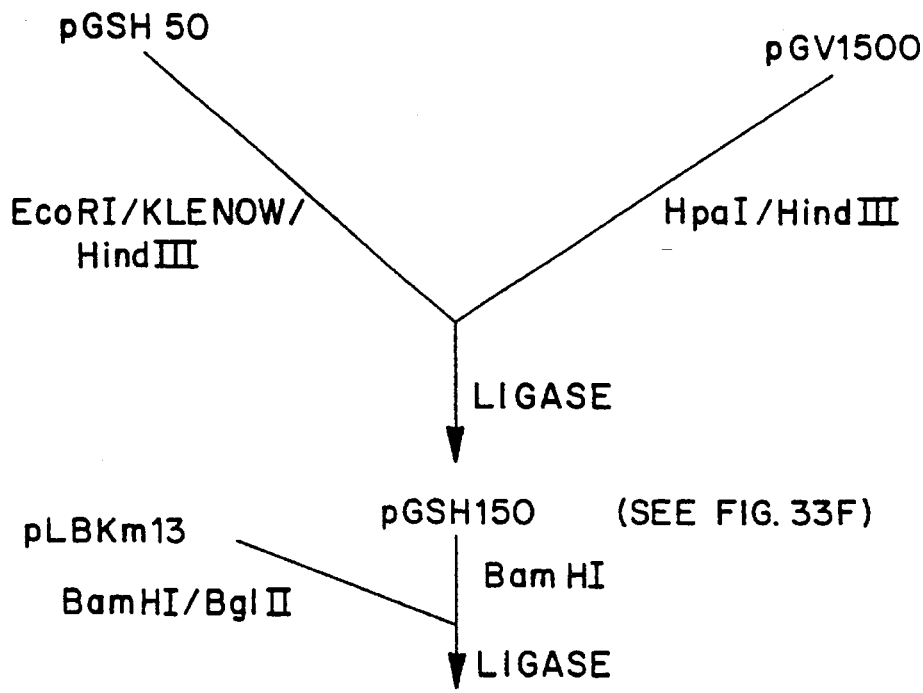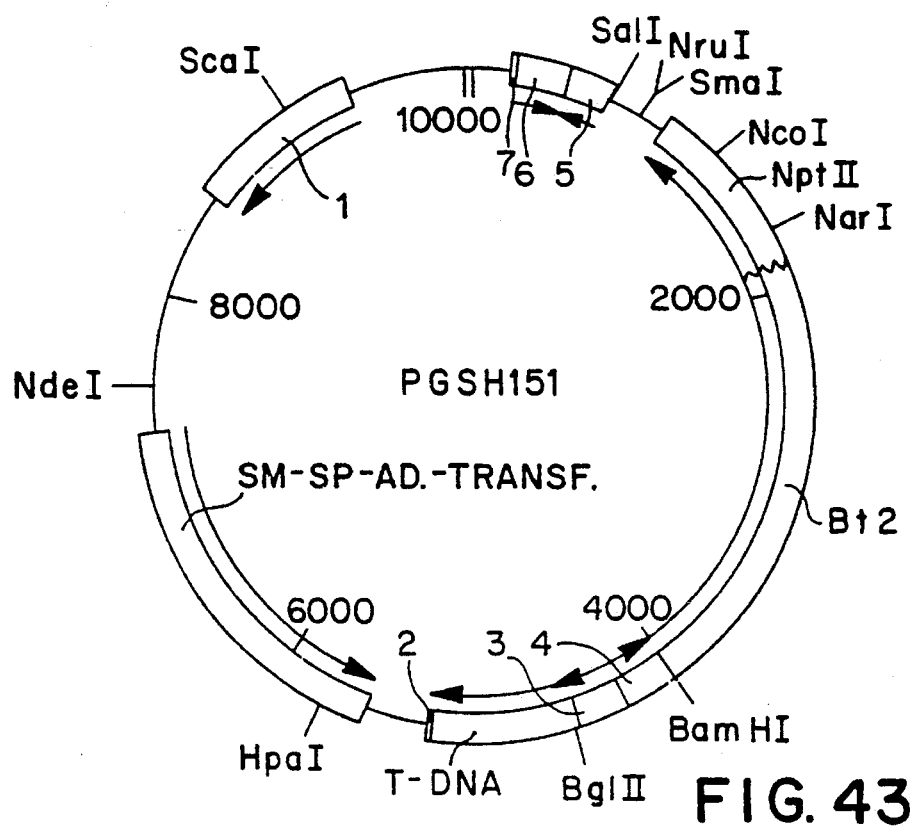
FIG. 43

TRANSFORMATION VECTORS ALLOWING EXPRESSION OF FOREIGN POLYPEPTIDE ENDOXINS FROM *BACILLUS THURINGIENSIS* IN PLANTS

This application is a continuation of U.S. Ser. No. 08/133,965, filed Oct. 8, 1993, now abandoned, which is a divisional of U.S. Ser. No. 08/014,148, filed Feb. 5, 1993, now U.S. Pat. No. 5,317,096, which is a divisional of U.S. Ser. No. 07/555,828, filed Jul. 23, 1990, now U.S. Pat. No. 5,254,799, which is a continuation of U.S. Ser. No. 06/821,582, filed Jan. 22, 1986, now abandoned, which is a continuation-in-part of U.S. Ser. No. 06/692,759, filed Jan. 18, 1985, now abandoned.

BACKGROUND OF THE INVENTION

This invention relates to the use of genetic engineering techniques in the modification of plants. More particularly, it concerns introduction and integration of a chimeric gene coding for a polypeptide toxin produced by *Bacillus thuringiensis* or having substantial sequence homology to a toxin gene described below in plant cells and obtaining an insect controlling level of expression of said polypeptide toxin intracellularly by transformed plant cells and their progeny.

Recombinant DNA technology is currently used to genetically engineer certain microorganisms such as bacteria and yeast to synthesize specific proteins. Genetic engineering of higher organisms within the present state of technology requires that one or a few cells be genetically engineered from which the entire organisms can develop. Among higher organisms, the cells of certain plants exhibit excellent regeneration capability and therefore are considered potentially good material for the genetic engineering of such plants. Furthermore, in higher plants, a known system is available to introduce foreign DNA into the plant genome. This system is provided by the tumor inducing plasmid from the gram negative soil bacterium *Agrobacterium tumefaciens*. Agrobacterium can genetically transform plant cells by stably integrating T-DNA, a well defined fragment of the Ti plasmid, into the plant cell genome. Recently, important progress has been made to facilitate the use of the Ti plasmid as a vector for plant genetic engineering. Small directly repeated sequences which flank the T-DNA (Border sequences) have been found to play a key role in the T-DNA integration. Nononcogenic Ti plasmid vectors have been constructed from which oncogenic tumor genes have been removed by an internal deletion in the T-DNA. These Ti plasmids still contain the border sequences and consequently transfer T-DNA without tumor induction. An example of such a Ti plasmid derived vector from plant genetic engineering is pGV3850 which contains a substitution of the internal T-DNA gene by the commonly used cloning vehicle pBR322. Several procedures have been developed to regenerate infected plants which contain the pGV3850. pGV3850 with the pBR322 sequences present in its T-DNA is an efficient acceptor plasmid for gene transfer experiments in plant cells. Indeed, genes cloned in pBR322 like plasmids are transferred to Agrobacterium and inserted via homologous recombination into the pGV3850 T-DNA in a single experimental step.

Another major advance in the development of plant engineering technique is the use of plant regulatory sequences to express chimeric genes in plants. In general, these chimeric genes contain a promoter region derived from a gene which is naturally expressed in plant cells, the sequence to be expressed, and preferentially a 3' non-translated region containing a polyadenylation site of a gene which is naturally expressed in plant cells. For example, using the nopaline synthase promoter and bacterial antibiotic resistance genes, dominant selectable markers for plant cells have been constructed.

Although certain chimeric genes have now successfully been expressed in transformed plant cells, such expression is by no means straightforward. Various lines of evidence indicate that the level of expression of the foreign genes of non-plant origin not only varies greatly in different transformed tissues but are in general very low. Such low levels of gene expression could be due to several reasons: first, incomplete transcription of the gene resulting from inadvertent transcription termination signals; second, inefficient processing of the messenger RNA; third, impaired transport of the messenger RNA from the nucleus to the cytoplasm; fourth, instability of the cytoplasm messenger RNA; fifth, inefficient translation of the cytoplasm messenger RNA; and sixth, instability of the protein due to its susceptibility to plant specific proteins. Consequently, the successful transformation of plant cells using vectors such as those described above is not necessarily predictable prior to attempting a desired transformation.

Engineering of differentiated plant cells and their progeny to express the Bt2 polypeptide and/or a truncated version thereof and/or a polypeptide having substantial sequence homology thereto is far more difficult than other genes such as antibiotic resistance genes or other plant genes such as thaumatin due to one or more of the following: (1) the large size of the Bt2 toxin, even in its truncated form; (2) the particular properties of the Bt2 polypeptide (such as, but not limited to, solubility of the polypeptide); (3) the potential toxicity of the Bt2 polypeptide toward the plant cells; or (4) the Bt2 polypeptide synthesized in plant cells and their progeny must retain substantially the same properties as the crystal protein synthesized in bacteria.

*Bacillus thuringiensis* (referred to at times herein as *B.t.*) bacteria includes approximately 19 known varieties that produce polypeptide toxins which form parasporal crystals during sporulation. The crystal protein made by *B.t.* is toxic to the larvae of certain insects. The toxins produced by a particular variety exhibit strong insecticidal activity, against certain Lepidoptera and/or Ceoleoptera and/or Diptera larva. See e.g., Tyrell D. J. et al., *J. Bacteriology,* (81) 145 (No. 2): p. 1052–1062. When ingested by insect larvae, the crystals are solubilized and processed in the insect midgut to yield at least one active polypeptide toxin which is believed to act on the midgut cell membrane. Studies have revealed that individual crystal polypeptides exhibit insecticidal activity. Yamamoto, T. et al., *Current Microbiology,* (83) 9: p. 279–284; Yamamoto, T. et al., *Arch. Biochem. Biophysics,* (83) 227: (No. 1): p. 233–241; Lilley, M. et al., *J. Gen. Microbiol.,* (80) 118: p. 1–11; Bulla, L. A. et al., *J. Biol. Chem.,* (81) 256 (No. 6): p. 3000–3004.

The toxic activity of the crystal polypeptide produced by *Bacillus thuringiensis* varieties is highly specific to particular insect species and is recognized as safe to higher vertebrates.

Preparations containing the crystals are used commercially as a biological insecticide. For example: Bactospeine, distributed by Biochem Products Ltd., Dipel Abbott Laboratories; and Thuricide, Sandoz AG. The efficacy of preparations obtained from bacterial hosts is, however, limited as adequate control of pests requires repeated and precisely timed applications. In addition, costs associated with the production of such preparations have made it difficult for them to compete effectively with other commercially available products, such as pyrethoid derivatives.

Molecular genetics studies have demonstrated that at least some polypeptide toxins produced by *Bacillus thuringiensis* are encoded by plasmids. Stahly, D. P. et al., (1978), *Biochem. Biophys. Res. Commun.*, 84, p. 581–588; Debaboc, V. G. et al., (1977), *Genetika*, 13, p. 496–501. Genes encoding toxic crystal polypeptides from different *B.t.* strains have been cloned and expressed in other bacterial hosts. (Schnepf & Whiteley, *PNAS* (81) 78:2993–2897. Klier, A. et al., *EMBO J.* (82) 1 (No. 7), p. 791–799; Adang et al., *Gene*, (36), p. 289, 1985; Schnepf et al., *J. Biol. Chem.*, (20), p. 6264, 1985; Shibano et al., *Gene*, (34), 1985.

Considering the major importance of plants both for consumption and for production of valuable products, it would be highly desirable to genetically modify plants such that plant cells could synthesize polypeptide toxins substantially similar to those toxins produced by *Bacillus thuringiensis*, without adverse effects to the plants. By stably integrating exogenous DNA fragments coding for polypeptide toxins produced by *Bacillus thuringiensis* into the plant cell genome and obtaining an insect controlling level of expression of said exogenous DNA fragments in plants, plant cells and their progeny so transformed would thereby become resistant to certain insect pests. Plant cells and their progeny genetically engineered in this way would provide an economically advantageous substitute to existing commercial varieties by substantially obviating the need for specific chemical or biological insecticides, and provide a more reliable means of controlling particular insect pests, while retaining normal morphological characteristics.

It is one object of this invention to provide novel chimeric genes coding for the polypeptide toxin produced by *Bacillus thuringiensis*, or coding for a polypeptide toxin having substantial sequence homology to a toxin gene described herein. The chimeric genes' plant regulatory sequences direct expression in transformed plant cells.

Another object of present invention is to provide novel hybrid plasmid vectors containing said chimeric genes that allow the introduction and integration and expression of said chimeric genes in a plant cell genome.

A further object of the present invention is to provide a process for preparing genetically transformed plant cells comprising the transformation of plant cells with said hybrid plasmid vectors containing said chimeric genes.

Other objectives, features and advantages of the present invention will become apparent to those skilled in the art from the following description taken in conjunction with the accompanying drawings.

SUMMARY OF THE INVENTION

In accordance with the present invention, there are provided: chimeric genes capable of being expressed in differentiated plant cells comprising:
  (a) a DNA fragment comprising a promotor region derived from a gene which is naturally expressed in a plant cell; and
  (b) at least one DNA fragment coding for a polypeptide toxin produced by *Bacillus thuringiensis* or having substantial sequence homology thereto.

Said chimeric genes include those where DNA fragment (b) codes for a Bt2 protein, an insecticidally active truncated Bt2 protein, a DNA fragment having substantial sequence homology to Bt2 or the truncated Bt2, or where DNA fragment (b) is fused to a DNA fragment (c) coding for an enzyme capable of being expressed in differentiated plant cells and permitting identification of plant cells expressing DNA fragment (b) where said DNA fragments (b) and (c) encode a fusion polypeptide.

Also in accordance with the present invention there are provided: hybrid plasmid vectors comprising:
  (a) a DNA fragment substantially homologous with that portion of a Ti plasmid essential for transfer of a T-region of a Ti plasmid to a plant cell genome (the virulence region of a Ti plasmid);
  (b) at least one DNA fragment which delineates a DNA fragment to be integrated into a plant cell genome (the border sequences of the T-DNA portion of a Ti plasmid; where only one border sequence is present, preferably it is the right border sequence); and
  (c) at least one chimeric gene comprising:
    (i) a DNA fragment comprising a promotor region derived from a gene which is naturally expressed in a plant cell; and
    (ii) at least one DNA fragment coding for a polypeptide toxin produced by *Bacillus thuringiensis* or at least one DNA fragment having substantial sequence homology thereto.

Said chimeric genes include those where DNA fragment (b) codes for a Bt2 protein, an insecticidally active truncated Bt2 protein, a DNA fragment having substantial sequence homology to Bt2 or the truncated Bt2, or where DNA fragment (b) is fused to a DNA fragment (c) coding for an enzyme capable of being expressed in differentiated plant cells and permitting identification of plant cells expressing DNA fragment (b) where said DNA fragments (b) and (c) express a fusion polypeptide.

Further, in accordance with the present invention, there are provided: intermediate plasmid vectors containing at least one chimeric gene, said chimeric gene comprising:
  (a) a DNA fragment comprising a promotor region derived from a gene which is naturally expressed in a plant cell; and
  (b) at least one DNA fragment coding for a polypeptide toxin produced by *Bacillus thuringiensis*, or at least one DNA fragment having substantial sequence homology thereto.

Said chimeric genes include those where DNA fragment (b) codes for a Bt2 protein, an insecticidally active truncated Bt2 protein, a DNA fragment having substantial sequence homology to Bt2 or the truncated Bt2, or where DNA fragment (b) is fused to a DNA fragment (c) coding for an enzyme capable of being expressed in differentiated plant cells and permitting identification of plant cells expressing DNA fragment (b) where said DNA fragments (b) and (c) express a fusion polypeptide.

Further, in accordance with the present invention, there are provided insecticidal compositions and methods of using transformed plant cells and their progeny.

Still further in accordance with the present invention there are provided: plants which include in their cells genome and express the chimeric gene as described above; and plant seeds which are capable of germinating into a plant which expresses the chimeric gene as described above.

Transformed plant cells and their progeny intracellularly express a polypeptide toxin substantially similar to the polypeptide toxins produced by *Bacillus thuringiensis* and are substantially toxic to certain insects. Transformed plant cells and their progeny may be used in controlling said insects.

Track 1: *B.t.* kurstaki crystal protein preparation;

Track 2: *B.t.* berliner crystal protein preparation;

Track 3: Molecular weight markers
- a: phosphorylase B (92,500 dalton);
- b: bovine serum albumin (66,300 dalton);
- c: ovalbumin (45,000 dalton); and
- d: carbonic anhydrase (31,000 dalton).

Figure 2:
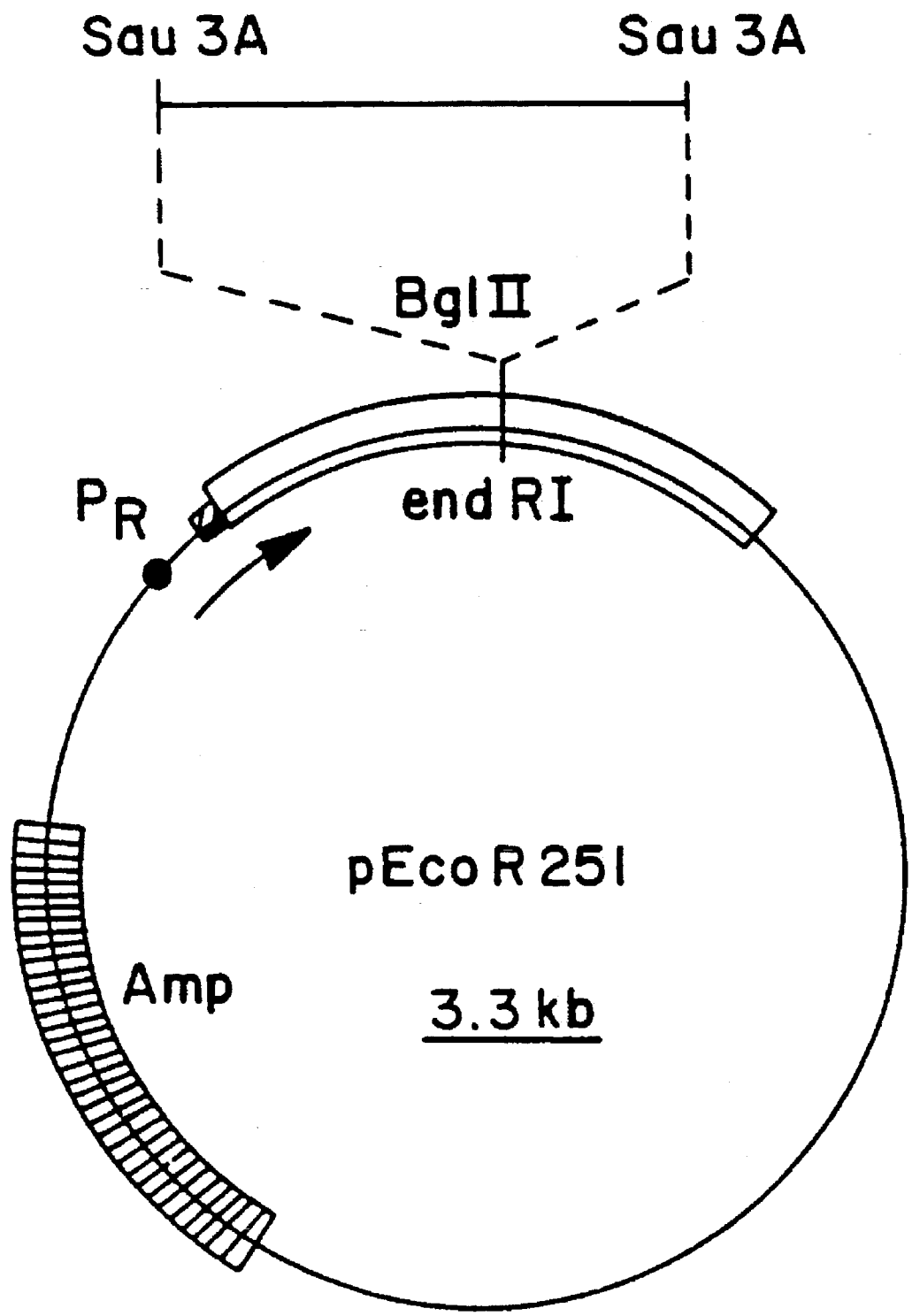

FIG. 2 is a schematic diagram of plasmid pEcoR251. The EcoRI endonuclease gene (EndRI) is fused to the $P_R$ promotor ($P_R$) and contains a unique BglII cloning site. Amp: beta-lactamase gene.

Figure 3:
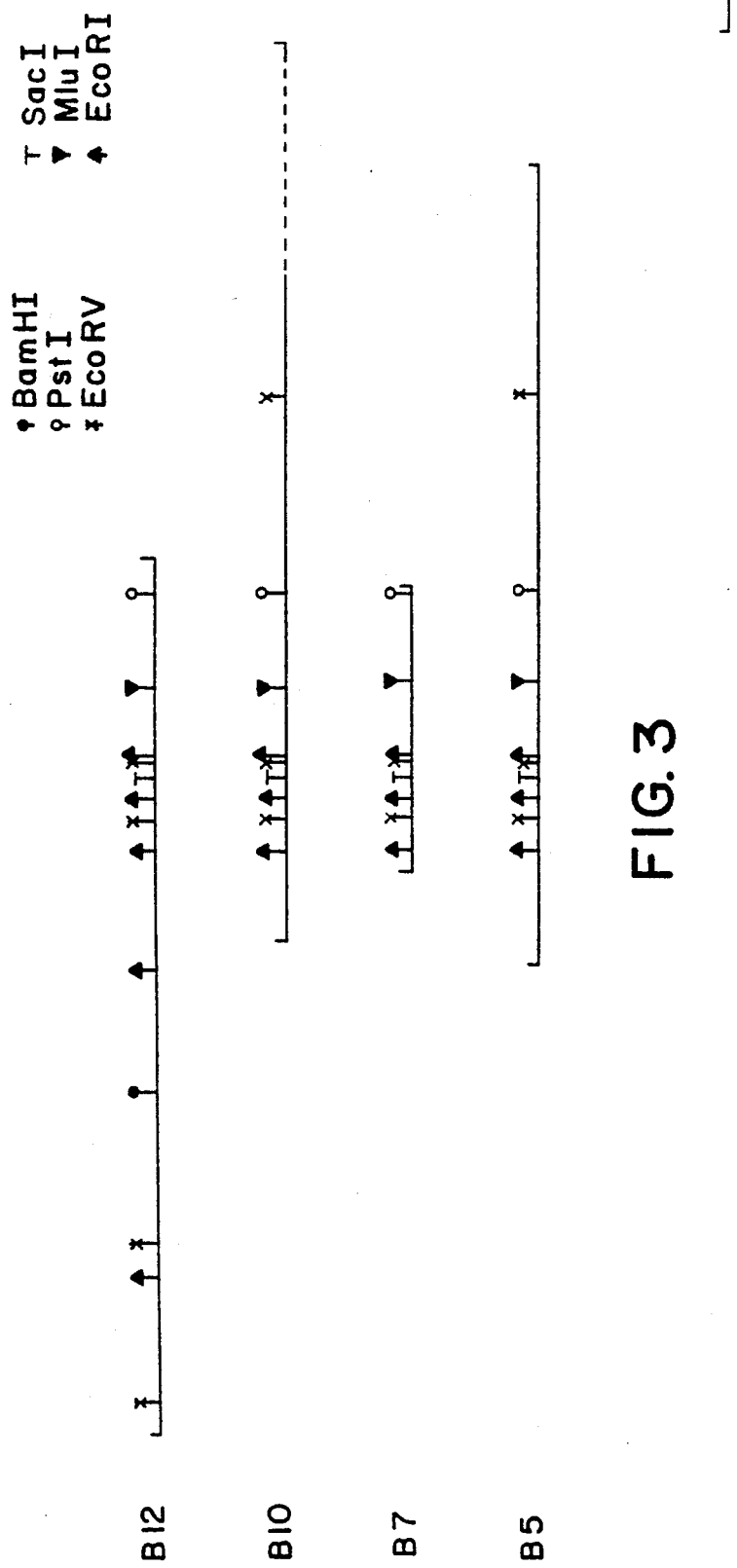

FIG. 3 shows restriction enzyme maps of the inserts present in 4 immunopositive partial Sau3A digest clones of *B.t.* berliner 1715 plasmid DNA cloned in pEcoR251.

Figure 4:
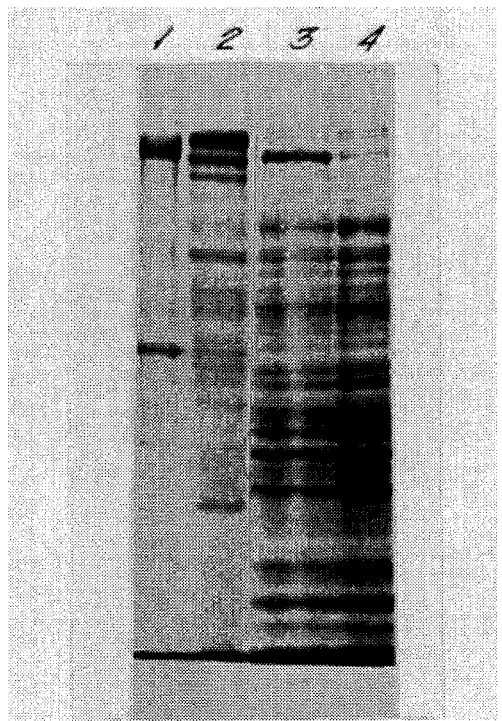

FIG. 4 is a photograph showing a 7.5% SDS PAGE stained with Coomassie Blue.

Figure 1:
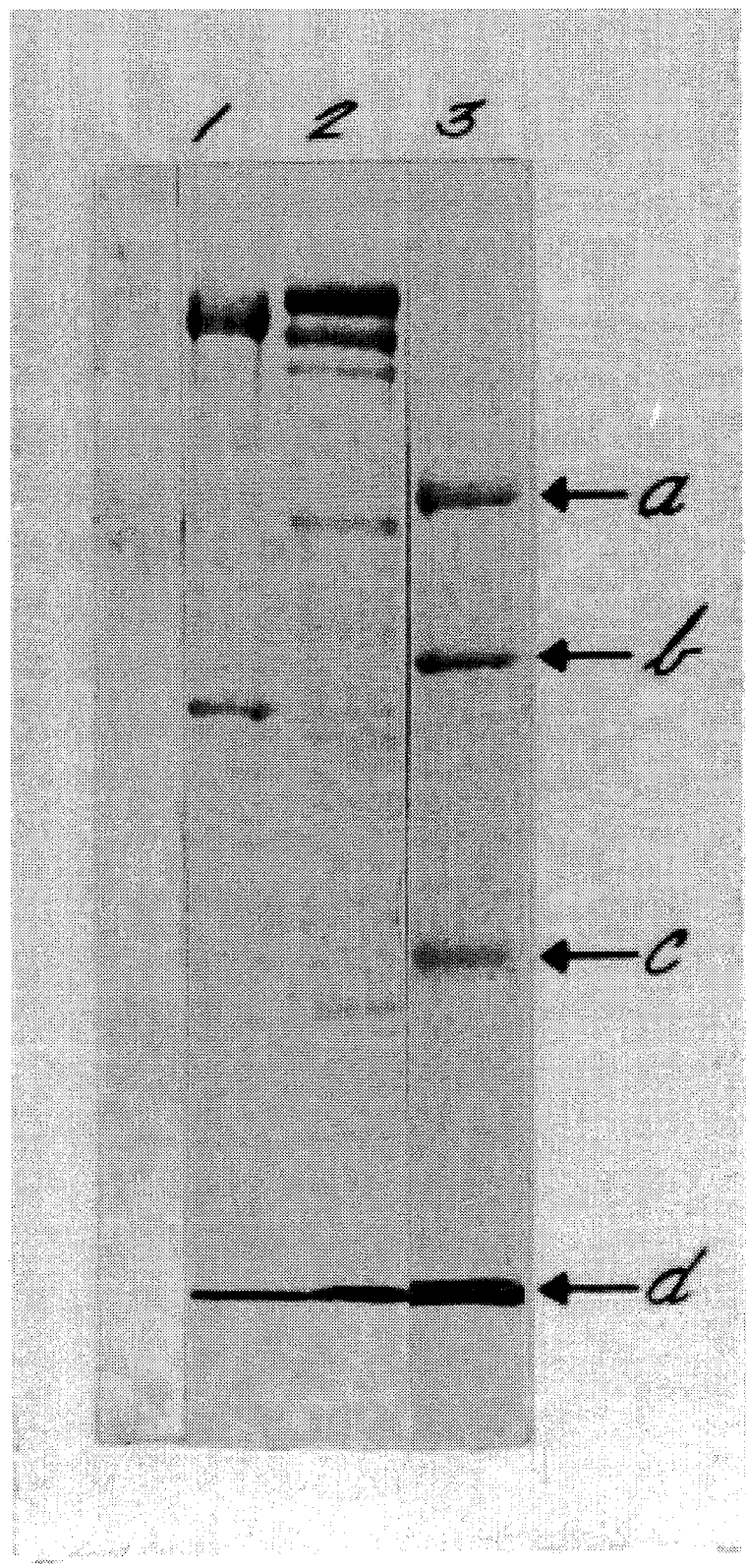
FIG. 1 is a photograph showing a 7.5% SDS PAGE stained with Coomassie Blue.

Track 1: *B.t.* kurstaki crystal protein preparation (identical with FIG. 1, Track 1);

Track 2: *B.t.* berliner crystal protein preparation (identical with FIG. 1, Track 2);

Track 3: Total lysate of *E. coli* K514 containing the Bt200 plasmid; and

Track 4: Control (total lysate of *E. coli* K514 without Bt200 plasmid).

FIG. 5 is a photograph showing the results of immunoblotting experiment using a rabbit anti-*B.t.* kurstaki crystal serum.

Track 1: *B.t.* berliner crystal protein preparation;

Track 2: *B.t.* kurstaki crystal protein preparation;

Track 3: Total lysate of *E. coli* K514 harboring the pBt200 plasmid; and

Track 4: Control (total lysate of *E. coli* K514 without pBt200.

FIG. 6 is a photograph showing the results of an immunoblotting experiment using a rabbit anti-kurstaki crystal serum (A) and a rabbit anti-berliner crystal serum (B). Part C shows a Coomassie staining of the 7.5% SDS PAGE after the blotting procedure (the same gel used for blotting shown in Part A).

Track 1: Bt2 protein (purified as described in Section 5-1);

Track 2: *B.t.* berliner crystal proteins; and

Track 3: *B.t.* kurstaki crystal proteins.

FIG. 7 is a photograph showing a Coomassie staining of an SDS PAGE.

Track 1: Totally lysate of *E. coli* K514 harboring pBt200;

Track 2: Purified Bt2 protein prepared from the *E. coli* K514 harboring pBt200.

FIG. 8 is a graph showing the results of an ELISA experiment. Binding curves of Bt2 protein and solubilized *B.t.* crystal proteins using a goat anti-*B.t.* crystal serum as goat-antibody and a mouse anti-Bt2 serum as first antibody.

FIG. 9 is a graph showing the results of an ELISA experiment showing reactivity of the different anti-berliner crystal monoclonal antibodies with:

FIG. 9(A) shows total berliner crystal proteins; and

FIG. 9(B) shows purified Bt2 protein.

FIG. 10 shows a comparison of N-terminal amino acid sequences of the 130 Kd crystal proteins:

1) deduced from the DNA sequence published by Wong et al., *J. Biol. Chem.* 258, p. 1960–1967 (1983) (termed *B.t.* W);

2) determined for the Bt2 protein.

FIG. 11 summarizes the immunological detection of polypeptides using Western blotting with a rabbit anti-*B.t.* berliner crystal serum. Polypeptides are encoded by pBt200 derivatives containing various deletions generated by restriction enzyme cleavage as indicated in the figure.

FIG. 12 A—shows the restriction map of the HpaI-NdeI fragment containing the entire Bt2 gene indicated as a box. B—shows the sequenced regions of the Bt2 gene. Boxes represent the stretches which have been sequenced from each strand. C—shows sequencing strategy. Restriction fragments were end labeled with polynucleotide kinase, strand isolated and sequenced using the Maxam and Gilbert method. The arrows indicate the length of the region sequenced in each experiment.

FIG. 13A–C shows the DNA sequence of the complete Bt2 gene indicating the open reading frame (position 21 to 3605) and the corresponding deduced amino acid sequence (1155 amino acids). The amino acid sequence of the Bt2 protein which was experimentally determined is indicated by a line above the corresponding amino acids.

FIG. 14A–C shows a comparison of the deduced amino acid sequences of the Bt2 gene (berliner) with the deduced sequences from three other *B.t.* crystal protein genes, cloned from other *B.t.* strains:

*B.t.* kurstaki HD73 (Adang et al., *Gene.* 36, p. 289, 1985)
*B.t.* kurstaki HDl (Schnepf et al., *J.B.C.* 20, p. 6264, 1985)
*B.t.* sotto (Shibano et al., *Gene* 34, p. 243, 1985)

In the latter 3 sequences, only those amino acids are represented that differ from those present in the Bt2 sequence at the homologous position. Eventually, gaps were introduced (marked by "—") in order to align the sequences.

FIG. 15 is a schematic outline of the construction of the Bt2 gene cassette pHD160.

FIG. 16 is a schematic representation of the different Bt2 gene cassettes.

FIG. 17 shows the experimental strategy used for the construction of plasmid pLB10. Also shown here is the structure of plasmids pLK54 and pLK57, described in J. Botterman et al. (in preparation).

FIG. 18 shows the construction and structure of pLBKm25.

FIG. 19 shows the strategy used to construct Bt:NPTII fusions and Bt2 deletions.

FIG. 20 is a schematic representation of the different Bt2 3' end deletion mutants, used in the mapping of the 3' end of the minimal toxin encoding fragment. Arrows represent the positions of the 3' ends.

FIG. 21 is a photograph showing the results of an immunoblotting experiment using a rabbit anti-berliner crystal serum. Samples analyzed are total extracts from Bt2 deletion clones specified in FIG. 20 and in Section 7.

FIG. 22 shows the 3' end points of deletion clones pLB834 and pLB879 on the Bt2 sequence, used to delineate the minimal gene fragment encoding an active toxin. Also shown is the deduced amino acid sequence and the position of a putative trypsin cleavage site.

FIG. 23 is a schematic representation of the construction of the Bt2:NPTII fusion gene cassettes pLBKm23, pLBKm33 and pLBKm14. Also represented are the 5' upstream sequences of the Bt2:NPTII fusions in the different constructs (sequences corresponding to a BamHI site are underlined).

FIG. 24 is a schematic representation of different Bt:NPTII fusion gene cassettes.

FIG. 25 is a photograph showing the results of a NPTII assay as described by Reiss et al. (*Gene,* 30, p. 217, 1984).

The samples analyzed are the supernatants of cell extracts of bacterial clones producing NPTII or different Bt2-NPTII fusion proteins.

23 means K514 (lambda) (pLBKm23)

860 means K514 (lambda) (pLBKm860)

865 means K514 (lambda) (pLBKm865)

NPT means HB101 (lambda dv) (a gift from Julian Davis, formerly of Biogen)

Figure 26:
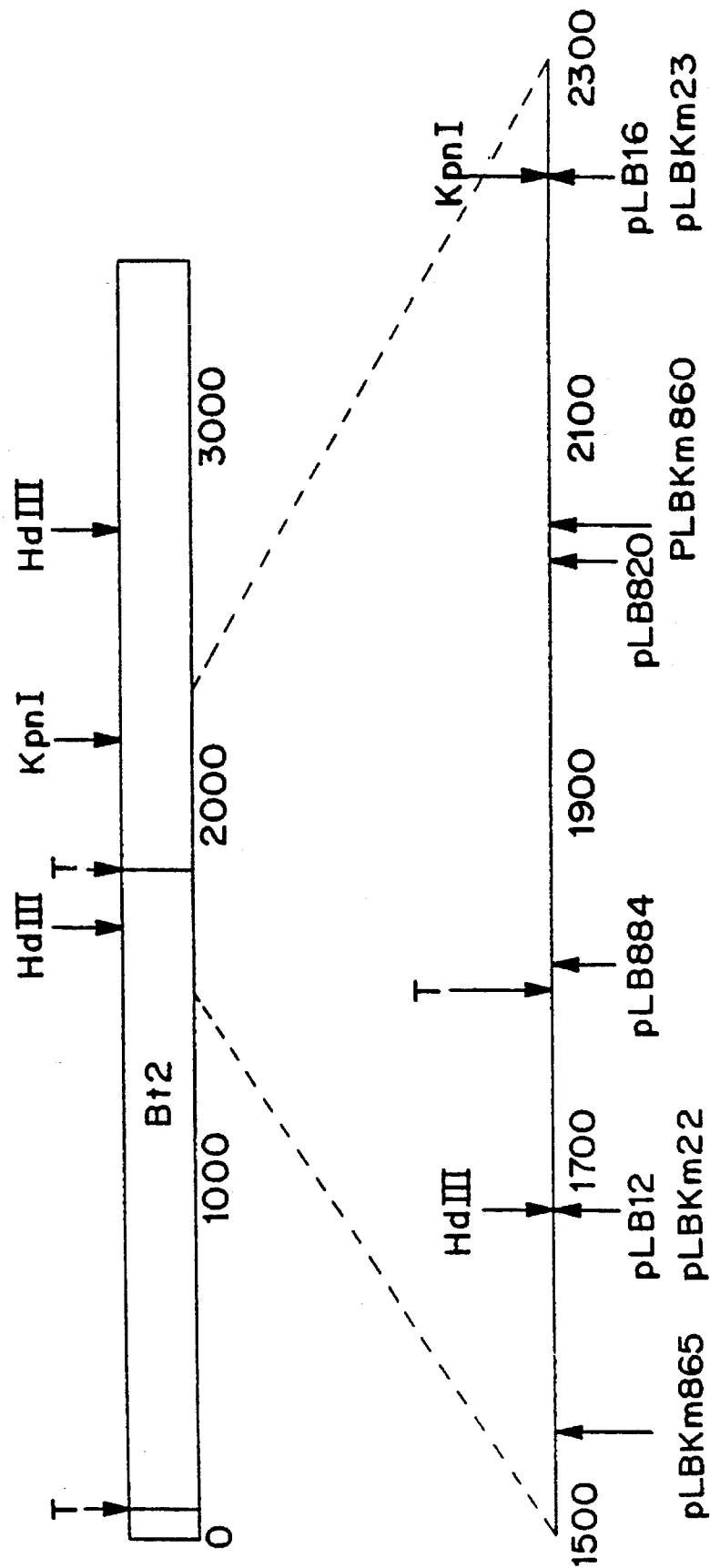

FIG. 26 shows the approximate positions of the 3' ends of the Bt sequences in different deletions and Bt:NPTII fusions (indicated by arrows).

Figure 27:
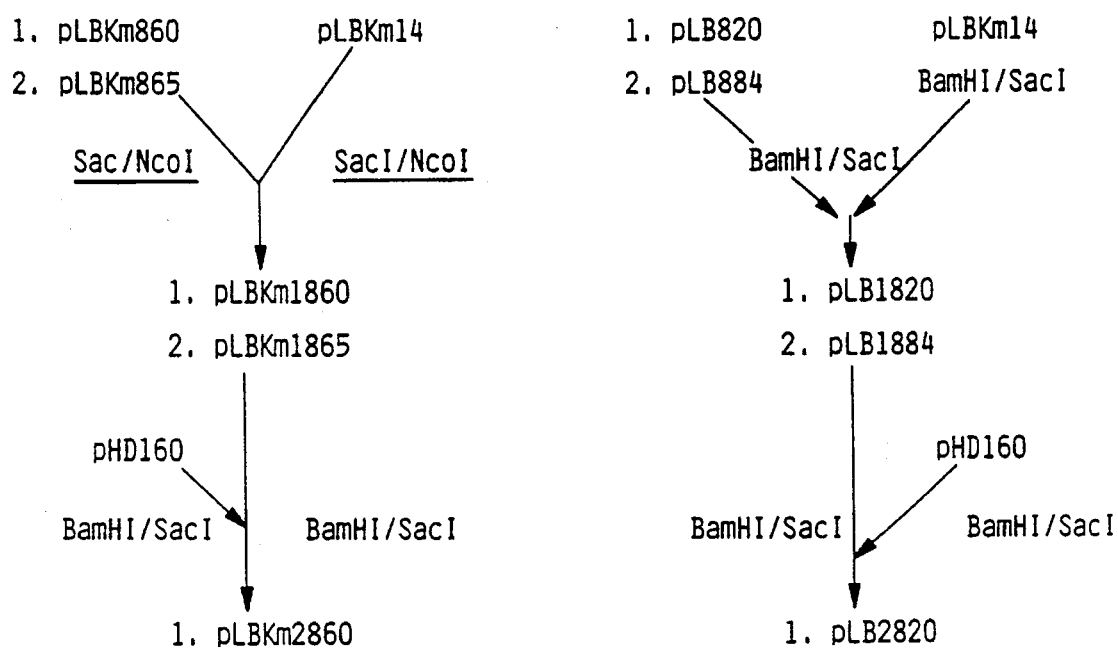
Figure 29:
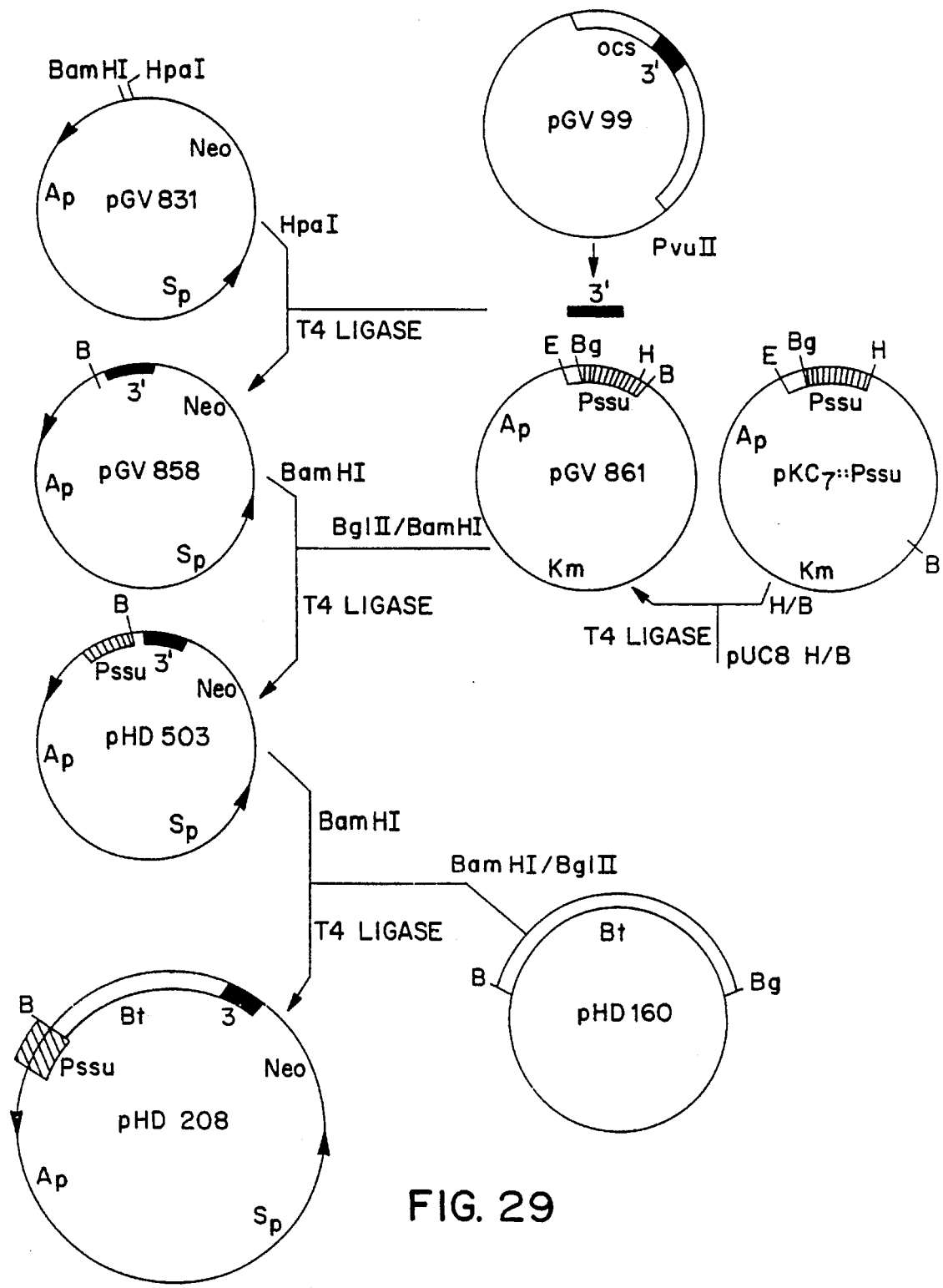
Figure 30:
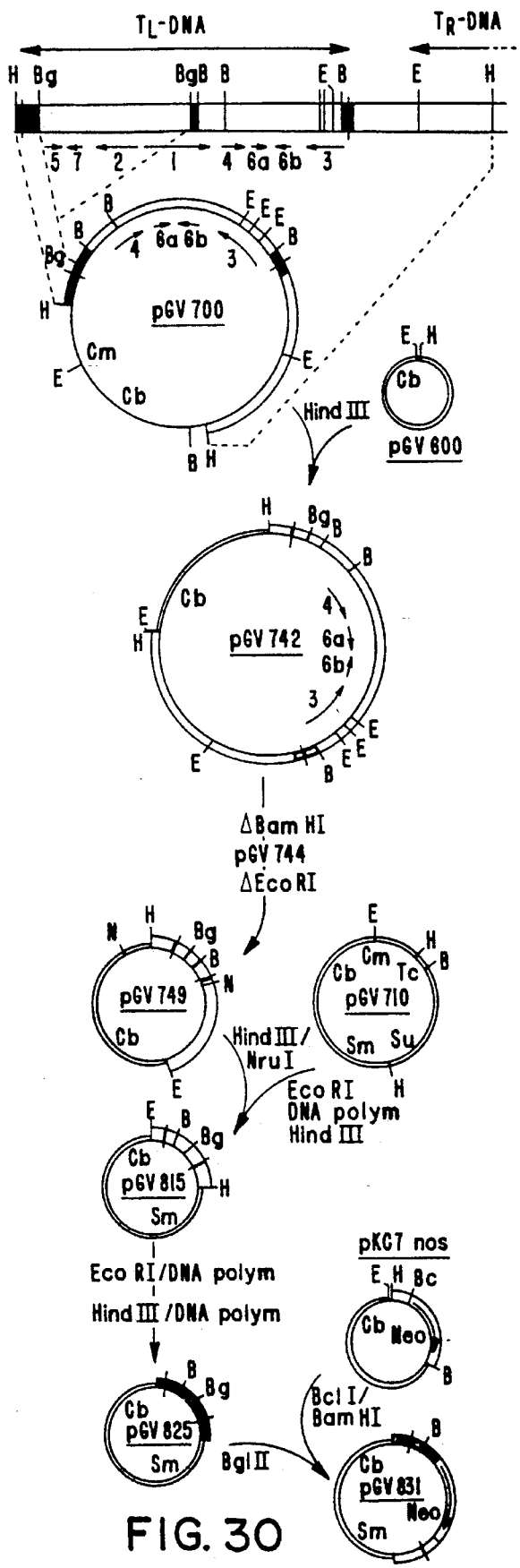

FIG. 27 shows the strategy used for the adaptation of the Bt2 and the Bt2:NPTII cassettes for expression in plant cells.

FIG. 28 shows the DNA sequences at the junction between the promotor regions and the coding sequence of the Bt gene cassettes as they are present in the different engineered Ti plasmids. Sequences derived from the original promotor regions and from the coding sequence of the Bt2 gene are underlined. Some relevant restriction enzyme sites which have been involved in the assembly of the chimeric genes are indicated. The ATG initiation codon is boxed.

FIG. 29 is a schematic representation of the construction of pHD208 as described in Section 8 Example 2.

B: BamHI, Hp: HpaI, H: HindIII, E: EcoRI, Bg: BglII.

FIG. 30 is a schematic representation of the construction of pGV831: pGV831 has been constructed by R. Deblaere, Lab of Genetical Virology, Free University Brussels, Belgium. It is a derivative of pGV700, as described in European Patent Application No 83112985.3. Recombinant DNA techniques used followed Maniatis et al., *Molecular Cloning* (1982), Cold Spring Harbor Laboratory.

The HindIII fragment present in pGV700 was subcloned into pGV600 (Leemans et al., *J. Mol. Appl. Genet.*, 1, 149–164, 1981). Recombinant plasmid pGV742 was isolated as a $Cb^R$ $Cm^S$ $Tc^S$ recombinant. An internal deletion was created in pGV742 by digestion with BamHI and recirculization. This produced pGV749. An internal deletion was created in pGV744 by digestion with EcoRI and recirculization to yield pGV749. The HindIII-NruI fragment from pGV749 was cloned in pGV710. pGV710 had been digested with EcoRI, the 5' protruding end filled in using DNA polymerase and had been subsequently digested with HindIII. The resulting plasmid pGV815 was isolated as a $Sm^R$, $Cb^R$ recombinant Both the EcoRI site and the HindIII site of pGV815 were removed by digestion with these enzymes and by filling in the protruding ends with DNA polymerase, followed by recirculization. Finally, a chimeric gene containing the nopaline synthase promotor and the neomycin phosfotransferase gene from Tn5 was isolated as a BclI-BamHI fragment from pKC7/:nos and was cloned in the BglII site from pGV825. The $Sp^R$, $Km^R$ recombinant plasmid pGV831 was obtained.

FIG. 31 is a schematic representation of the T region of Ti-plasmid pGV3850 and of the intermediate vector pHD205. The crossed lines indicate the regions which were involved in cointegration of pGV3850 with pHD205 to produce pHD1050. The T region of hybrid Ti plasmid pHD1050 is represented.

H: HindIII

Bt: chimeric Bt2 gene under control of the nopaline synthase promotor nos: nopaline synthase gene Ap, Km: genes encoding ampicillin and kanamycin resistance FIG. 32 is a schematic representation of the T region of Ti plasmid pGV2260 and of the intermediate vector pHD208. The crossed lines indicate the regions which were involved in cointegration of pGV2260 with pHD208 to produce pHD1076. The T-region of hybrid Ti-plasmid pHD1076 is represented.

1: vector fragment

2: T-DNA border region

3: Bt2 gene cassette

4: Pssu promotor fragment

5: Pnos promotor fragment

6: neomycin phosfotransferase gene cassette

7: T-DNA border region

8: vector fragment

Black triangles represent T-DNA border regions

Ap, Sp, Fun: genes encoding respectively ampicillin, spectinomycin and kanamycin resistance Pnos: nopaline synthase promotor Pssu: small subunit of ribulose biphosphate carboxylase promotor

*B.t.*: Bt2 gene cassette

FIG. 33 shows schematic representations of the different intermediate expression vectors.

A: Schematic representation of pLGV2382.

B: Schematic representation of pGV857.

C: Schematic representation of pD508.

D: Schematic representation of pAC6.

E: Schematic representation of pGV874.SEQ.

F: Schematic representation of pGSH150.

G: Schematic representation of pGSH160.

H: Schematic representation of pAGS007-9.5 kb.

I: Schematic representation of pGSJ250.

J: Schematic representation of pGSJ260.

FIG. 34 is a graph showing the results of an ELISA assay of tobacco callus tissue transformed with C58Cl $Rif^R$ pHD1076, as described in Section 11 Example 1. The coating antibody is goat anti-*B.t.* crystal serum. Rabbit anti-Bt2 is used as first antibody.

Numbers 1 to 14 are transformed calli.

The optical density (O.D.) corresponding to a level of 4 ng Bt2 protein per gram of tissue, determined in a reconstruction experiment, is indicated in the figure.

FIG. 35 is a graph showing the results of an ELISA assay of tobacco callus tissue transformed with C58Cl $Rif^R$ pHD1076, as described in Section 11 Example 1. The coating antibody is goat anti-*B.t.* crystal serum. Rabbit anti-Bt2 serum is used as first antibody.

Numbers 1 to 21 are transformed calli.

The O.D. value corresponding to a level of 4 ng Bt2 protein per gram of tissue, determined in a reconstruction experiment, is indicated in the figure.

FIG. 36 is a graph showing the results of an ELISA assay of tobacco callus tissue transformed with $C58ClRif^R$ pHD1076, as described in Section 11.2, Example 1. Coating antibody is goat anti-*B.t.* crystal serum. Different monoclonal antibodies were used as first antibody. Reactivity with untransformed SR1 callus tissue (used as a negative control) is also shown.

FIG. 37A and B is a description of the experimental protocol used for the preparation of callus tissue extracts, used for the Immunological detection of Bt2 expressed in this callus.

FIG. 38A and B is a graph showing the growth rate of 1st instar *M. sexta* larvae feeding on leaves from transformed tobacco plants obtained as described in Section 10, Example 5. Open bars represent the number of larvae (on a total of 20 larvae tested) that went to the L2 stage after 3 days of feeding.

Figure 38A:
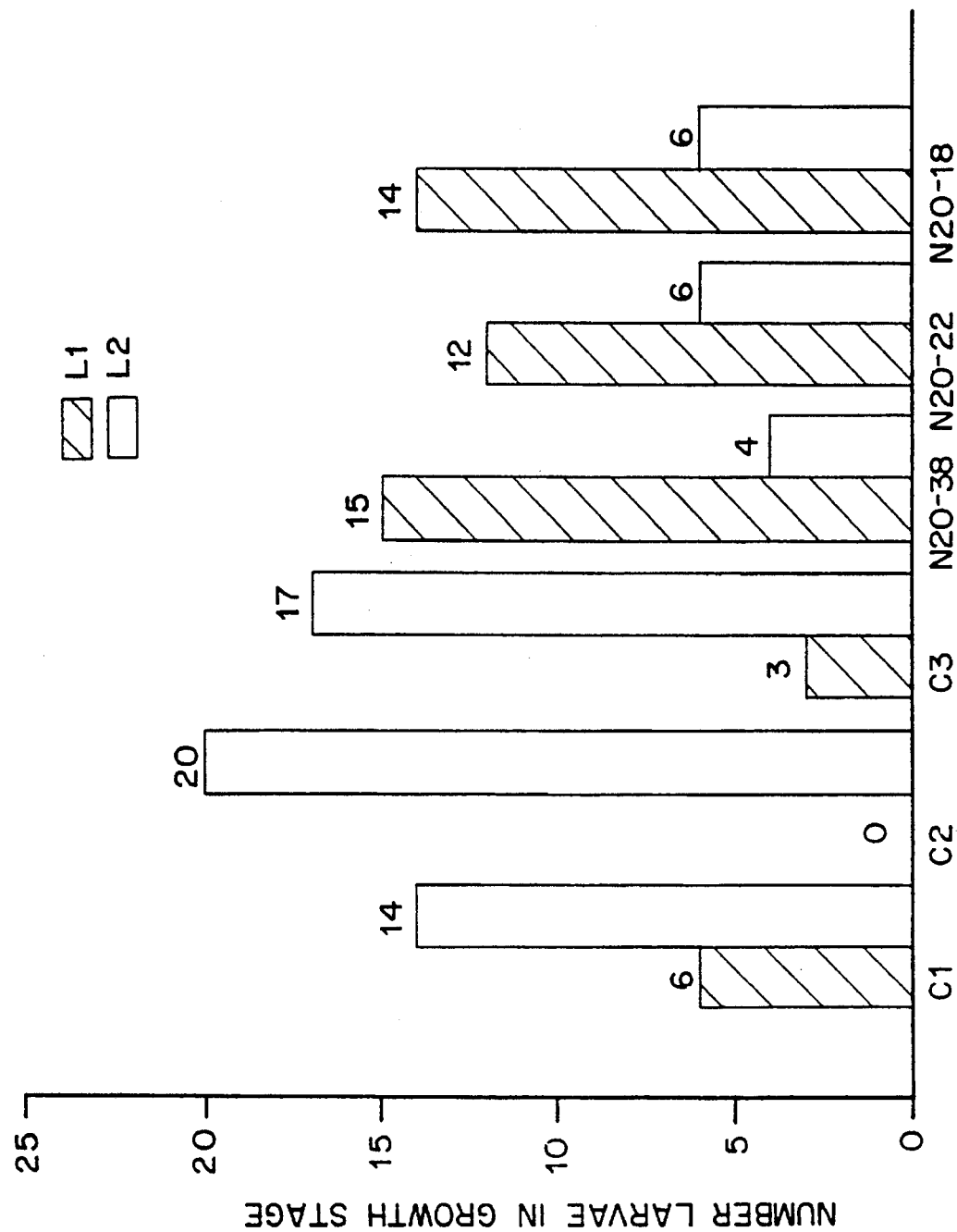
Figure 38B:
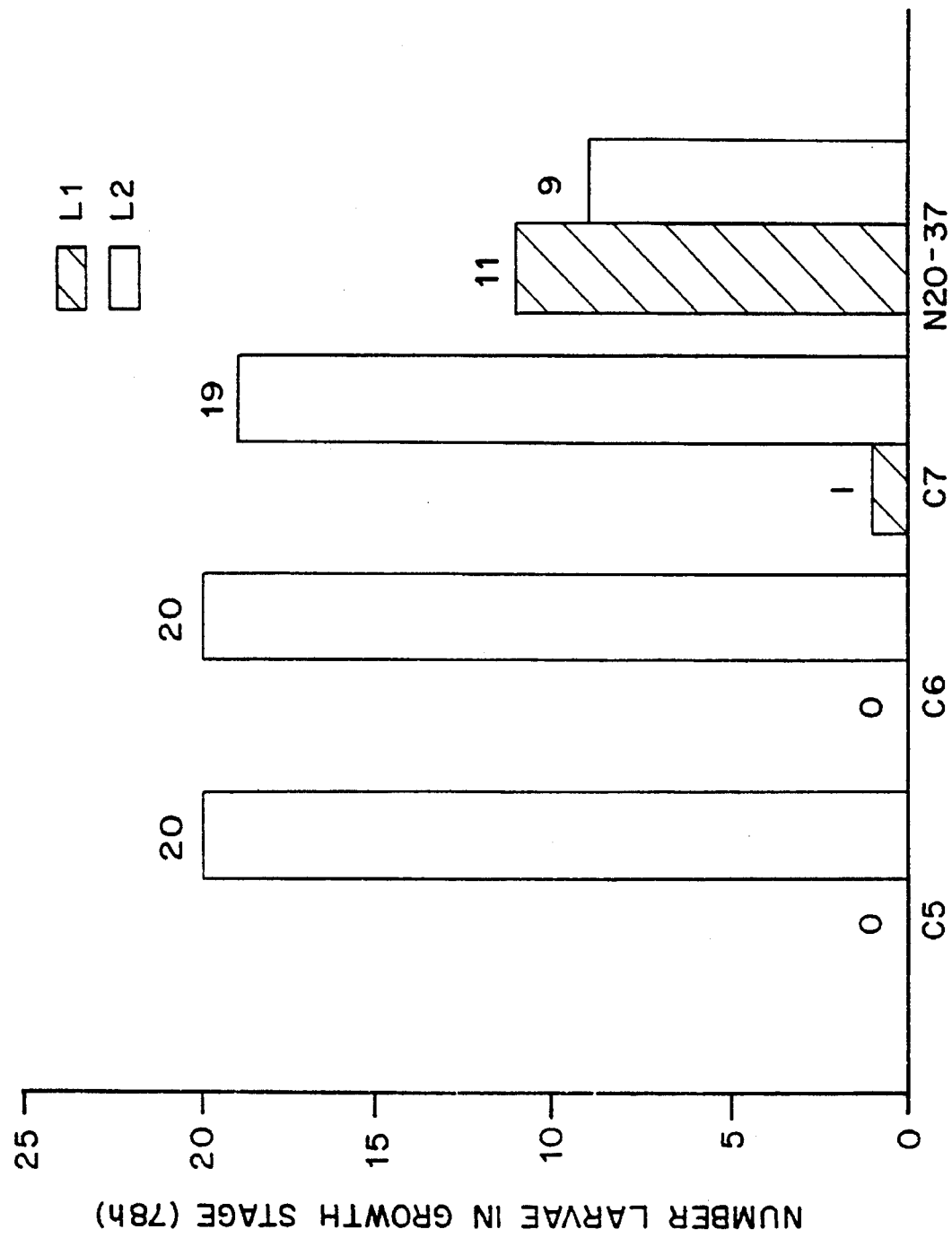
Figure 39A:
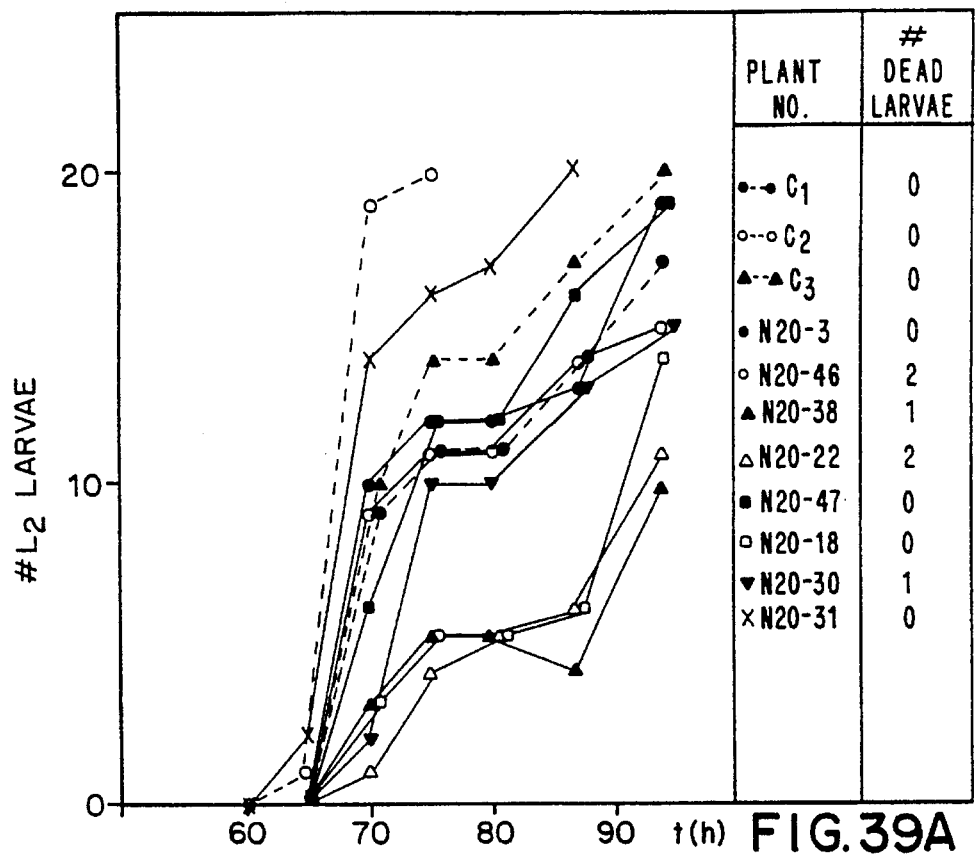

FIG. 39A and B is a graph showing complete growth rate curves over a 4 day period, for *M. sexta* larvae feeding on leaves of transformed tobacco (data are from same experiments as those represented in FIG. 38). The represented values are the numbers of larvae that were in the L2 stage at a certain point in time (per plant, 20 larvae were tested). $C_1$–$C_4$ are control plants (transformed with the Pnos-NPTII gene only). The other numbers (N20-1, N20-46) refer to individual plants putatively transformed with pGS1110.

FIG. 40 shows the DNA sequences of the P35S-1 and P35-2 promotor fragments derived from cauliflower mozaic virus Cm4-184 (Gardner et al., 1981, *Nucl. Acid Res.*, 9, 2871–2888).

Figure 41:
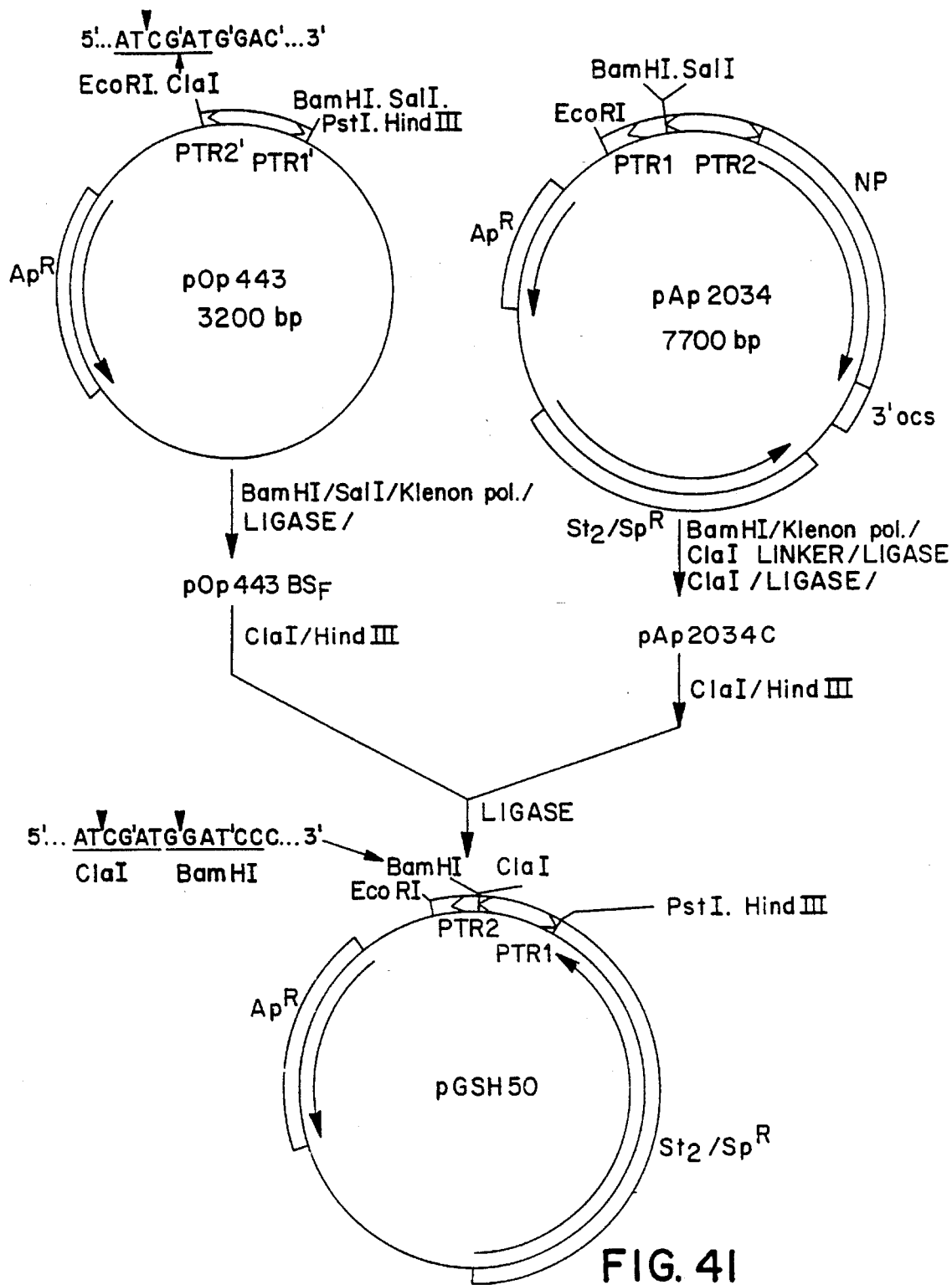

FIG. 41 is a schematic representation of the construction of pGSH50.

Figure 42:
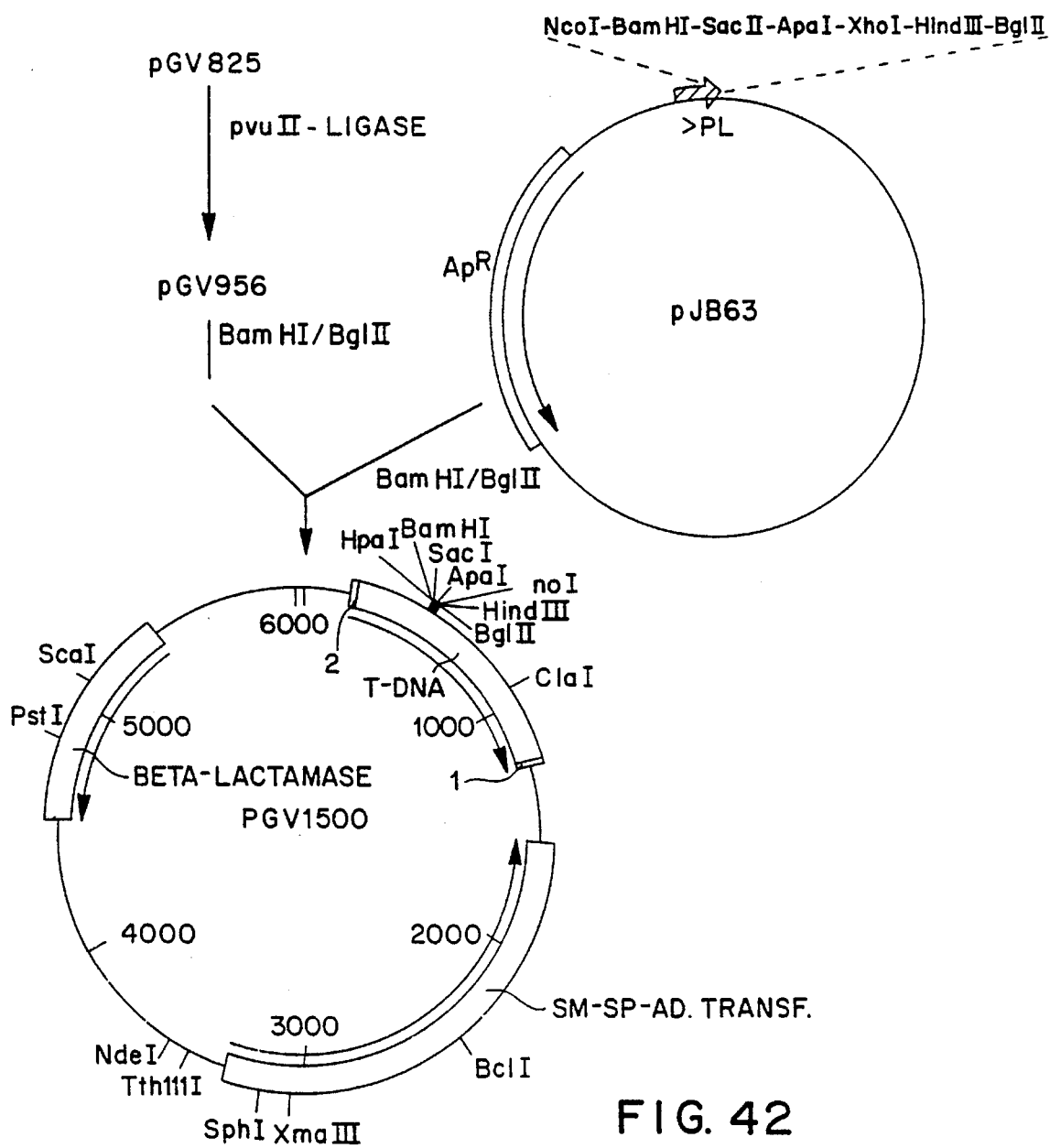

FIG. 42 is a schematic representation of the construction of pGV1500.

FIG. 43 is a schematic representation of the construction of pGSH150 and pGSH151.

Figure 44:
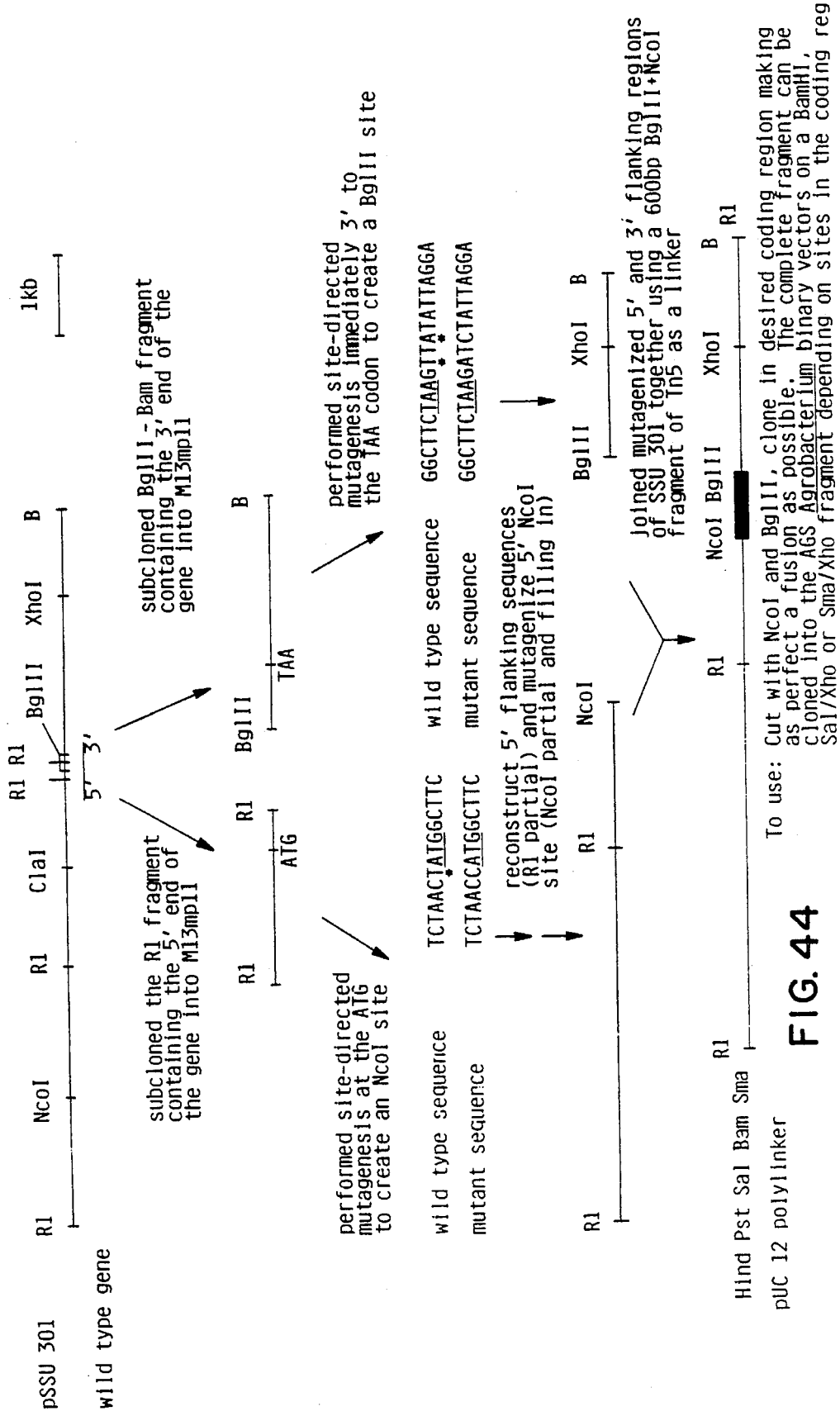

FIG. 44 is a schematic representation of the construction of pAGS007 from Pssu301 whild type gene.

DESCRIPTION OF THE PREFERRED EMBODIMENTS

As used herein, the term "polypeptide" should be understood as meaning an intact protein or fragments thereof.

"Plant" should be understood as referring to a multicellular differentiated organism capable of photosynthesis including angiosperms (monocots and dicots) and gymnosperms. "Plant cells" should be understood as referring to one or more cells derived from a plant. "Plant cell progeny" should be understood as referring to any cell or tissue derived from plant cells including callus; plant parts such as stems, roots, fruits, leaves or flowers; plants; plant seed; pollen; and plant embryos. "Chimeric gene" should be understood as a hybrid DNA segment comprising a regulatory signal essential for transcription referred to as a promotor, fused to at least one structural gene sequence coding for a specific polypeptide. "Substantial sequence homology" should be understood as referring to either: a DNA fragment having a nucleotide sequence sufficiently similar to another DNA fragment to produce a protein having similar properties; or a polypeptide having an amino acid sequence sufficiently similar to another polypeptide to exhibit similar properties. "Identification" should be understood as referring to selection or scoring of cells harboring and expressing the desired gene. Selectable markers permit growth (selection) under otherwise lethal conditions such as kanamycin resistance ($Km^R$). Scorable markers add on identifiable trait (scoring) foreign to non-tranformed cells. "Naturally expressed gene" should be understood as meaning a DNA fragment whether originally part of a plant's genome or introduced by agents such as bacteria or viruses which produces RNA, protein or both in the plant in the absence of human intervention.

A chimeric gene may also include a nontranslated DNA fragment positioned on the 3' side (downstream) of the structural gene sequence, which in turn may include a regulatory signal referred to as a polyadenylation signal preferably derived from a gene which is naturally expressed in plants.

A naturally expressed gene includes a 3' non-translated region which in turn includes a polyadenylation signal, both of which code for the corresponding messenger RNA (mRNA) regions. These corresponding mRNA regions are located on the 3' side of a stop codon in a monocistronic mRNA. The 3' non-translated region of mRNA is believed to be involved in the processing, stability and/or transport of the mRNA. This 3' non-translated region of mRNA is also believed to contain a sequence of bases, polyadenylation signal, which is recognized by an enzyme in the cell. This enzyme adds a substantial number of adenosine residues to the mRNA molecule to form a poly-A "tail" on the mRNA.

Figure 13C:
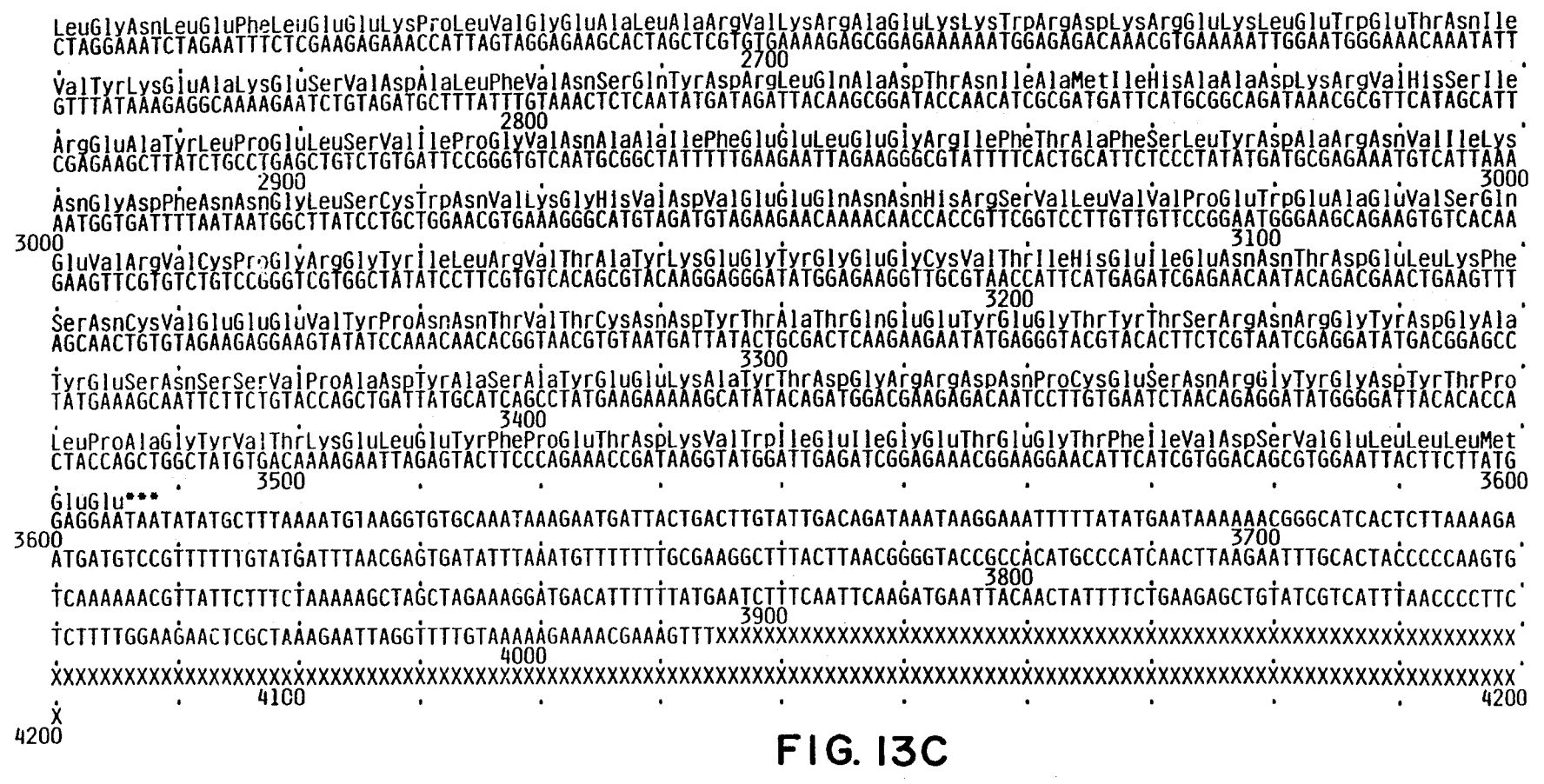

Generally, the process used to arrive at the present invention is described in European Patent Application Publication No. 0116718 entitled "Process for the Introduction of Expressible Genes into Plant Cell Genomes and Agrobacterium Strains Carrying Hybrid Ti Plasmid Vectors Useful for this Process." The introduction and integration of one or more chimeric genes coding for polypeptide toxins produced by *Bacillus thuringiensis* or having substantial sequence homology to Bt2 (see FIG. 13) into a plant cell genome is achieved by:

(1) isolation of at least one DNA fragment from *Bacillus thuringiensis* coding for a polypeptide toxin by digestion of bacterial DNA and inserting the mixture of DNA fragments obtained into a cloning vehicle harbored in a bacterial host; and (2) identification of bacterial clones harboring DNA fragments coding for said polypeptide toxin; and (3) characterization of the structure of the DNA fragment coding for said polypeptide toxin; and (4) removal of unwanted DNA sequences flanking the desired DNA fragment; or (5) synthesis of a DNA fragment having substantial sequence homology and exhibiting a similar structure to a DNA fragment coding for Bt2; or (6) construction of a DNA fragment containing the DNA fragment from (4) fused to a DNA fragment encoding an identification polypeptide to produce a fusion polypeptide; and (7) insertion of said DNA fragment from (4) or (5) or (6) into plasmid vectors under the control of plant regulator sequences harbored in a bacterial host; and (8) introduction of plasmids from (7) by conjugation (or mobilization) in a bacterial host harboring suitable helper plasmids; and (9) conjugation of bacterial clones from (8) to *Agrobacterium tumefaciens* harboring an acceptor Ti plasmid vector; and

(10) identification of *Agrobacterium tumefaciens* which contain the desired chimeric gene; and

(11) contacting plant cells with *Agrobacterium tumefaciens* from (10); and

(12) identification of transformed plant cells from appropriate culture media; and

(13) immunological detection of Bt2 antigens present in extracts from transformed plant cells; and

(14) propagate transformed plant cells to regenerate a differentiated plant.

It is contemplated that cloning vectors and bacterial host strains other than those described below in the examples can be used. Ti-based vectors like pGV3850 into which recombinant plasmids integrate before transfer to plant cells are known as cis-type vectors. There are also Ti-based vector systems in which the recombinant plasmids do not integrate into the resident Ti plasmid or in which large portions of the naturally occurring Ti plasmid are deleted. These binary-type systems, Hoekema et al., *Nature,* Vol. 303, 179 (1983), or mini-Ti plasmids, Framond et al., *Biotechnology,* Vol. 1, 262 (1983), have also been shown to introduce DNA into plant cells. These plasmids contain a border sequence (at least one, preferably two) flanking the gene to be introduced into plants. A marker which is selectable or scorable in plant cells is useful but not essential. Such plasmids are capable of autonomous replication in *A. tumefaciens* and need not integrate into a resident Ti plasmid. Virulence functions needed to effect transfer of DNA, such as the chimeric genes of the present invention, to plant cells can be provided in trans. Hoekema et al., *Nature,* Vol. 303, 179 (1983). See also Fraley, R. T. et al., *Biotechnology,* Vol. 3,629 (1985); and Klee et al., *Biotechnology,* Vol. 3, 637 (1985).

*A. tumefeciens* is not the only means of introducing genes into plants. DNA can be introduced by physical means such as electroporation or chemical means such as polyethylene glycol (PEG) fusion. It is believed any technique which introduces DNA, such as the chimeric genes of the present invention can be used. Further, RNA viral vectors which introduce an RNA copy of an insecticidal chimeric gene may also be used.

Further, plasmid vectors containing plant regulatory sequences other than those described below in the examples can be used. For example, enhancers can be included before, or after, or in such proximity to the chimeric gene to exert their function.

Plant cells transformed with the novel plasmid vectors of the present invention may then be cultured on suitable medium, preferably selectable growth medium, and plants which express the polypeptide toxin may be regenerated from the resulting callus. Subsequent generations of plant cells and their progeny should also exhibit expression of the polypeptide toxin.

Transformed plant cells and their progeny should express a polypeptide toxin substantially similar to polypeptide toxins being produced by *Bacillus thuringiensis* or a DNA fragment having substantial sequence homology to Bt2.

The present invention contemplates that the hybrid plasmid transformation vectors may be used to develop plant cells and their progeny exhibiting insect resistant properties. It is contemplated that plants, particularly dicotyledonous plants, other than those described below in the examples can be transformed such as cotton, sugarbeet, soybean, rape and vegetables such as cabbage, lettuce and beans. Transformed plant cells and their progeny are protected against certain insect pests by expressing an insect controlling amount of polypeptide toxin. By controlling is meant a toxic (lethal) or combative (sublethal) amount of polypeptide toxin. The transformed plants should be morphologically normal and may be cultivated in their usual manner for consumption and/or production of products. Further, said transformed plants should substantially obviate the need for chemical or biological insecticides directed toward combatting Lepidoptera and Coleoptera larvae. Since the genes coding for the polypeptide toxin are stably integrated in the plant cell genome and are thus heritable, seed obtained from said transformed plants should also produce plants expressing the polypeptide toxin at substantially the same level and thereby also be protected against certain insect pests.

In addition, it is contemplated that transformed plant cells and their progeny could be used to control certain insect pests by applying to the pests and/or the habitat of said pests (i.e., the locus to be protected, for example, to a growing crop or to an area where a crop is to be grown) an effective (controlling) amount of transformed plant matter alone or together with other components.

By way of example, but not limitation, transformed plant cells and their progeny could be used alone or as one component in a formulation or composition. For practical applications, plant cells and their progeny could be used as the active material or as a solid carrier in conventional pesticide compositions and formulations. Such compositions and formulations may also contain adjuvants such as surfactants and stabilizers. Examples of such composition and formulations include pastes, dusting powders, wettable powders, granules, baits and aerosol compositions.

Compositions and formulations are prepared in a known manner. The amount of transformed plant matter to be used depends on a variety of factors, for example, the kind of pest, the formulation or composition used, the state of the crop infected with the pest and the prevailing weather conditions. In general, transformed plant cells and their progeny may constitute from about 0.1 to about 100% by weight of the composition or formulation and preferably from about 1.0 to about 99% by weight.

Known insecticidal, fungicidal, biocidal, herbicidal and fertilizer compounds and compositions compatible with the polypeptide toxins may be included as components in the above described compositions and formulations to provide additional benefits and advantages.

In practice, certain Lepidoptera or Coleoptera larvae attempt to feed on transformed plants. A small amount of transformed plant matter is ingested. The ingested matter is processed in the insect midgut yielding the active polypeptide toxin which acts on the midgut cell membrane to kill or inhibit growth of the pest.

Also in practice, when used alone or as one component in a formulation or composition, certain Lepidoptera and/or Coleoptera larva attempt to feed on plants treated with said formulations or compositions. A small amount of treated plant matter is ingested. The ingested matter containing the formulation or composition is processed in the insect midgut yielding the polypeptide toxin which acts on the midgut cell membrane to kill or inhibit growth of the pest.

Engineering of the present invention was generally accomplished as follows:

1. Isolation and preparation of antibodies specific for *B.t.* crystal polypeptides
   A. Isolation of *Bacillus thuringiensis* (*B.t.*) crystal polypeptides
   B. Preparation of antibodies (polyclonal and monoclonal) against *B.t.* crystal polypeptides
2. Preparations of *B.t.* Gene Bank
   A. Preparation of total DNA or plasmid DNA from *B.t.*, preferably plasmid DNA
   B. Partial digestion of the purified DNA with a suitable restriction enzyme
   C. Cloning DNA fragments into a suitable *E. coli* plasmid expression vector
3. Isolation of recombinant plasmids containing *B.t.* polypeptide genes
   A. Screening of the transformed *E. coli* cells with anti-*B.t.* crystal protein serum
   B. Identification and isolation of bacterial clones expressing the polypeptide
4. Characterization of Bt2 protein
   A. Purification of the polypeptide encoded by the cloned *B.t.* gene
   B. Testing to confirm that polypeptide expressed by clones is immunologically the same as *B.t.* crystal polypeptide
   C. Testing to confirm that polypeptide expressed by clones is insecticidal
5. Mapping and subcloning of Bt2, including restriction enzyme analysis, subcloning and DNA sequence determination 6. Construction of toxin gene cassette including removal of undesired flanking ATG triplets preceding the initiator ATG and addition of suitable restriction enzyme cleavage sites using synthetic oligonucleotide linkers
7. Construction of Intermediate Vectors
8. Construction of Hybrid Ti Plasmids
9. Engineering of Plants
   A. Identification of transformed plant tissues producing the toxin using the immunoassays and quantification of the toxin levels produced
   B. Regeneration of plants from tissues
10. Detection of Bt2 toxin in engineered plants
11. Determine toxicity of engineered plants toward insects Different types of chimeric genes (promotor-gene fusions), have been used to genetically transform plant cells, and basically 3 different types of plant specific promoters can be distinguished:

Promoters:
1. Ti plasmid derived promoters (Pries, PTR at times referred to herein as PTR2)
2. Plant promoters (Pssu pea, Pssu301)
3. Plant virus promoters (P35S from cauliflower mozaic virus)

Types of chimeric genes:
1. Type I:
   Straight promotor-gene fusions in which the entire Bt2 coding sequence is inserted behind the promotor fragment. Examples are: Pnos-Bt2 (pHD1050, pHD1060), Pssu pea-Bt2 (pHD1076), PTR2-Bt 2 (pGS1161), Pssu301-Bt2 (pGS1181), P35S-1-Bt2 (pGS1261), P35S-2-Bt2 (pGS1271). Some of the constructs do not contain the intact 5' untranslated region of the original transcript (Pnos, Pssu pea), but others do (PTR, Pssu301).
2. Type II:
   Chimeric Pssu-Tp-Bt2 gene fusion in which the Bt2 gene is fused to the transit peptide (Tp) sequence of the small subunit of RuBisco and expressed under the control of the Pssu promotor. In this case a fusion protein preferably is made from the natural translation initiation signal of the ssu gene. Van Den Broeck et al. (1985) demonstrated the transport of the bacterial NPTII protein into plant chloroplasts using a fusion between the transit peptide of the ssu of RuBisco and the NPTII coding region. In view of these results, we constructed the chimeric gene Pssu-Tp:Bt2. Both the Pssu promotor and the transit peptide (Tp) fragment were derived from the pea gene used by Van Den Broeck et al. (1985). The DNA sequence at the junction site is shown in FIG. 28. It is worth mentioning that the original 5' untranslated region of the pea m-RNA is maintained in Pssu-Tp:Bt2, so that the chimeric gene is translated from the genuine ssu translation initiation site (pHD1080).
3. Type III:
   Straight promotor-gene fusions in which only part of the Bt2 coding sequence is used ("truncated Bt2"). Fragments of the Bt2 sequence still encoding an active toxin are inserted behind the plant specific promotors: The toxic polypeptides produced in the plant cells using these constructs should have biological and biophysical properties distinct from the intact Bt2 protein such as specific toxic activity or solubility.

Examples: pGS1162, pGS1163, pGS126.
4. Type IV:
   Straight promotor-gene fusions in which a Bt:NPTII fusion gene (also referred to at times at Bt2:NPTII) is inserted behind the promotor. Fusion genes were constructed, consisting of a fragment of the Bt2 coding sequence (still encoding an active toxin) fused to the coding sequence of the NPTII enzyme. The Bt:NPTII fusion genes used here, specify stable fusion proteins comprising amino terminal parts of the Bt2 protein fused to an intact Neomycin phosphotransferase (NTPII) enzyme. These fusion proteins have a specific toxicity comparable to the intact Bt2 protein and retain neomycin phosphotransferase enzyme activity. Thus, expression of the Bt:NPTII fusion proteins in plant cells allows direct selection for the production of this protein by isolating Kanamycin resistant ($Km^R$) transformed cells. Furthermore, the level of $Km^R$ should be directly correlated to the amount of protein synthesized. Thus, selection of plants resistant to a high level of Kanamycin should identify, among all possible transformations, those which produce high levels of the toxic fusion protein. Further, expression of the fusion protein by a Bt:NPTII fusion gene might have other desirable properties such as stability in plant cells; for example, mRNA may be more stable. Differences in results obtained with these Type IV fusion genes might be due to intrinsic differences in the properties of the fusion protein expressed as compared to the intact Bt2 protein.
   Examples: pGS1110, pGS1151, pGS1152, pGS1171, pGS1251, pGS1253, pGS1281.

Alternative constructions of the desired transformation vectors described herein are also contemplated. For example, plant specific exogenous promoters other than those disclosed herein may be used. The use of a different exogenous promotor sequence may be useful for directing expression of the inserted exogenous DNA in a regulated fashion. Examples of other types of regulation which may be used include tissue-specific expression (leaves, roots, stems or flowers); and inducible expression (temperature, light or chemical factors). Additionally, given the DNA sequence data coding for the polypeptide endotoxins produced by *Bacillus thuringiensis*, a transformation vector could be constructed containing an artificially created DNA fragment substantially similar to the Bt2 DNA fragment described herein. This artificially created DNA fragment could then be used to transform plants in substantially the same manner as described herein.

The following examples are offered by way of illustration and should not be construed as limiting the scope of the present invention.

EXPERIMENTAL

1. Isolation of *Bacillus thuringiensis* (*B.t.*) Crystal Proteins
   Crystals were isolated and purified from spore preparations of strains *B.t.* berliner 1715 (received from Dr. A. Klier, *EMBO J.* 1, No. 7, p. 791–799, 1982) and *B.t.* var. kurstaki, (*J. Bacteriol.* 145, No. 2, p. 1052, 1981) as described by Mahillon and Delcour (*J. Microbiol. Meth.*, Vol. 3, No. 2, p. 69–76, 1984). The crystal proteins were solubilized by incubating the purified crystals at 37° C. for 2 h in 0.2M thioglycolate, 0.1M $NaHCO_3$ pH 9.5, whereafter the insoluble material was removed by low speed centrifugation. This procedure solubilizes more than 80% of the proteins present in the crystals. Solubilized crystal proteins were analyzed on 7.5% sodium dodecyl sulfate polyacrylamide gel (SDS PAGE). The crystal protein preparation from Bt berliner contained at least two major protein species in the high molecular weight region (apparent HW of 140 and 130 Kd) and a less abundant protein of about 120 Kd, as revealed by staining the gels with Coomassie brilliant blue (FIG. 1). The solubilized crystal proteins of strain kurstaki showed one major 130 Kd protein band and a weaker 60 Kd band (FIG. 1).

These solubilized crystal proteins exhibited a strong toxic activity towards third instar larvae of the cabbage butterfly *Pieris brassicae* (L.D. 50 values of 0.5 ng/larva for kurstaki and 0.65 ng/larva for berliner) using the toxicity assay described in section 5.2 below.

2. Preparation of Antibodies Specific for *B.t.* Crystal Proteins 2.1 Polyclonal Antisera Antisera against *B.t.* crystal proteins (berliner 1715 and kurstaki) were prepared separately in rabbits and mice. Antiserum against *B.t.* crystal proteins (kurstaki) prepared in goat was received courtesy of Dr. L. Bulla, University of Idaho. To the best of applicant's knowledge and belief, the antiserum was prepared by known procedures substantially similar to those described for rabbit and mouse.

Rabbits were injected subcutaneously with 0.5 mg of a solubilized crystal protein preparation (0.25 ml dialysed qagainst PBS pH 7.4) mixed with an equal volume of complete Freund's adjuvant (CFA). After three months, the rabbits received another injection of the same type of preparation, and three weeks later blood samples were taken. BALBc mice were injected intraperitoneally with 100 ug of crystal protein solution, mixed with CFA (1/1 vol.). Four to six weeks later they received a booster injection of 50 ug crystal protein PBS, and four days later blood samples were taken. Antigen reactivity of the sera was confirmed by immunodiffusion tests (Ouchterlony assay). A strong cross-reaction between berliner 1715 and kurstaki crystal protein preparations was observed, indicating that they contained antigenically related components.

Some of the mice were sacrificed and the spleens removed asceptically for cell fusion experiments (see 2.2).

2.2 Monoclonal Antibodies

Although not essential for the identification of toxin expressing clones as described herein, hybridomas producing monoclonal antibodies against *B.t.* crystal proteins were generated following the procedure originally described by Koehler and Milstein (*Nature* 256: 495–497, 1975). Monoclonal antibodies were used as an additional and more specific means of determining toxin presence in bacterial clones and plant cells.

Spleen cells from immunized BALBc mice (see 2.1) were fused with the SP2/0 myeloma cell line (Shulman, M. et al., *Nature* 276, p. 269, 1978). Cells were plated at $3.10^5$ per well in microtiter plates and 10–14 days later the supernatants were screened for the presence of anti-crystal protein antibodies using an enzyme immuno assay (Engvall and Pesce, *Scand. J. Immunol.*, suppl. 7, 1978) with alkaline phosphatase labelled goat anti-mouse immunoglobulin as the second antibody (Sigma, A-5153). Approximately 4% of the wells were positive for the antigen (crystal protein). Positive clones were subcloned twice by limiting dilution. Positive subclones were selected, grown up and their culture supernatants containing the monoclonal antibodies were collected. A total number of 17 hybridoma cell lines producing monoclonal antibodies reactive with *B.t.* berliner crystal proteins were generated.

3. Construction of a Gene Bank from Plasmid DNA of *B.t.* Strain Berliner 1715

Kronstad et al., *J. Bacteriol.*, 54, p. 419–428 (1983) reported that *B.t.* berliner 1715 contains two related toxin genes which are both located on plasmids. Intact endotoxin genes were isolated from a gene bank from total *B.t.* berliner 1715 plasmid DNA using partial Sau3A digests of plasmid DNA. *B.t.* berliner 1715 cells were grown in LB medium (Miller, *Experiments in Molecular Genetics*, (1972), Cold Spring Harbor Laboratory, New York) overnight at 37° C. Plasmid DNA was isolated from *B.t.* berliner 1715 using the denaturation-renaturation method described by Kronstad et al., *J. Bacteriol.*, 54, p. 419–428 (1983). Analysis of the plasmid DNA on 0.5% agarose gels revealed that this plasmid DNA preparation contained several different plasmid species present in different molar concentrations. To construct the gene bank thirty ug of plasmid DNA was partially digested with Sau3A at 37° C. in a total volume of 500 ul. 100 ul samples were taken after respectively 10, 20, 30, 45 and 60 minutes of incubation and phenol-chloroform extracted. The Sau3A digested DNA was size fractionated on a 10 to 40% sucrose gradient, and the size of the DNA fragments in the different fractions was estimated on a 0.8% agarose gel. The fractions containing DNA in the 6–10 Kb size range were pooled and ligated to BglII digested pEcoR251 vector DNA. The pEcoR251 plasmid is a derivative of plasmid pBR322 in which the EcoRI-PuvII fragment has been replaced by a chimeric EcoRI endonuclease gene which is fused to a $P_R$ promotor fragment derived from plasmid pLK5 (Zabeau and Stanley, *EMBO Journal*, 1, 1217–1224 (1982)) as depicted in FIG. 2. The pEcoR251 contains a unique BglII site in the EcoRI endonuclease gene, where insertion will inactivate the gene. The pEcoR251 vector is a suicide vector similar to the positive-selection cloning vehicle pSCC31 described by Cheng and Modrich (*J. Bacteriol.* 154, 1005–1008, 1983). Sau3A DNA fragments were ligated into BglII digested pEcoR251. Recombinant plasmids were selected by transforming the ligation mix into competent *E. coli* K514 cells (Colson et al., *Genetics* 52, p. 1043–1050, 1965) as described by Dagert and Ehrlich, *Gene* 6 (1980), 23–28. Cells were plated on LB medium (Miller, *Experiments in Molecular Genetics* (1972), Cold Spring Harbor Laboratory, New York), supplemented with ampicillin (100 ug/ml).

Several gene banks were constructed each containing between 600 and 1500 recombinant clones. Analysis of the recombinant plasmids present in 12 randomly chosen clones confirmed that in each gene bank at least 10 out of the 12 clones contained inserted fragments with sizes ranging from 5 to 15 Kb.

4. Isolation of Recombinant Plasmids Containing *B.t. Crystal Protein Genes*

The colonies of the gene bank were screened for bacteria producing crystal proteins using a rabbit serum raised against purified *B.t.* berliner crystal proteins (see Section 2.1 above). The procedures used are slightly modified from Helfman et al., (*PNAS* 80: 31–35 1983). Bacterial colonies, grown on 150 mm square Petri dishes, were replica plated on nitrocellulose sheets (Schleicher & Schuell, 0.45 um, 401196). Sheets were soaked in 0.1M NaOH until colonies lysed. The sheets were then air dried, washed in phosphate buffered saline (PBS) pH 7.4 for 30 minutes and incubated overnight at 4° C. or for 2 hours at room temperature with gentle agitation in PBS containing 1% crude ovalbumine (Sigma, A-5253). Nitrocellulose sheets were rinsed in PBS and incubated for 2 hours in rabbit anti-crystal serum diluted in PBS, 1% ovalbumin, 0.2% Triton X-100, at room temperature with gentle agitation. After additional washing the sheets were incubated with peroxidase-labeled goat anti-rabbit antibodies (Sigma, A-6154) (2 hours at room temperature). After extensive washing with PBS/0.2% Triton, the sheets were reacted with substrate solution (substrate was 4-chloro-1-naphtol, Sigma, C-8890). Positive colonies developed as dark blue dots. Using serial dilutions of purified crystal protein solution, the detection limit of this test was estimated to be 1–10 ng protein/ml. In total, 4 different immunopositive clones were isolated from a gene bank of 1250 clones. Plasmid DNA was prepared from each clone following the procedure of Zabeau and Stanley, EMBO J., 1, 1217–1224, 1982. Primary restriction maps were constructed by performing single and simultaneous restriction enzyme digestions. Comparison of the restriction maps for the enzymes EcoRI, EcoRV, BamHI, SacI, MluI and PstI (See FIG. 3) revealed that all 4 plasmids carried DNA fragments of different sizes which showed a clear region of overlap. These results show that the Bt2 gene must be encoded by a 4.2 Kb region common in the 4 different recombinant plasmids. For further study we subcloned a 7.5 Kb BamHI-PstI fragment from clone B12 (see FIG. 3) into the plasmid PUC8 (J. Viera and J. Messing, Gene, 19, p. 259–268, 1982) and this recombinant plasmid was termed pBt200.

5. Characterization of the Bt2 Protein 5.1 Identification of a 130 Kd Crystal Protein Encoded by pBt200

The E. coli strain K514 containing the pBt200 plasmid (see Section 4), showed a strong positive reaction in the colony assay. This was further confirmed using an enzyme linked immune sorbent assay (ELISA) (Engvall & Pesce, 1978, Scand. J. Immunol., Suppl. 7). For the ELISA screening the following procedure was used: Flexible polyvinyl microtiter plates, coated with goat anti-Bt crystal protein antibodies, were incubated with lysate of bacterial colonies (lysates were obtained by freeze-thawing pelleted cells, followed by incubation in 0.1M NaOH for 15 minutes, and subsequent neutralization with 0.1M HCl). After washing, a diluted rabbit or mouse anti-B.t. crystal protein serum was added. After 1–2 hours incubation, plates were washed and incubated with rabbit or mouse anti-B.t. crystal serum (appropriately diluted). After 1–2 h incubation, plates were washed and incubated with goat anti-rabbit or anti-mouse IgG antibodies, alkaline phosphatase labeled (Sigma A-8025, A-5153). After incubation and washing the substrate (p-nitro phenyl phosphate, Sigma, 104–105) was added and the reaction monitored by measuring optical density (O.D.) at 405 nm. Detection limit of the test for purified solubilized crystal protein was estimated to be in the range of 0.1–1 ng/ml.

Figure 5:
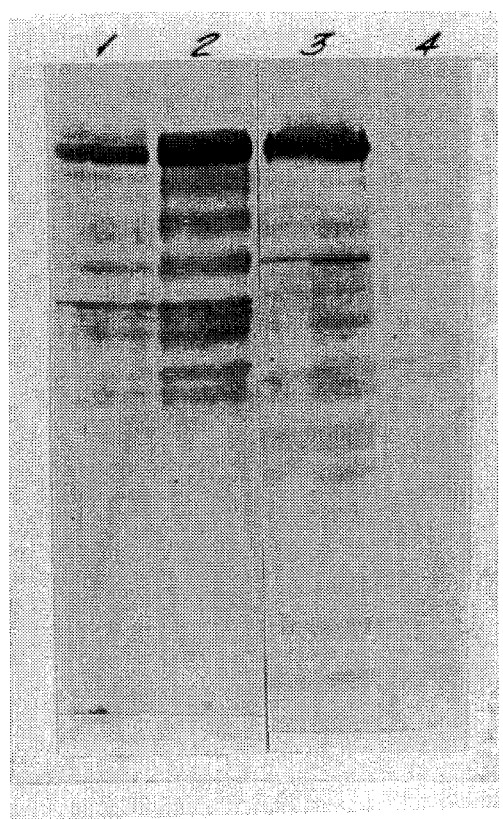
Figure 6:

Total cell protein extracts of E. coli strains harboring pBt200 were analyzed on SDS PAGE. An intense new protein band was visible in the high molecular weight range, corresponding to a M. W. of about 130 Kd. This band was not present in K514 cells containing the pUC8 vector plasmid without insert. This new protein also comigrated on SDS PAGE with one of the major crystal proteins of B.t. berliner and with the major crystal protein of Bt kurstaki (see FIG. 4). The relationship of this protein, which was termed Bt2, with B.t. crystal proteins was confirmed by immunoblotting. Western blotting experiments were carried out using both rabbit anti-Bt kurstaki crystal serum and rabbit anti-Bt berliner crystal serum. Strong reaction of the Bt2 protein with both antisera was observed (see FIGS. 5 and 6).

These results demonstrate that the cloned Bt2 gene codes for one of the crystal proteins of B.t. berliner which is immunologically related to the 130 Kd crystal protein of B.t. kurstaki.

Figure 7:
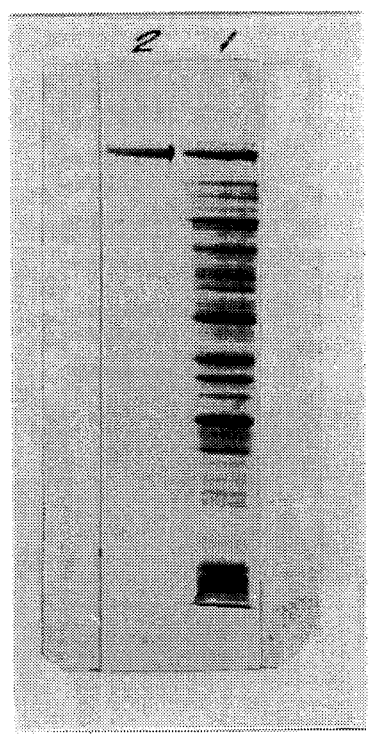

The amount of positively reacting material in bacterial extracts was quantitated using an ELISA assay. Using purified crystal protein as a standard, the amount of crystal protein produced in E. coli harboring pBt200 was estimated to be in the range of 5–10% of the total cell protein content. The estimate agrees well with the observed intensity of the band the Bt2 protein band on SDS PAGE after staining with Coomassie blue. To further characterize the 130 Kd protein encoded by the pBt200 plasmid (termed Bt2 protein) we developed a rapid purification procedure, taking advantage of the relative insolubility of the protein. 5 g cells obtained from a 2 litre overnight culture of K514 (pBt200) were resuspended in 50 ml 50 mM TRIS pH 7.9, 50 mM EDTA, 15% sucrose, treated with lysozyme (100 ug/ml), sonicated (30 minutes at 400 watts in a Labsonic 1510), mixed with 200 ml of PBS, pH 7 containing 2% Triton X100 and incubated for 30 min. on ice. The lysate was centrifuged at 15000 g and the supernatant was discarded. The pellet containing the Bt2 protein was resuspended in the same buffer and the procedure was repeated. Whereafter the pellet was washed twice with 200 ml PBS. To solubilize the Bt2 protein the pellet was resuspended in 50 ml extraction buffer 0.2N thioglycolate and 0.1M $NaHCO_3$, pH 9.5 for 2 hr. at 37° C. An efficient (>90%) and selective solubilization of Bt2 protein was obtained in this way (FIG. 7).

Figure 8:
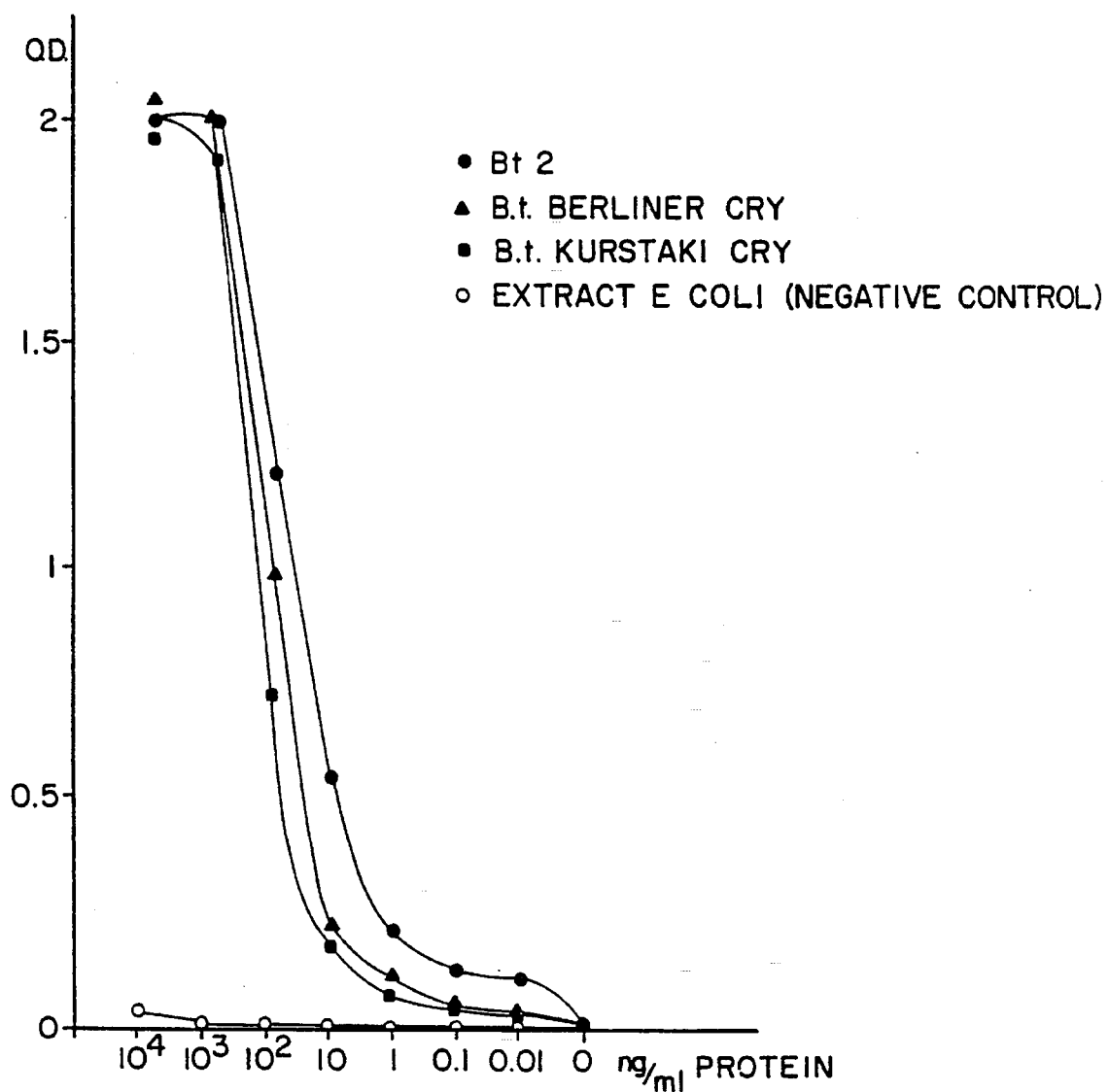

These semi-purified protein preparations were used for further studies. Antisera were raised against Bt2 protein in rabbits and mice using a similar immunization protocol as described in Section 2.1. These antisera reacted equally well with solubilized crystal proteins from B.t. berliner and kurstaki as with Bt2 itself, in the ELISA assay described above (FIG. 8 shows results with the mouse serum).

A similar positive reaction was observed using antibodies purified, from anti-Bt crystal serum, by affinity chromatography on an immunoadsorbent of Bt2 (Bt2 protein coupled onto CNBr activated Sepharose LB, Pharmacia). These antibodies also reacted in Western blotting with a 130 Kd protein present in both B.t. berliner and kurstaki crystals.

Figure 9A:
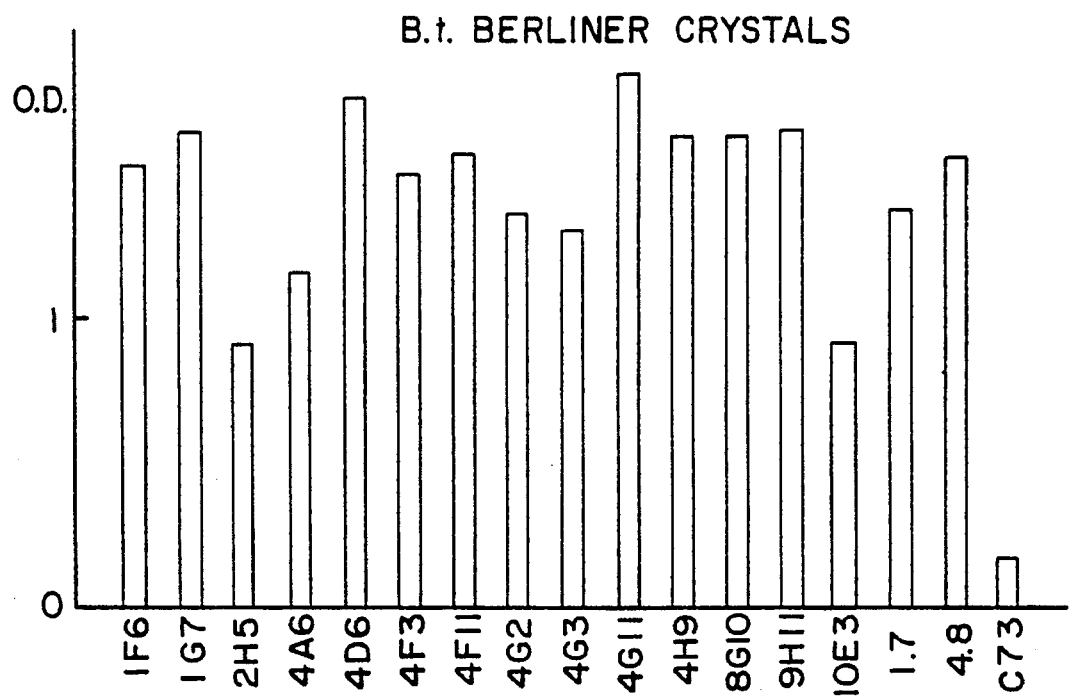
Figure 9B:
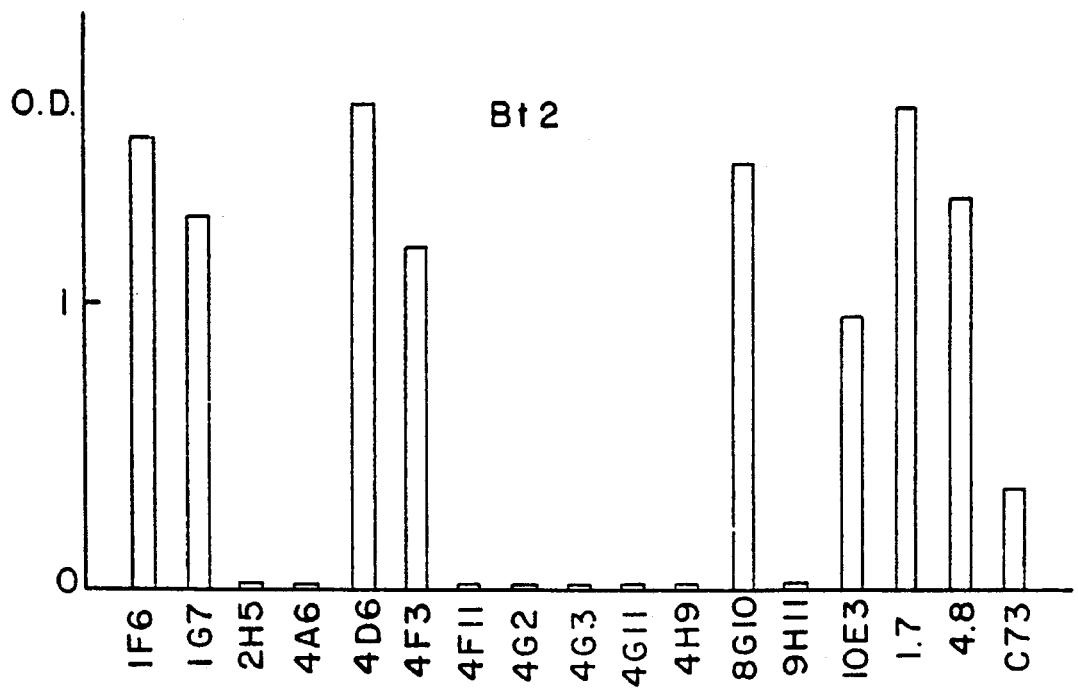

Finally, in the ELISA, 9 out of the 17 monoclonal antibodies raised against total B.t. berliner crystal proteins, were also reactive with the Bt2 protein. (Code numbers: 1F6, 167, 4D6, 4F3, 8G10, 10E3, 1.7, 4.8, C73) (FIG. 9). The same 9 antibodies were also reactive with B.t. kurstaki crystal proteins.

In general both the Bt2 protein and the major 130 Kd crystal proteins from B.t. require alkaline pH and the presence of reducing reagents for complete solubilization. Also they both precipitate at pH 4–5.

Thus, the cloned gene product Bt2 exhibits biochemical properties similar to those of the major 130 Kd crystal protein from B.t. berliner and B.t. kurstaki and is immunologically related to these crystal proteins.

The Bt2 protein was purified further by DEAE-ion exchange chromatography and by Sephacryl gel filtration. The amino-terminal sequence of this purified protein was determined with the use of a gas-phase sequencer (Applied Biosystems), operated according to Hewick et al., J. Biol. Chem., 256, 7990–7997, 1981).

The sequence of the first 20 N-terminal amino acids was found to be substantially identical to the N-terminal sequence deduced from the DNA sequence or a cloned B.t. kurstaki gene, Wong et al., J. Biol. Chem., 258 (3), 1960–1967 (1983) (FIG. 10).

5.2 Insect Toxicity of the Bt2 Protein

Crystals from B.t. are known to be particularly toxic against larvae of certain Lepidoptera species. In order to test whether Bt2 protein exhibited a similar toxic activity, toxicity tests were performed on larvae of the cabbage butterfly *Pieris brassicae*. Protein solutions of known concentration, expressed as ppm (1 ppm=1 ug/ml) were serially diluted in water. Small discs (0.25 cm$^2$) were cut from fresh cabbage leaves and on each disc 5 ul or a test solution was applied. Discs were air dried and each disc was placed in a vial containing one larva. Third instar larvae were obtained from a synchronized culture of *P. brassicae*. During a 10 h period before moulting, these larvae were incubated in separate vials in the absence of food. Immediately after moulting they were given one leaf disc. When the first disc was consumed, the larva was offered a fresh disc without sample. For each sample dilution, 50 larvae were tested. Feeding and viability were monitored every 24 h up to 120 h. As can be seen from Table 1, Bt2 sample preparations exhibited similar degrees of toxicity for *P. brassicae* larvae as solubilized crystals from *B.t.* berliner 1715.

To test the effect of sublethal doses of Bt2 toxin on the growth of *P. brassicae* larvae, the following experimental design was used: cabbage leaves were dipped in a solution containing a known concentration of Bt2 protein (0.01–1 ppm) and dried. Groups of 100 third instar larvae (from synchronized cultures) were fed on Bt2 coated leaves. The leaves were regularly replaced by new leaves treated in the same way. Growth of the larvae was followed over a period of seven days, which corresponds to the time period needed to develop from 3rd to 5th instar. As can be seen from the results presented in Table 2 the Bt2 protein induced a significant growth inhibition in *P. brassicae* larvae at doses that were sublethal. Growth inhibition was evident at a concentration of 0.01 ppm which corresponded to 2.67 ng protein/gram leaf. During the first 48 h the larvae feeding on leaves coated with 0.01 ppm ate 3.6 cm$^2$ of leaf (83 mg) and consequently ingested about 0.22 ng of Bt2 protein. At this time, 93% of the larvae were still in the L3 stage while only 33% of the control larvae were in this stage. Thus an inhibitory effect on growth can be observed with toxin doses that are significantly below the LD$_{50}$ values (1.65 mg/larva, see Table 1).

These results indicate which levels of Bt2 protein synthesis must be reached in transformed plant cells in order to express insect resistance against *P. brassicae*. A level of 2.7 ng Bt2 protein/g tissue is sufficient to retard the growth of the larvae. This might already be adequate as such to halt a devastating spread of the larvae in the field. Toxicity assays with Bt2 protein were also performed on larvae of the Tobacco Hornworm, (*Manduca sexta*). As shown in Table 3, Bt2 protein is slightly more toxic than total berliner crystal proteins (100% mortality at 12.5 ng/cm$^2$). In addition, significant growth inhibition is observed at sublethal doses (2.5 ng/cm$^2$): 4.4 mg body weight after 7 days, as compared to 30.5 mg for control larvae. Due to the fact that Manduca is fed on an artificial diet, (ref: Bell, R. A. & Joachim, F. G. (1976) *Ann. Entomol. Soc. Am.*, 69: 365–373), results are expressed somewhat differently, namely as ng toxin applied per cm$^2$ of agar medium.

6. Characterization of the Bt2 Gene

To locate the Bt2 toxin gene on the 7.2 Kb BamHI-PstI fragment of the pBt200 plasmid a series of deletions were made in the 7.2 Kb DNA fragment with respectively HpaI, KpnI and IbaI. The proteins encoded by these deletion plasmids were analyzed immunologically, using the ELISA technique and Western blotting (also referred herein to as immunoblotting) (Towbin et al., PNAS, U.S.A., 76: 4350–4354, 1979 and Burnette, W. N. *An. Biochemistry*, 112, p. 195–203, 1981).

Figure 11:
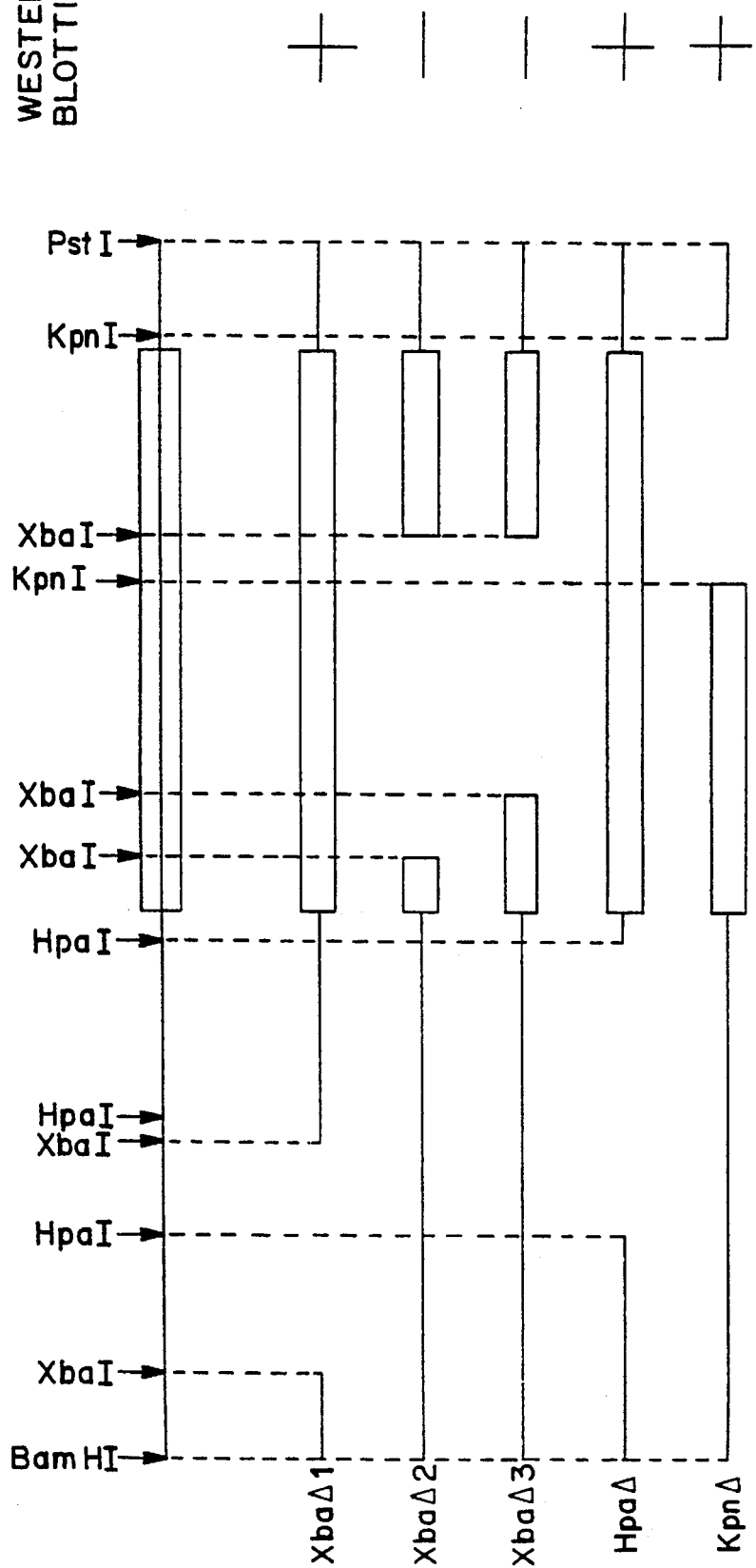

The results (diagrammed in FIG. 11) can be summarized as follows: (1) Deletion of the HpaI fragment results in the synthesis of an intact Bt2 protein at a lower level. This finding indicates that the deletion only affects the regulatory region but not the structural part of the gene. (2) Deletion of the Kpn fragment results in a approximately 70 Kd protein fragment still detectable by immunoblotting. (3) The Xba deletions closer to the 5' end do not give rise to protein fragments detectable by Western blotting procedure. These results show that the intact gene encoding the 130 Kd protein is located on a 4.3 Kb HpaI-PstI fragment (see FIG. 11). To determine the precise structure of the Bt2 gene, the complete nucleotide sequence of the 4,060 base pairs (bp) HpaI-NdeI fragment was determined by the Maxam and Gilbert sequencing method. The sequencing strategy used is diagrammed in FIG. 12.

The proposed nucleotide sequence was confirmed primarily by sequencing the complementary strand. Examination of the sequence revealed the presence of a single large open reading frame starting at position 141 and ending at position 3605, which could code for a protein of 1,155 amine acids with a molecular weight of 127 Kd. This is in agreement with the molecular weight of 130 Kd of the Bt2 protein as determined by SDS polyacrylamide gel electrophoresis. Furthermore, the amine-terminal amine acid sequence predicted from the nucleotide sequences agrees with the amine acid sequence determined on the purified Bt2 protein (see FIGS. 10 and 13).

The complete amine acid sequence of the Bt2 toxin shows extensive homology with the deduced amine acid sequences from 3 other *B.t.* crystal proteins from which the genes were cloned and sequenced: *B.t.* kurstaki HD1 (Dipel) (Schnepf et al., *J. Biol. Chem.*, 20, p. 6264, 1985), *B.t.* kurstaki HD73 (Adang et al., *Gene*, 36, p. 289, 1985) and *B.t.* sotto (Shibano et al., *Gene*, 34, p. 243, 1985).

Comparison of these other *B.t.* sequences with our Bt2 at the amino acid level (FIG. 14) reveals that they encode similar but distinct proteins, showing regions of striking homology but also stretches which diverge significantly.

7. Construction of the "Toxin Gene" Cassettes

7.1 Construction of a Cassette Carrying the Intact Bt2 Gene

Inspection of the DNA sequence of the Bt2 gene revealed that the 160 bp region immediately upstream of the ATG translation initiation codon contains 5 ATG triplets. Translation of eucaryotic genes usually starts at the first AUG in the message (In RNA U replaces T). These AUG triplets might act as initiator AUG's and could be recognized preferentially over the genuine Bt2 initiation codon and could thus reduce the level of expression in transformed plant cells. Moreover, these AUG's are in other reading frames and would give rise to nonsense polypeptides. To prevent initiation of translation at these AUG triplets, the sequences upstream of the Bt2 gene were removed by exonucleolytic treatment, prior to insertion of the pBt2 gene in the Ti expression vectors. To this end, deletion derivatives of the pBT200 plasmid in which upstream sequences were deleted up to the initiator ATG were constructed. Thirty-five ug of pBt200 DNA was digested with HpaI and treated with 6 units of Bal31 exonuclease (Biolabs, New England) for 1, 1.30, 2, 2.30 and 3 minutes in 300 ul of 12 mM MgCl$_2$, 12 mM CaCl$_2$, 0.6M NaCl, 1 mM EDTA and 20 mM tris-HCl—pH 8.0, at 30° C. One ug of Bal31-treated molecules of each reaction were ligated at 4° C. to 0.13 ug phosphorylated BamHI linkers (Biolabs, New England) with 2 units T4 DNA ligase in a total volume of 20 ul.

After the T4 ligase was inactivated at 68° C. for 10 minutes, each ligation mix was digested with 20 units BamHI for 1 h at 37° C. Subsequently, 50 ng DNA was recirculated with 0.1 unit T4 DNA ligase in a total volume of 100 ul for 20 h at 4° C.

One-fifth of this ligation mixture was transformed into competent *E. coli* K514 cells (Colson et al., *Genetics* 52 (1965), 1043–1050) as described by Dagert and Ehrlich, *Gene* 6 (1980), 23–28. Cells were plated on LB medium (Miller, *Experiments in Molecular Genetics*, (1972), Cold Spring Harbor Laboratory, New York), supplemented with carbenicillin (100 ug/ml).

The deletion end points in the plasmids were first analyzed by measuring the size of the newly generated EcoRI fragments of the recombinant plasmids on a 2% agarose gel. The nucleotide sequences of the exact deletion end points in plasmids with deletions ending just before the start of the Bt2 gene were determined. Clone pHD100 has a deletion ending 8 bp before the initiator ATG and removes all upstream non-initiator ATG's. Clone pBa3.3 contains the BamHI linker fused to the 4th bp of the coding sequence and clone pBa23-3 contains the Bam linker fused to bp −33.

In a second engineering step, the non-coding sequences at the 3' end of the toxin gene were deleted using Bal31 exonuclease (Biolabs, New England). Thirty ug of pHD100 plasmid DNA were digested with NdeI and treated with Bal31 exonuclease for 3, 4, 5, 6 and 8 minutes at 30° C. in buffer. At each time interval, 60 ul aliquots (each containing 6 ug of Bal31 treated DNA molecules) were removed. After addition of phosphorylated BglII linkers (Biolabs, New England) to the Bal31 treated DNA molecules, the DNA molecules were recircularized with 0.1 U T4 ligase overnight at 4° C. The ligation mixture was transformed into competent *E. coli* K514 cells (Colson et al., *Genetics* 52 (1965), 1043–1050) as described by Dagert and Ehrlich, *Gene* 6 (1980), 23–28. Cells were plated on LB medium (Miller, *Experiments in Molecular Genetics*, (1973), Cold Spring Harbor Laboratory, New York) supplemented with carbenicillin (100 ug/ml). After determination of the size of the deletion in several plasmids, using restriction enzyme digestion and agarose gel electrophoresis, pHD160, pHD162, pHD163 were retained for further experiments. In pHD160, the BglII site is positioned at approximately 300 bp behind the TAA stopcodon of the Bt2 gene; in pHD162 the BglII is at approximately 250 bp behind TAA; and in pHD163 the BglII is at position 3342 (bp) in the Bt2 coding sequence. Construction of pHD160 is schematically diagrammed in FIG. 15. In this way, we constructed toxin gene cassettes carrying the Bt2 gene on a BamHI-BglII fragment which will be excised and inserted in the BamHI site of the T1 expression vectors. In order to construct pHD164, the BamHI-SacI fragment of pHD160 containing the 5' end of the coding sequence was replaced with the corresponding BamHI-SacI fragment of pBa3.3. To construct pHD159, the BamHI-SacI fragment of pHD163 was replaced by the BamHI-SacI fragment of pBa3.3 (FIG. 16).

Figure 17:
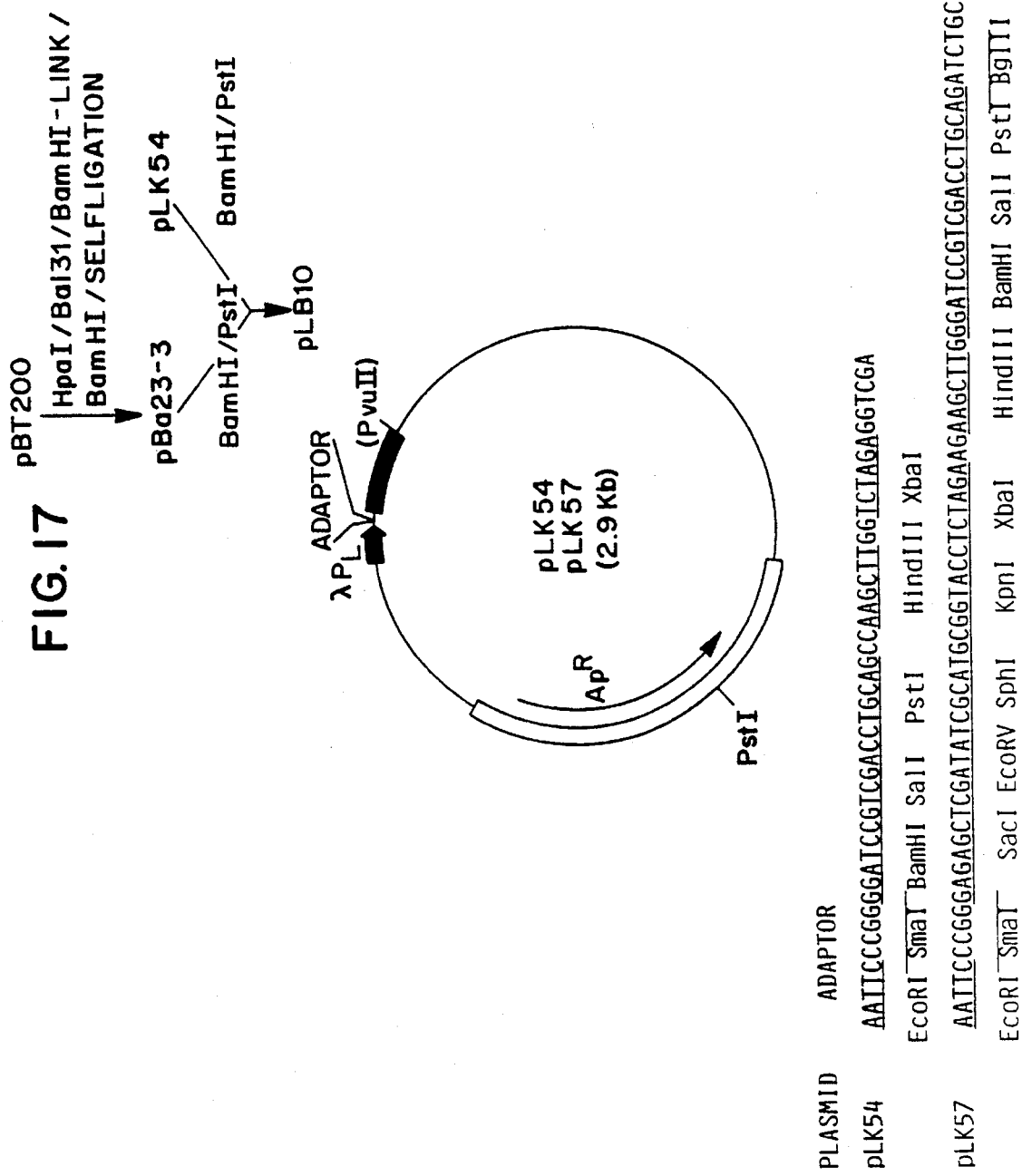
Figure 18:
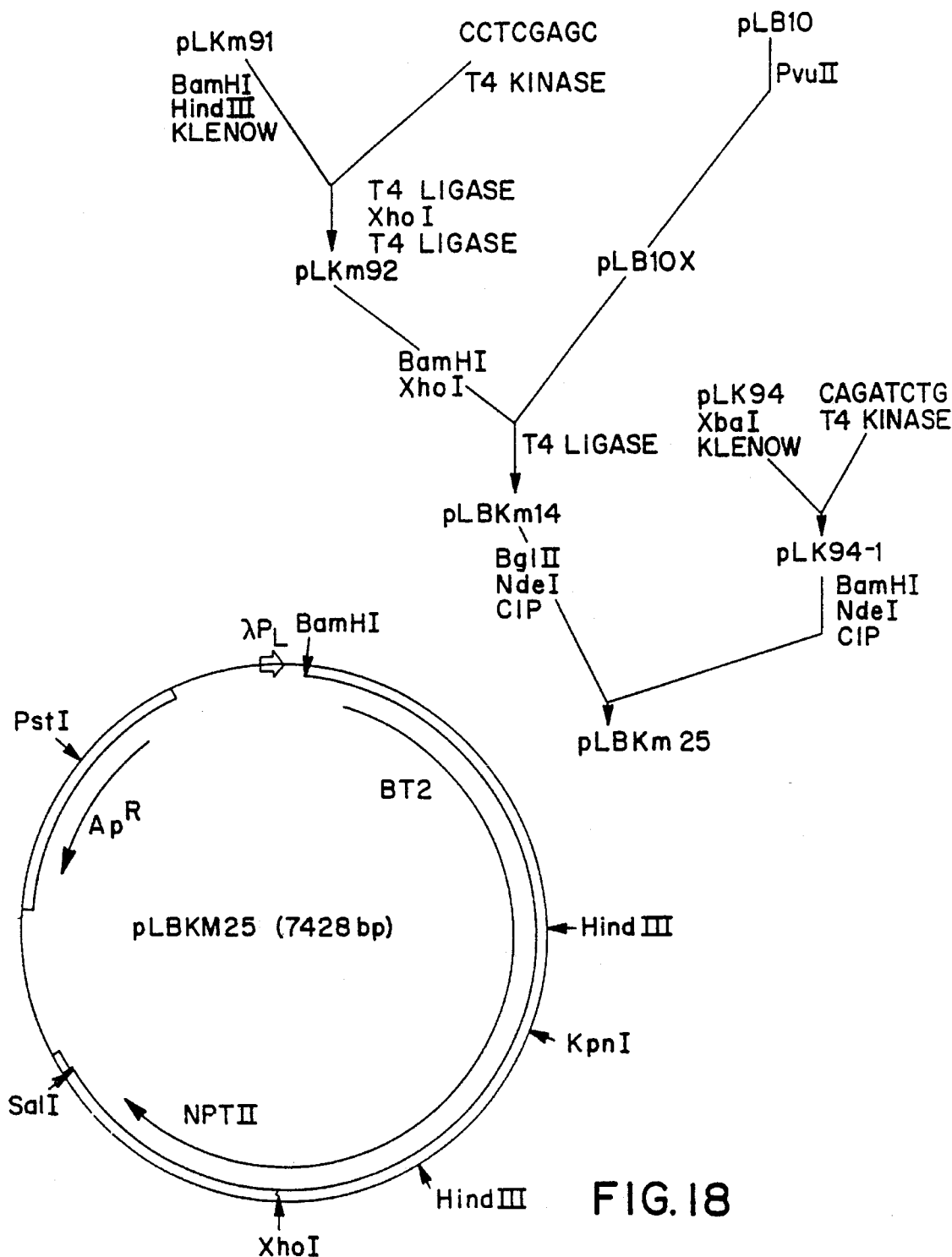
Figure 19:
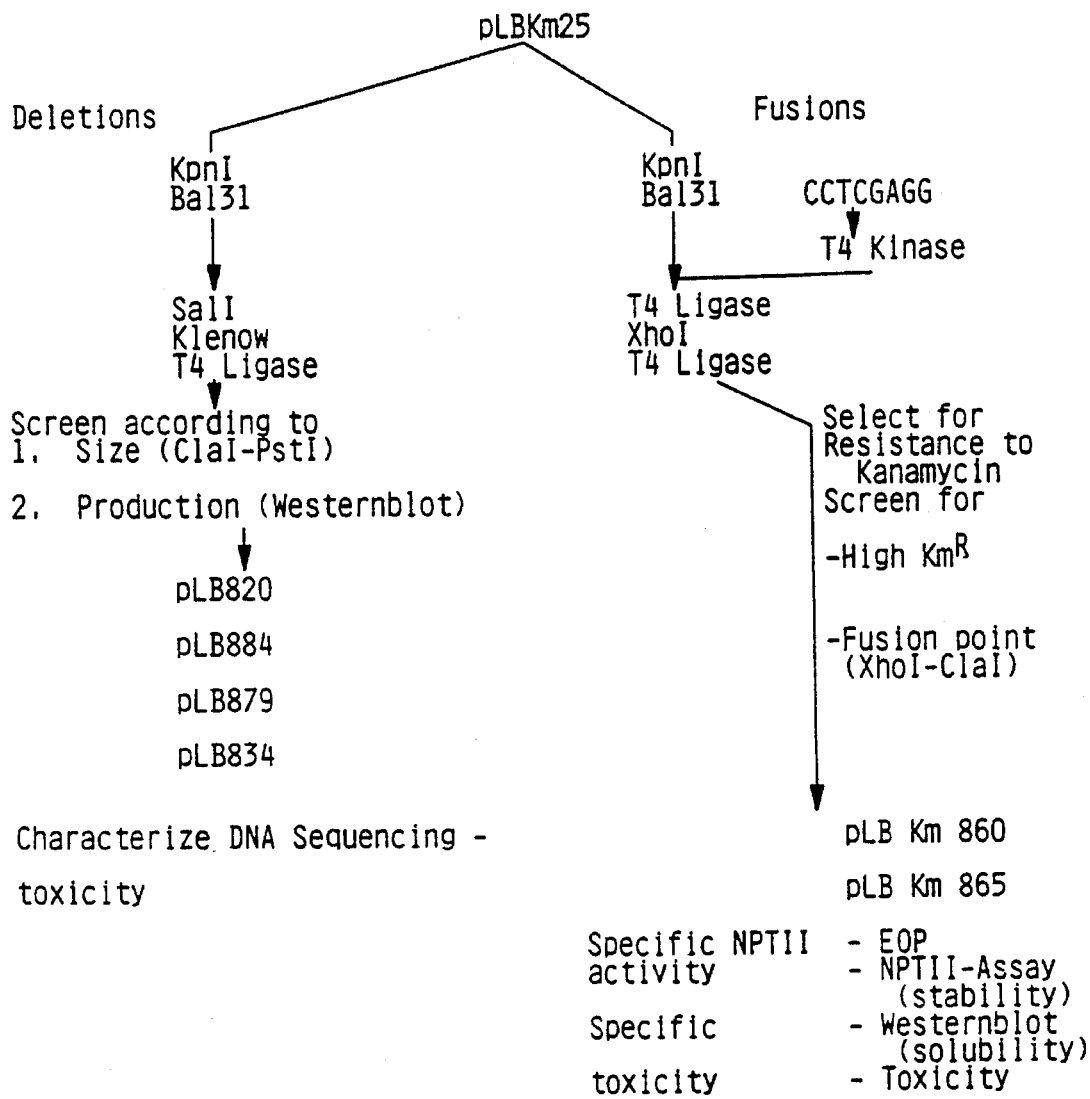
Figure 20:
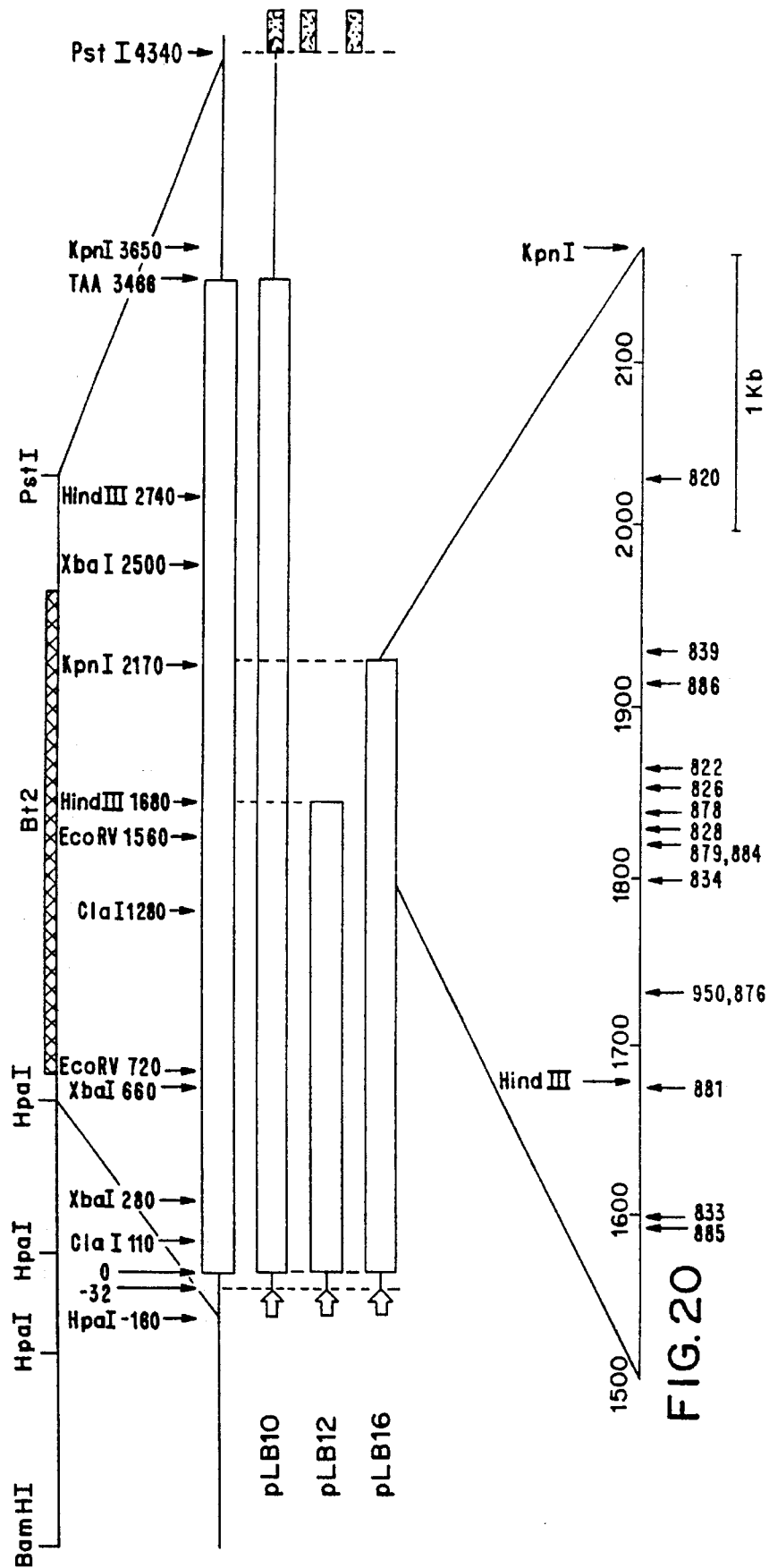
Figure 21:
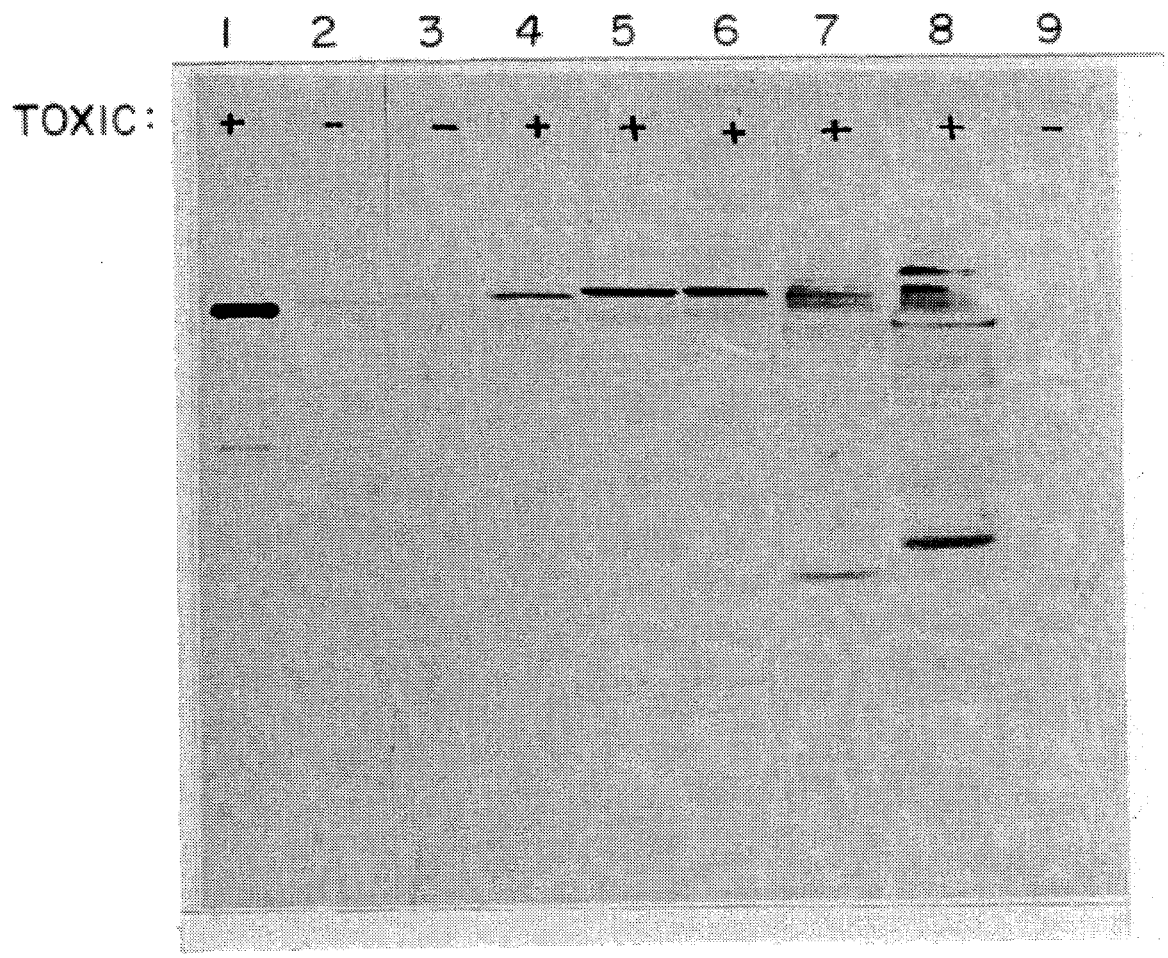
Figure 23:
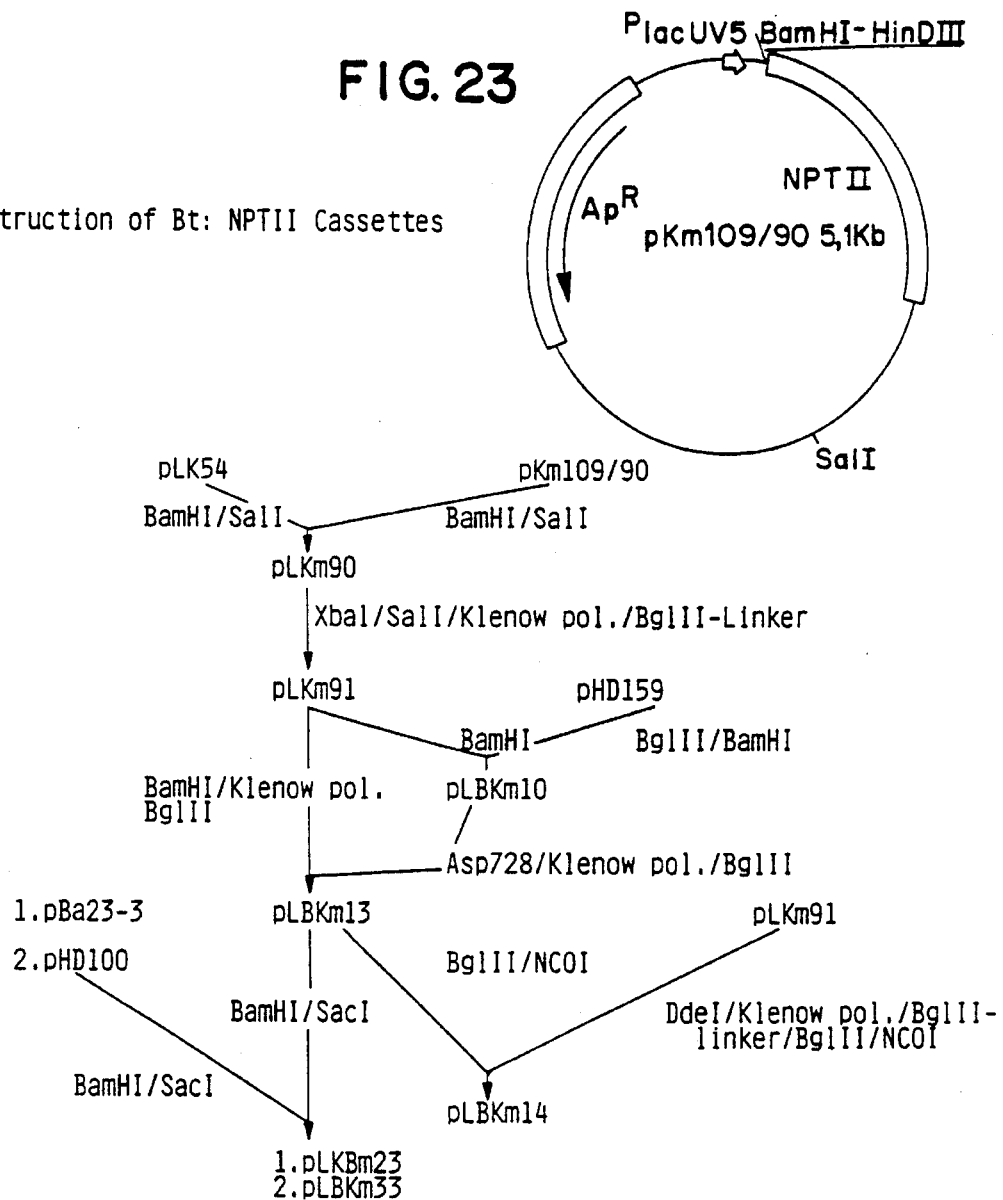
Figure 24:
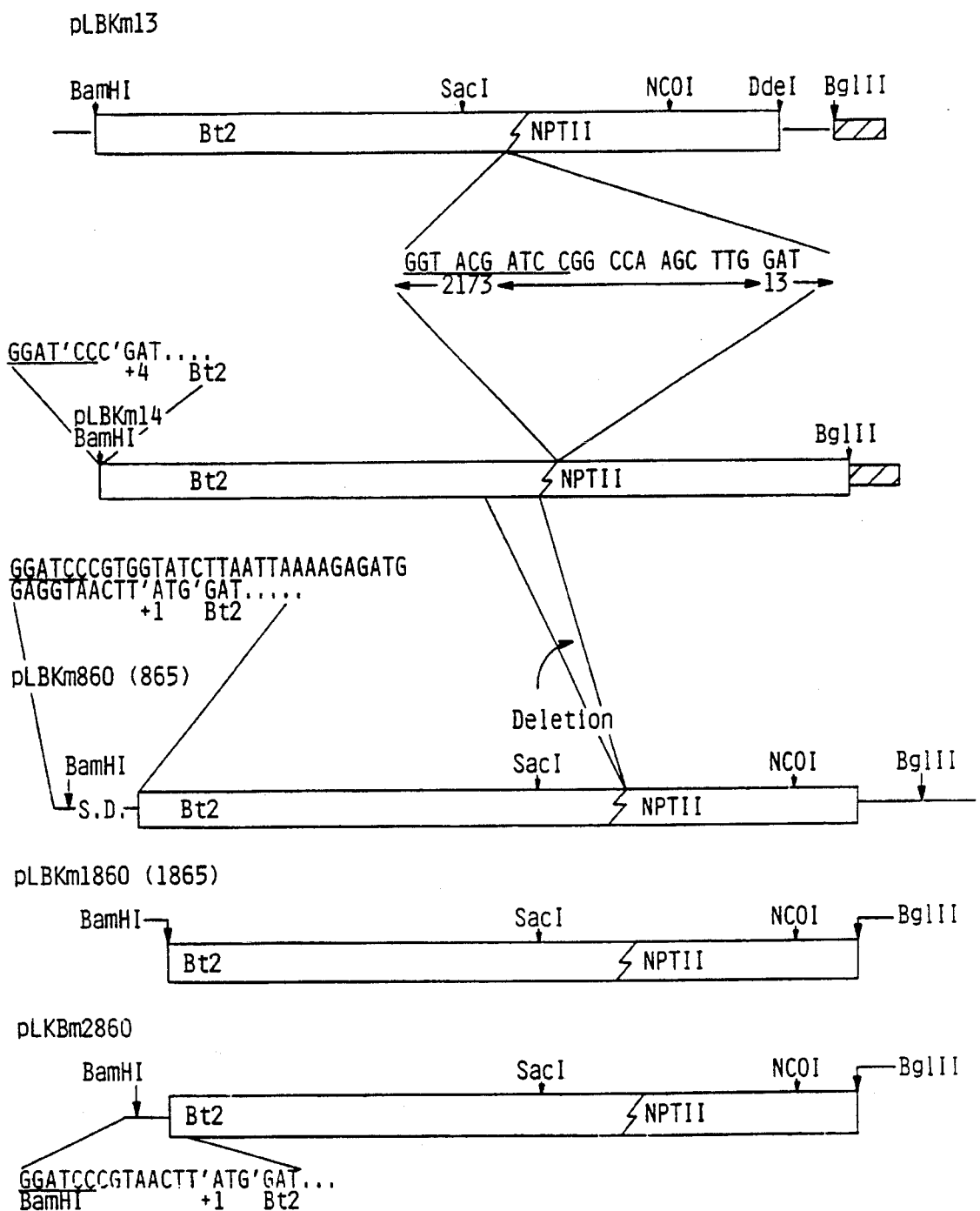
Figure 25:
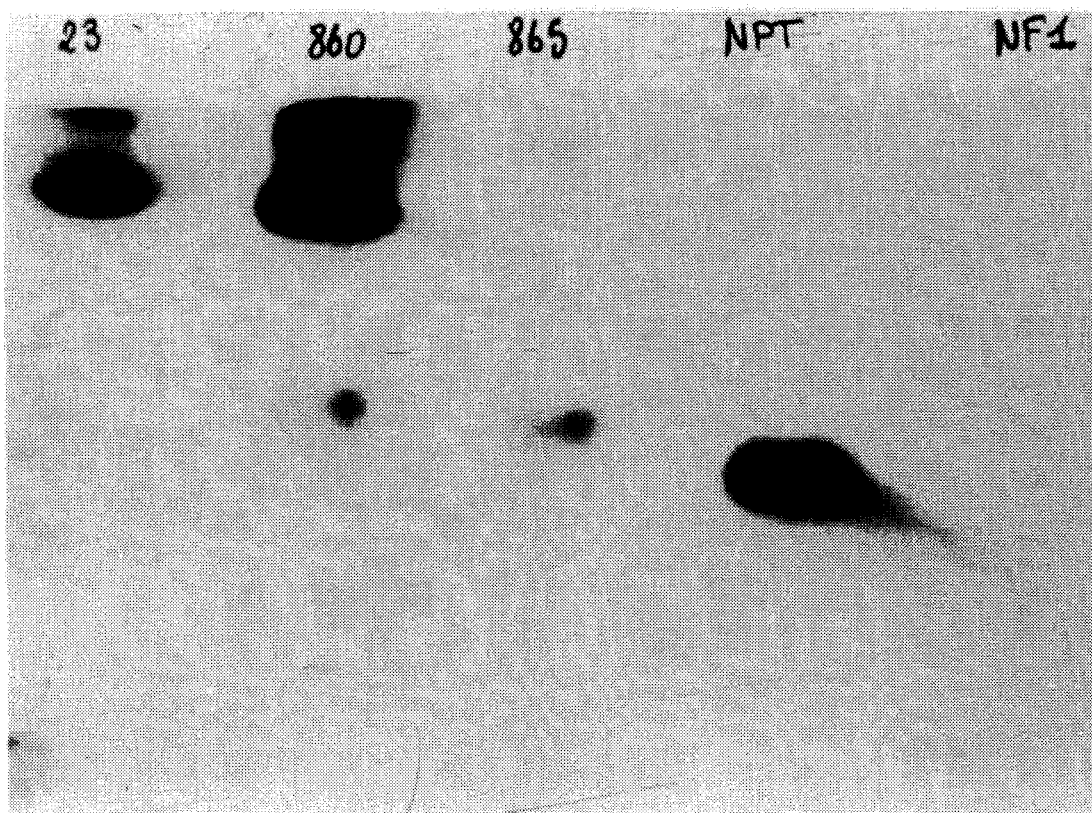

In order to create plasmid pDC3 (FIG. 16), plasmid pHD164 was digested with DraI, ligated to BglII linkers, and the fragment containing the Bt2 gene was cloned in the BglII site of pLK57 (FIG. 17). In this way, the BglII site of the BamHI-BglII cassette was placed in close proximity of the TAA stop codon of Bt2.

7.2 Construction of Cassettes Containing Engineered Bt2 Genes

7.2.1 Truncated Bt2 Genes

7.2.1.1 Rational

Results from basic research on the functional properties of *B.t.* crystal proteins indicate that the large approximately 130 Kd crystal proteins are relatively insoluble and, in addition, are protoxins which need processing in the insect midgut towards lower molecular weight active toxins, able to exert their toxic effects on insects (Bulla, L. A., Jr., D. B. Bechtel, K. J. Kramer, Y. I. Shetna, A. I. Aronson and P. C. Fitz-James, 1980, *Rev. Microbiol.*, 8: 147–203; Bulla, L. A., Jr., K. J. Kramer, D. J. Cox, B. L. Jones, L. I. Davidson and G. L. Lookhart, 1981, *Biol. Chem.*, 256:3000–3004; T. A. Angus, *Can. J. Microbiol.*, 2:416 (1956); M. M. Lecadet, "Microbial Toxins", Vol. II, ed. by T. C. Montie and S. Kadis, Academic Press, Inc., New York and London, 1970, pp. 437–471). The specific activity of the Bt toxin when ingested by the insects as part of a composition of engineered plant material will be determined, not only by the total quantity of toxin present but also by the degree of accessibility of active toxin, released in the midgut. It has been shown that some insects species are more efficient than others in solubilizing and/or "processing" (enzymatically degrade) *B.t.* protoxins (Presentation by Dr. P. Luthy in "Second Workshop Bacterial Protein Toxins", Wepion Belgium: Jun. 30–Jul. 4, 1985; to be published in congress proceedings). Therefore, it might be advantageous in the engineering of insect resistant plants to construct truncated toxins derived from Bt2 which have the properties of being: 1) already processed or partially processed toxin, exhibiting full toxic activity; and 2) more soluble than the original Bt2 protein. Plants expressing such truncated polypeptides might exhibit higher specific toxicity against insects than plants expressing intact Bt2 at the same level.

7.2.1.2 Construction of the Deletion Mutants

1. Positioning of the Toxin Gene Behind the $P_L$ Promotor

A gene coding for a 130 Kd crystal protein toxin of *B.t.* berliner 1715 has been cloned into pUC8 (Viera and Messing, *Gene* 1, 259–268, 1982) giving rise to pBt200. Characteristics of this gene, called Bt2, and the resulting toxin (Bt2 protein) have been described in Sections 5 and 6.

In order to assure a regulatable, high-level expression in *E. coli*, the Bt2 gene was positioned behind the $P_L$ promotor (FIG. 17). To this end, the plasmid pBt200 carrying the Bt2 gene on a 7.7. Kb BamHI PstI fragment was cut with HpaI, treated with Bal31, ligated to BamHI linkers, cut with BamHI and self-ligated (as described in Section 7.1). From the resulting clones, deletion derivatives with varying lengths of upstream sequences were selected, and inserted behind the $P_L$ promotor of the expression plasmid pLK54 (see FIG. 17 and Botterman et al., in press, *Gene* 1986) making use of the restriction enzymes BamHI and PstI.

The resulting plasmids were assessed for the production of Bt2 protein and one of those producing the highest levels of Bt2, termed pLB10 was selected for further experiments. Plasmid pLB10 originated from pBa23-3 (FIG. 17, Section 7.1).

2. Construction of Deletions

From the internal deletions previously made in pBt200 with XbaI and KpnI, only the KpnI deletion gave rise to immunologically detectable Bt2-derived protein (see Section 6). Deletions were made in pLB10 using restriction enzymes KpnI and HindIII. Western blotting analysis and ELISA showed that only the KpnI deletion mutant, containing the largest fragment extending from the start towards position 2167 of the Bt2 gene, produced a stable approximately 80 Kd polypeptide. The polypeptide encoded by the HindIII deletion derivative probably is highly sensitive to *E. coli* proteases.

Interestingly, the KpnI deletion mutant-encoded polypeptide exhibited an insecticidal activity that was equivalent to that of the intact Bt2 protein: in one experiment the $LD_{50}$ value on 3rd instar *P. brassicae* larvae was determined to be 2.5 ng/larva for the Kpn deletion mutant as compared to 2 ng/larva for the intact Bt2. This result indicates that the truncated Bt2 gene product, arising from the KpnI deletion, comprises the entire active toxic unit.

The previous data suggests that the smallest gene fragment of Bt2, encoding an active toxin is contained within the KpnI deletion fragment but extends further than the HindIII site. To map the exact endpoint of the minimal fragment coding for the active toxin, deletion mutants were constructed which contained N-terminal fragments of decreasing size. To achieve this, we used a strategy which allowed us to construct simultaneously deletion-mutants and translational fusions to the NPTII-gene (see Section 7.2.2). The construction of the intermediate plasmid pLBKm25 is outlined in FIG. 18. As shown in FIG. 18, pLBKm25 is derived from pLB10 (see previous section) and pLKm91 which will be described in Section 7.2.2.2.

As shown, this plasmid is provided with a DNA sequence with stopcodons in the three reading frames behind a unique SalI site. This construct was cut with KpnI, digested with Bal31, cut with SalI, treated with Klenow polymerase and religated (FIG. 19). In this way, the deleted coding region is fused to a stopcodon with a minimum of nonsense coding sequence. An overview of the deletion clones is given in FIG. 20. Total cellular extracts were made of the clones (after induction) and analyzed in Western blotting and ELISA for the quantitative detection of Bt2-like polypeptides and in an insect toxicity assay to screen for active toxin. The results are presented in FIG. 21 and indicate that detection of a stable polypeptide decreases gradually when the endpoint of the coding region is coming closer to the HindIII site.

From a certain position on (still downstream of HindIII), almost no Bt2-like protein was detectable anymore. Furthermore, toxicity of the extracted material from these clones, drops abruptly when the 3' endpoint is passing a particular position between HindIII and KpnI. The two clones characterizing the smallest toxic (pLB879) and the largest non-toxic (pLB834) polypeptide were verified by DNA sequence analysis. This analysis showed that the critical endpoint for a stable active toxin maps between positions 1797 and 1820 on the Bt2 gene (FIG. 22). Therefore all N-terminal gene fragments of Bt2, ending downstream of position 1820 (bp) comprise a gene fragment encoding an active toxin. Interestingly, total cellular extract of one clone (pLB820) showed a much stronger reaction with a polyclonal antiserum and a monoclonal antibody in Western blotting. Moreover, the protein produced by this clone was more soluble in *E. coli* than the KpnI deletion gene product and still exhibited full toxic activity.

7.2.2 Fusion genes to NPTII 7.2.2.1 Rationale

It is known that amino-terminal fusions at the NPTII gene can generate fusion proteins that still confer kanamycin resistance in bacteria (Reiss et al., *EMBO J.* 3, p. 3317, 1984).

Since NPTII is a most suitable selection marker in plant engineering, such gene fusions could have very promising applications. Indeed when using such NPTII fusion proteins to transform plants, a selection for high kanamycin resistance would allow direct selection for a high expression of the fusion product. Therefore, toxin gene fusions with NPTII might be used to transform plants and select for transformed plants expressing high levels of toxin, by selection for kanamycin resistance.

7.2.2.2 Construction of the Fusion Gene Cassettes

Different fragments of the Bt2 gene were fused to the N-terminus of NPTII.

One of the fusion proteins termed Bt:NPT2 is described in more detail below.

1. Construction of the Bt:NPT2 Fusion Gene

The construction of the Bt:NPT2 gene is shown in FIG. 23. pLK54 is a pBR322 derivative containing the $P_L$ promotor and 2 phase fd transcription terminators in tandem (Section 7.2.1.2). pKm109/90 contains the NPTII gene of Tn5 on pBR322 (Reiss et al., *EMBO J.*. 1984) (FIG. 24).

A 1141 bp gene fragment of pKm109/90 containing the NPTII gene was cloned in pLK54 giving rise to pLKm90. In order to create a BglII site behind the NPTII gene, BglII linkers were ligated at the XbaII and the SalI site after Klenow polymerase treatment. This gives rise to pLKm91.

pHD159 is a derivative of pBt200 (Section 7.1) whereby a BamHI linker has been fused to the 4th bp and a BglII linker to bp 3342 (after Bal31 treatment). The BamHI BglII fragment of this plasmid containing the deleted Bt2 gene was inserted in the BamHI site of pLKm91, in one orientation, giving rise to a Bt2:NPTII fusion gene on pLBKm10.

To construct pLBKm13 an Asp 728, Klenow treated BglII fragment was inserted between the BamHI site (after filling in) and the BglII site of pLKm91.

In order to produce the Bt:NPTII fusion proteins in *E. coli,* analogous constructs to pLBKm10 and 13 were made containing 5' leader sequences of the Bt2 gene with a ribosome binding site. Therefore, from another Bal31 deletion derivative of pBt200, pBa23-3 (Section 7.1), with the BamHI linker at position −33 we exchanged the BamHI-SacI fragment with pLBKm13, giving rise to pLBKm23.

For the expression of the fusion protein Bt:NPT2 behind the Pnos promotor and the 35S promotor, the BamHI-SacI fragment of pHD160 (described in Section 7.1) was cloned between the same sites in pLBKm13 giving pLBKm33.

Finally for the construction with the Petunia ssu-promotor (see Section 8) we used a modified Bt:NPTII cassette wherein the 3' non-coding region was removed up to the stopcodon of NPTII. To achieve this the NCoI-BglII fragment of pLBKm13 containing the 3' end of the NPTII gene was replaced by a NCoI BglII-fragment generated from pLKm91 (FIG. 23). This plasmid was cut with DdeI, treated with Klenow polymerase, and ligated to a BglII linker, whereafter the resulting DNA was cut by NCoI and BglII. FIG. 23 also shows the 5' Bt2 sequences in the different constructs.

In summary, the Bt:NPT2 gene contains (FIG. 24):

1) The 5' end of the Bt2 gene starting 8 bp upstream of the initiation ATG codon or at pos +4 or at position −33 and extending towards nucleotide position 2173.

2) a 16 bp linker fragment.

3) the NPTII coding region starting at nucleotide position 13.

2. Characteristics of the Fusion Protein Expressed in *E. coli*

The fusion gene Bt:NPT2, placed behind the $P_L$ promotor In plasmid construction pLBKm23 (FIG. 23), was expressed in *E. coli* to study the properties of the fusion protein.

2.1 Identification of the Fusion Protein in *E. coli*

An *E. coli* clone transformed with pLBKm23 was analyzed in SDS-PAGE and in Western blotting. Coomassie staining of the complete bacterial extract in SDS PAGE showed the presence of a new protein band having an apparent molecular weight corresponding to the expected size of the fusion protein (approximately 110 Kd).

The protein could also be visualized in Western blotting using either anti-Bt2 serum or anti-NPTIII serum. Again the positively reacting band showed the expected size of the fusion protein. The protein is quite stable in *E. coli* since only limited amount of degradation products was detected (bands of lower M.W.).

2.2 Kanamycin Resistance of the Engineered *E. coli* Clone and NPTII Activity of the Bt:NPT2 Protein The *E. coli* clone containing pLBKm23 gene was indeed resistant to kanamycin. Bacteria were able to grow on 100 ug/ml Km (for comparison, the wild type NPTII gene confers resistance to more than 1000 ug/ml).

NPTII activity of the Bt-NPT2 fusion protein was evaluated using an NPTII assay as described elsewhere (Reiss et al., *Gene* 30, p. 217, 1984). A cell extract of the *E. coli* clone expressing the Bt:NPT2 protein was run on gel in nondenaturing conditions, in parallel with an extract from an *E. coli* clone producing the wild type NPTII. Cell extracts were prepared as follows. The *E. coli* clones were grown during about 4 hrs. at 28° C. in 20 ml cultures (containing LB medium), centrifuged and resuspensed in 1 ml TES buffer, sonicated for 2 times 2 minutes at 50 watts in Labsonic 1510 and centrifuged for 30 minutes at 15,000 rpm; the supernatant was used in our experiment. The position and NPTII-specific activity of the proteins was determined by in situ phosphorylation of kanamycin, using $^{32}$P-ATF (Reiss et al., 1984, *Gene,* 30, 217–223). A gel containing the same samples was run in parallel and used in a Western blotting procedure (with anti-Bt2 and anti-NPTII antibodies). By comparison with dilution series of purified Bt2 and purified NPTII protein samples, which were included on this gel, the amount of protein present in the samples used for activity measurement could be determined; the results indicated that the specific activity of the Bt:NPT2 protein was roughly the same as that of NPTII (FIG. 25).

2.3 Behavior of the Bt:NPT2 Fusion Protein in *E. coli*

The results in the previous section indicate that specific NPTII enzyme activities of intact NPTII enzyme and of the fusion protein were substantially equivalent. This seems somewhat incompatible with the "in vivo" behavior of the protein. While an *E. coli* producing wild type NPTII is resistant to more than 1000 ug/ml Km, the Bt:NPT2 engineered *E. coli* expressing comparable levels of protein are only resistant to a level of 100 ug/ml.

It is known, however, that proteins produced in *E. coli* at high levels (such as is the case here, using the strong $P_L$ promotor), tend to precipitate within the cell. One might expect that if a substantial fraction of the Bt:NPT2 protein is present in a precipitated form in *E. coli* (and most of the protein is enzymatically inactive) the result is a low resistant phenotype.

Analysis of a bacterial extract of the Bt:NPT2 clone using a Western blotting indicated that indeed nearly all the protein was present in an insoluble form. After lysis of the cells and centrifugation, most of detectable Bt:NPT2 was found in the pellet (this in contrast to the NPTII wild type protein which is mostly present in the supernatant fraction). Only a minor fraction of the Bt:NPT2 protein was present in the supernatant. To solubilize the fusion protein, present in the pellet fraction, 8M urea+2% ME (mercapto ethanol) was required. After dialysis, to renature the solubilized protein an enriched Bt:NPT2 protein preparation was obtained which could be tested in insect toxicity assays (see 2.4).

2.4 Toxicity of the Bt:NPT2 Protein

Previous toxicity assays have shown that the polypeptide encoded by the KpnI deletion fragment of Bt2 has still 100% of the toxic activity of the intact Bt2 protein (Section 7.2.1.2). In addition, our studies on the identification of minimal active toxic fragments have shown that this Kpn fragment comprises a (approximately 60 Kd) active toxin which exhibits the complete toxic activity of the Bt2 molecule. In the following, we wanted to determine whether the Bt:NPT2 fusion protein had still the same degree of toxicity.

To this end, toxicity levels towards insect larvae, of enriched Bt:NPT2 and purified Bt2 protein were compared. The exact amount of fusion protein in the samples was determined using ELISA (with a monoclonal antibody specific for the N-terminal region of Bt2:4D6) and Western blotting (comparison of band intensity of dilutions of the fusion protein and purified Bt2). The results showed that the specific toxic activity on *M. sexta* and *P. brassicae* larvae was substantially the same for Bt:NPT2 fusion protein as for intact Bt2 (Tables 4 and 5).

Taken together the above data indicate that the Bt:NPT2 protein has NPTII activity both "in vivo" and "in vitro" and in addition that it has an equally potent insecticidal activity as the Bt2 toxin. Therefore, this truncated toxin clearly represents a valuable alternative in the engineering of plants expressing high level of insect toxicity.

2.5 Selection of Additional Bt2:NPTII Fusions Expressing a Higher Kanamycin Resistance Phenotype The results obtained with the previously constructed Bt:NPTII gene were very promising since this fusion protein conferred kanamycin resistance, showed normal levels of toxicity and was relatively stable. However, the kanamycin resistance conferred by the Bt:NPT2 fusion was relatively low as compared to the wild type cells. Since the isolated purified Pnos-Bt:NPT2 protein had a specific NPTII activity comparable to the wild type NPTII protein, we concluded that the low kanamycin resistance was due to the low solubility of the fusion protein in *E. coli.* A relatively low resistance phenotype might interfere with an efficient selection system in plants. Therefore, we considered the possibility that other Bt-NPTII fusions could have different physicochemical properties leading to a higher Km resistance phenotype "in vivo". We designed an experiment to fuse the NPTII gene at random to the Bt2 sequence in the region between the KpnI site and the processing site. The experiment was as follows:

We used plasmid pLBKm25 (FIG. 18) containing the following elements of interest: a $P_L$ promotor and the Bt2 gene, fused at 1100 bp downstream of the KpnI site, to the NPTII gene (see FIG. 19). A unique XhoI site separates the Bt from the NPTII gene. This plasmid was linearized by KpnI digestion and treated with Bal31 exonuclease. The Bal31 reaction was titrated such that the deletions did not proceed far beyond the HindIII site which is localized upstream of the C-terminal processing site. The Bal31 treated plasmid was ligated to XhoI linkers, digested with XhoI and self-ligated. As a result, the NPTII is fused to fragments of the Bt2 gene varying in size. These plasmids, transformed in *E. coli,* conferred kanamycin resistance on condition the NPTII gene was fused in frame to the Bt2 gene. Transformants were selected on plates containing low levels of kanamycin (20 ug/ml) and screened for the ability to grow on higher kanamycin concentrations.

145 kanamycin resistant transformants were screened for their ability to grow on higher kanamycin concentrations. 8 transformants proved more resistant and were able to grow on concentrations higher than 200 ug/ml of kanamycin. The fusion point in all 8 clones was determined by restriction enzyme mapping with an accuracy of 20 bp. Surprisingly 7 out of 8 clones had their fusion point around the HindIII site at position 1680 of the Bt gene. One clone (pLBKm860) mapped at position approximately 2050. Although the majority of the deletions were fused around position 1800, none of these conferred a higher kanamycin resistant phenotype. The 7 clones which have their fusion point positioned around the HindIII site are too short to encode an active toxin. However, one of the clones (pLBKm860) was:

More stable, since more protein per amount of total cellular extract was detected in Western blot analysis; and More soluble since more truncated Bt protein was detected in the supernatant.

The positions of the 3' end points in the Bt2 coding sequences in clones 860 and 865 are represented in FIG. 26.

Toxicity of the fusion proteins and truncated Bt2 gene products is illustrated in Table 6.

7.3 Adaption of Cassettes Containing Truncated Bt Genes or Bt Gene Fusions for Expression in Plant Cells Plasmids pLBKm860 and 865 were modified as described in FIG. 27 to generated plasmids pLBKm1860 and pLBKm1865 respectively. pLBKm2860 was derived from (FIG. 27) pLBKm860.

By replacing the BamHI-SacI fragment from pLB820 and 884 for the BamHI-SacI fragment of pLBKm14, the new plasmids called pLB1820 and 1884 respectively, were generated. pLB2820 was derived from pLB1820. As an example, the final constructs pLBKm1860, pLBKm1865 and pLBKm2860 are shown in FIG. 24.

8. Construction of Intermediate Expression Vectors Containing the Toxin Gene 8.1 Overview Table 7 gives an overview of the engineered plasmids which have been constructed and used in the plant tranformation experiments. Each engineered Ti plasmid is the result of a cointegration of a receptor Ti plasmid with an intermediate vector. Each intermediate vector contains a chimeric toxin gene comprising a plant promotor sequence derived from the indicated expression vector and a Bt gene cassette.

Assembly of Chimeric Genes

Table 7 gives the plasmids from which the Bt gene cassettes are isolated. The construction of these plasmids has been described in previous parts. The detailed maps of the expression vectors mentioned in Table 7 are given in FIG. 33 (A–J).

The detailed construction of the two chimeric genes present in pHD205 and pHD208 are described as an example. The experimental procedure uses standard recombinant DNA techniques and experimental protocols have been followed, according to Maniatis (Cold Spring Harbor, 1982).

The different plant promotors which have been used are (Table 7):

Pnos: a constitutive and relatively week promotor derived from the T-DNA encoded nopaline synthase gene.

Pssu-pea: derived from a weekly expressed member of the family of smell Subunit of Ribulose biphosphate-carboxylase genes of pea. Expression is light inducible in green tissues.

PTR2: A constitutive promotor derived from the $T_R$-DNA of the octopine Ti plasmid (Velten et al., 1984, *EMBO J.*, 3, 2723). In the expression vectors pGSH150 and pGSH160 the duel promotor fragment is derived from pop443 (Velten et al., 1984, *EMBO J.*, 3, 2723). The 5' untranslated region of the 2' promotor has been completed by adding a BamHI linker to produce the sequence

. . . ATCGATGGATCC

ClaI BamHI

Cloning into the BamHI site thus leaves the 5' untranslated region of the 2' gene intact and fuses the Bt gene cassette at the initiation ATG of the 2' gene.

The importance of an intact 5' untranslated region for obtaining high levels of expression of chimeric genes has been demonstrated (Jones et al., *EMBO J.*, 4, 2411, 1985).

Pssu301: is the promotor of an rbs (ribulose bisphosphate carboxylase small subunit) gene of Petunia from which about 50% of the *Petunia rbs* mRNA is transcribed (Dean et al., *EMBO J*, 1984, 4, No. 12). Via site directed mutagenesis the sequence around the initiation codon (TAACTATGGCTT) has been changed to TAACCATGGCTT, creating an NcoI site on the initiation codon. Similarly, modification around the TAA stopcodon from GGCTTCTAAGTT to GGCTTCTAAGATCTT created a BglII site.

BglII

As a result, the coding region of the ssu-301 gene could be precisely removed by NcoI-BglII digest and substituted by the Bt gene cassettes described under 7.2.

Isolation and characterization of the promotor fragment (Pssu PET) and 3' end (ssu-PET) is described in Dean et al., *PNAS*, U.S.A., Vol. 82, 4964 (1985). Construction of pAGS007 (FIG. 33H) is described in FIG. 44.

P35S: is a strong constitutive promotor derived from cauliflower mosaic virus (CAMV). The P35S-1 promotor fragment is derived from CAMV isolate Cm4-184. It contains a fragment (nt6492–7454) of the CAMV genome (Gardner et al., 1981, *Nucl. Acid Res.*, 9, 2871–2899 and a downstream BamHI site for cloning (FIG. 40).

P35S-2 contains CAMV sequences from 6492 to 7466 followed by a ClaI site.

P35S-1 and P35S-2 thus only differ in the length of the 5' untranslated sequences of the 35S CAMV transcript.

Promotor-Bt Gene Junctions

FIG. 28 gives the DNA sequences at the junction between the promotor regions and the coding sequence of the Bt gene cassettes as they are present in the different engineered Ti plasmids. Sequences derived from the original promotor regions and from the coding sequence of the Bt2 gene are underlined. Some relevant restriction enzyme sites which have been involved in the assembly of the chimeric genes are indicated. The ATG initiation codon is boxed.

Junctions Between Bt Gene Cassettes and the 3' Ends

All chimeric genes are provided at the 3' end with a sequence which contains the 3' untranslated region, including the polyadenylation site, of a gene which is naturally expressed in plant cells. The following sequences have been used:

3'ocs (in pHD1060, pHD1076, pHD1080)

A 706 bp PvuII fragment containing the 3' untranslated region of the octopine synthase gene (pos 11939–11233 according to Gielen et al., *EMBO* 4, p. 835, 1984).

3't7 (pOS1151, pGS1161, pGS1152, pGS1153, pGS1162, pGS1163, pGS1251, pGS1261, pGS1253, pGS1262, pGS1271, pGS1281

A 212 bp EcoRV-ClaI fragment containing the 3' untranslated region of T-DNA gene 7, cloned into the SmaI site of pUC8 and reisolated as a EcoRI-SalI fragment (pos 2317–2105 according to Gielen et al., *EMBO* 4, p. 835, 1984).

3'nos (in pGS1110)

A 182 bp TAgI-ClaI fragment, containing the 3' untranslated region of the nopaline synthase gene (pos 1290–1472 according to Depicker et al., *J.M.A.G* 1, p. 561, 1982)

3'SSu301 (in pGS1171, pGS1181)

An approximately 1.2 Kb BglII-BamHI fragment derived from the 3' end of the ssu301 gene was constructed by site-directed mutagenesis as follows:

|  | stop coding region | (which is TAA) |
|---|---|---|
| ssu301 | ... TTC<u>TAA</u>GTTATA |  |
| coding | ... TTC<u>TAA</u>GATCTATA |  |
| sequence | BglII | Construction of a BglII site through site-directed mutagenesis |

EXAMPLE 1

This example describes the construction of pHD205, an intermediate vector containing a chimeric Bt2 toxin gene comprising: the nopaline synthase promotor, the Bt2 toxin gene cassette from pHD160 and a DNA fragment containing the 3' untranslated region of the nopaline synthase gene including the polyadenylation site. In the chimeric gene the Bt2 gene cassette is oriented such that the expression of the Bt2 protein can be obtained from the nopaline synthase promotor. The Bt2 gene cassette was excised from pHD160 with BamHI and BglII and inserted in the BamHI site of pLGV2382 (Herrera-Estrella et al., *EMBO J.*, 2, 987–995, 1983). Two ug of pHD160 DNA were totally digested with respectively 2 units of BglII and BamHI (Boehringer Mannheim) for 1 h at 37° C. in a final volume of 20 ul, using the incubation buffer described by Maniatis et al. (*Molecular Cloning* (1982), Cold Spring Harbor Laboratory, 133–134). Five ug of pLGV2382 DNA was totally digested with BamHI under the same conditions. Subsequently the terminal 5' phosphates were removed from the DNA treatment with calf intestinal alkaline phosphatase (CIP) (Boehringer Mannheim) using the conditions described by Maniatis et al., *Molecular Cloning* (1982), Cold Spring Harbor Laboratory, 133–134). One-fifth of BamHI digested and CIP treated pLGV2382 DNA was ligated to 0.1 ug of BamHI-BglII digested pHD160 DNA with 0.01 units of T4 DNA ligase (Boehringer Mannheim) in a final volume of 20 ul. Ligation buffer and incubation are as recommended Boehringer Mannheim (Brochure "T4 ligase", Boehringer Mannheim, August 1980, 10.M.880.486). The ligation mixture was transformed into competent *E. coli* K514 cells (Colson et al., *Genetics* 52 (1965), 1043–1050) according to Dagert and Ehrlich, *Gene,* 6 (1980) 23–28. Cells are plated on LB medium (Miller, *Experiments in Molecular Genetics* (1972) Cold Spring Harbor Laboratory, New York) supplemented with cerbenicillin (100 ug/ml). Transformants were screened for the presence of recombinant plasmids by microscale DNA preparations, performed according to Birnboim and Doly (*Nucl. Acids Res.* 7 (1979), 1513–1523). The orientation of the BamHI-BglII fragment in the BamHI site of pLGV2382 was determined by BamHI-PstI double digestion. Double digestion pattern of recombinant plasmids shows 4 fragments after agarose gel electrophoresis. In the alpha-orientation there are fragments of approximately 5700 bp, 3000 bp, 2300 bp and 920 bp, whereas in the beta-orientation there are fragments of approximately 6200 bp, 3000 bp, 1800 bp and 920 bp. A recombinant plasmid with the alpha-orientation (the toxin gene under the control of the nopaline synthase promotor) is used in subsequent experiments and called pHD205.

EXAMPLE 2

This example describes the construction of pHD208. The intermediate vector pHD208 contains a chimeric Bt2 toxin gene comprisimg the promotor from a pea gene encoding a small subunit of ribulose biphosphate carboxylase (Pssu), the Bt2 toxin gene cassette from pHD160 and the 3' untranslated region of the octopine synthase gene including the polyadenylation site. The fragments of the chimeric gene were assembled in the cloning vector pGV831 as described in this example and as diagrammed in FIG. 29. The construction of pGV831 is summarized in FIG. 30.

Step 1: Insertion of a 706 bp PvuII fragment containing the 3' untranslated region of the octopine synthase gene into pGV831, to yield pGV858.

Five ug of pGV831 DNA was totally digested with 5u HpaI at 37° C. 0 for 1 h, using the incubation buffer described by Maniatis et al., *Molecular Cloning* (1982). Subsequently, the terminal 5' phosphates are removed from the DNA by treatment with CIP using the conditions as described by Maniatis et al., *Molecular Cloning,* 1982. Twenty ug of pGV99 DNA (De Greve et al., *J. Mol. Appl. Genet.* 1, 499–512, 1982) was digested with 20 units of PvuII for 1 hour at 37° C.

The resulting DNA fragments were separated by electrophoresis on a horizontal agarose gel (0.8% agarose in TBE buffer). The agarose band containing the 706 bp PvuII fragment was cut out and the DNA was recovered by electroelution. After phenolisation and ether extraction, DNA was precipitated with ethanol by centrifugation in an Eppendorf centrifuge for 10 minutes, washed with 70% ethanol, dried and resuspended in 20 ul $H_2O$.

0.03 ug HpaI digested and CIP treated pGV831 was ligated to 0.1 ug of the purified 706 bp fragment with 1U of T4 ligase in a final volume of 10 ul. The ligation mixture was transformed into competent *E. coli* K514 cells. (Colson et al., *Genetics* 52 (1965), 1043–1050) as described by Dagert and Ehrlich, *Gene* 6 (1980), 23–28. Cells were plated on LB medium (Miller, *Experiments in Molecular Genetics* (1972), Cold Spring Harbor Laboratory, New York), supplemented with carbenicillin (100 ug/ml). The resulting recombinant plasmids were characterized by double digestion with PstI and ApaI digestion. One of the resulting plasmids, pGV858, yielded the desired digestion fragments of approximately 5300, 1700, 1500 and 900 bp and was used further.

Step 2: Construction of a modified Pssu fragment and insertion of this fragment in pGV858 to yield pHD503.

A BamHI site was positioned immediately downstream of the Pssu promotor by inserting the HindIII-BamHI polylinker from pUC8 (Vierra and Messing, *Gene* 19, p. 259–266, 1982) into pKC7::Pssu. pKC7::Pssu was provided by the Lab of Genetics, State University, Gent, Belgium. It contains the EcoRI-HindIII fragment which includes the promotor for one of the pea genes encoding the small subunit (ssu) of Ribulose biphosfate carboxylase (RUDPcase) (Herrera-Estrella, *Nature* 310; 115–120, 1984) cloned in vector pKC7 (Rao and Rogers, *Gene* 7, 1979). 1 ug of pKC7::Pssu was digested with 1 U HindIII and 1 U BamHI. 1 ug pUC8 DNA was digested with 1 U HindIII and 1 U BamHI at 37° C. for 1 hr. 0.1 ug of each digested DNA were mixed and ligated with 0.01 unit of T4 DNA ligase in a final volume of 20 ul. The ligation mixture was transformed into competent *E. coli* K514 cells (Dagert and Erhlich, *Gene* 6 (1980) 23–18). Cells were plated on LB medium (Miller, *Experiments in Molecular Genetics* (1972), Cold Spring Harbor Laboratory, New York) supplemented with 100 ug/ml carbenicillin. In one of the resulting recombinant plasmids, pGV861, the HindIII-BamHI fragment containing the $Km^R$ gene of pKC7 was substituted by the 20 bp HindIII-BamHI polylinker of pUC8.

Five ug of pGV858 were digested with 5 units of BamHI for 1 h at 37° C. in a final volume of 20 ul, using the incubation buffer described by Maniatis et al., *Molecular Cloning*, Cold Spring Harbor Laboratory, 133–134, (1982). Subsequently, the terminal 5' phosphates were removed from the DNA by treatment with CIP using the conditions described by Maniatis et al., *Molecular Cloning*, Cold Spring Harbor Laboratory, 133–134 (1982). Two ug of pGV861 were digested with 2 units of BglII, BamHI and PvuI for 1 h at 37° C. in a final volume of 20 ul, using the incubation buffer described by Maniatis et al., *Molecular Cloning*, Cold Spring Harbor Laboratories 1982.

0.2 ug BamHI digested and CIP treated pGV858 was ligated to 0.05 ug BamHI-BglII-PvuI digested pGV861 with 0.01 units of T4 DNA ligase (Boehringer Mannheim) in a final volume of 20 ul. The ligation mixture was transformed into competent *E. coli* K514 cells (Colson et al., *Genetics* 52 (1965), 1043–1050) according to Dagert and Ehrlich, *Gene*, 6 (1980), 23–28. Cells are plated on LB medium (Miller, *Experiments in Molecular Genetics* (1972) Cold Spring Harbor Laboratory, New York) supplemented with carbenicillin (100 ug/ml). Carbenicillin resistant clones were screened for the presence of recombinant plasmids by restriction enzyme digestion of DNA prepared by the microscale technique described by Birnboim and Doly (*Nucl. Acids. Res.* 7 (1979), 1513–1523).

In one of the recombinant plasmids, pHD503, the BglII-BamHI fragment including the pea ssu promoter is inserted in the correct orientation in front of the 3' end of the octopine synthase gene. pHD503 contains a unique BamHI site, located between the Pssu promoter and the 3' end of the octopine synthase gene.

Step 3: Insertion of the BamHI-BglII Bt2 gene cassette into the BamHI site of pHD503 to yield the intermediate expression vector pHD208. Two ug of pHD160 DNA were completely digested with 2 units of BglII and 2 units of BamHI for 1 hour at 37° C. in a final volume of 20 ul. Five ug of pHD503 DNA were digested with 5 units of BamHI to completion under the same conditions, treated with CIP using the conditions described by Maniatis et al., *Molecular Cloning* (1982), (Cold Spring Harbor Laboratory, 133–134) to remove the terminal 5' phosphates from the DNA. 0.1 ug of BamHI-BglII digested pHD160 DNA was ligated to 0.2 ug of BamHI digested and CIP treated pHD503 DNA with 0.01 U T4 DNA ligase in a final volume of 20 ul.

The ligation mixture was transformed into competent *E. coli* K514 cells (Dagert and Erhlich, *Gene* 6 (1980) 23–18). Cells were plated on LB medium (Miller, *Experiments in Molecular Genetics* (1972), Cold Spring Harbor Laboratory, New York) supplemented with streptomycin (20 ug/ml) and spectinomycin (50 mg/ml). Streptomycin-spectinomycin resistant clones were screened for the presence of recombinant plasmids by restriction enzyme digestion of DNA prepared from these clones by the microscale technique described by Birnboim and Doly (*Nucl. Acids Res.* 7, 1513–1523, 1979). pHD208, a recombinant plasmid containing the Bt2 gene cassette in the correct orientation with respect to the Pssu promotor was isolated and used in further experiments.

EXAMPLE 3

This example describes the construction of pGSH151. The intermediate vector pGSH151 contains a chimeric Bt:NPTII fusion gene comprising: the promotor of transcript 2 of the TR-DNA of the octopine Ti plasmid (PTR2) (Velten et al., 1984, *Embo J.*, 3, 2723), the Bt:NPTII fusion gene cassette from pLBKm13 and the 3' untranslated region of the gene 7 of the T-DNA of the octopine Ti plasmid.

The fragments of the chimeric gene were assembled as described in this example. All the techniques were performed as described in Maniatis et al., *Molecular Cloning* (1982).

Step 1: Construction of pGSH50 (FIG. 41)

This plasmid contains the TR promotor PTR2 with a completely intact 5' untranslated region, followed by an ATG-initiation codon, followed by a unique BamHI site, and the 3' untranslated end of the transcript 7 gene.

pOP443 (Velten et al., 1984) contains a ClaI-HdIII fragment comprising the PTR2 and the PTR1 of the octopine Ti plasmid. To eliminate the BamHI site, pOP443 was totally digested with BamHI and SalI, the sticky ends treated with the Klenow fragment of *E. coli* polymerase I and self-ligated with T4 -ligase.

After transformation, ampicillin-resistant colonies were selected and their plasmids were screened for the absence of BamHI and SalI sites, yielding pOP4433SF.

In order to create a ClaI site in front of the 3' untranslated end of transcript 7 in pAP2034 (Velten et al., 1984), pAP2034 was totally digested with BamHI, treated with the Klenow fragment of *E. coli* polymerase I and ligated to kinated ClaI-linkers. The DNA was subsequently totally digested with ClaI and self-ligated with T4-ligase; among the $Amp^R$ transformants pAP2043C was selected.

From pOP443BSF, the ClaI-HindIII fragment containing the TR-promotors was cloned between the corresponding sites of pAP2034C giving rise to pGSH50.

Step 2: Construction of pGV1500 (FIG. 42)

pGV825 is described in Deblaere et al., *NAR*, 13, 4777 (1985); to reduce its size, pGV825 was digested with PvuII and self-ligated. The resulting plasmid pGV956 contains a unique BamHI and a unique BglII-site within the T-DNA. pJB63 is described in Botterman et al. (in press, *Gene*, (1986)). The BamHI-BglII fragment containing several unique restriction sites was cloned between the corresponding sites in pGV956 giving rise to pGV1500.

Step 3: Construction of pGSH150 (FIG. 43)

pGSH50 was digested with EcoRI, treated with the klenow fragment of *E. coli* polymerase I and digested with HindIII. The resulting fragment, containing the TR-promotors was cloned between the HpaI and the HindIII site of plasmid pGV1500.

Step 4: Construction of pGSH151 (FIG. 3)

The BamHI-BglII fragment of pLBKm13 containing the Bt2 gene was cloned in the BamHI site of pGSH150 creating an in-frame fusion of the Bt2 gene starting at the and codon to an ATG-initiation codon behind the PTR2.

9. Introduction of the intermediate expression vectors containing the toxin gene into Agrobacterium The introduction of intermediate expression vectors into acceptor Ti plasmids of Agrobacterium is accomplished in two steps: first, the intermediate expression vector is transformed into *E. coli* strain GJ23 carrying two helper plasmids: R64 drd 11 containing tra functions and p GJ28 containing the mob functions (Finnegan et al., *Mol. Gen. Genet.* 185 (1982), 344–351). Secondly, the *E. coli* strain carrying all three plasmids is conjugated to an Agrobacterium strain containing an acceptor Ti plasmid carrying a region of homology with the intermediate expression vector essentially as described by Van Haute et al., (*EMBO J*, 2 411–418, 1983). The recombinant Ti plasmid, resulting from a single crossover event, is isolated by selecting for the antibiotic resistance marker carried by the intermediate expression vector.

Figure 31:
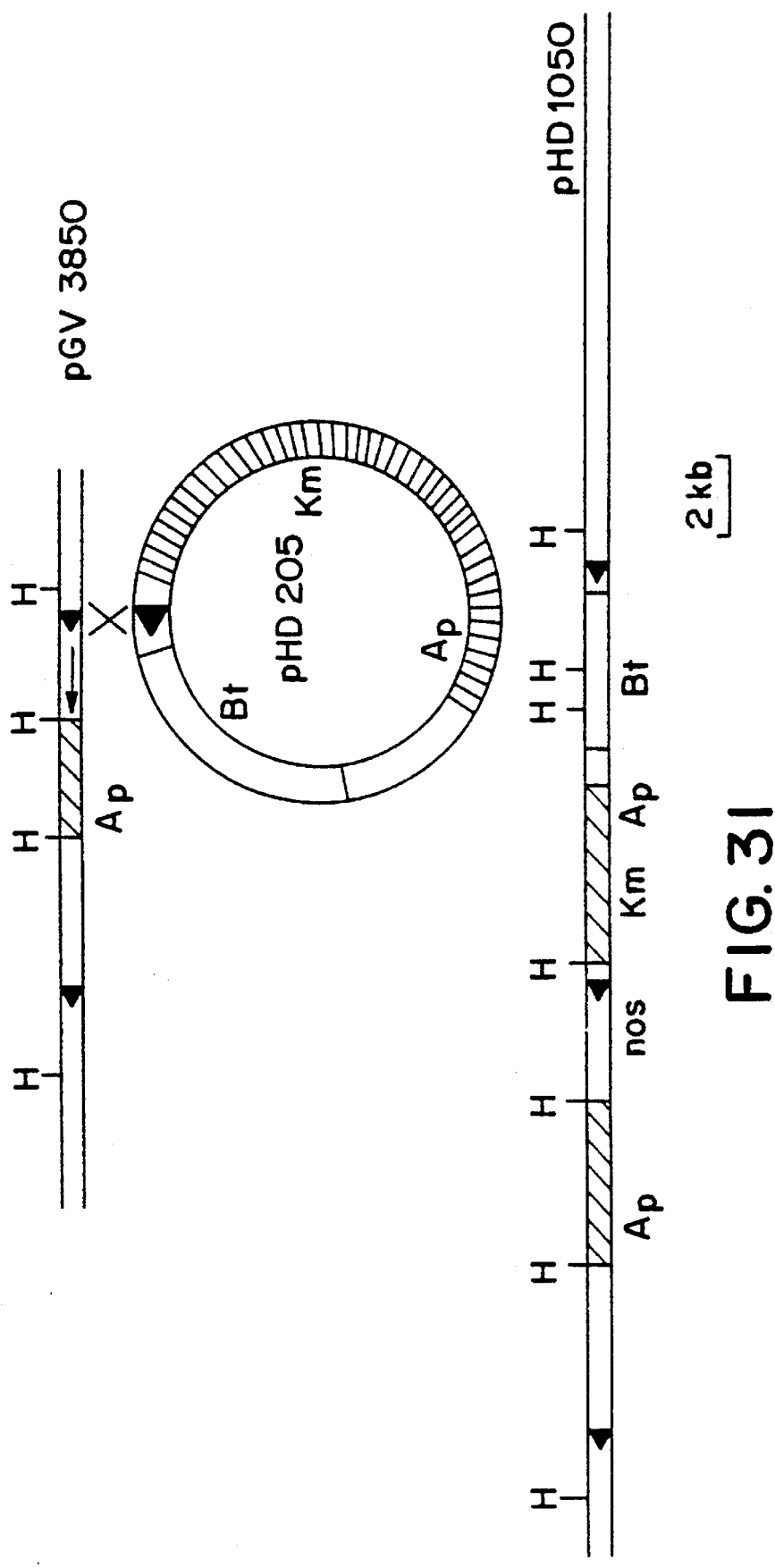

As an example, the cointegration of pHD205 with pGV3850 and of pHD208 with pGV2260 is described. Intermediate vectors and receptor Ti plasmids used are listed in Table 7 and represented in FIGS. 31–33.

EXAMPLE 1:

The intermediate expression vector pHD205 was inserted into the acceptor T1 plasmid pGV3850 to yield the hybrid Ti plasmid pHD1050. As diagrammed in FIG. 31, pHD1050 contains the chimeric Bt2 gene under the control of the Pnos promotor, as well as the nopaline synthase gene positioned between T-DNA border fragments.

The plasmid pHD205 was introduced into competent *E. coli* GJ23 cells by transformation according to Dagert and Ehrlich (*Gene* 6 (1981, 23–28). To select for *E. coli* GJ23 cells transformed with pHD205, the cells were plated on LB medium (Miller, *Experiments in Molecular Genetics* (1972), Cold Spring Harbor Laboratory, New York ) supplemented with carbenicillin (100 ug/ml ).

Liquid LB medium was innoculated with one of the pHD205 transformed *E. coli* GJ23 colonies and cultured overnight (about 18 hours ). 0.1 ml of this culture is conjugated with 0.1 ml of an overnight culture of the C58C1 Rif$^R$ (also called GV3101, Van Larebeke et al., *Nature* 252, 169–170, 1974) containing (pGV3850) Zambryski et al (*EMBO J.* 2, 2143–2156, 1983) and cultured overnight at 28° C. on solid LB medium (Miller, *Experiments in Molecular Genetics* (1972), Cold Spring Harbor Laboratory, New York).

Agrobacterium strains containing hybrid Ti plasmids, resulting from a single cross-over event, were isolated by selecting for the kanamycin-neomycin marker carried by the pHD205 plasmid on minimal A medium (Miller, *Experiments in Molecular Genetics* (1972), Cold Spring Harbor Laboratory, New York) supplemented with neomycin (400 ug/ml). After purification of transconjugants on LB medium (Miller, *Experiments in Molecular Genetics* (1972), Cold Spring Harbor Laboratory, New York) supplemented with rifampicin (100 ug/ml) and kanamycin (25 ug/ml). The physical structure of the T region of one of the transconjugants, pHD1050, was determined according to the method described by Dhaese et al., (*Nucl. Acids Res.* 7 (1979), 1837–1849) by hybridization of P$^{32}$ labelled pHD205 against HindIII digested to total DNA of C58C1 Rif$^R$ pHD1050. The structure of the T region of pHD1050 is diagrammed in FIG. 31.

EXAMPLE 2

The intermediate expression vector pHD208 was inserted into the acceptor Ti plasmid pGV2260 to yield the hybrid Ti plasmid pHD1076. As diagrammed in FIG. 32 pHD1076 contains the chimeric Bt2 gene under the control of the Pssu promotor as well as a chimeric gene containing the neomycin phosphotransferase gene under the control of the Pnos promotor, positioned between T-DNA border fragments. The Ti plasmid pGV2260 is described in European Patent Application Number 83112985.3 (Publication Number 0116718). The plasmid pHD208 was introduced into competent *E. Coli* GJ23 cells by transformation according to Dagert and Ehrlich (*Gene* 6 (1980), 23–28). To select for *E. coli* GJ23 cells transformed with pHD208, the transformation mixture was plated on LB medium (Miller, *Experiments in Molecular Genetics* (1972), Cold spring Harbor Laboratory, New York) supplemented with carbenicillin (100 ug/ml ).

Liquid LB medium was inoculated by one of the transformed *E. coli* colonies and cultured overnight. 0.1 ml of the overnight culture of the *E. coli* strain carrying all 3 plasmids was conjugated overnight with an overnight culture of the C58C1 Rif$^R$ (pGV2260) at 28° C. on LB medium (Miller, *Experiments in Molecular Genetics* (19.72), Cold Spring Harbor Laboratory, N.Y.). Agrobacterium strains containing hybrid Ti plasmid, resulting from a single cross-over event between pGV2260 and pHD208 were isolated by selecting for the streptomycin-spectinomycin marker carried by the pHD208 plasmid on minimal A medium (Miller, *Experiments in Molecular Genetics* (1972), Cold Spring Harbor Laboratory, N.Y.) supplemented with spectinomycin (300 ug/ml) and streptomycin (300 ug/ml) and streptomycin (1 ug/ml ).

Figure 32:
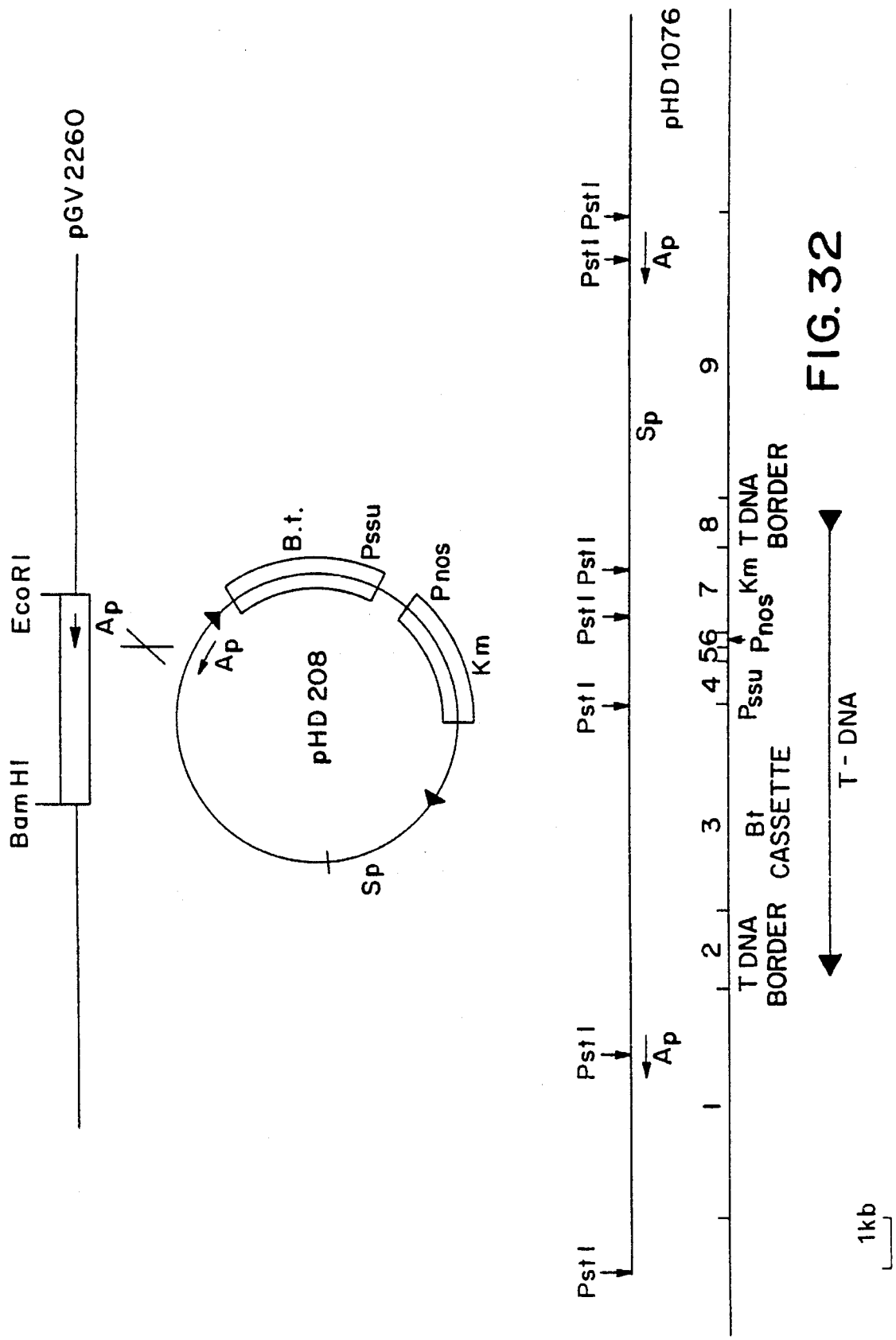
Figure 33A:
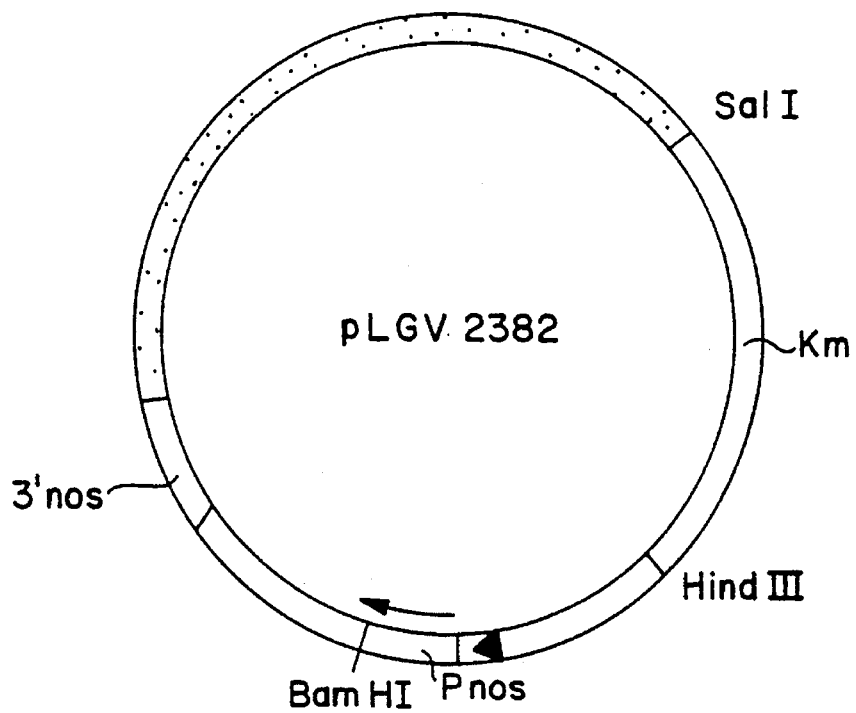
Figure 33B:
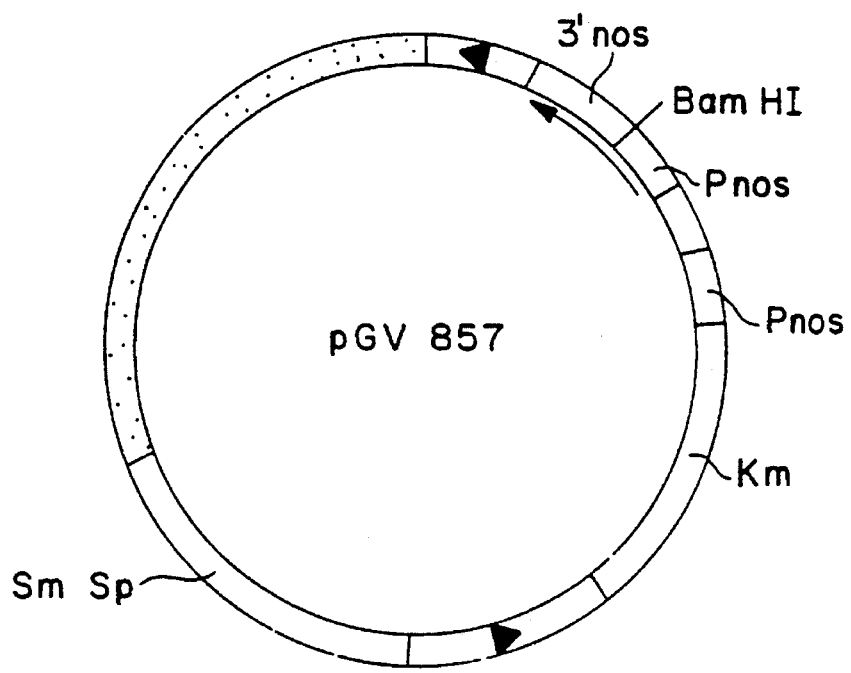
Figure 33C:
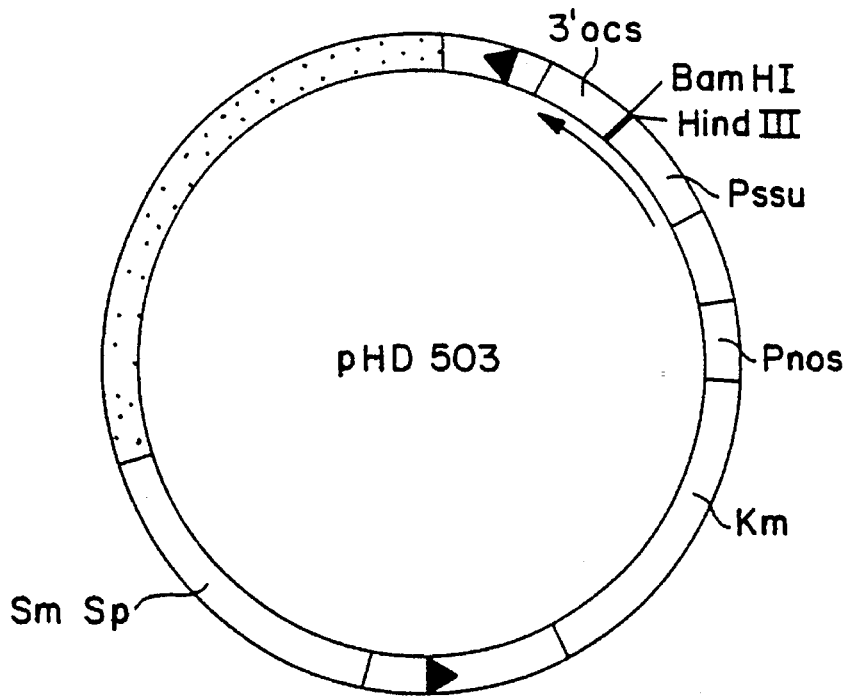
Figure 33D:
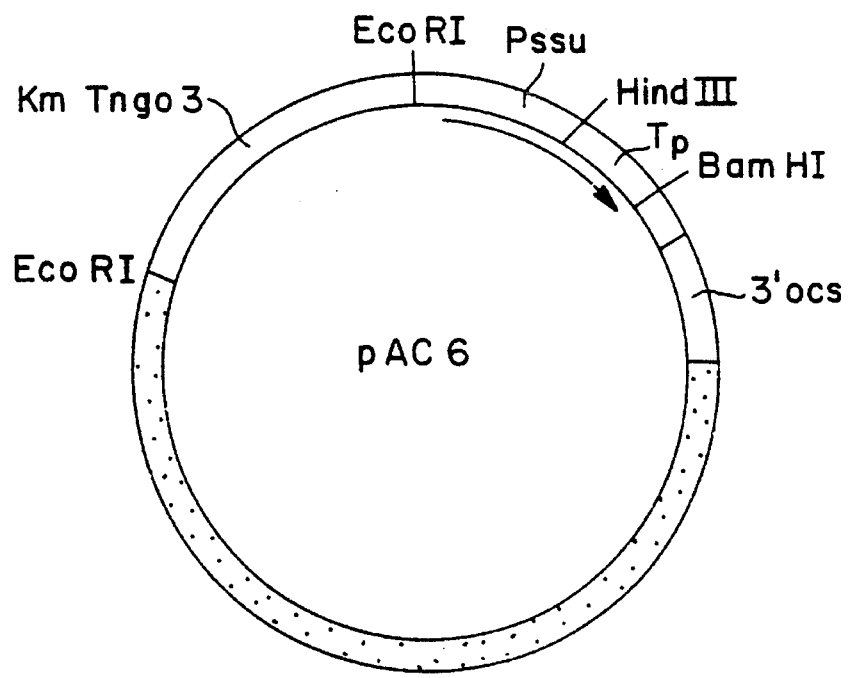
Figure 33E:
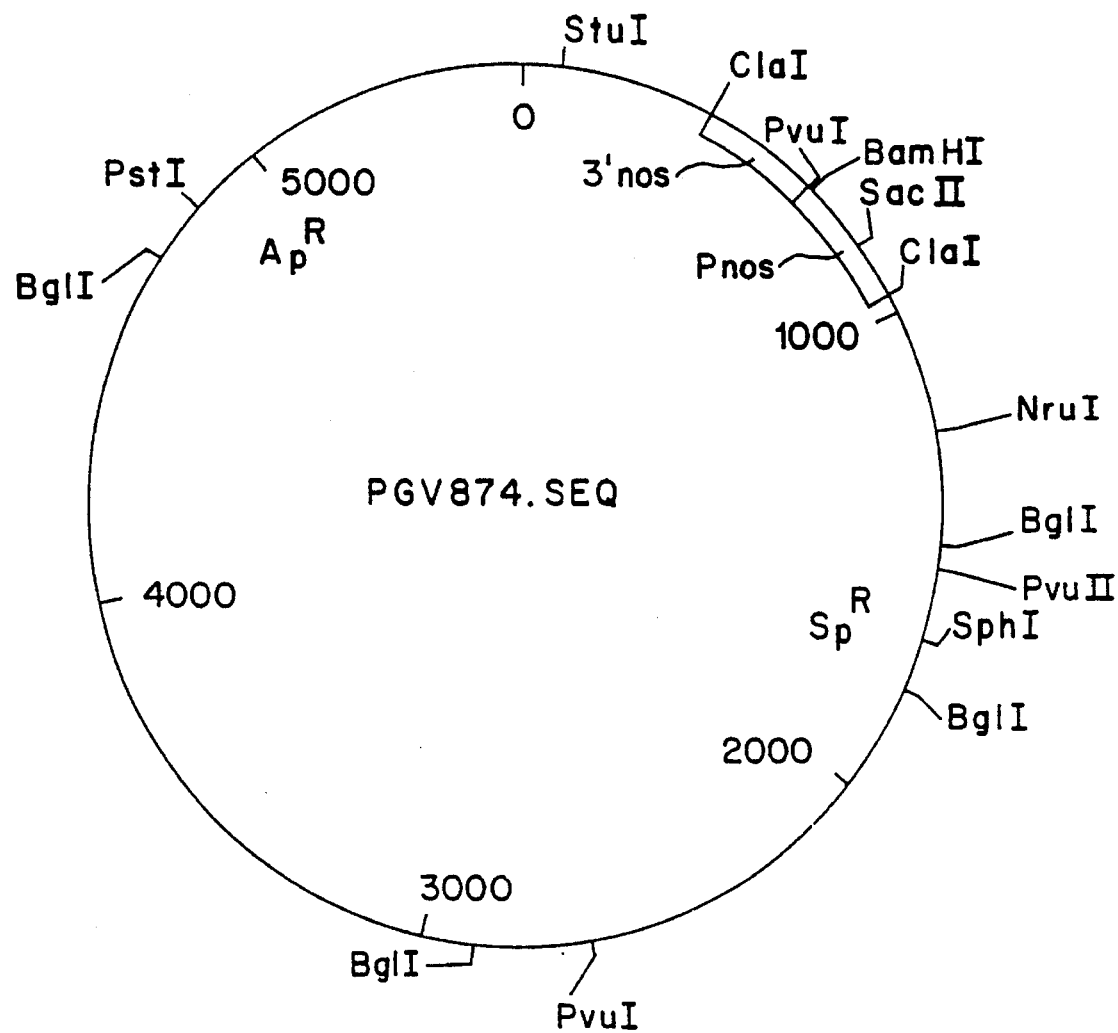
Figure 33F:
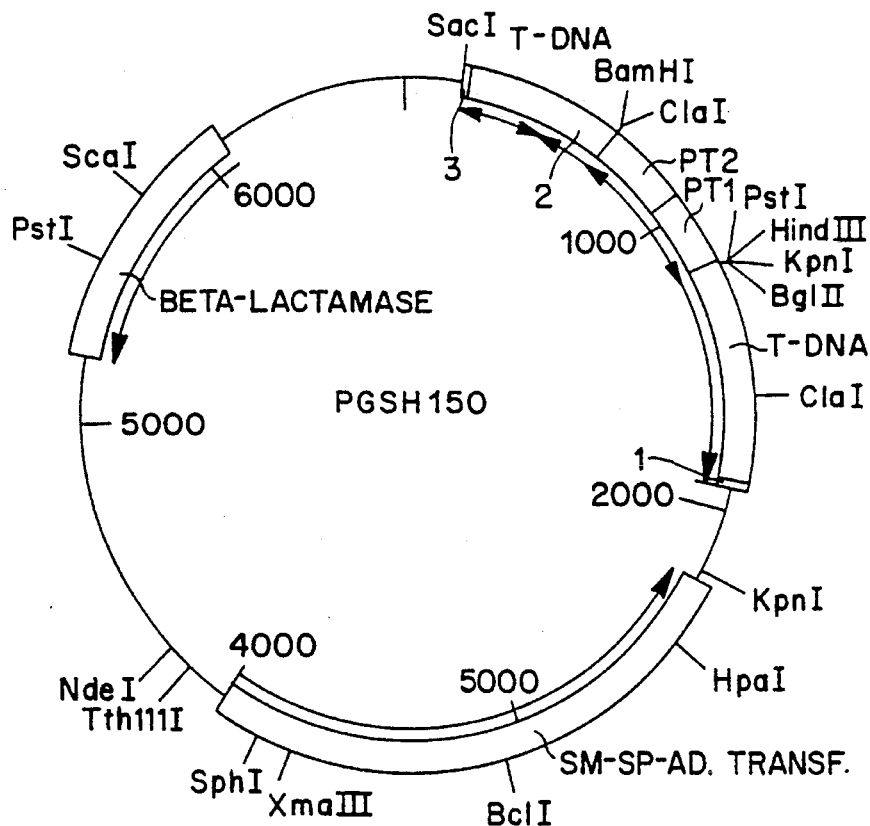
Figure 33G:
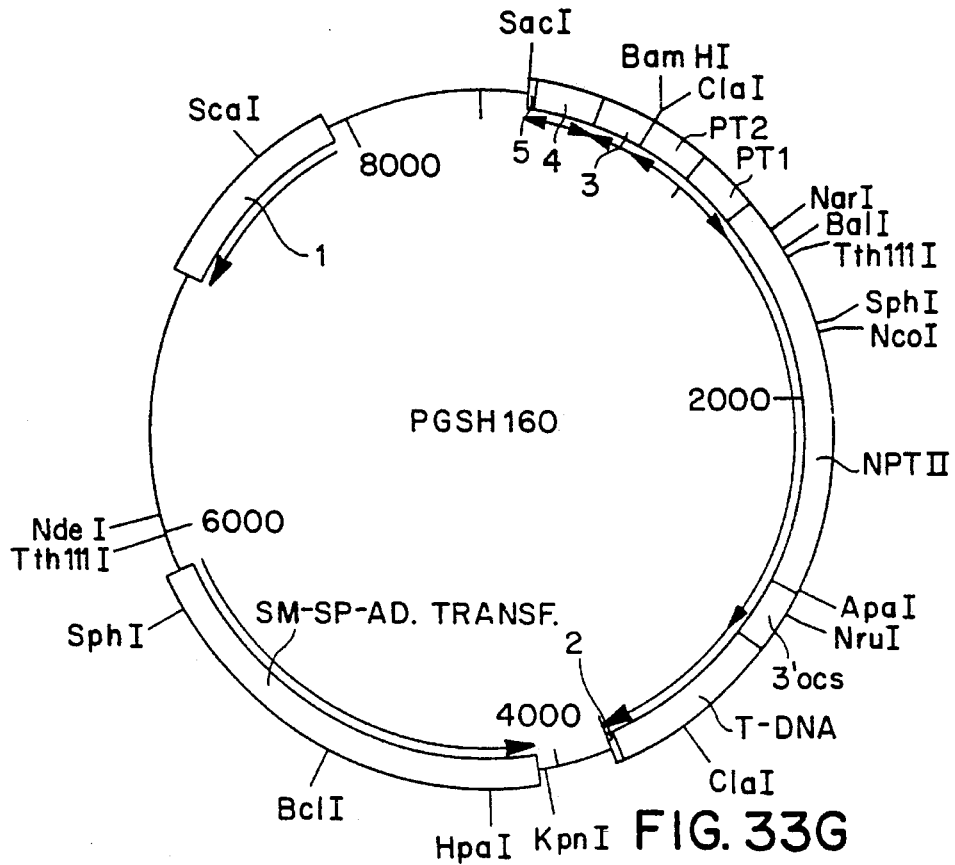
Figure 33H:
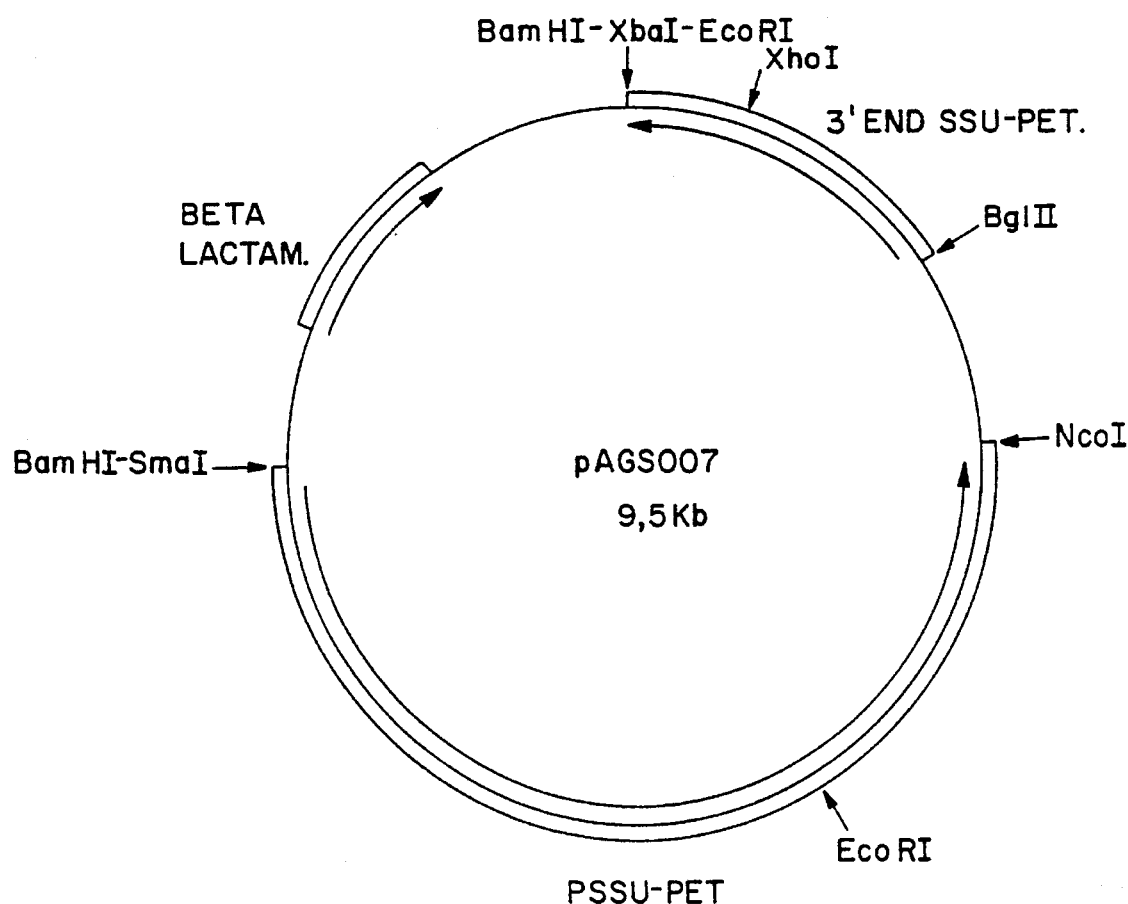
Figure 33I:
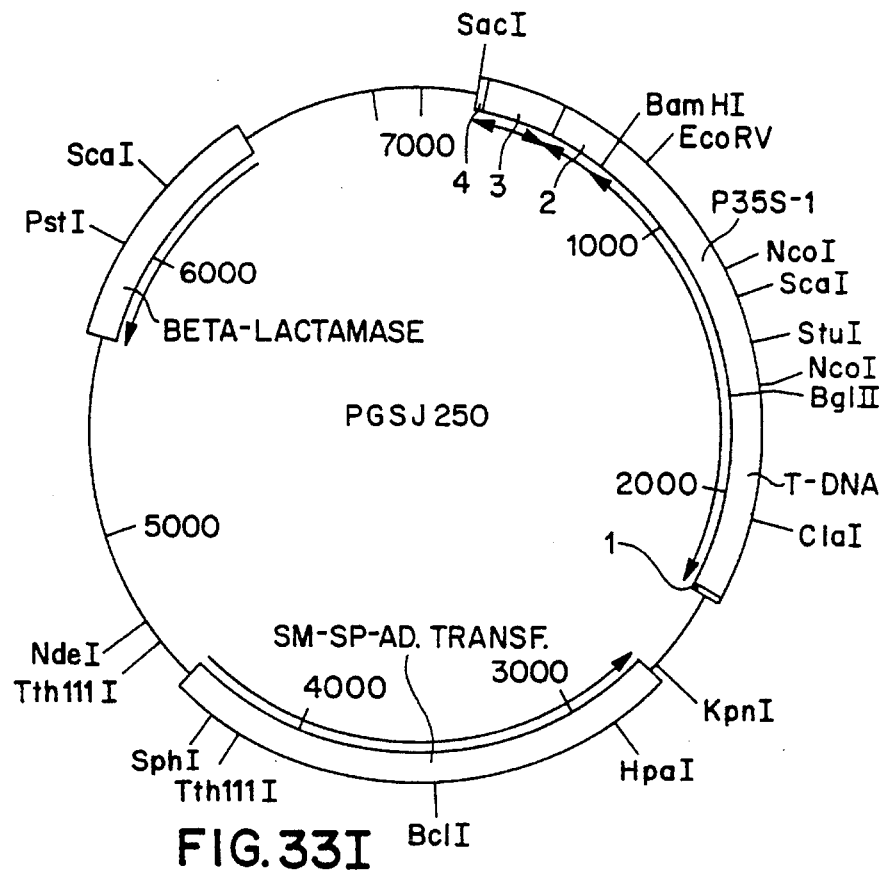
Figure 33J:
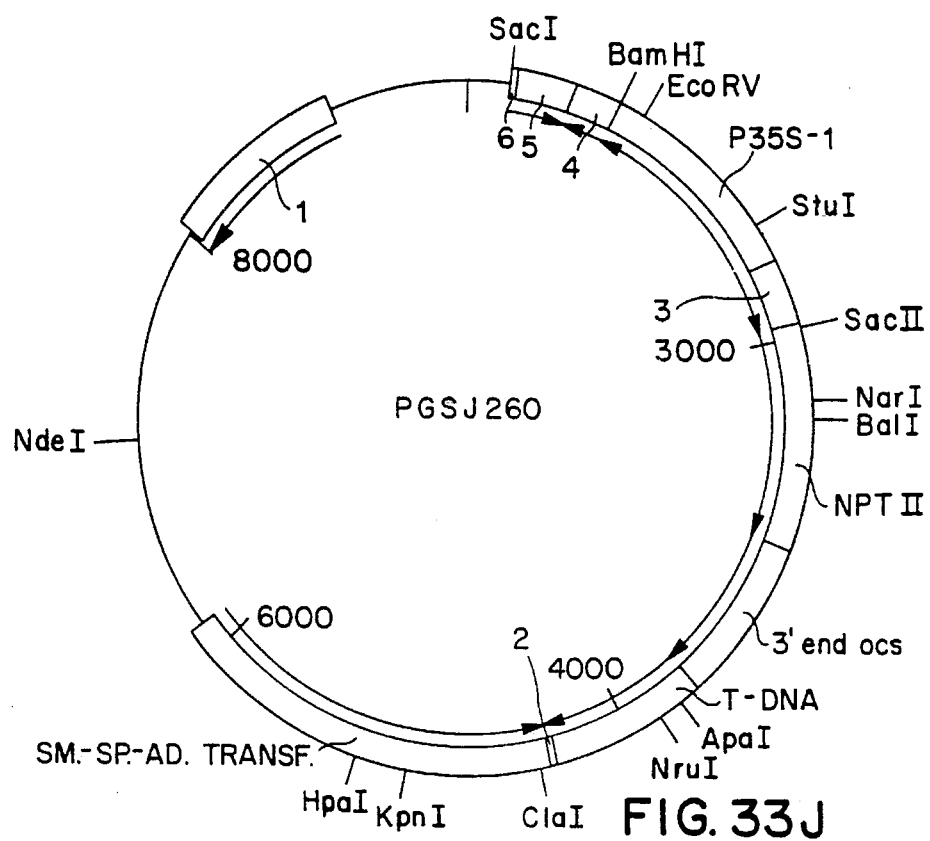
Figure 34:
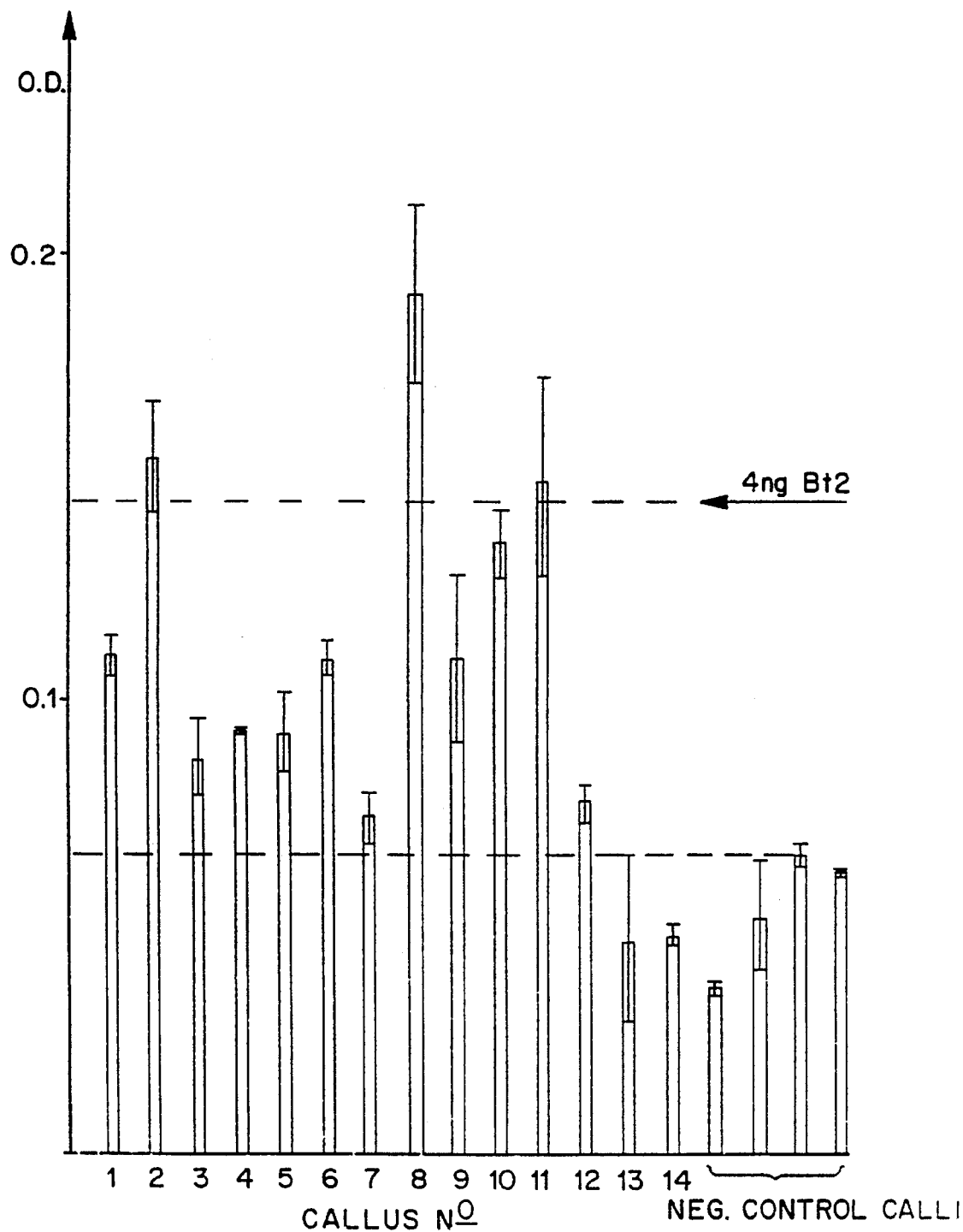
Figure 35:
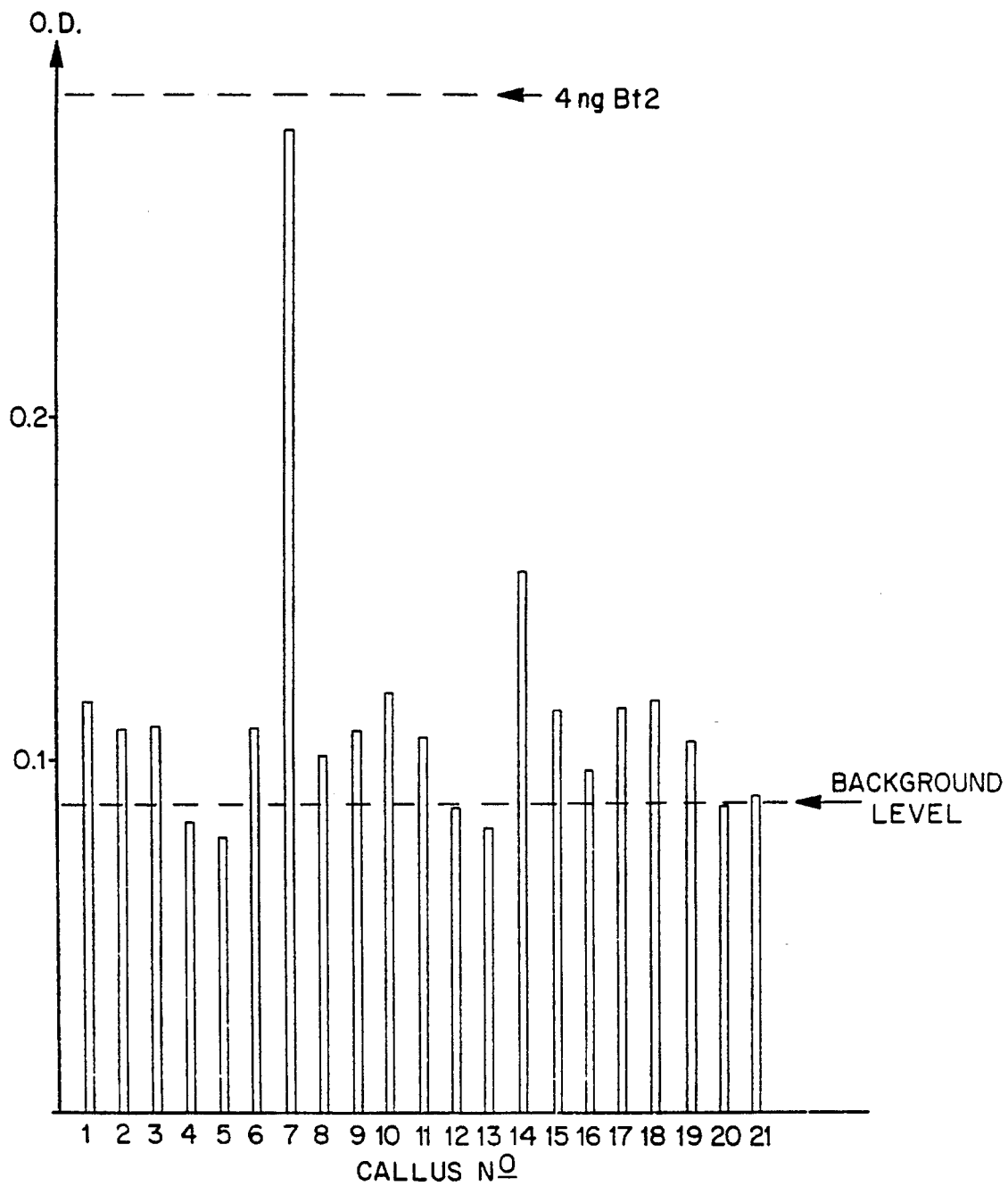
Figure 36:
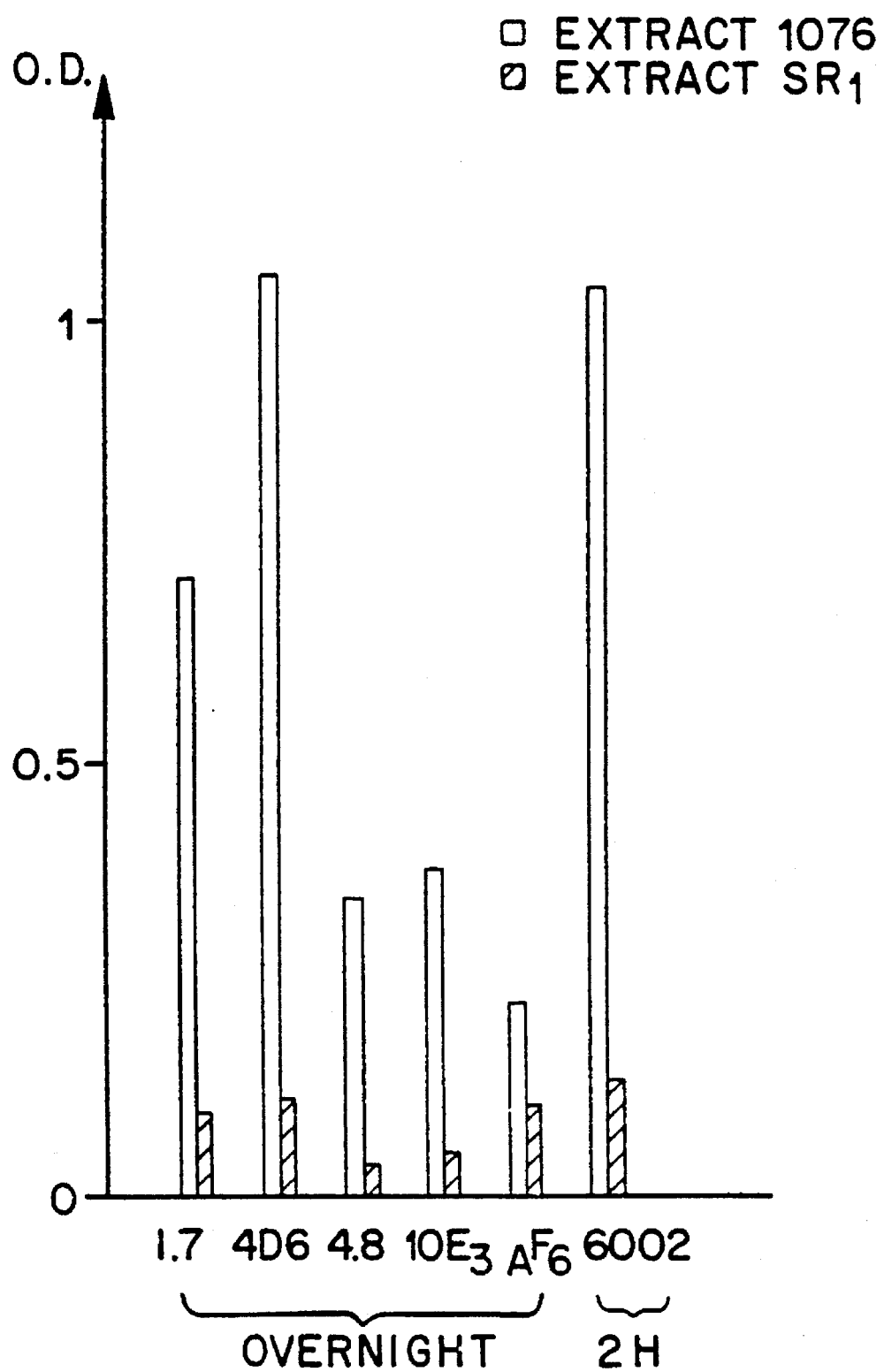

Transconjugants were purified on LB medium (Miller, *Experiments in Molecular Genetics* (1972), Cold Spring Harbor Laboratory, N.Y.) supplemented with rifampicin (100 ug/ml ), spectinomycin (100 ug/ml ) and streptomycin (300 ug/ml). The physical structure of one of the transconjugants, pHD1076, was determined by hybridizing P$^{32}$ labelled pHD208 against PstI digested total DNA of C58C1 Rif$^R$ pHD1076 according to the method described by Dhaese et al., (*Nucl. Acids Res.* 7 (1979), 1837–1849). The physical structure of pHD1076 is shown in FIG. 32.

EXAMPLE 3

The intermediate expression vector pGSH151 was inserted into the acceptor Ti plasmid pGV2260 to yield the hybrid Ti plasmid pGS1151.

The method used was a triparental cross according to Dittag et al. (1980), *PNAS*, 77, 7347–7351.

Liquid LB medium was inoculated with one of the pGSH151 transformed *E coli* K514 colonies and cultured overnight at 37° C. 0.1 ml of this culture was plated together with 0.1 ml of overnight cultures of HB101 (pRK2013) Figurski & Helinski (1979), *PNAS*, 76, 1648–1652 and 0.1 ml of C58C1 Rif$^R$ (Van Larebeke et al., *Nature,* 252, 169–170) on LB plates and grown overnight at 28° C.

The cells were collected from the LB plates and dilutions were plated on minimal A. medium (Miller, *Experiments in Molecular Genetics,* 1972, Cold Spring Harbor Laboratory, N.Y.) supplemented with spectinomycin (300 ug/ml) and streptomycin (1 mg/ml). Transconjugants were purified on LB medium containing rifampicin (100 ug/ml ), spectinomycin (100 ug/ml ) and streptomycin (300 ug/ml). The physical structure of one of the transconjugants, pGS1151, was determined by hybridizing P$^{32}$ labeled pGSH151 against PstI-BamHI digested total DNA of C58C1 Rif$^R$ (pGS1151) according to Dhaese et al., *N.A.R.,* 7 (1979) 1837–1849.

10. Isolation of plant cells and plants containing the chimeric toxin gene inserted in their genome Procedures:

Two different protocols are described here for the transformation of tobacco plant cells with transformation vectors such as those described in Section 9 and for the generation of callus tissue and/or differentiated plants from these transformed cells.

Procedure 1: Cocultivation of protoplasts

This procedure describes the cocultivation of tobacco protoplasts with Agrobacterium C58C1 Rif$^R$ and the isolation of transformed tobacco cell lines by screening for the presence of a scorable marker such as nopaline or for the expression of a selectable marker such as kanamycin resistance and the regeneration of whole plants from transformed callus lines.

Step 1: Preparation of Protoplasts a) Grow 10–12 cm high *Nocotiana tabacum* cv. Petit Havana SR-1 aseptic plants for 4 weeks in vitro in medium containing half strength of the mineral components as well as half strength of the vitamins and sucrose of the Murashige and Skoog medium. (Murashige and Skoog, *Physiol. Plant*, 15, 473–497, (1962)).

b) Incubate leaf segments of 3 well developed young leaves with 20 ml of 1.4% cellulase Onozuka R-10 and 0.4% macerozyme Onozuka (both from Yakult Pharmaceutical Industry, Co., Ltd., Japan) in the following solution:

KCl 2.5 g/l $MgSO_4 7H_2O$ 1 g/l $KH_2PO_4$ 0.136 g/l

Sorbitol 73 g/l

Polyvinyl pyrolidone-10 0.3 g/l c) Incubate overnight at 24° C. in the dark;

d) Filter through a nylon filter with a mesh size of 50 micrometer;

e) Centrifuge in 15 ml tubes at 80 g for 10 minutes, remove the supernatant and resuspend the pellet in 20 ml of the same solution but without enzymes;

f) Centrifuge for 10 minutes at 80 g to remove excess of enzymes and remove the supernatant;

g) Resuspend pellet in 20 ml of ½ strength Murashige and Skoog medium supplemented with 0.225% $CaCl_2 \cdot 2 H_2O$ and 0.4M mannitol pH 5.6;

h) Centrifuge for 10 minutes at 80 g, remove supernatant;

i) Resuspend the pellets in 20 ml of medium 55 (see below);

j) Count protoplasts and dilute to a density of $10^5$ pp/ml. Incubate in 5 cm petri dishes (2.5 ml per petri dish) in the dark about four days.

Step 2: Cocultivations with Agrobacterium strain C58C1 Rif$^R$ containing the hybrid Ti plasmid (section 9).

a) A culture of Agrobacterium C58C1 Rif$^R$ was grown until saturation in LB medium, centrifuged for 1 minute in an Eppendorf centrifuge, supernatant removed and the cells resuspended in an equal volume of 0.01M $MgCl_2$. When about 30% of the protoplasts have started their first cell division, 50 ul of the bacterial suspension was added to 2.5 ml of the protoplast suspension (this represents about 100–500 bacteria per protoplast).

b) Incubate 48 hrs. in the dark.

c) Transfer the cell suspension to a centrifuge tube, wash the petri dish with the same volume of medium 55 supplemented with Claforan 500 mg/l, and add it to the centrifuge tube. Centrifuge for 10 minutes at 80 g, remove the supernatant and resuspend the pellet in the same volume of medium 55 supplemented with Claforan 500 mg/l.

d) Transfer to 5 cm petri dishes (2.5 ml/dish) at this moment the cell density is approximately $10^4$ cells/ml.

Incubate under 400 lux, 16 hours a day, at 23° C. for 1–2 weeks until small aggregates of 4–8 cells are formed.

e) Add an equal volume of medium 56 (see below).

f) After 3–4 weeks colonies are plated on medium 56 solidified with 0.7% agarose, with reduced mannitol concentration (0.2M instead of 0.44M), and supplemented with Claforan 250 mg/l. At this stage the colonies must contain more than 50 cells/colony. In case Km$^R$ is used as a selectable marker 50 ug/ml of Km is added to the medium as a selection agent.

g) Incubate 2–3 weeks at 800 lux, 16 hours a day, 23° C.

h) Transfer isolated calli to the same medium. Shoot induction occurs. At this stage, callus tissue is taken to screen for the presence of nopaline using the procedure as described by Aerts et al, *Plant Sci. Lett.* 17, 43–50 (1979), in case nopaline is used as scorable marker.

Step 3: Regeneration of transformed tobacco plants.

a) Grow nopaline positive or kanamycin resistant calli for 4 weeks.

b) Transfer the differentiating calli on hormone free Murashige and Skoog.

c) Grow for 3 weeks.

d) Separate shoots and transfer to the same medium, grow for 2–3 weeks till plants form roots.

e) At this stage small plants are transferred to grow in 250 ml containers containing 50 ml of half strength hormone free Murashige and Skoog medium.

f) Grow for 2–3 weeks. Remove a lower leaf for nopaline detection or screening of kanamycin resistance activity and for immunological detection of the toxin.

The leaf disc (also at times referred to herein as leaf segments) assay for testing Km resistance of a plant is performed as follows. Small discs are cut out from "in vitro" grown plants and transferred to petri dishes containing callus inducing medium (M&S macro and micronutrients and vitamins 3% sucrose, 500 mg/l Claforan, 1 mg/l NAA and 0.1 mg/l BAP) with various kanamycin sulphate concentrations (50–500 mg/l).

After three weeks incubation in a plant tissue culture room, callus growth on the leaf discs is monitored. The Km resistance level of the plant is determined as the highest concentration of Km on which the leaf discs still give rise to callus tissue.

Screening for the presence of nopaline (nopaline assay) is performed according to the procedures described in Aerts M., Jacobs M., Hernalsteens J. P., Van Montagu M. and Schell J. (1979) *Plant Sci. Letters* 17, 43–50.

Composition of medium 55:

Half strength of the Macronutrients of the Murashige and Skoog salts

- 1 ml/l of 1000 x Micronutrients Heller modified

- 1 ml/l of 1000 x vitamins Morel & Wetmore

- 100 ml/l Inositol

- 10 ml/l of a stock solution containing $FeSO_4$ 5.57 g/l and $Na_2EDTA$ 7.45 g/l

- Benzylaminopurine 1 ml/l

Naphthalene acetic acid 3 mg/l

- Mannitol 80 g/l (0.44M)

Sucrose 20 g/l

| 1000 x Vitamins Morel and Wetmore for 100 ml | Micronutrients Heller modified (500 ml) |
|---|---|
| Ca pantotenate 100 mg; | 500 mg $ZnSO_4.7H_2O$ |
| Biotine 1 mg; | 50 mg $H_3BO_3$; |
| Niacine 100 mg; | 50 mg $MnSO_4.4H_2O$ |
| Pyridoxine 100 mg; | 50 mg $CuSO_4.5H_2O$ |
| Thiamine 100 mg; | 15 mg $AlCl_3$; |
|  | 15 mg $NiCl_2$ |

Composition of Medium 56:

Medium 56 is the same as medium 55 except for the addition of naphthalene acetic acid at 0.2 mg/l and glutamine 1 mM.

Procedure 2: Infection of leaf segments with Agrobacterium strain C5.81 $Rif^R$ containing a hybrid Ti plasmid This procedure describes the infection of leaf segments with C58C1 $Rif^R$ and the isolation of transformed cell lines by selection on kanamycin containing medium.

Sterile *Nicotiana tabacum* cv. Petite Havana SR-1 plants were grown in vitro in plant nutrient agar containing half strength of the complete Murashige & Skoog (M&S) salt mixture complemented with half strength of the organic nutrients and sucrose of complete M&S medium. Twenty SR-1 leaf segments of approximately 1 $cm^2$ were floated on 5 ml liquid M&S medium (without hormones) in a 9 cm petri dish containing 0.1 ml of a washed bacterial suspension of C58C1 $Rif^R$. Incubation occurred on a shaker at 60 rmp in the dark for 48 h at 25° C. Subsequently, leaf segments were rinsed twice with M&S medium (without hormones) containing 500 mg/l Claforan, and then placed on a medium allowing both callus and shoot formation. This medium contains M&S macro- and micronutrients and vitamins, 3% sucrose, 500 mg/l Claforan, 500 mg/l kanamycinsulfate, 0.1 mg/l NAA and 1.0 mg/l BAP. The final pH of the medium is 5.8. Six leaf discs are placed per 9 cm petri dish containing about 30 ml medium and are incubated for 3 weeks at 23° C. (approximately 1° C.) under a 16 hours 2000 lux/day illumination cycle. After 3 weeks discs bearing callus and small shoots are transferred to the same medium for another 3 weeks. At that time shoots over 1 cm in length are transferred to M&S medium without hormones and without Km containing 500 mg/l Claforan. Afterwards, shoots are transferred about every three weeks on half strength M&S without hormones and the Claforan concentration is gradually decreased (1st transfer: 250 ug/ml, 2nd: 125 ug/ml, 3rd: 0 ug/ml Claforan). During the first transfer to ½ strength M&S, leaf material is removed to test kanamycin resistance. Leaf discs are transferred to petri dishes containing callus inducing medium (M&S macro and micronutrients and vitamins, 3% sucrose, 500 mg/l Claforan, 1 mg/l NAA and 0.1 mg/l BAP) containing different kanamycin sulphate concentrations (50–500 mg/l). Plants are retested for Km resistance on medium without Claforan when the material has been proved to be free of Agrobacteria.

EXAMPLE 1

Callus and Plants Transformed with pHD1050

T-DNA: Pnos-Bt2 (Bt2 gene fused to Pnos).

Marker: nopaline synthase as marker gene with additional border sequence between the Bt gene and the nos gene.

Transformation method: protoplast infection

Approximately 250 calli have been screened for nopaline and 19% were $Nos^+$, which represents a high efficiency of transformation.

In total 180 different callus lines, both $nos^+$ and $nos^-$, generated from these transformation experiments have been screened for the presence of Bt2 using the sensitive ELISA described above (Section 5.1). Most of the clones were tested early after transformation during the initial phase of propagation (when only 5 mm diameter) and some were retested after a period of subculturing (3 months later). On the basis of the immunoassay results, a number (25) of callus lines were selected for plant regeneration. From each callus several plants were regenerated, and each of them received a distinct number (total of 149 plants).

The 149 plants were propagated "in vitro" and subsequently 138 were transferred to the greenhouses. All these plants appeared fully normal, flowered and set seeds. Some plants were tested for insect toxicity assays. From callus lines 161, 165 and 206, total DNA was prepared and the integration of the Bt2 gene was analyzed in Southern blotting. Integration of at least 1 copy of the Bt2 gene/ genome was detected.

EXAMPLE 2

Callus and Plants Transformed with pHD1060

T-DNA: Pnos-Bt2

Selectable marker: kanamycin resistance (Km)

Transformation method: protoplast infection (procedure 1) and leaf disc infection (procedure 2).

Following procedure 1, kanamycin resistant protoplast clones were obtained and grown as calli. Calli were selected at random and were put in generation medium for shoot formation. Shoots developed and isolated from these kanamycin resistant clones were propagated as plants "in vitro." Thereafter some of these plants were transferred to the greenhouse.

Following procedure 2, kanamycin resistant callus tissue and shoots were induced. Uncloned callus tissue was kept in continuous culture "in vitro." Kanamycin resistant shoots were isolated and were propagated "in vitro" as small plants (2–5 cm). These small plants were retested for kanamycin resistance using leaf disc assay (50 ug/ml Km). The shoots that were clearly resistant at this concentration of kanamycin were selected for further "in vitro" propagation. Plants were eventually transferred to the greenhouse. Using southern blotting analysis the presence of both the NPTII genes and the Bt2 genes was confirmed in the leaf tissue of these plants.

EXAMPLE 3

Calli and plants transformed with pHD1076

T-DNA: Pssu-Bt2 (Bt2 gene fused to Pssu)

Selectable marker: kanamycin resistance

Transformation method: leaf disc infection.

Using conditions described in procedure 2 either callus transformation of shoot induction was performed on the infected leaf discs. Using the callus induction protocol, a number of calli were obtained by partial purification and maintained as separated semi clones. On the basis of positive immunoassay results 5 of these lines were selected for further propogation (1076-4, 10, 11, 12, 13). From the shoot induction protocol used in the initial stage of leaf disc infection a number (72) of kenamycin resistant plants were regenerated (selection on 50 ug/ml Km).

When retested by leaf disc assay 65% of these proved to be truly resistant to 50 ug/ml Km. From leaves of some "in vitro" propagated plants, callus tissue was generated and propagated "in vitro" for further testing. Example 4

Calli end plants transformed with pHD1080

T-DNA: Pssu - Transit peptide (Tp) Bt2

Selectable marker: kanamycin resistance/(Nos)

Transformation method: leaf disc infection.

Kanamycin resistant calli and shoot were induced following procedure 2. Approximately 20 kanamycin resistant callus lines were analyzed for nopaline expression and all were found positive. 86 kanamycin resistant shoots were selected, propagated "in vitro" and retested for kenamycin resistance (using the leaf disc assay) and for nopaline expression.

52 plants (60%) were both kanamycin resistant and nopaline positive, and these were further propagated "in vitro." Approximately 10% of the plants expressed only one of the two markers.

EXAMPLE 5

Plants Transformed with pGS1110

T-DNA: Pnos-Bt:NPTII (fusion)

Selectable marker: kanamycin resistance/Nos

Tranformation method: leaf disc infection.

Leaf discs from "in vitro" maintained SR-1 plants were incubated during 48 hours with a suspension of *Agrobacterium tumefaciens*, C58C1 Rif$^R$ pGS1110 (procedure 2). Similar dilutions of different control strains containing chimeric genes encoding intact NPTII were included. After two weeks active shoot formation on M&S medium containing 50 mg/l kanamycin was observed both with the controls and pGS1110. However, after transfer to fresh selective M&S medium, a difference became apparent between the controls and pGS1110. Some shoots on discs inoculated with the latter strain turned yellow and were growing slowly. The best growing and green shoots were transferred to medium without kanamycin. Part of them could be rescued in this way and started growing normally after the second transfer on kanamycin free medium.

About 70 shoots were rescued from the pGS1100 transformation experiment. Screening among 35 of these shoots showed that 28 of these (85%) were real transformants since they produced nopaline. This important observation suggests that, although the shoots have not been maintained for a long period on. Km containing medium. phenotypical selection for the expression of the fusion protein had occurred.

The obtained shoots were propagated "in vitro" as small plants on nonselective medium. A number of these plants were tested for Km$^R$ resistance using the leaf disc assay. Most of them expressed a certain level of Km$^R$ since they formed callus on Km containing medium. Variable resistance levels were recorded in the range of 50–500 mg Km/liter. However, most of the plants were only resistant to low levels of Km. Two out of a total of 61 plants showed resistance to 200 ug/ml Km and partial resistance to 500 ug/ml Km (very weak callus growth).

For a number of plants, copies were transferred into vermiculite pots. When reaching 10–15 cm height a first insect toxicity test was performed on leaves of these plants (see section 13).

EXAMPLE 6

Plants Transformed with pGS1161

T-DNA: PTR2-Bt2

Selectable marker: kanamycin resistance

Transformation method: leaf disc infection.

Leaf discs from "in vitro" maintained SR-1 plants were incubated during 48 h with a suspension of *Agrobacterium tumefaciens* C58C1 Rif$^R$ pGS1161. As a control a *A. tumefaciens* C58C1 Rif$^R$ pGS1160 containing NPTII under control of pTR was included. After two weeks shoot formation on medium containing 50 mg/l kanamycin sulphate was observed. After three weeks discs were transferred to fresh selective medium and after another three weeks the best growing shoots were transferred to kanamycin free medium. The level of Km$^R$ is determined systematically using the leaf disc assay. Most plants showed high levels of resistance (callus formation on 500 ug/ml Km).

EXAMPLE 7

Plants Transformed with pGS1151

T-DNA: PTR2-Bt: NPT2 (fusion)

Selectable marker: kanamycin resistance

Transformation method: leaf disc infection.

Leaf discs from "in vitro" cultivated SR-1 plants were incubated during 48 hrs. with a suspension of *Agrobacterium tumefaciens* C58C1 Rif$^R$ pGS1151. As a control *A. tumefaciens* C58C1 Rif$^R$ pGS1160 containing NPTII under control of pTR was included.

Shoot formation and development of shoots on medium containing 50 mg/l kanamycin sulphate was slightly slower on discs treated with pGS1151 than in control discs (pGS1160). After three weeks discs were transferred to fresh selective medium and after another four weeks the best growing shoots were transferred to kanamycin free medium. The shoots were propagated "in vitro" as plants and the level of Km$^R$ of these plants was determined systematically using the leaf disc assay. A number of plants were completely resistant to 500 ug/ml Km (normal callus growth). This data indicates that the PTR promotor directs higher levels of fusion protein expression in tobacco leaves than the Pnos promotor (pGS1100, Example 5 in this section).

Copies of the plants were transferred to pots and grown in the greenhouse. On a selected set of plants, those showing high Km resistance, detailed insect toxicity tests were performed (see Section 13). The level of Km$^R$ is determined systematically using the leaf disc assay.

EXAMPLE 8

Plants transformed with pGS1162 or pGS1163

T-DNA: PTR2-Bt2/820 - PTR2/884

Selectable marker: kanamycin resistance

Transformation method: leaf disc infection.

Leaf discs obtained from "in vitro" grown SR-1 plants were infected with *Agrobacterium tumefaciens* C58C1 Rif$^R$ pGS1162, pGS1163 or pGS1160 (as control). Discs were transferred to media containing different Km concentrations (50–100–200 mg/l). Shoots obtained on all three concentrations are transferred to Km free medium. Km resistance was checked by leaf disc test on callus inducing medium containing 50–500 ug/ml Km.

EXAMPLE 9

Plants Transformed with pGS1152

T-DNA: pTR2-Bt: NPT860

Selectable marker: kanamycin resistance

Transformation method: leaf disc infection.

Leaf discs obtained from "in vitro" grown SR-1 plants were infected with *Agrobacterium tumefaciens* C58C1 Rif$^R$ pGS1152. Discs infected with *Agrobacterium tumefaciens* C58C1 Rif$^R$ pGS460 were included as a control. Discs were transferred to media containing different Km concentrations (50–100–200 ml/l). Shoots were obtained on all three concentrations, although less abundant than in control discs infected with C58C1 Rif$^R$ GS1160.

11. Immunological detection of Bt2 protein in engineered plant tissues

Expression of Bt2 in engineered plants (either callus tissue or differentiated plants) was monitored using the ELISA described in Section 5 and adapted for assaying plant extracts.

Conditions for preparing and assaying plant extracts were established in reconstruction experiments in which purified Bt2 protein was mixed with plant extracts.

In reconstruction experiments we observed no significant loss in antigenic activity of Bt2 protein (less than 20%) due to the presence of plant extracts. In the ELISA assay, as little as 0.1 mg/ml purified Bt2 protein was still detectable. However, In reconstruction experiments a certain variability in background occurs, probably caused by plant proteins present in extracts. Therefore, reliable detection limit in these conditions was of the order of 1 ng/g tissue, which corresponds to a level of 2 ng Bt2 protein per g of plant tissue.

11.1 Screening of individual calli

For the immunological screening of individual calli, the following experimental procedure was established:

Two hundred mg of callus tissue was mixed with 150–200 ul of extraction buffer. Extraction buffer had the following composition: 50% of a solution of $Na_2CO_3$ 500 mM and DIT 100 mM and 50% fetal calf serum. The tissue was homogenized by crunching with a spatula whereafter the cell debris were centrifuged. Fifty ul of supernatants was added to 50 ul of PBS pH 7.4+10% fetal calf serum in wells of a microtiter plate coated with goat antibodies against B.t. crystal protein as described. During the entire procedure the samples were kept in ice and the microtiter plates were incubated at 4° C. for 1.5–2 hours. Thereafter the ELISA procedure was continued as described in 5.1 for detection of Bt2 protein with either rabbit anti-Bt2 serum or with a mixture of monoclonal anti-Bt2 antibodies 4D6, 10E3, 1.7, and 4.8 (under the form of culture supernatants).

EXAMPLE 1

Analysis of calli transformed with C58C1 $Rif^R$ pHD1050.

Transformed callus clones were obtained through the protoplast cocultivation method as described in Section 10 Example 1. Since 19% of the clones were found to express nopaline ($Nos^+$), at least 19% of them were transformed. However, due to an additional border sequence in the intermediate expression vector (pLGV2382) the nos gene and the Bt2 gene can be inserted independently as well as tandemly. Therefore both $Nos^+$ and $Nos^-$ clones were screened in the ELISA assay.

A total of 180 callus clones (130 $nos^-$, 50 $nos^+$) were tested. Some of the clones were retested once or twice at different time intervals after the initial propagation from protoplast culture. In none of the cases could a clear positive signal be recorded. When the substrate reaction times of the assay were prolonged (overnight incubation at 4° C.) some of the clones (both $nos^+$ and $nos^-$) produced a very weak signal above the background (background being control callus without Bt2 gene). However, since the obtained values were clearly below the reliable detection limit of the test system, no firm conclusions could be drawn concerning the expression of Bt2 protein in these calli.

EXAMPLE 2

Detection of Bt2 protein in tobacco callus tissue transformed with C58C1 $Rif^R$ pHD1076.

Transformed callus tissue obtained from leaf segment infections using Agrobacterium strain C58C1 $Rif^R$ (pHD1076) (see Section 10, Example 3), were screened immunologically for the presence of Bt2 protein.

After initial propagation calli were transferred for a second time after 20 days. When they reached optimal growth, 200 mg was used from each callus line for immunological screening in the ELISA. In a first experiment 9 out of 14 transformed calli showed a positive signal clearly above the background obtained with the control calli (untransformed SR-1 callus), when reacted with a specific rabbit anti Bt2 serum. (see FIG. 34). Three transformed calli generated a signal corresponding to approximately 5 ng Bt2 protein per gram tissue, as determined by comparison with a positive control (control SR-1 mixed with a known amount of Bt2 protein). All samples have signals equal to background level signals (obtained with SR-1 control callus) when reacted with normal rabbit serum as a negative control. In a second experiment 13 out of 21 transformed calli yielded a signal significantly above background (FIG. 35). One of the calli generated a signal corresponding to 4 ng of Bt2 per gram tissue. These results indicate that Bt2 protein is produced at a detectable level in a fraction of the calli transformed with pHD1076.

About 5 weeks after the first ELISA experiments, 4 selected lines (1076–10, 11, 12 and 13) which in the initial screening gave high positive values, were retested in ELISA. From each line several "subclones" were tested (the original callus had been divided in pieces which were propagated independently in the next growth cycle; each new piece is referred herein to as a subclone). From 1076-10, one subclone was positive, one negative, from 1076-12, 2 subclones were positive, from 1076-13, 3 subclones were positive, 2 were negative. These results indicate that callus tissue originally scored as B.t. positive might, when further propagated, give rise to B.t. negative callus.

11.2 Detection of Bt2 in pooled callus extracts

In order to perform detailed immunoassay screenings with an increased sensitivity of detection, concentrated extracts from larger amounts of transformed callus tissues were prepared. The procedure developed here for obtaining an extract enriched in Bt2 protein, is based on the property of Bt2 to precipitate at pH 4–5.

EXAMPLE 1

Calli transformed with pHD1076.

Transformed calli using pHD1076 were grown on medium containing 0.05 mg/ml kanamycin sulfate and 140 g of uncloned transformed calli were collected (a pool of callus lines 1076-4, 10, 11, 12, 13 and a number of unscreened lines). An extract was made by homogenizing the calli in the presence of 70 ml extraction buffer ($Na_2CO_3$ 500 mM, pH 10, DIT 5 mM, PMFS 170 ug/ml).

The supernatant obtained after centrifugation at 15,000 rpm was diluted by adding 50 ml phosphate buffered saline pH 7.5. Subsequently the pH of the diluted extract was brought to pH 6 with 1M HCl and it was incubated for 20 minutes at 0° C. and the supernatant isolated by centrifugation and stored at 0° C. (fraction pH 6). When pH was brought down to 4.5 a new precipitate was isolated (fraction pH 4.5) in the same way. The pellets were washed once with $H_2O$ and subsequently incubated for 20 minutes at room temperature in the following buffer: $Na_2CO_3$ 500 mM pH 10, DTT 50 mM, PMSF 170 ug/ml (pellet pH 6 in 1.5 ml and pellet pH 4.5 in 2 ml).

The material solubilizing in these conditions was isolated after centrifugation at 15,000 rpm and these samples were called 1076 pH 6 and 1076 pH 4.5 respectively.

A completely identical procedure was used to prepare extracts from normal SR-1 callus material (used here as a negative control) and resulted in two preparations called SR-1 pH 4.5. Total protein content in these samples was:

| | |
|---|---|
| 1076 pH 6 | 600 ug/ml |
| 1076 pH 4.5 | 6560 ug/ml |
| SR-1 pH 6 | 380 ug/ml |
| SR-1 pH 4.5 | 3840 ug/ml |

In order to evalaute the efficiency of the procedure a reconstruction experiment was done in which 1 ug of purified Bt2 was added to 20 g of SR-1 control callus tissue at the initiation of the sample homogenization. Presence of Bt2 protein in these extracts was determined using the ELISA (with goat anti-Bt crystal serum and rabbit anti Bt2, 6002). A strong reaction was recorded in fraction 1076 pH 4.5 as compared to the negative control (SR-1). Fraction 1076 pH 6 gave a signal which was only slightly higher than SR-1 pH 6, indicating that this fraction only contained a minor part of the Bt2 protein content.

In the ELISA, fraction 1076 pH 4.5 also gave a significant reaction with five different monoclonal antibodies, specific for Bt2 protein, namely 1.7, 4D6, 4.8, 10E3 and 1F6 (see FIG. 36). This strongly indicates that fraction 1076 pH 4.5 contains Bt2 protein which is in the same configuration as the bacterial Bt2.

In the following we attempted to remove Bt2 protein from the extract using a procedure of immunoprecipitation. A 5% volume of rabbit anti-Bt2 serum was added to the extract which was incubated at 4° C. for 1 hour. Subsequently a 5% volume of goat anti-rabbit Ig serum was added, followed by 1.5 hours incubation at 4° C. The precipitate was removed by centrifugation and the supernatant was tested in the ELISA. This supernatant contained at least 10 times less Bt2 activity than the original 1076 pH 4.5 fraction, indicating that the material which generated the positive signals in ELISA could be specifically removed by anti-Bt2 antibodies, again confirming the Bt2 nature of the positively reacting substance in ELISA.

In a next experiment the above samples were dialysed against carbonate buffer pH 10. A quantitative determination of the Bt2 content of extract 1076 pH 4.5 was performed by testing dilutions of the extract and a solution of purified Bt2 protein as a standard in the ELISA. The value determined was 122 ng Bt2/ml extract (total volume 2 ml). Reconstruction experiments (Bt2 added to SR-1 control callus at the beginning of the extraction), indicated that only 20% of Bt2 protein is lost during the extraction procedure and that 80% is contained in the pH 4.5 fraction. Based on these results, one could calculate that the total amount of Bt2 protein originally present in 140 g callus was 305 ng, which is 2.2 ng/g, a result that agrees well with the original estimates made for the screening of individual calli (see FIGS. 34 and 35). These data show that Bt2 protein present in extracts from transformed calli can be specifically concentrated using a precipitation procedure at pH 4.5 as described above, allowing us to quantify more accurately the amount of Bt2 protein produced in these plant tissues.

EXAMPLE 2

Calli transformed with pHD1050.

A 500 g pool of selected callus clones (on the basis of previous ELISA tests on individual calli, approximately 25 callus lines, which gave values above background, were selected) and homogenized in the presence of 1000 ml extraction buffer using the same procedure as described in Example 1.Material which remained soluble at pH 6, but precipitated at pH 4.5 was isolated by centrifugation and subsequently redissolved in a small volume of carbonate buffer pH 10 (see Example 1). Analysis of the material in ELISA revealed positive signals corresponding to 60 ng/ml Bt2 or 1.2 ng/g callus tissue (Table 8).

EXAMPLE 3

Calli transformed with pHD1060 and pHD1080.

In this example a slightly different and more extensive extraction protocol was used for the isolation of Bt2 protein from the engineered plant material. A protocol was developed to recover eventual residual Bt2 protein that would not be solubilized in a single extraction step as used in the procedures of Examples 1 and 2. Such could be the case, since Bt2 protein contains some highly hydrophobic regions which possibly interact with plant cell membrane structures and therefore would be difficult to solubilize in the absence of detergents. The step by step procedure used here would allow the recovery of additional proteins associated with insoluble plant cell structure. A schematic representative of the protocol is given in FIG. 37.

A first protein fraction is obtained by extraction in carbonate buffer pH 10+DTT and concentration through acid precipitation (pH 4.5) (fraction I). This fraction corresponds to the pH 4.5 extract obtained using the procedure in Examples 1 and 2.

Material not solubilized in this first extraction step and remaining in the pellet is then treated with the same extraction buffer containing 1% Triton X-100. Proteins, solubilizing in these conditions and precipitating at pH 4.5 are contained in fraction II. The last step involves solubilization in 2% SDS followed by acetone precipitation, yielding fraction III. Fractions I and II are analysed in ELISA and Western blotting; fraction III, which contains SDS, is only analysed in Western blotting.

ELISA results are given in Table 8: positive signals were detected in fractions I and II of both constructions 1060 and 1080, corresponding to Bt2 levels of respectively 1.9 and 1.4 ng/g original tissue (fr. I) and 0.27 and 0.29 ng/g (ft. II). Western blotting of the SDS solubilized material (fraction III) revealed the presence of a faint approximately 130 Kd band for both 1060 and 1080 callus material (using rabbit anti-Bt2 serum). Detection limit of the Western blotting was 10 ng/lane, therefore these fractions contained at least 0.39 ng/g for 1060 and 0.5 ng/g for 1080.

Western blotting of fractions I of 1050, 1060 and 1080 did not reveal the presence of a 130 Kd band probably because the concentration of Bt2 protein is too low in these fractions.

The present results indicate that low levels of Bt2 protein are indeed expressed in calli transformed with pHD1060 and pHD1080. Although small scale analysis of individual calli might not allow detection of immunopositive clones in these constructions, a more rigorous extraction and concentration procedure on a pool of selected calli clearly results in reliable and quantitative detection of Bt2 protein. A substantial fraction of the Bt2 was strongly bound to insoluble plant material and could only be released upon use of detergents such as Triton and SDS.

11.3 Detection of Bt2 protein in leaves of regenerated transformed plants

For the routine testing of leaf samples the following procedure was established:

Green leaf tissue (200–400 mg) was taken from "in vitro" grown plants (5–10 cm high as described in Section 10, Example 1) and homogenized in the presence of extraction buffer (200 ul), containing 50% of: $Na_2CO_3$ 500 mM, 100 mM DDT, 480 ug/ml leupeptine (Sigma, L-2884), 2 mM PMSF, 2 mg/ml ascorbic acid (Sigma, A-7631), 2 mM EDTA and 50% of FCS. The tissue was homogenized by crunching with a spatula whereafter the cell debris were centrifuged. Thereafter the same ELISA procedure was followed as described for the screening of callus tissue (see Section 11.1).

EXAMPLE 1

Detection of Bt2 protein in tobacco plants transformed with C58C1 $Rif^R$ pHD 1050.

Leaves from the "in vitro" propagated plants (70 individual plants regenerated from 25 selected callus clones) were tested for Bt2 expression in the ELISA, using conditions described above.

From 70 plants tested, 5 gave a clear positive reaction above background obtained with leaves of untransformed SR-1 corresponding to Bt2 levels ranging from 6 to 25 ng per gram wet tissue (see Table 9).

One of the plants with the highest value (plant no 161-9: 25 ng) was studied In more detail. Leaf extract reacted positively with a rabbit anti-Bt2 serum and with a mixture of monoclonal antibodies specific for the Bt2 molecule (undiluted culture supernatants from clones 1.7, 4.8, 4D6, 10ES). Furthermore it did not react with a pool of monoclonals displaying an irrelevant specificity. The plant extract was retested at least twice after freezing at −20° C. and thawing, using the same reagents. Identical results were obtained each time, however, the level of Bt2 declines gradually with each cycle of freezing/thawing, probably as a result of Bt2 protein degradation.

Plant 161-9 was retested after it had been propagated in greenhouse conditions at a stage when it was about to flower. Again a clear positive signal was obtained, this time corresponding to a level of approximately 5 ng Bt2/gram tissue.

This result indicates that the levels of Bt2 protein detected in engineered plant leaves might vary considerably depending on the plants age, growth conditions, etc.

EXAMPLE 2

Screening of tobacco plants transformed with C58C1 $Rif^R$ pHD 1060.

Screening of 76 "in vitro" propagated kanamycin resistant plants did not yield clearly Bt2 positive plants using the ELISA method described in Example 1.

EXAMPLE 3

Screening of tobacco plants transformed with C58C1 $Rif^R$ pHD1076.

Leaf extracts from "in vitro" propagated plants obtained through the shoot induction method were screened in ELISA (method as in Example 1). Seventeen plants were tested and none of these gave a positive signal. Subsequently, an additional number (21) plants were screened when they were grown in pots and 15–20 cm high. Again no positive signal above background were recorded in ELISA upon screening of these plants.

EXAMPLE 4

Screening of tobacco plants transformed with pHD1080.

About 30 "in vitro" propagated plants were screened in ELISA. One plant (plant no 174) gave a positive signal corresponding to 20 ng/g Bt2 both with rabbit anti-Bt2 serum and a pool of monoclonal antibodies. The extract from this plant was consistently positive upon retesting in subsequent experiments.

11.4 Detection of Bt2 protein in callus tissue derived from leaves of transformed plants The data outlined in Section 11.1, Example 2, 11.3, Example 3 suggests that the Pssu promotor constructions used here (pHD1076) are less active in differentiated plant leaves than in callus.

To investigate this further, new callus tissue was generated from leaves of the same plants used in the previous assays. Leaf discs were cultured on callus inducing medium and a few weeks later the callus material was collected and analyzed in a similar procedure (the only difference being that a Tris pH 7.5 buffer was used in the Step I extraction instead of a $Na_2CO_3$ pH 10/DTT buffer).

Callus, induced simultaneously from untransformed SR-1 leaves, was used as negative control.

ELISA analysis of the pHD1076 transformed calli revealed detectable amounts of Bt2 protein (Table 10).

These results show that a chimeric gene with the Pssu promotor from pea in the construction used herein is functional and induces expression of Bt2 protein in tobacco callus tissue derived from leaves, that did not express detectable amounts of the same protein. Thus a chimeric gene that directs expression in undifferentiated callus tissue may not necessarily be active to the same extent if at all in differentiated plant leaves.

12. Insecticidal activity of the Bt2 protein produced in engineered calli

Procedures:

Toxicity assays were performed on first instar larvae of *Manduca sexta,* fed on artificial diet. Three to four ml of liquid artificial diet (Bell, R. A. & Joachim, F. G. (1976) *Ann. Entomol. Soc. Ann.* 69: 365–373) were dispensed in each compartment (4 $cm^2$) of square Petri dishes. Formaldehyde was omitted from the diet. After the diet had become solid, 200 ul of a known dilution of sample was applied on the surface of the diet and dried in a cool air flow. Four newly hatched larvae were placed into each compartment. Growth and mortality were followed over a period of 3–5 days.

EXAMPLE 1

Callus extract from calli transformed with pHD1076.

A concentrated extract from a pool of calli, transformed with pHD1076 was prepared as described in Section 11.2 Example 1. Extract dilutions were applied onto the surface of the diet and its toxicity was evaluated. The extracted material 1076 pH 4.5 clearly had a toxic effect on the

Figure 39B:
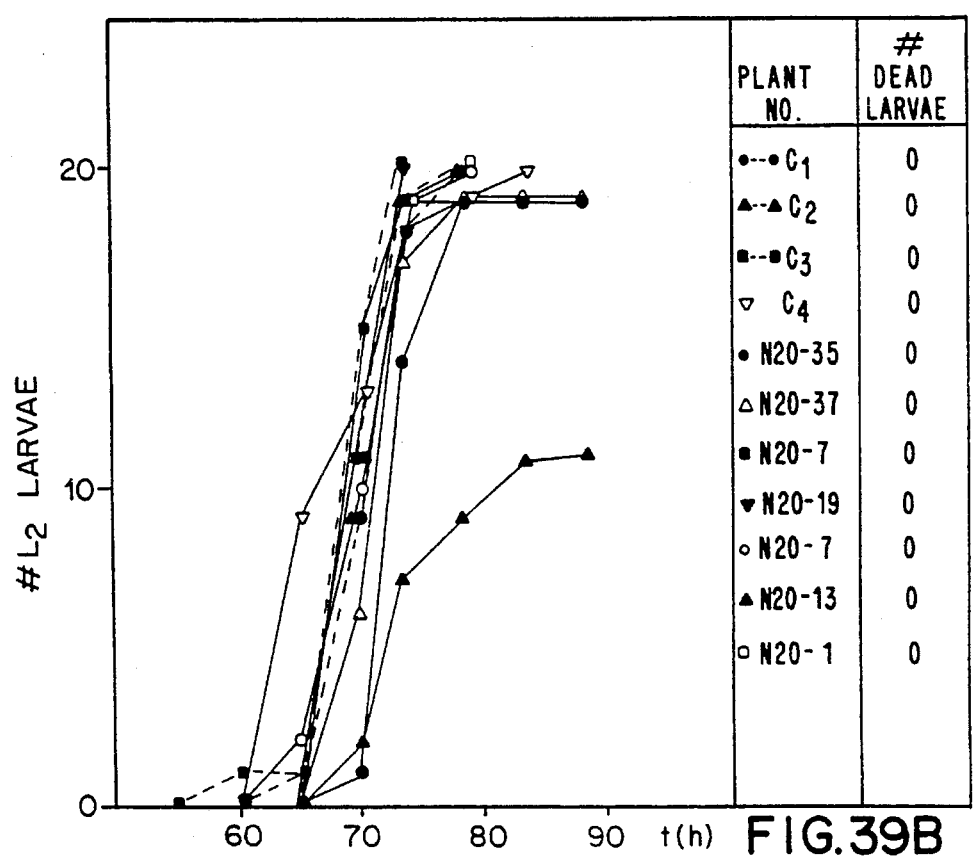

*Manduca sexta* larvae: at 12.5 ul/cm$^2$ all larvae showed growth inhibition and at 50 ul/cm$^2$ 100% died (Table 11). Toxic activity of this material was significantly diminished after immunoprecipitation (100% normal growth at 12.5 and 25 ul/cm$^2$ and only 37% death at 50 ul/cm$^2$), indicating that the toxic activity can be depleted by anti-Bt2 antibodies. Extract from untransformed SR-1 callus tissue, the negative control, was completely nontoxic. Since the presence of Bt2 protein in the extracts was quantified immunologically, we could correlate the observed toxicity with the determined Bt2 concentration. The immunoassay values indicated that 1076 pH 4 contained 122 ng/ml Bt2. Thus, 50 ul extract per $cm^2$ corresponds to 6.1 ng Bt2 protein/$cm^2$. Previous toxicity assays with Bt2 on Manduca (Section 5.2, Table 3) indicated that Bt2 at 12 ng/$cm^2$ is 100% lethal while 2.5 ng/$cm^2$ induces growth inhibition.

Together these results indicate that the Bt2, expressed in engineered callus tissue, is a functional toxin and displays toxicity which is in the same range of potency as the bacterial Bt2 gene product.

13. Insecticidal activity exhibited by leaves of transformed tobacco plants

Procedures:

In order to evaluate the insecticidal activity expressed in leaves of transformed tobacco plants the growth rate and mortality of *Manduca sexta* larvae feeding on these leaves was recorded and compared with the growth rate of larvae feeding on untransformed SR-1 leaves. The following procedures were used:

Procedure 1

Subsequent experiments were carried out on leaf discs placed in Petri dishes. Four leaf discs of 4 cm diameter were punched out, placed on wet filter paper on a Petri dish together with 4×10 first instar larvae of *M. sexta*. Preferentially young leaves from the upper part of the plant were used. Twenty-four hours later a second disc was added. Between 48 hours and 100 hours after initiation of the experiment, the number of moulted insects were counted at regular time intervals. From this we could calculate the $MT_{50}$ time at which 50% of the larvae had moulted. The whole experiment was conducted in a growth chamber at 26° C., 90% relative humidity and under a photoperiod of 16 hours light and 8 hours darkness.

In order to estimate the toxin levels required to have a notable effect on growth rate and viability of *Manduca sexta* larvae in the present experiment, a series of reconstruction experiments had to be included. To this end purified solubilized Bt2 protein (Section 5.1) was serially diluted in PBS containing 0.5% Triton X-100. Standard volumes of Bt2 solution were mechanically sprayed (to obtain a very homogenous coating) on tobacco leaf discs. Ten L1 (first instar) larvae were placed on each leaf disc, and 3 discs were used per Bt2 concentration. Growth rate and mortality of the larvae were followed over a 100 hour period.

Procedure 2

A procedure essentially similar to the previous one was also used. This experimental protocol was however somewhat more extensive in order to be more effective in reliably detecting very small effects on larval growth rate. The set up was different from the previous one in the following aspects:

- care was taken that all plants were in exactly the same stage and condition so that the effects on larval growth caused by differences in the condition of the leaf tissue would be minimal.
- larval growth was followed up to the $L_3$ stage (unlike previous experiments where growth was only monitored up to $L_2$).
- not only the moulting time of the larvae was recorded but also larval weight in the final stage was measured.

The plants used in this set up were grown in the greenhouse until they reached a height of 60–80 cm, but were not flowering yet. Leaf discs were cut out, placed on wet filter paper in Petri dishes and 10 first instar larvae were placed on each disc. Per plant, five groups of 10 larvae were used (5 leaf discs).

Growth rate and mortality were followed over a 7 day period (at this time nearly 100% of the controls were in the $L_3$ stage).

EXAMPLE 1

Plants transformed with pHD1050, 1060, 1076 and 1080 were screened in the insect assay following procedure 1. No significant effect on growth rate and viability of the larvae could be recorded using this procedure. Results of a reconstruction experiment with purified bacterial Bt2 protein were as follows:

Growth inhibition but no mortality was observed at 25 ng/g and approximately 50% mortality at 50 ng/g.

EXAMPLE 2

An extensive toxicity test using procedure 2 was done on a number of transformed plants that were previously scored as Bt+ in immunoassays. These plants were 161-9 (Pnos-Bt2, nos+) (pHD1050 Example 1 Section 10)

147 (Pnos-Bt2, nos+) (pHD1050 Example 1 Section 10)

174 (Pssu-Tp-Bt2, Km+, nos+) pHD1080 Example 4 Section 10)

As controls a $Bt^-$ plant (161-6) and an untransformed SR-1 were used. Results are presented in Table 12.

A) The number-of larvae that were still in the $L_2$ stage, or already went to $L_3$, or died, at 150 hours after initiation of the test. Clearly the $L_2$–$L_3$ transition somewhat earlier in the groups of larvae feeding on SR-1 and 161-6 as compared to those feeding on the $Bt^+$ plants 161-9, 147 and 174. In none of the groups has significant mortality been recorded (10% or less is considered as background).

B) Mean larval weight at the end of the experiment is presented in the upper row (larvae in 5 groups of 10, deviation is calculated on the mean values of these groups).

Below are the weight values calculated for the 5 largest larvae from each group of 10. These results are compatible with the kinetics of the L3-L4 transition: control larvae are somewhat larger than larvae feeding on $Bt^+$ plants.

EXAMPLE 3

Insect toxicity assays were done on leaves of plants obtained from the transformation procedure with pGS1110 (Section 10, Example 5). Plants were 10–20 cm and tests were performed following procedure 1. L1–$L_2$ transition was monitored and 2 groups of 10 larvae were used per plant. A significant growth inhibition effect, exhibited by some of the plants on *M. sexta* larvae, was observed. Data on the L1–$L_2$ ratio after about 3 days of feeding, are presented in Table 13. Control plants included in these experiments were transformed with vectors containing Pnos-NPTII only. In Exp. 1, from the 8 plants putatively transformed with pGS1110, 3 produced growth inhibition (N20-38, N20-22, N20-18) as compared to the 3 control plants (C1, C2, C3). In Exp. 2, one plant (N20-37) out of 6 produced growth inhibition when compared to the 4 control plants (C4, C5, C6, C7). The differences in growth rate are apparent when complete growth rate curves are compared (see FIGS. 38 and 39).

The same plants were also screened for the presence of nopaline end for resistance against kanamycin, in order to determine whether they were real transformants. The results of the screening data on the plants used in the present insect tests are compiled in Table 14. All four plants that showed an effect on larval growth are among the positive transformants, since they are Kanamycin resistant ($Km^R$) and nopaline positive (nos+).

EXAMPLE 4

Insect toxicity assays were performed on leaves of plants generated through transformation with pGS1151 (Section 10, Example 7). Plants were 15–30 cm high at the time of testing and had been grown in greenhouse conditions.

Two independent experiments are described below: some of the plants tested in the first experiment were retested in Experiment II, in order to confirm the observed toxicity effects.

EXPERIMENT I:

The test was performed as described in Procedure 2 (this section) except that only two groups of ten larvae were used per plant (newly hatched *Manduca sexta* larvae).

Growth rate and mortality of the larvae were followed over a 7 day period and the larval weight at the end of this period was determined. Detailed results from Experiment I are represented in Table 15 and indicate that larvae feeding on several plants transformed with pGS1151 show significant growth inhibition in the initial stage of the experiment, as compared to larvae feeding on a control plant. For example, after 71 h, 60% of the larvae feeding on control plant N21-107 have gene to the L2 stage, while the number of L2 larvae is only 15% or less on plants N21-18, 43, 53, 50 and 11. When followed over a longer period, significant mortality was recorded in the larvae feeding on pGS1151 transformed plants. On one of the plants (N21-11), mortality reached 100% after less than 7 days. Mortality on the control plant only reached 15% on day 7 and 45% of the larvae had already gene to the L3 stage (this in contrast to the other plants having substantially no L3 larvae on day 7).

EXPERIMENT II:

Results from a second insect test (II) involving newly hatched *M. sexta* larvae was performed on some of the plants also used in Exp. I, following Procedure 1. Results are presented in Table 16. A high mortality rate was recorded in the plants transformed with pGS1151 (75–100% death) while nearly all the larvae feeding on the control plants N21-102, 104 and 107 were still viable after 4 days. A complete list of all the plants used in insect tests I and II is given in Table 17. Also indicated are the Km resistance levels determined for the plants transformed with pGS1151; the percentage mortality of the larvae feeding on these plants after several days; and the mean weight of the larvae that survived after 7 days in Experiment I.

CONCLUSION

Tobacco plants transformed with pGS1151 and selected for high Km resistance clearly induce severe toxic effects on larvae feeding on these plants. The effects on insect larvae observed here, are the same as those induced by the B.t. toxin of bacterial origin (see Section 5.2, Tables 2 and 3); that is, growth inhibition in the initial stage (retardation in the transition from one instar to the next) followed by death.

It is apparent from Table 17 that the plants exhibiting the highest levels of Km resistance (500 ug/ml Km) also induce the highest mortality rates. Thus, using the fusion protein construction, we were able to select for efficient expression of toxicity by selecting for Km resistance.

It should be noted that the use of a fusion protein, as described herein, may represent a particular advantage, not only because direct slection for transformants of interest can be done, but also because the fusion protein itself might have some intrinsic useful properties. For example, Bt2:NPTII fusion proteins might be more stable in plant cells than intact Bt2 protein and/or the messenger RNA derived from the fusion genes might be more stable than intact Bt2 RNA.

14. Stable inheritance of new phenotype, acquired through transformation

A substantial fraction of the plants transformed with the transformation vectors described herein will contain, stably inserted into their genome, a fragment of newly acquired DNA containing both a chimeric Bt toxin gene end a marker gene (nos, NPTII). This was confirmed by the results of southern blotting experiments. The new phenotypic traits acquired through this transformation method (expression of Bt Toxin, antibiotic resistance, nopaline production) will be inherited according to classic Mendelian genetics. To verify stable inheritance of the new traits, $F_1$ descendants from transformed plants were analysed for the expression of Bt toxin and synthesis of nopaline.

Transformed tobacco plants were allowed to flower and give seed. Care was taken that no cross pollination occurred. From 4 plants previously identified as $Bt^+$ (161-9, $10^{-1}$, $147^{-8}$, 174), seeds were germinated in agar medium end $F_1$ plants were analysed for the presence of nopaline (nopaline synthase being present as marker gene in the parental plants). Plants were tested 3 weeks after germination (approximately 1 cm in height) or later at 6–7 weeks (2–4 cm). The results are depicted in Table 18.

From plants 10-1 and 147-8 about ¾ of the $F_1$ were $nos^+$, which is expected from Mendelian inheritance of a single locus (1:2:1). For $F_1$ plants from 161-9, the nopaline signal was very weak when plantlets were tested at approximately 3 weeks after germination. Due to this weak expression the nopaline signals were not clearly visible end therefore the number of positives might be underestimated at this stage. However at 7 weeks a clear positive signal was detected in a ¾ of the plants. The reason for the low expression in the early age of the plants is not known.

In the $F_1$ from plant 174, of the 45 plants analysed, 43 were $nos^+$. This high percentage (95%) of $nos^+$ indicates that the nos gene is inserted in the genome on more than one independent locus. $F_1$ plants were also analysed for the expression of Bt2 toxin using the ELISA. Data from ELISA assays on leaf tissue indicated that $Bt2^+$ phenotype was correlated with $nos^+$. Therefore the $Bt2^+$ trait is stably inherited.

Cultures of cells containing intermediate cloning vectors and hybrid plasmid vectors have been deposited with Deutsche Sammlung von Miko-organism (DSM) Gesellschaft fur Biotechnologische Forschung mbH, Grisbachstr 8D-3400, Gottingen, Federal Republic of Germany and have been assigned accession numbers as follows:

| | |
|---|---|
| E. coli K514 (pHD208) | DSM 3127 |
| E. coli K514 (pHD205) | DSM 3128 |
| A. tumefaciens C58Cl Rif$^R$ (pHD1076) | DSM 3129 |
| A. tumefaciens C58Cl Rif$^R$ (pHD1050) | DSM 3130 |

Cultures of B.t. berliner 1715 have also been deposited with the same depository and been assigned an accession number of DSM 3131. *Nicotiana tabacum* cv. Petit Havana SR-1 has been deposited with the United States Department of Agriculture, National Seed Storage Laboratory, Colorado State University, Ft. Collins, Colo., 80523 and assigned Ser. No. 191197 and is freely available upon request.

Cultures of cells containing intermediate cloning vectors and hybrid plasmid vectors have been deposited with American Type Culture Collection (ATCC) and have been assigned accession numbers as follows:

| | |
|---|---|
| E. coli K514 (pLBKm25) | ATCC 53390 |
| E. coli K514 (pLBKm33) (without lambda repressor) | ATCC 53389 |
| E. coli K514 (pLBKm1820) | ATCC 53388 |
| E. coli JM83 K12 (pSSU301) | ATCC 53391 |
| E. coli K514 (pLBKm1860) | ATCC 53387 |
| A. tumefaciens C58Cl Ery$^R$ Cml$^R$ (pHD1080) | ATCC 53385 |
| A. tumefaciens C58Cl Rif$^R$ (pGS1110) | ATCC 53386 |
| A. tumefaciens C58Cl Rif$^R$ (pGS1151) | ATCC 53392 |
| A. tumefaciens C58Cl Rif$^R$ (pGS1161) | ATCC 53393 |
| A. tumefaciens C58Cl Rif$^R$ (pGS1152) | ATCC 53394 |
| A. tumefaciens C58Cl Rif$^R$ (pGS1163) | ATCC 53395 |
| A. tumefaciens C58Cl Rif$^R$ (pGS1171) | ATCC 53396 |
| A. tumefaciens C58Cl Rif$^R$ (pGS1181) | ATCC 53397 |
| A. tumefaciens C58Cl Rif$^R$ (pGS1182) | ATCC 53398 |
| A. tumefaciens C58Cl Rif$^R$ (pGS1251) | ATCC 53399 |
| A. tumefaciens C58Cl Rif$^R$ (pGS1261) | ATCC 53400 |
| A. tumefaciens C58Cl Rif$^R$ (pGS1253) | ATCC 53401 |
| A. tumefaciens C58Cl Rif$^R$ (pGS1262) | ATCC 53402 |

Cultures of *E. coli* K514 are commercially available.

It is to be understood that changes and variations may be made without departing from the spirit and scope of this invention as defined by the appended claims.

TABLE 1

Toxicity (Toward *P. brassicae* Larvae) of Bt2 and B.t. Crystal Proteins

| Sample | Toxicity (mean value ± S.D.*) LD$_{50}$ (ng/larva) |
|---|---|
| Solubilized B.t. berliner 1715 crystals | 0.65 ± 0.35 |
| Purified Bt2 protein | 1.65 ± 1.3 |

*S.D. is Standard Deviation.

TABLE 2

Effect of Bt2 Protein on Growth Kinetics of *P. brassicae* Larvae
(Results Expressed in % of Larvae In a Certain Stage); 1 ppm = 267 ng/gram leaf

| | Bt2 Concentration | | | | | | | | | | | | | | | |
|---|---|---|---|---|---|---|---|---|---|---|---|---|---|---|---|---|
| | 0 | | | | | | 0.01 ppm | | | | | | 0.1 ppm | | | | |
| Time (hours) | Stage L3 | WC | L4 | WC | L5 | % mort | L3 | WC | L4 | WC | L5 | % mort | L3 | WC | L4 | WC | L5 | % mort |
| 24 | 100 | | | | | 0 | 100 | | | | | 0 | 100 | | | | | 0 |
| 48 | 33 | 67 | | | | 0 | 93 | 7 | | | | 0 | 100 | | | | | — |
| 52 | 16 | 50 | 34 | | | 0 | 70 | 30 | | | | 0 | 100 | | | | | — |
| 57 | | 30 | 70 | | | 0 | 55 | 45 | | | | 0 | 100 | | | | | — |
| 71 | | 3 | 97 | | | 0 | 44 | 15 | 41 | | | 0 | 100 | | | | | 60 |
| 77 | | | 100 | | | 0 | 15 | 18 | 67 | | | 0 | 100 | | | | | — |
| 95 | | | 100 | | | 0 | 3 | 5 | 92 | | | 0 | 100 | | | | | 85 |
| 102 | | | 89 | 11 | | 0 | 3 | 5 | 92 | | | 0 | 100 | | | | | 85 |
| 119 | | | 63 | 30 | 7 | 0 | | 3 | 97 | | | 0 | 100 | | | | | 95 |
| 127 | | | 36 | 40 | 24 | 0 | | | 97 | 3 | | 0 | | | | | | 100 |
| 143 | | | 7 | 58 | 35 | 0 | | | 45 | 51 | 4 | 0 | | | | | | |
| 151 | | | 6 | 22 | 72 | 0 | | | 24 | 70 | 6 | 0 | | | | | | |
| 167 | | | | | 100 | 0 | | | 15 | 27 | 58 | 0 | | | | | | |

TABLE 3

Toxicity of Bt2 and Total B.t. berliner Crystal Proteins Towards Larvae of *Manduca sexta*, Expressed as Percentage Mortality

| | Control E. coli Extracts | Bt2 | | | | | B.t. berliner Crystals | | | | |
|---|---|---|---|---|---|---|---|---|---|---|---|
| Time (days) | | dose (ng protein/cm) | | | | | | | | | |
| | 1250 | 2.5 | 12.5 | 25 | 125 | 250 | 2.5 | 12.5 | 25 | 125 | 250 |
| 1 | 0 | 0 | 0 | 0 | 0 | 0 | 0 | 0 | 0 | 0 | 0 |
| 2 | 0 | 0 | 4 | 8 | 28 | 36 | 0 | 0 | 0 | 20 | 20 |
| 3 | 0 | 0 | 64 | 92 | 100 | 100 | 0 | 32 | 64 | 92 | 100 |

TABLE 3-continued

Toxicity of Bt2 and Total B.t. berliner Crystal Proteins Towards
Larvae of Manduca sexta, Expressed as Percentage Mortality

| Time (days) | Control E. coli Extracts | Bt2 | | | | | B.t. berliner Crystals | | | | |
|---|---|---|---|---|---|---|---|---|---|---|---|
| | | dose (ng protein/cm) | | | | | | | | | |
| | 1250 | 2.5 | 12.5 | 25 | 125 | 250 | 2.5 | 12.5 | 25 | 125 | 250 |
| 4 | 0 | 4 | 80 | 100 | | | 0 | 72 | 92 | 100 | |
| 5 | 0 | 4 | 88 | | | | 0 | 81 | 100 | | |
| 6 | 0 | 8 | 100 | | | | 0 | 88 | | | |
| 7 | 0 | 8 | | | | | 0 | 88 | | | |

TABLE 4

Toxicity of Bt:NPT2 Fusion Protein on 3rd Instar
P. brassicae (% Mortality After 4 Days)

| Bt protein | Toxin dose (ug/ml) | | | | |
|---|---|---|---|---|---|
| | 0.1 | 0.2 | 0.3 | 0.6 | 1 |
| Bt2 | 70 | NT(*) | 90 | N TABLE 7-continued Summary of Engineered Ti Plasmids and Their Intermediate Vectors

| Ti Plasmid | Ti Plasmid Receptor | Intermediate Vectors | Expr. Vector | Bt Cassette from | Plant Prom. | Plant Marker | 3' End |
|---|---|---|---|---|---|---|---|
| pGS1152 | pGV2260 | pGSH152 | pGSH150 | pLBKm1860 | PTR2 | KmF | t7 |
| pGS1162 | pGV2260 | pGSH162 | pGSH160 | pLB1820 | PTR2 | Km | t7 |
| pGS1163 | pGV2260 | pGSH163 | pGSH160 | pLB1884 | PTR2 | Km | t7 |
| pGS1171 | pGV2260 | pGSH171 | pAGS007 | pLBKm14 | Pssu301 | Hyg | ssu301 |
| pGS1181 | pGV2260 | pGSH181 | pAGS007 | pDC3 | Pssu301 | Km | ssu301 |
| pGS1182 | pGV2260 | pGSH182 | pAGS007 | pLB1820 | Pssu301 | Km | ssu301 |
| pGS1251 | pGV2260 | pGSJ251 | pGSJ250 | pLBKm33 | P35S-1 | KmF | t7 |
| pGS1261 | pGV2260 | pGSJ261 | pGSJ260 | pHD162 | P35S-1 | Km | t7 |
| pGS1253 | pGV2260 | pGSJ253 | pGSJ250 | pLBKm2860 | P35S-1 | KmF | t7 |
| pGS1262 | pGV2260 | pGSJ262 | pGSJ260 | pLB2820 | P35S-1 | Km | t7 |
| pGS1271 | pGV2260 | pGSJ271 | pGSJ270 | pHD162 | P35S-2 | Km | t7 |
| pGS1281 | pGV2260 | pGSJ281 | pGSJ280 | pLBKm33 | P35S-2 | KmF | t7 |

*KmF indicates Kanamycin fusions.

TABLE 8

Results Immunoassays on Pooled Callus Extracts

| Construction | Extract Fraction | Protein Content ug/ml | Total Volume Extract (ml) | Bt2 in ELISA ng/ml | ng/g | Western Blotting Volume (ul) | 130 Kd |
|---|---|---|---|---|---|---|---|
| pHD1050 (500 g) | I | 9650 | 10 | 60 | 1.2 | 50 | – |
| pHD1060 (392 g) | I | 7800 | 8 | 95 | 1.9 | 50 | – |
|  | II | 640 | 1 | 105 | 0.27 | 200 | ± |
|  | III | N.D.$^{(x)}$ | 0.3 | N.D. | N.D. | 20 | + |
| pHD1080 (100 g) | I | 4150 | 2 | 72 | 1.2 | 50 | – |
|  | II | 326 | 1 | 29 | 0.29 | N.D. | N.D. |
|  | III | N.D. | 0.5 | N.D. | N.D. | 100 | + |

$^{(x)}$N.D. = Not Determined

TABLE 9

Levels of Bt2 Protein Detected in Leaves from 5 Immunopositive Plants Transformed by pHD1050

| Plant Isolation Number | ng Bt2/g Plant Tissue |
|---|---|
| 161-9 | 25.0 |
| 10-1 | 7.6 |
| 10-2 | 6.0 |
| 147-8 | 14.0 |
| 147-9 | 9.2 |

TABLE 10

Immunoassays on Extracts of Calli Derived from Leaves of Transformed Tobacco

| Construction | Fraction | Protein Content (ug/ml) | Volume Extract (ml) | Bt2 Detected in ELISA (ng/g) |
|---|---|---|---|---|
| pHD1076 (59 g) | I | 6200 | 7 | 1.6 |
|  | II | 1520 | 1.5 | 0.4 |

TABLE 11

Toxicity of Callus Extract on Manduca Sexta Larvae

| Extract | Volume Per cm$^2$ (ul) | Total Number Larvae | Results After L1 | WC | L2 | Dead |
|---|---|---|---|---|---|---|
| 1076 pH 4.5 | 12.5 | 4 | 3 | 1 |  |  |
|  | 50 | 4 |  |  |  | 4 |
|  | 100 | 4 |  |  |  | 4 |
| SR-1 pH 4.5 | 50 | 8 |  |  | 8 |  |
| (Control No Plant Extract) |  | 44 |  | 1 | 43 |  |
| After Immunoprec: 1076 pH 4.5 | 25 | 12 |  |  | 12 |  |
|  | 50 | 8 |  | 1 | 3 | 4 |
| SR-1 pH 4.5 | 50 | 8 |  |  | 8 |  |

TABLE 12

Growth Rate and Mortality of *Manduca Sexta* Larvae Feeding on Transformed Tobacco Leaves A. Larval Stage at 150 h: (Number of Larvae)

| Plant | 161-9 | 147 | 174 | SR-1 | 161-6 |
|---|---|---|---|---|---|
| L2 | 22 | 22 | 24 | 9 | 5 |
| L3 | 25 | 27 | 23 | 36 | 41 |
| Dead | 3 | 1 | 3 | 5 | 4 |

B. Larval Weight at 164 h:

| | 161-9 | 147 | 174 | SR-1 | 161-6 |
|---|---|---|---|---|---|
| Mean Weight Per Larva (mg) | 59.5 ±4.7 | 48.7 ±6.1 | 50.6 ±10.4 | 65.7 77.0 | 74.9 86.5 |
| Mean Weight 5 Largest | 67.6 ±6.5 | 61.9 ±6.4 | 60.0 ±1.3 | 77.0 ±2.5 | 86.5 ±7.2 |

TABLE 13

Growth Rate of *Manduca sexta* Larvae Feeding on Tobacco Leaves from Plants Transformed with pGS1110

Exp. 1: Number of Larvae in a Certain Stage After 87 h:

| Plant No: | C1 | C2 | C3 | N20-3 | N20-46 | N20-38 | N20-22 | N20-47 | N20-18 | N20-30 | N20-3 |
|---|---|---|---|---|---|---|---|---|---|---|---|
| Stage L1 | 6 | 0 | 3 | 7 | 5 | 15 | 12 | 4 | 14 | 6 | 0 |
| L2 | 14 | 20 | 17 | 13 | 14 | 4 | 6 | 16 | 6 | 13 | 20 |
| Dead | 0 | 0 | 0 | 0 | 1 | 1 | 2 | 0 | 0 | 1 | 0 |

Exp. 2: Number of Larvae in a Certain Stage after 78 h:

| Plant No: | C4 | C5 | C6 | C7 | N20-35 | N20-37 | N20-7(*) | N20-7(*) | N20-19 | N20-13 | N20-1 |
|---|---|---|---|---|---|---|---|---|---|---|---|
| Stage L1 | 0 | 0 | 0 | 1 | 1 | 11 | 1 | 0 | 0 | 1 | 0 |
| L2 | 20 | 20 | 20 | 19 | 19 | 9 | 19 | 20 | 20 | 19 | 20 |
| Dead | 0 | 0 | 0 | 0 | 0 | 0 | 0 | 0 | 0 | 0 | 0 |

(*)Two copies of this plant were tested in this experiment.

TABLE 14

Characteristics of Plants from Experiment No. 20

| Plant Number | Nos. | Km$^R$ | Insect Tox. |
|---|---|---|---|
| N20-4 | + | + | − |
| N20-30 | + | + | − |
| N20-18 | N.T.(*) | + | + |
| N20-22 | + | + | + |
| N20-3 | − | + | − |
| N20-46 | N.T. | N.T. | − |
| N20-38 | + | + | + |
| N20-31 | + | + | − |
| N20-37 | + | + | + |
| N20-7 | + | + | − |
| N20-35 | + | + | − |
| N20-13 | − | N.T. | − |
| N20-19 | + | N.T. | − |
| N20-1 | − | N.T. | − |

(*)N.T. = Not Tested

TABLE 15

Growth Rate and Mortality of *Manduca sexta* Larvae
Feeding on Leaves From Tobacco Plants Transformed
with pGS1151 (Experiment I)
Represented are:
Numbers of larvae in a certain stage (L1, L2 or L3)
or dead (D) from groups of 20 larvae after a period of
feeding on the tobacco leaves.

| Time | Plant N21-50 | | | | N21-35 | | | | N21-11 | | | | N21-56 | | | |
|---|---|---|---|---|---|---|---|---|---|---|---|---|---|---|---|---|
| (Hours) | D | L1 | L2 | L3 | D | L1 | L2 | L3 | D | L1 | L2 | L3 | D | L1 | L2 | L3 |
| 0 | | 20 | | | | 20 | | | | 20 | | | | 20 | | |
| 55 | | 20 | | | 5 | 15 | | | | 20 | | | | 20 | | |
| 61 | 1 | 19 | | | 5 | 14 | 1 | | 1 | 19 | | | | 20 | | |
| 66 | 1 | 19 | | | 5 | 11 | 4 | | 1 | 19 | | | | 19 | | |
| 71 | 1 | 19 | | | 6 | 5 | 9 | | 3 | 19 | | | 1 | 9 | 10 | |
| 76 | 1 | 18 | 1 | | 7 | 4 | 9 | | 5 | 15 | | | 1 | 8 | 11 | |
| 81 | 1 | 18 | 1 | | 7 | 4 | 9 | | 5 | 15 | | | 2 | 7 | 11 | |
| 87 | 1 | 18 | 1 | | 7 | 4 | 9 | | 5 | 15 | | | 2 | 7 | 11 | |
| 92 | 2 | 17 | 1 | | 8 | 3 | 9 | | 8 | 12 | | | 2 | 3 | 15 | |
| 119 | 11 | 7 | 2 | | 12 | 1 | 7 | | 18 | 2 | | | 3 | 1 | 16 | |
| 136 | 12 | 4 | 4 | | 12 | | 8 | | 19 | 1 | | | 4 | | 16 | |
| 144 | 12 | 4 | 4 | | 15 | | 5 | | 19 | 1 | | | 4 | | 16 | |
| 159 | 13 | 3 | 4 | | 17 | | 3 | | 20 | | | | 4 | | 16 | |
| 168 | 15 | 1 | 4 | | 17 | | 2 | 1 | 20 | | | | 4 | | 15 | 1 |

| Time | N21-107(*) | | | | N21-18 | | | | N21-43 | | | | N21-53 | | | |
|---|---|---|---|---|---|---|---|---|---|---|---|---|---|---|---|---|
| (Hours) | D | L1 | L2 | L3 | D | L1 | L2 | L3 | D | L1 | L2 | L3 | D | L1 | L2 | L3 |
| 0 | | 20 | | | | 20 | | | | 20 | | | | 20 | | |
| 55 | | 20 | | | | 20 | | | 1 | 19 | | | | 20 | | |
| 61 | | 19 | 1 | | | 20 | | | 1 | 19 | | | | 20 | | |
| 66 | 1 | 10 | 9 | | | 20 | | | 1 | 19 | | | | 20 | | |
| 71 | 2 | 6 | 12 | | 1 | 16 | 3 | | 1 | 16 | 3 | | | 20 | | |
| 76 | 2 | 6 | 12 | | 1 | 14 | 5 | | 2 | 15 | 3 | | | 16 | 4 | |
| 81 | 2 | 6 | 12 | | 1 | 13 | 6 | | 2 | 15 | 3 | | 4 | 13 | 3 | |
| 87 | 2 | 2 | 16 | | 1 | 12 | 7 | | 3 | 14 | 3 | | 5 | 11 | 4 | |
| 92 | 2 | | 18 | | 1 | 12 | 7 | | 4 | 12 | 4 | | 8 | 9 | 3 | |
| 119 | 2 | | 18 | | 9 | 3 | 8 | | 6 | 7 | 7 | | 17 | 1 | 2 | |
| 136 | 2 | | 18 | | 4 | | 6 | | 9 | 4 | 7 | | 18 | 1 | 1 | |
| 144 | 2 | | 18 | | 16 | | 4 | | 10 | 4 | 6 | | 18 | | 2 | |
| 159 | 2 | | 12 | 6 | 17 | | 3 | | 12 | 2 | 6 | | 18 | | 2 | |
| 168 | 3 | | 8 | 9 | 17 | | 3 | | 15 | | 5 | | 18 | | 2 | |

*Plant N21-107 is a control plant transformed with the same type of vector but comprising only a PTR:NPTII chimeric gene and no Bt2 sequences.

TABLE 16

Growth Rate and Mortality of *Manduca sexta* Larvae Feeding on Leaves from
Tobacco Plants Transformed with pGS1151 (Experiment II) (See also Legend for Table 15)

| | | | | | | | | | | | | | | | | Controls | | | | | | |
|---|---|---|---|---|---|---|---|---|---|---|---|---|---|---|---|---|---|---|---|---|---|---|---|
| Time | N21-50 | | N21-18 | | N21-43 | | N21-11 | | N21-56 | | N21-35 | | N21-53 | | N21-33 | | N21-102 | | | N21-104 | | | N21-107 | |
| (hours) | D | L1 | D | L1 | D | L1 | D | L1 | D | L1 | D | L1 | D | L1 | D | L1 | D | L1 | L2 | D | L1 | L2 | D | L1 | L2 |
| 0 | | 20 | | 20 | | 20 | | 20 | | 20 | | 20 | | 20 | | 20 | | 20 | | | 20 | | | 20 | |
| 29 | | | | | | | | | | | | 20 | | 20 | | 20 | | 20 | | | 20 | | | 20 | |
| 47 | | | | | | | | | | | 5 | 15 | 6 | 14 | 8 | 12 | | 20 | | | 20 | | | 20 | |
| 51 | 9 | 11 | 8 | 12 | 2 | 18 | 18 | 2 | 2 | 18 | | | | | | | | | | | | | | | |
| 57 | | | | | | | | | | | 8 | 12 | 15 | 5 | 15 | 5 | | 20 | | | 20 | | | 20 | |
| 69 | 16 | 4 | 16 | 4 | 10 | 10 | 20 | | 3 | 17 | | | | | | | | | | | | | | | |
| 79 | 19 | 1 | 18 | 2 | 11 | 9 | 20 | | 3 | 17 | 16 | 4 | 18 | 2 | 20 | | | 14 | 6 | | 15 | 5 | | 20 | |
| 96 | | | | | | | | | | | 17 | 3 | 20 | | 20 | | | 4 | 16 | | 12 | 8 | 1 | 18 | 1 |
| 100 | 19 | 1 | 18 | 2 | 14 | 6 | 20 | | 10 | 10 | | | | | | | | | | | | | | | |
| 118 | 20 | | 19 | 1 | 18 | 2 | 20 | | 15 | 5 | | | | | | | | | | | | | | | |
| 120 | | | | | | | | | | | 18 | 2 | 20 | | 20 | | | | 20 | | | 20 | 1 | 13 | 6 |

*Plants N21-102, 104, 107 are control plants transformed with PTR:NPTII.

TABLE 17

Percentage mortality and mean weight of *Manduca sexta* larvae after a certain period of feeding on tobacco leaves from plants transformed with pGS1151. Complete results from the 2 independent Experiments I and II (Tables 15 and 16) are compiled. Kanamycin resistance levels of the plants expressing the Bt:NPT2 fusion protein are also given (ug/ml Km on which good callus growth still occurs).

| Plant No. | Km<sup>R</sup> (ug/ml Km) | % Mortality Exp. I (after 168 h) | Exp. II (after 118 h) (or 120 h*) | Mean Weight Surviving Larvae (mg/larva) Exp. I (after 168 h) |
|---|---|---|---|---|
| N21-3 | 200 | 15 | N.T. | 34.0 |
| 5 | 200 | 30 | N.T. | 52.4 |
| 11 | 500 | 100 | 100 | — |
| 12 | 500 | 40 | N.T. | 16.6 |
| 16 | 200 | 45 | N.T. | 25.3 |
| 17 | 500 | 75 | N.T. | 13.4 |
| 18 | 500 | 85 | 95 | 9.0 |
| 23 | 500 | 90 | 100* | 12.5 |
| 29 | 200 | 55 | N.T. | 21.9 |
| 32 | 200 | 50 | N.T. | 27.4 |
| 33 | 500 | 40 | N.T. | 27.7 |
| 35 | 500 | 85 | 90 | 18.7 |
| 40 | 200 | 20 | N.T. | 28.6 |
| 41 | 200 | 15 | N.T. | 29.1 |
| 42 | 200 | 55 | N.T. | 18.7 |
| 43 | 500 | 75 | 90 | 15.5 |
| 45 | 200 | 30 | N.T. | 13.7 |
| 50 | 500 | 75 | 100 | 10.7 |
| 53 | 500 | 90 | 100* | 12.5 |
| 56 | 200 | 20 | 75 | 22.4 |
| Controls: | | | | |
| N21-102 | — | N.T. | 0* | N.T. |
| 104 | — | N.T. | 0* | N.T. |
| 107 | — | 15 | 5* | 44.1 |

N.T. = Not Tested

TABLE 18

Frequency of Nopaline Positive Plants in the F<sub>1</sub> Generation Derived from Transformed Tobacco Plants

| Plant No of Parental Plant | Age of the Seedlings Tested (wks) | Total Number of Plants Tested | Nopaline Positive | % Nopaline Positives |
|---|---|---|---|---|
| 147-8 | 3 | 74 | 56 | 76% |
|  | 7 | 13 | 11 | 85% |
| 10-1 | 3 | 25 | 20 | 80% |
|  | 7 | 9 | 7 | 78% |
| 161-9 | 3 | 66 | 18<sup>(x)</sup> | 27% |
|  | 7 | 107 | 81 | 76% |
| 174 | 6 | 45 | 43 | 95% |

<sup>(x)</sup>Nopaline Signal Very Weak.

---

We claim:

1. A chimeric gene comprising:
(1) a DNA fragment encoding an insecticidal *Bacillus thuringiensis* Bt2 toxin of about 60 to about 80 kD, wherein said Bt2 toxin comprises the amino acid sequence of SEQ ID No. 1 from amino acid position 29 to amino acid position 607; and
(2) a promoter region of a gene naturally expressed in plant cells, wherein said DNA fragment is under the control of said promoter region.

2. The chimeric gene as defined in claim 1, wherein said Bt2 toxin comprises the amino acid sequence of SEQ ID No. 1 from amino acid position 1 to an amino acid position between amino acid position 607 and amino acid position 725.

3. The chimeric gene as defined in claim 1, wherein said Bt2 toxin comprises the amino acid sequence of SEQ ID No. 1 from amino acid position 29 to an amino acid position between amino acid position 607 and amino acid position 725.

4. The chimeric gene as defined in claim 1, wherein said Bt2 toxin comprises the amino acid sequence of SEQ ID No. 1 from amino acid position 1 to amino acid position 607.

5. The chimeric gene as defined in claim 1, wherein said Bt2 toxin comprises the amino acid sequence of SEQ ID No. 1 from amino acid position 1 to amino acid position 725.

6. The chimeric gene as defined in claim 1, wherein said Bt2 toxin comprises the amino acid sequence of SEQ ID No. 1 from amino acid position 29 to amino acid position 725.

7. The chimeric gene as defined in claim 1, wherein said DNA fragment is artificially made.

8. The chimeric gene as defined in any of claims 2 to 6, wherein said DNA fragment is artificially made.

9. A chimeric gene comprising:
(1) a DNA fragment encoding an insecticidal *Bacillus thuringiensis* Bt2 toxin of about 60 to about 80 kD, wherein said DNA fragment comprises the DNA sequence of SEQ ID No. 1 from nucleotide position 225 to nucleotide position 1961; and
(2) a promoter region of a gene naturally expressed in plant cells, wherein said DNA fragment is under the control of said promoter region.

10. The chimeric gene as defined in claim 9, wherein said DNA fragment encoding an insecticidal *Bacillus thuringiensis* Bt2 toxin of about 60 to about 80 kD comprises the sequence of SEQ ID No. 1 from nucleotide position 141 to a nucleotide position between nucleotide position 1961 and nucleotide position 2314.

11. The chimeric gene as defined in claim 9, wherein said DNA fragment encoding an insecticidal *Bacillus thuringiensis* Bt2 toxin of about 60 to about 80 kD comprises the sequence of SEQ ID No. 1 from nucleotide position 225 to a nucleotide position between nucleotide position 1961 and nucleotide position 2314.

12. The chimeric gene as defined in claims 1 or 9, wherein said promoter region is from a ribulose bisphosphate carboxylase small subunit gene, a TR-DNA gene, a Cauliflower Mosaic Virus 35S gene, or a nopaline synthase gene.

13. The chimeric gene as defined in claims 1 or 9, wherein said promoter region regulates tissue-specific or inducible expression in a plant.

14. The chimeric gene as defined in claim 1 or 9, which further comprises a 3' untranslated region, including a polyadenylation site, of a gene naturally expressed in plant cells.

15. The chimeric gene as defined in claim 14, wherein said 3' untranslated end, including a polyadenylation site, is from an octopine synthase gene, a T-DNA gene 7, a nopaline synthase gene or a ribulose bisphosphate small subunit gene.

* * * * *

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
      ( A ) LENGTH: 4014 base pairs
      ( B ) TYPE: nucleic acid
      ( C ) STRANDEDNESS: double
      ( D ) TOPOLOGY: linear ( i i ) MOLECULE TYPE: DNA (genomic)

( v i ) ORIGINAL SOURCE:
      ( A ) ORGANISM: Bacillus thuringiensis
      ( B ) STRAIN: berliner 1715

( i x ) FEATURE:
      ( A ) NAME/KEY: CDS
      ( B ) LOCATION: 141..3608

( x i ) SEQUENCE DESCRIPTION: SEQ ID NO: 1:

```
CAAAAATTGA  TATTTAGTAA  AATTAGTTGC  ACTTTGTGCA  TTTTTTCATA  AGATGAGTCA        60

TATGTTTTAA  ATTGTAGTAA  TGAAAAACAG  TATTATATCA  TAATGAATTG  GTATCTTAAT       120

AAAAGAGATG  GAGGTAACTT  ATG GAT AAC  AAT CCG AAC  ATC AAT GAA  TGC            170
                         Met Asp Asn  Asn Pro Asn  Ile Asn Glu  Cys
                          1            5                         10
```

| | | | | | | | | | | | | | | | | |
|---|---|---|---|---|---|---|---|---|---|---|---|---|---|---|---|---|
| ATT | CCT | TAT | AAT | TGT | TTA | AGT | AAC | CCT | GAA | GTA | GAA | GTA | TTA | GGT | GGA | 218 |
| Ile | Pro | Tyr | Asn | Cys | Leu | Ser | Asn | Pro | Glu | Val | Glu | Val | Leu | Gly | Gly | |
| | | | | 15 | | | | 20 | | | | | | 25 | | |
| GAA | AGA | ATA | GAA | ACT | GGT | TAC | ACC | CCA | ATC | GAT | ATT | TCC | TTG | TCG | CTA | 266 |
| Glu | Arg | Ile | Glu | Thr | Gly | Tyr | Thr | Pro | Ile | Asp | Ile | Ser | Leu | Ser | Leu | |
| | | | 30 | | | | | 35 | | | | 40 | | | | |
| ACG | CAA | TTT | CTT | TTG | AGT | GAA | TTT | GTT | CCC | GGT | GCT | GGA | TTT | GTG | TTA | 314 |
| Thr | Gln | Phe | Leu | Leu | Ser | Glu | Phe | Val | Pro | Gly | Ala | Gly | Phe | Val | Leu | |
| | | | 45 | | | | | 50 | | | | | 55 | | | |
| GGA | CTA | GTT | GAT | ATA | ATA | TGG | GGA | ATT | TTT | GGT | CCC | TCT | CAA | TGG | GAC | 362 |
| Gly | Leu | Val | Asp | Ile | Ile | Trp | Gly | Ile | Phe | Gly | Pro | Ser | Gln | Trp | Asp | |
| | | 60 | | | | | 65 | | | | | 70 | | | | |
| GCA | TTT | CTT | GTA | CAA | ATT | GAA | CAG | TTA | ATT | AAC | CAA | AGA | ATA | GAA | GAA | 410 |
| Ala | Phe | Leu | Val | Gln | Ile | Glu | Gln | Leu | Ile | Asn | Gln | Arg | Ile | Glu | Glu | |
| 75 | | | | | 80 | | | | | 85 | | | | | 90 | |
| TTC | GCT | AGG | AAC | CAA | GCC | ATT | TCT | AGA | TTA | GAA | GGA | CTA | AGC | AAT | CTT | 458 |
| Phe | Ala | Arg | Asn | Gln | Ala | Ile | Ser | Arg | Leu | Glu | Gly | Leu | Ser | Asn | Leu | |
| | | | | 95 | | | | | 100 | | | | | 105 | | |
| TAT | CAA | ATT | TAC | GCA | GAA | TCT | TTT | AGA | GAG | TGG | GAA | GCA | GAT | CCT | ACT | 506 |
| Tyr | Gln | Ile | Tyr | Ala | Glu | Ser | Phe | Arg | Glu | Trp | Glu | Ala | Asp | Pro | Thr | |
| | | | 110 | | | | | 115 | | | | | 120 | | | |
| AAT | CCA | GCA | TTA | AGA | GAA | GAG | ATG | CGT | ATT | CAA | TTC | AAT | GAC | ATG | AAC | 554 |
| Asn | Pro | Ala | Leu | Arg | Glu | Glu | Met | Arg | Ile | Gln | Phe | Asn | Asp | Met | Asn | |
| | | 125 | | | | | 130 | | | | | 135 | | | | |
| AGT | GCC | CTT | ACA | ACC | GCT | ATT | CCT | CTT | TTT | GCA | GTT | CAA | AAT | TAT | CAA | 602 |
| Ser | Ala | Leu | Thr | Thr | Ala | Ile | Pro | Leu | Phe | Ala | Val | Gln | Asn | Tyr | Gln | |
| | 140 | | | | | 145 | | | | | 150 | | | | | |
| GTT | CCT | CTT | TTA | TCA | GTA | TAT | GTT | CAA | GCT | GCA | AAT | TTA | CAT | TTA | TCA | 650 |
| Val | Pro | Leu | Leu | Ser | Val | Tyr | Val | Gln | Ala | Ala | Asn | Leu | His | Leu | Ser | |
| 155 | | | | | 160 | | | | | 165 | | | | | 170 | |
| GTT | TTG | AGA | GAT | GTT | TCA | GTG | TTT | GGA | CAA | AGG | TGG | GGA | TTT | GAT | GCC | 698 |
| Val | Leu | Arg | Asp | Val | Ser | Val | Phe | Gly | Gln | Arg | Trp | Gly | Phe | Asp | Ala | |
| | | | | 175 | | | | | 180 | | | | | 185 | | |
| GCG | ACT | ATC | AAT | AGT | CGT | TAT | AAT | GAT | TTA | ACT | AGG | CTT | ATT | GGC | AAC | 746 |
| Ala | Thr | Ile | Asn | Ser | Arg | Tyr | Asn | Asp | Leu | Thr | Arg | Leu | Ile | Gly | Asn | |
| | | | 190 | | | | | 195 | | | | | 200 | | | |
| TAT | ACA | GAT | CAT | GCT | GTA | CGC | TGG | TAC | AAT | ACG | GGA | TTA | GAG | CGT | GTA | 794 |
| Tyr | Thr | Asp | His | Ala | Val | Arg | Trp | Tyr | Asn | Thr | Gly | Leu | Glu | Arg | Val | |
| | | 205 | | | | | 210 | | | | | 215 | | | | |
| TGG | GGA | CCG | GAT | TCT | AGA | GAT | TGG | ATA | AGA | TAT | AAT | CAA | TTT | AGA | AGA | 842 |
| Trp | Gly | Pro | Asp | Ser | Arg | Asp | Trp | Ile | Arg | Tyr | Asn | Gln | Phe | Arg | Arg | |
| | 220 | | | | | 225 | | | | | 230 | | | | | |
| GAA | TTA | ACA | CTA | ACT | GTA | TTA | GAT | ATC | GTT | TCT | CTA | TTT | CCG | AAC | TAT | 890 |
| Glu | Leu | Thr | Leu | Thr | Val | Leu | Asp | Ile | Val | Ser | Leu | Phe | Pro | Asn | Tyr | |
| 235 | | | | | 240 | | | | | 245 | | | | | 250 | |
| GAT | AGT | AGA | ACG | TAT | CCA | ATT | CGA | ACA | GTT | TCC | CAA | TTA | ACA | AGA | GAA | 938 |
| Asp | Ser | Arg | Thr | Tyr | Pro | Ile | Arg | Thr | Val | Ser | Gln | Leu | Thr | Arg | Glu | |
| | | | | 255 | | | | | 260 | | | | | 265 | | |
| ATT | TAT | ACA | AAC | CCA | GTA | TTA | GAA | AAT | TTT | GAT | GGT | AGT | TTT | CGA | GGC | 986 |
| Ile | Tyr | Thr | Asn | Pro | Val | Leu | Glu | Asn | Phe | Asp | Gly | Ser | Phe | Arg | Gly | |
| | | | 270 | | | | | 275 | | | | | 280 | | | |
| TCG | GCT | CAG | GGC | ATA | GAA | GGA | AGT | ATT | AGG | AGT | CCA | CAT | TTG | ATG | GAT | 1034 |
| Ser | Ala | Gln | Gly | Ile | Glu | Gly | Ser | Ile | Arg | Ser | Pro | His | Leu | Met | Asp | |
| | | 285 | | | | | 290 | | | | | 295 | | | | |
| ATA | CTT | AAC | AGT | ATA | ACC | ATC | TAT | ACG | GAT | GCT | CAT | AGA | GGA | GAA | TAT | 1082 |
| Ile | Leu | Asn | Ser | Ile | Thr | Ile | Tyr | Thr | Asp | Ala | His | Arg | Gly | Glu | Tyr | |
| | 300 | | | | | 305 | | | | | 310 | | | | | |
| TAT | TGG | TCA | GGG | CAT | CAA | ATA | ATG | GCT | TCT | CCT | GTA | GGG | TTT | TCG | GGG | 1130 |
| Tyr | Trp | Ser | Gly | His | Gln | Ile | Met | Ala | Ser | Pro | Val | Gly | Phe | Ser | Gly | |
| 315 | | | | | 320 | | | | | 325 | | | | | 330 | |

| | | | | | | | | | | | | | | | | |
|---|---|---|---|---|---|---|---|---|---|---|---|---|---|---|---|---|
| CCA | GAA | TTC | ACT | TTT | CCG | CTA | TAT | GGA | ACT | ATG | GGA | AAT | GCA | GCT | CCA | 1178 |
| Pro | Glu | Phe | Thr | Phe 335 | Pro | Leu | Tyr | Gly | Thr 340 | Met | Gly | Asn | Ala | Ala 345 | Pro | |
| CAA | CAA | CGT | ATT | GTT | GCT | CAA | CTA | GGT | CAG | GGC | GTG | TAT | AGA | ACA | TTA | 1226 |
| Gln | Gln | Arg | Ile 350 | Val | Ala | Gln | Leu | Gly 355 | Gln | Gly | Val | Tyr | Arg 360 | Thr | Leu | |
| TCG | TCC | ACT | TTA | TAT | AGA | AGA | CCT | TTT | AAT | ATA | GGG | ATA | AAT | AAT | CAA | 1274 |
| Ser | Ser | Thr 365 | Leu | Tyr | Arg | Arg | Pro 370 | Phe | Asn | Ile | Gly | Ile 375 | Asn | Asn | Gln | |
| CAA | CTA | TCT | GTT | CTT | GAC | GGG | ACA | GAA | TTT | GCT | TAT | GGA | ACC | TCC | TCA | 1322 |
| Gln | Leu 380 | Ser | Val | Leu | Asp | Gly | Thr 385 | Glu | Phe | Ala | Tyr | Gly 390 | Thr | Ser | Ser | |
| AAT | TTG | CCA | TCC | GCT | GTA | TAC | AGA | AAA | AGC | GGA | ACG | GTA | GAT | TCG | CTG | 1370 |
| Asn 395 | Leu | Pro | Ser | Ala | Val 400 | Tyr | Arg | Lys | Ser | Gly 405 | Thr | Val | Asp | Ser | Leu 410 | |
| GAT | GAA | ATA | CCG | CCA | CAG | AAT | AAC | AAC | GTG | CCA | CCT | AGG | CAA | GGA | TTT | 1418 |
| Asp | Glu | Ile | Pro | Pro 415 | Gln | Asn | Asn | Asn | Val 420 | Pro | Pro | Arg | Gln | Gly 425 | Phe | |
| AGT | CAT | CGA | TTA | AGC | CAT | GTT | TCA | ATG | TTT | CGT | TCA | GGC | TTT | AGT | AAT | 1466 |
| Ser | His | Arg | Leu 430 | Ser | His | Val | Ser | Met 435 | Phe | Arg | Ser | Gly | Phe 440 | Ser | Asn | |
| AGT | AGT | GTA | AGT | ATA | ATA | AGA | GCT | CCT | ATG | TTC | TCT | TGG | ATA | CAT | CGT | 1514 |
| Ser | Ser | Val | Ser 445 | Ile | Ile | Arg | Ala | Pro 450 | Met | Phe | Ser | Trp | Ile 455 | His | Arg | |
| AGT | GCT | GAA | TTT | AAT | AAT | ATA | ATT | CCT | TCA | TCA | CAA | ATT | ACA | CAA | ATA | 1562 |
| Ser | Ala | Glu 460 | Phe | Asn | Asn | Ile | Ile 465 | Pro | Ser | Ser | Gln | Ile 470 | Thr | Gln | Ile | |
| CCT | TTA | ACA | AAA | TCT | ACT | AAT | CTT | GGC | TCT | GGA | ACT | TCT | GTC | GTT | AAA | 1610 |
| Pro 475 | Leu | Thr | Lys | Ser | Thr 480 | Asn | Leu | Gly | Ser | Gly 485 | Thr | Ser | Val | Val | Lys 490 | |
| GGA | CCA | GGA | TTT | ACA | GGA | GGA | GAT | ATT | CTT | CGA | AGA | ACT | TCA | CCT | GGC | 1658 |
| Gly | Pro | Gly | Phe | Thr 495 | Gly | Gly | Asp | Ile | Leu 500 | Arg | Arg | Thr | Ser | Pro 505 | Gly | |
| CAG | ATT | TCA | ACC | TTA | AGA | GTA | AAT | ATT | ACT | GCA | CCA | TTA | TCA | CAA | AGA | 1706 |
| Gln | Ile | Ser | Thr 510 | Leu | Arg | Val | Asn | Ile 515 | Thr | Ala | Pro | Leu | Ser 520 | Gln | Arg | |
| TAT | CGG | GTA | AGA | ATT | CGC | TAC | GCT | TCT | ACC | ACA | AAT | TTA | CAA | TTC | CAT | 1754 |
| Tyr | Arg | Val 525 | Arg | Ile | Arg | Tyr | Ala 530 | Ser | Thr | Thr | Asn | Leu 535 | Gln | Phe | His | |
| ACA | TCA | ATT | GAC | GGA | AGA | CCT | ATT | AAT | CAG | GGG | AAT | TTT | TCA | GCA | ACT | 1802 |
| Thr | Ser | Ile 540 | Asp | Gly | Arg | Pro | Ile 545 | Asn | Gln | Gly | Asn | Phe 550 | Ser | Ala | Thr | |
| ATG | AGT | AGT | GGG | AGT | AAT | TTA | CAG | TCC | GGA | AGC | TTT | AGG | ACT | GTA | GGT | 1850 |
| Met 555 | Ser | Ser | Gly | Ser | Asn 560 | Leu | Gln | Ser | Gly | Ser 565 | Phe | Arg | Thr | Val | Gly 570 | |
| TTT | ACT | ACT | CCG | TTT | AAC | TTT | TCA | AAT | GGA | TCA | AGT | GTA | TTT | ACG | TTA | 1898 |
| Phe | Thr | Thr | Pro | Phe 575 | Asn | Phe | Ser | Asn | Gly 580 | Ser | Ser | Val | Phe | Thr 585 | Leu | |
| AGT | GCT | CAT | GTC | TTC | AAT | TCA | GGC | AAT | GAA | GTT | TAT | ATA | GAT | CGA | ATT | 1946 |
| Ser | Ala | His | Val 590 | Phe | Asn | Ser | Gly | Asn 595 | Glu | Val | Tyr | Ile | Asp 600 | Arg | Ile | |
| GAA | TTT | GTT | CCG | GCA | GAA | GTA | ACC | TTT | GAG | GCA | GAA | TAT | GAT | TTA | GAA | 1994 |
| Glu | Phe | Val 605 | Pro | Ala | Glu | Val | Thr 610 | Phe | Glu | Ala | Glu | Tyr 615 | Asp | Leu | Glu | |
| AGA | GCA | CAA | AAG | GCG | GTG | AAT | GAG | CTG | TTT | ACT | TCT | TCC | AAT | CAA | ATC | 2042 |
| Arg | Ala | Gln 620 | Lys | Ala | Val | Asn | Glu 625 | Leu | Phe | Thr | Ser | Ser 630 | Asn | Gln | Ile | |
| GGG | TTA | AAA | ACA | GAT | GTG | ACG | GAT | TAT | CAT | ATT | GAT | CAA | GTA | TCC | AAT | 2090 |
| Gly | Leu | Lys | Thr | Asp 640 | Val | Thr | Asp | Tyr | His 645 | Ile | Asp | Gln | Val | Ser 650 | Asn | |

| | | | | | | | | | | | | | | | | |
|---|---|---|---|---|---|---|---|---|---|---|---|---|---|---|---|---|
| TTA | GTT | GAG | TGT | TTA | TCT | GAT | GAA | TTT | TGT | CTG | GAT | GAA | AAA | AAA | GAA | 2138 |
| Leu | Val | Glu | Cys<br>655 | Leu | Ser | Asp | Glu | Phe<br>660 | Cys | Leu | Asp | Glu | Lys | Lys<br>665 | Glu | |
| TTG | TCC | GAG | AAA | GTC | AAA | CAT | GCG | AAG | CGA | CTT | AGT | GAT | GAG | CGG | AAT | 2186 |
| Leu | Ser | Glu | Lys<br>670 | Val | Lys | His | Ala<br>675 | Lys | Arg | Leu | Ser | Asp<br>680 | Glu | Arg | Asn | |
| TTA | CTT | CAA | GAT | CCA | AAC | TTT | AGA | GGG | ATC | AAT | AGA | CAA | CTA | GAC | CGT | 2234 |
| Leu | Leu | Gln<br>685 | Asp | Pro | Asn | Phe | Arg<br>690 | Gly | Ile | Asn | Arg | Gln<br>695 | Leu | Asp | Arg | |
| GGC | TGG | AGA | GGA | AGT | ACG | GAT | ATT | ACC | ATC | CAA | GGA | GGC | GAT | GAC | GTA | 2282 |
| Gly | Trp<br>700 | Arg | Gly | Ser | Thr | Asp<br>705 | Ile | Thr | Ile | Gln | Gly<br>710 | Gly | Asp | Asp | Val | |
| TTC | AAA | GAG | AAT | TAC | GTT | ACG | CTA | TTG | GGT | ACC | TTT | GAT | GAG | TGC | TAC | 2330 |
| Phe | Lys | Glu | Asn<br>715 | Tyr | Val | Thr | Leu<br>720 | Leu | Gly | Thr | Phe<br>725 | Asp | Glu | Cys | Tyr<br>730 | |
| TTA | ACG | TAT | TTA | TAT | CAA | AAA | ATA | GAT | GAG | TCG | AAA | TTA | AAA | GCC | TAT | 2378 |
| Leu | Thr | Tyr | Leu | Tyr<br>735 | Gln | Lys | Ile | Asp | Glu<br>740 | Ser | Lys | Leu | Lys | Ala<br>745 | Tyr | |
| ACC | CGT | TAC | CAA | TTA | AGA | GGG | TAT | ATC | GAA | GAT | AGT | CAA | GAC | TTA | GAA | 2426 |
| Thr | Arg | Tyr | Gln<br>750 | Leu | Arg | Gly | Tyr | Ile<br>755 | Glu | Asp | Ser | Gln | Asp<br>760 | Leu | Glu | |
| ATC | TAT | TTA | ATT | CGC | TAC | AAT | GCC | AAA | CAC | GAA | ACA | GTA | AAT | GTG | CCA | 2474 |
| Ile | Tyr | Leu | Ile<br>765 | Arg | Tyr | Asn | Ala | Lys<br>770 | His | Glu | Thr | Val | Asn<br>775 | Val | Pro | |
| GGT | ACG | GGT | TCC | TTA | TGG | CGC | CTT | TCA | GCC | CCA | AGT | CCA | ATC | GGA | AAA | 2522 |
| Gly | Thr<br>780 | Gly | Ser | Leu | Trp | Arg<br>785 | Leu | Ser | Ala | Pro | Ser<br>790 | Pro | Ile | Gly | Lys | |
| TGT | GCC | CAT | CAT | TCC | CAT | CAT | TTC | TCC | TTG | GAC | ATT | GAT | GTT | GGA | TGT | 2570 |
| Cys<br>795 | Ala | His | His | Ser | His<br>800 | His | Phe | Ser | Leu | Asp<br>805 | Ile | Asp | Val | Gly | Cys<br>810 | |
| ACA | GAC | TTA | AAT | GAG | GAC | TTA | GGT | GTA | TGG | GTG | ATA | TTC | AAG | ATT | AAG | 2618 |
| Thr | Asp | Leu | Asn | Glu<br>815 | Asp | Leu | Gly | Val | Trp<br>820 | Val | Ile | Phe | Lys | Ile<br>825 | Lys | |
| ACG | CAA | GAT | GGC | CAT | GCA | AGA | CTA | GGA | AAT | CTA | GAA | TTT | CTC | GAA | GAG | 2666 |
| Thr | Gln | Asp | Gly<br>830 | His | Ala | Arg | Leu | Gly<br>835 | Asn | Leu | Glu | Phe | Leu<br>840 | Glu | Glu | |
| AAA | CCA | TTA | GTA | GGA | GAA | GCA | CTA | GCT | CGT | GTG | AAA | AGA | GCG | GAG | AAA | 2714 |
| Lys | Pro | Leu | Val<br>845 | Gly | Glu | Ala | Leu | Ala<br>850 | Arg | Val | Lys | Arg | Ala<br>855 | Glu | Lys | |
| AAA | TGG | AGA | GAC | AAA | CGT | GAA | AAA | TTG | GAA | TGG | GAA | ACA | AAT | ATT | GTT | 2762 |
| Lys | Trp<br>860 | Arg | Asp | Lys | Arg | Glu<br>865 | Lys | Leu | Glu | Trp | Glu<br>870 | Thr | Asn | Ile | Val | |
| TAT | AAA | GAG | GCA | AAA | GAA | TCT | GTA | GAT | GCT | TTA | TTT | GTA | AAC | TCT | CAA | 2810 |
| Tyr | Lys<br>875 | Glu | Ala | Lys | Glu | Ser<br>880 | Val | Asp | Ala | Leu | Phe<br>885 | Val | Asn | Ser | Gln<br>890 | |
| TAT | GAT | AGA | TTA | CAA | GCG | GAT | ACC | AAC | ATC | GCG | ATG | ATT | CAT | GCG | GCA | 2858 |
| Tyr | Asp | Arg | Leu | Gln<br>895 | Ala | Asp | Thr | Asn | Ile<br>900 | Ala | Met | Ile | His | Ala<br>905 | Ala | |
| GAT | AAA | CGC | GTT | CAT | AGC | ATT | CGA | GAA | GCT | TAT | CTG | CCT | GAG | CTG | TCT | 2906 |
| Asp | Lys | Arg | Val<br>910 | His | Ser | Ile | Arg | Glu<br>915 | Ala | Tyr | Leu | Pro | Glu<br>920 | Leu | Ser | |
| GTG | ATT | CCG | GGT | GTC | AAT | GCG | GCT | ATT | TTT | GAA | GAA | TTA | GAA | GGG | CGT | 2954 |
| Val | Ile | Pro<br>925 | Gly | Val | Asn | Ala | Ala<br>930 | Ile | Phe | Glu | Glu | Leu<br>935 | Glu | Gly | Arg | |
| ATT | TTC | ACT | GCA | TTC | TCC | CTA | TAT | GAT | GCG | AGA | AAT | GTC | ATT | AAA | AAT | 3002 |
| Ile | Phe | Thr | Ala<br>940 | Phe | Ser | Leu | Tyr | Asp<br>945 | Ala | Arg | Asn | Val | Ile<br>950 | Lys | Asn | |
| GGT | GAT | TTT | AAT | AAT | GGC | TTA | TCC | TGC | TGG | AAC | GTG | AAA | GGG | CAT | GTA | 3050 |
| Gly | Asp | Phe | Asn<br>955 | Asn | Gly | Leu | Ser<br>960 | Cys | Trp | Asn | Val | Lys<br>965 | Gly | His | Val<br>970 | |

| | | | | | | | | | | | | | | | |
|---|---|---|---|---|---|---|---|---|---|---|---|---|---|---|---|
| GAT | GTA | GAA | GAA | CAA | AAC | AAC | CAC | CGT | TCG | GTC | CTT | GTT | GTT | CCG | GAA | 3098 |
| Asp | Val | Glu | Glu | Gln | Asn | Asn | His | Arg | Ser | Val | Leu | Val | Val | Pro | Glu | |
| | | | 975 | | | | | 980 | | | | | 985 | | |

```
TGG  GAA  GCA  GAA  GTG  TCA  CAA  GAA  GTT  CGT  GTC  TGT  CCG  GGT  CGT  GGC      3146
Trp  Glu  Ala  Glu  Val  Ser  Gln  Glu  Val  Arg  Val  Cys  Pro  Gly  Arg  Gly
               990                      995                     1000

TAT  ATC  CTT  CGT  GTC  ACA  GCG  TAC  AAG  GAG  GGA  TAT  GGA  GAA  GGT  TGC      3194
Tyr  Ile  Leu  Arg  Val  Thr  Ala  Tyr  Lys  Glu  Gly  Tyr  Gly  Glu  Gly  Cys
               1005                     1010                    1015

GTA  ACC  ATT  CAT  GAG  ATC  GAG  AAC  AAT  ACA  GAC  GAA  CTG  AAG  TTT  AGC      3242
Val  Thr  Ile  His  Glu  Ile  Glu  Asn  Asn  Thr  Asp  Glu  Leu  Lys  Phe  Ser
               1020                    1025                     1030

AAC  TGT  GTA  GAA  GAG  GAA  GTA  TAT  CCA  AAC  AAC  ACG  GTA  ACG  TGT  AAT      3290
Asn  Cys  Val  Glu  Glu  Glu  Val  Tyr  Pro  Asn  Asn  Thr  Val  Thr  Cys  Asn
1035                     1040                    1045                    1050

GAT  TAT  ACT  GCG  ACT  CAA  GAA  GAA  TAT  GAG  GGT  ACG  TAC  ACT  TCT  CGT      3338
Asp  Tyr  Thr  Ala  Thr  Gln  Glu  Glu  Tyr  Glu  Gly  Thr  Tyr  Thr  Ser  Arg
               1055                    1060                     1065

AAT  CGA  GGA  TAT  GAC  GGA  GCC  TAT  GAA  AGC  AAT  TCT  TCT  GTA  CCA  GCT      3386
Asn  Arg  Gly  Tyr  Asp  Gly  Ala  Tyr  Glu  Ser  Asn  Ser  Ser  Val  Pro  Ala
               1070                    1075                     1080

GAT  TAT  GCA  TCA  GCC  TAT  GAA  GAA  AAA  GCA  TAT  ACA  GAT  GGA  CGA  AGA      3434
Asp  Tyr  Ala  Ser  Ala  Tyr  Glu  Glu  Lys  Ala  Tyr  Thr  Asp  Gly  Arg  Arg
               1085                    1090                     1095

GAC  AAT  CCT  TGT  GAA  TCT  AAC  AGA  GGA  TAT  GGG  GAT  TAC  ACA  CCA  CTA      3482
Asp  Asn  Pro  Cys  Glu  Ser  Asn  Arg  Gly  Tyr  Gly  Asp  Tyr  Thr  Pro  Leu
               1100                    1105                     1110

CCA  GCT  GGC  TAT  GTG  ACA  AAA  GAA  TTA  GAG  TAC  TTC  CCA  GAA  ACC  GAT      3530
Pro  Ala  Gly  Tyr  Val  Thr  Lys  Glu  Leu  Glu  Tyr  Phe  Pro  Glu  Thr  Asp
1115                     1120                    1125                    1130

AAG  GTA  TGG  ATT  GAG  ATC  GGA  GAA  ACG  GAA  GGA  ACA  TTC  ATC  GTG  GAC      3578
Lys  Val  Trp  Ile  Glu  Ile  Gly  Glu  Thr  Glu  Gly  Thr  Phe  Ile  Val  Asp
               1135                    1140                     1145

AGC  GTG  GAA  TTA  CTT  CTT  ATG  GAG  GAA  TAATATATGC TTTAAAATGT                   3625
Ser  Val  Glu  Leu  Leu  Leu  Met  Glu  Glu
               1150                    1155

AAGGTGTGCA  AATAAAGAAT  GATTACTGAC  TTGTATTGAC  AGATAAATAA  GGAAATTTTT              3685

ATATGAATAA  AAAACGGGCA  TCACTCTTAA  AAGAATGATG  TCCGTTTTTT  GTATGATTTA              3745

ACGAGTGATA  TTTAAATGTT  TTTTGCGAA   GGCTTTACTT  AACGGGTAC   CGCCACATGC              3805

CCATCAACTT  AAGAATTTGC  ACTACCCCCA  AGTGTCAAAA  AACGTTATTC  TTTCTAAAAA              3865

GCTAGCTAGA  AAGGATGACA  TTTTTTATGA  ATCTTTCAAT  TCAAGATGAA  TTACAACTAT              3925

TTTCTGAAGA  GCTGTATCGT  CATTTAACCC  CTTCTCTTTT  GGAAGAACTC  GCTAAAGAAT              3985

TAGGTTTTGT  AAAAAGAAAA  CGAAAGTTT                                                   4014
```

( 2 ) INFORMATION FOR SEQ ID NO: 2:

( i ) SEQUENCE CHARACTERISTICS:
        ( A ) LENGTH: 1155 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Asp  Asn  Asn  Pro  Asn  Ile  Asn  Glu  Cys  Ile  Pro  Tyr  Asn  Cys  Leu
  1                 5                    10                       15

Ser  Asn  Pro  Glu  Val  Glu  Val  Leu  Gly  Gly  Glu  Arg  Ile  Glu  Thr  Gly
                20                   25                           30
```

```
Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                      70              75                      80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460
```

| | | | | | | | | | | | | | | | |
|---|---|---|---|---|---|---|---|---|---|---|---|---|---|---|---|
| Ile | Ile | Pro | Ser | Ser | Gln | Ile | Thr | Gln | Ile | Pro | Leu | Thr | Lys | Ser | Thr |
| 465 | | | | | 470 | | | | 475 | | | | | | 480 |
| Asn | Leu | Gly | Ser | Gly | Thr | Ser | Val | Val | Lys | Gly | Pro | Gly | Phe | Thr | Gly |
| | | | | 485 | | | | | 490 | | | | | 495 | |
| Gly | Asp | Ile | Leu | Arg | Arg | Thr | Ser | Pro | Gly | Gln | Ile | Ser | Thr | Leu | Arg |
| | | | 500 | | | | | 505 | | | | | 510 | | |
| Val | Asn | Ile | Thr | Ala | Pro | Leu | Ser | Gln | Arg | Tyr | Arg | Val | Arg | Ile | Arg |
| | | 515 | | | | | 520 | | | | | 525 | | | |
| Tyr | Ala | Ser | Thr | Thr | Asn | Leu | Gln | Phe | His | Thr | Ser | Ile | Asp | Gly | Arg |
| | 530 | | | | | 535 | | | | | 540 | | | | |
| Pro | Ile | Asn | Gln | Gly | Asn | Phe | Ser | Ala | Thr | Met | Ser | Ser | Gly | Ser | Asn |
| 545 | | | | | 550 | | | | | 555 | | | | | 560 |
| Leu | Gln | Ser | Gly | Ser | Phe | Arg | Thr | Val | Gly | Phe | Thr | Thr | Pro | Phe | Asn |
| | | | | 565 | | | | | 570 | | | | | 575 | |
| Phe | Ser | Asn | Gly | Ser | Ser | Val | Phe | Thr | Leu | Ser | Ala | His | Val | Phe | Asn |
| | | | 580 | | | | | 585 | | | | | 590 | | |
| Ser | Gly | Asn | Glu | Val | Tyr | Ile | Asp | Arg | Ile | Glu | Phe | Val | Pro | Ala | Glu |
| | | | 595 | | | | 600 | | | | | 605 | | | |
| Val | Thr | Phe | Glu | Ala | Glu | Tyr | Asp | Leu | Glu | Arg | Ala | Gln | Lys | Ala | Val |
| | | 610 | | | | 615 | | | | | 620 | | | | |
| Asn | Glu | Leu | Phe | Thr | Ser | Ser | Asn | Gln | Ile | Gly | Leu | Lys | Thr | Asp | Val |
| 625 | | | | | 630 | | | | | 635 | | | | | 640 |
| Thr | Asp | Tyr | His | Ile | Asp | Gln | Val | Ser | Asn | Leu | Val | Glu | Cys | Leu | Ser |
| | | | | 645 | | | | | 650 | | | | | 655 | |
| Asp | Glu | Phe | Cys | Leu | Asp | Glu | Lys | Lys | Glu | Leu | Ser | Glu | Lys | Val | Lys |
| | | | 660 | | | | | 665 | | | | | 670 | | |
| His | Ala | Lys | Arg | Leu | Ser | Asp | Glu | Arg | Asn | Leu | Leu | Gln | Asp | Pro | Asn |
| | | 675 | | | | | 680 | | | | | 685 | | | |
| Phe | Arg | Gly | Ile | Asn | Arg | Gln | Leu | Asp | Arg | Gly | Trp | Arg | Gly | Ser | Thr |
| | 690 | | | | | 695 | | | | | 700 | | | | |
| Asp | Ile | Thr | Ile | Gln | Gly | Gly | Asp | Asp | Val | Phe | Lys | Glu | Asn | Tyr | Val |
| 705 | | | | | 710 | | | | | 715 | | | | | 720 |
| Thr | Leu | Leu | Gly | Thr | Phe | Asp | Glu | Cys | Tyr | Leu | Thr | Tyr | Leu | Tyr | Gln |
| | | | | 725 | | | | | 730 | | | | | 735 | |
| Lys | Ile | Asp | Glu | Ser | Lys | Leu | Lys | Ala | Tyr | Thr | Arg | Tyr | Gln | Leu | Arg |
| | | | 740 | | | | | 745 | | | | | 750 | | |
| Gly | Tyr | Ile | Glu | Asp | Ser | Gln | Asp | Leu | Glu | Ile | Tyr | Leu | Ile | Arg | Tyr |
| | | 755 | | | | | 760 | | | | | 765 | | | |
| Asn | Ala | Lys | His | Glu | Thr | Val | Asn | Val | Pro | Gly | Thr | Gly | Ser | Leu | Trp |
| | 770 | | | | | 775 | | | | | 780 | | | | |
| Arg | Leu | Ser | Ala | Pro | Ser | Pro | Ile | Gly | Lys | Cys | Ala | His | His | Ser | His |
| 785 | | | | | 790 | | | | | 795 | | | | | 800 |
| His | Phe | Ser | Leu | Asp | Ile | Asp | Val | Gly | Cys | Thr | Asp | Leu | Asn | Glu | Asp |
| | | | | 805 | | | | | 810 | | | | | 815 | |
| Leu | Gly | Val | Trp | Val | Ile | Phe | Lys | Ile | Lys | Thr | Gln | Asp | Gly | His | Ala |
| | | | 820 | | | | | 825 | | | | | 830 | | |
| Arg | Leu | Gly | Asn | Leu | Glu | Phe | Leu | Glu | Glu | Lys | Pro | Leu | Val | Gly | Glu |
| | | 835 | | | | | 840 | | | | | 845 | | | |
| Ala | Leu | Ala | Arg | Val | Lys | Arg | Ala | Glu | Lys | Lys | Trp | Arg | Asp | Lys | Arg |
| | 850 | | | | | 855 | | | | | 860 | | | | |
| Glu | Lys | Leu | Glu | Trp | Glu | Thr | Asn | Ile | Val | Tyr | Lys | Glu | Ala | Lys | Glu |
| 865 | | | | | 870 | | | | | 875 | | | | | 880 |
| Ser | Val | Asp | Ala | Leu | Phe | Val | Asn | Ser | Gln | Tyr | Asp | Arg | Leu | Gln | Ala |

|   |   |   |   |   | 885 |   |   |   |   | 890 |   |   |   |   | 895 |   |
|---|---|---|---|---|---|---|---|---|---|---|---|---|---|---|---|---|

Asp Thr Asn Ile Ala Met Ile His Ala Ala Asp Lys Arg Val His Ser
            900           905           910
Ile Arg Glu Ala Tyr Leu Pro Glu Leu Ser Val Ile Pro Gly Val Asn
        915           920           925
Ala Ala Ile Phe Glu Glu Leu Glu Gly Arg Ile Phe Thr Ala Phe Ser
930               935               940
Leu Tyr Asp Ala Arg Asn Val Ile Lys Asn Gly Asp Phe Asn Asn Gly
945           950           955               960
Leu Ser Cys Trp Asn Val Lys Gly His Val Asp Val Glu Glu Gln Asn
            965           970           975
Asn His Arg Ser Val Leu Val Val Pro Glu Trp Glu Ala Glu Val Ser
        980           985           990
Gln Glu Val Arg Val Cys Pro Gly Arg Gly Tyr Ile Leu Arg Val Thr
        995           1000          1005
Ala Tyr Lys Glu Gly Tyr Gly Glu Gly Cys Val Thr Ile His Glu Ile
        1010          1015          1020
Glu Asn Asn Thr Asp Glu Leu Lys Phe Ser Asn Cys Val Glu Glu Glu
1025          1030          1035          1040
Val Tyr Pro Asn Asn Thr Val Thr Cys Asn Asp Tyr Thr Ala Thr Gln
            1045          1050          1055
Glu Glu Tyr Glu Gly Thr Tyr Thr Ser Arg Asn Arg Gly Tyr Asp Gly
        1060          1065          1070
Ala Tyr Glu Ser Asn Ser Ser Val Pro Ala Asp Tyr Ala Ser Ala Tyr
        1075          1080          1085
Glu Glu Lys Ala Tyr Thr Asp Gly Arg Arg Asp Asn Pro Cys Glu Ser
        1090          1095          1100
Asn Arg Gly Tyr Gly Asp Tyr Thr Pro Leu Pro Ala Gly Tyr Val Thr
1105          1110          1115          1120
Lys Glu Leu Glu Tyr Phe Pro Glu Thr Asp Lys Val Trp Ile Glu Ile
            1125          1130          1135
Gly Glu Thr Glu Gly Thr Phe Ile Val Asp Ser Val Glu Leu Leu Leu
            1140          1145          1150
Met Glu Glu
        1155

( 2 ) INFORMATION FOR SEQ ID NO: 3:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Bacillus thuringiensis ( i x ) FEATURE:
        ( A ) NAME/KEY: Peptide
        ( B ) LOCATION: 1..19
        ( D ) OTHER INFORMATION: /note="N-terminal amino acids of
            Bt Whiteley protein"

( x i ) SEQUENCE DESCRIPTION: SEQ ID NO: 3:

Met Asp Asn Asn Pro Asn Ile Asn Glu Cys Ile Pro Tyr Asn Cys Leu
1               5                   10                  15
Ser Asn Pro (2) INFORMATION FOR SEQ ID NO: 4:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
        (A) ORGANISM: Bacillus thuringiensis
        (B) STRAIN: berliner 1715

(ix) FEATURE:
        (A) NAME/KEY: Peptide
        (B) LOCATION: 1..19
        (D) OTHER INFORMATION: /note="N-terminal amino acids of
            130 kD Bt2 protein, determined after N-terminal
            sequencing (Xaa=unknown)"

(xi) SEQUENCE DESCRIPTION: SEQ ID NO: 4:

| Xaa | Asp | Asn | Asn | Pro | Asn | Ile | Asn | Glu | Xaa | Ile | Pro | Tyr | Asn | Xaa | Leu |
|---|---|---|---|---|---|---|---|---|---|---|---|---|---|---|---|
| 1 | | | | 5 | | | | | 10 | | | | | 15 | |

| Xaa | Asn | Pro |
|---|---|---|

(2) INFORMATION FOR SEQ ID NO: 5:

(i) SEQUENCE CHARACTERISTICS:
        (A) LENGTH: 1178 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..1178
        (D) OTHER INFORMATION: /note="deduced amino acid sequence
            of B.t. kurstaki HD73 gene (Adang et al., Gene 36,
            p.289, 1985)"

(xi) SEQUENCE DESCRIPTION: SEQ ID NO: 5:

| Met | Asp | Asn | Asn | Pro | Asn | Ile | Asn | Glu | Cys | Ile | Pro | Tyr | Asn | Cys | Leu |
|---|---|---|---|---|---|---|---|---|---|---|---|---|---|---|---|
| 1 | | | | 5 | | | | | 10 | | | | | 15 | |
| Ser | Asn | Pro | Glu | Val | Glu | Val | Leu | Gly | Gly | Glu | Arg | Ile | Glu | Thr | Gly |
| | | | 20 | | | | | 25 | | | | | 30 | | |
| Tyr | Thr | Pro | Ile | Asp | Ile | Ser | Leu | Ser | Leu | Thr | Gln | Phe | Leu | Leu | Ser |
| | | 35 | | | | | 40 | | | | | 45 | | | |
| Glu | Phe | Val | Pro | Gly | Ala | Gly | Phe | Val | Leu | Gly | Leu | Val | Asp | Ile | Ile |
| | 50 | | | | | 55 | | | | | 60 | | | | |
| Trp | Gly | Ile | Phe | Gly | Pro | Ser | Gln | Trp | Asp | Ala | Phe | Leu | Val | Gln | Ile |
| 65 | | | | | 70 | | | | 75 | | | | | | 80 |
| Glu | Gln | Leu | Ile | Asn | Gln | Arg | Ile | Glu | Glu | Phe | Ala | Arg | Asn | Gln | Ala |
| | | | | 85 | | | | | 90 | | | | | 95 | |
| Ile | Ser | Arg | Leu | Glu | Gly | Leu | Ser | Asn | Leu | Tyr | Gln | Ile | Tyr | Ala | Glu |
| | | | 100 | | | | | 105 | | | | | 110 | | |
| Ser | Phe | Arg | Glu | Trp | Glu | Ala | Asp | Pro | Thr | Asn | Pro | Ala | Leu | Arg | Glu |
| | | 115 | | | | | 120 | | | | | 125 | | | |
| Glu | Met | Arg | Ile | Gln | Phe | Asn | Asp | Met | Asn | Ser | Ala | Leu | Thr | Thr | Ala |
| | 130 | | | | | 135 | | | | | 140 | | | | |
| Ile | Pro | Leu | Phe | Ala | Val | Gln | Asn | Tyr | Gln | Val | Pro | Leu | Leu | Ser | Val |
| 145 | | | | | 150 | | | | | 155 | | | | | 160 |

```
Tyr Val Gln Ala Ala Asn Leu His Leu Ser Val Leu Arg Asp Val Ser
                165                 170                 175
Val Phe Gly Gln Arg Trp Gly Phe Asp Ala Ala Thr Ile Asn Ser Arg
                180                 185                 190
Tyr Asn Asp Leu Thr Arg Leu Ile Gly Asn Tyr Thr Asp Tyr Ala Val
                195                 200                 205
Arg Trp Tyr Asn Thr Gly Leu Glu Arg Val Trp Gly Pro Asp Ser Arg
    210                 215                 220
Asp Trp Val Arg Tyr Asn Gln Phe Arg Arg Glu Leu Thr Leu Thr Val
225                 230                 235                 240
Leu Asp Ile Val Ala Leu Phe Pro Asn Tyr Asp Ser Arg Arg Tyr Pro
                245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Ser Ala Gln Gly Ile Glu
                275                 280                 285
Arg Ser Ile Arg Ser Pro His Leu Met Asp Ile Leu Asn Ser Ile Thr
    290                 295                 300
Ile Tyr Thr Asp Ala His Arg Gly Tyr Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
                355                 360                 365
Arg Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
                420                 425                 430
Val Ser Met Phe Arg Ser Gly Phe Ser Asn Ser Ser Val Ser Ile Ile
                435                 440                 445
Arg Ala Pro Met Phe Ser Trp Ile His Arg Ser Ala Glu Phe Asn Asn
    450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
                485                 490                 495
 Asp Leu Val Arg Leu Asn Ser Ser Gly Asn Asn Ile Gln Asn Arg Gly
                 500                 505                 510
Tyr Ile Glu Val Pro Ile His Phe Pro Ser Thr Ser Thr Arg Tyr Arg
                515                 520                 525
Val Arg Val Arg Tyr Ala Ser Val Thr Pro Ile His Leu Asn Val Asn
    530                 535                 540
Trp Gly Asn Ser Ser Ile Phe Ser Asn Thr Val Pro Ala Thr Ala Thr
545                 550                 555                 560
Ser Leu Asp Asn Leu Gln Ser Ser Asp Phe Gly Tyr Phe Glu Ser Ala
                565                 570                 575
Asn Ala Phe Thr Ser Ser Leu Gly Asn Ile Val Gly Val Arg Asn Phe
                580                 585                 590
```

```
Ser Gly Thr Ala Gly Val Ile Ile Asp Arg Phe Glu Phe Ile Pro Val
    595             600             605
Thr Ala Thr Leu Glu Ala Glu Tyr Asn Leu Glu Arg Ala Gln Lys Ala
610             615             620
Val Asn Ala Leu Phe Thr Ser Thr Asn Gln Leu Gly Leu Lys Thr Asn
625             630             635             640
Val Thr Asp Tyr His Ile Asp Gln Val Ser Asn Leu Val Thr Tyr Leu
                645             650                         655
Ser Asp Glu Phe Cys Leu Asp Glu Lys Arg Glu Leu Ser Glu Lys Val
            660             665             670
Lys His Ala Lys Arg Leu Ser Asp Glu Arg Asn Leu Leu Gln Asp Ser
    675             680             685
Asn Phe Lys Asp Ile Asn Arg Gln Pro Glu Arg Gly Trp Gly Gly Ser
    690             695             700
Thr Gly Ile Thr Ile Gln Gly Gly Asp Asp Val Phe Lys Glu Asn Tyr
705             710             715             720
Val Thr Leu Ser Gly Thr Phe Asp Glu Cys Tyr Pro Thr Tyr Leu Tyr
            725             730             735
Gln Lys Ile Asp Glu Ser Lys Leu Lys Ala Phe Thr Arg Tyr Gln Leu
            740             745             750
Arg Gly Tyr Ile Glu Asp Ser Gln Asp Leu Glu Ile Tyr Leu Ile Arg
        755             760             765
Tyr Asn Ala Lys His Glu Thr Val Asn Val Pro Gly Thr Gly Ser Leu
770             775             780
Trp Pro Leu Ser Ala Gln Ser Pro Ile Gly Lys Cys Gly Glu Pro Asn
785             790             795             800
Arg Cys Ala Pro His Leu Glu Trp Asn Pro Asp Leu Asp Cys Ser Cys
                805             810             815
Arg Asp Gly Glu Lys Cys Ala His His Ser His His Phe Ser Leu Asp
            820             825             830
Ile Asp Val Gly Cys Thr Asp Leu Asn Glu Asp Leu Gly Val Trp Val
            835             840             845
  Ile Phe Lys Ile Lys Thr Gln Asp Gly His Ala Arg Leu Gly Asn Leu
  850             855             860
Glu Phe Leu Glu Glu Lys Pro Leu Val Gly Glu Ala Leu Ala Arg Val
865             870             875             880
Lys Arg Ala Glu Lys Lys Trp Arg Asp Lys Arg Glu Lys Leu Glu Trp
            885             890             895
Glu Thr Asn Ile Val Tyr Lys Glu Ala Lys Glu Ser Val Asp Ala Leu
            900             905             910
Phe Val Asn Ser Gln Tyr Asp Gln Leu Gln Ala Asp Thr Asn Ile Ala
        915             920             925
Met Ile His Ala Ala Asp Lys Arg Val His Ser Ile Arg Glu Ala Tyr
    930             935             940
Leu Pro Glu Leu Ser Val Ile Pro Gly Val Asn Ala Ala Ile Phe Glu
945             950             955             960
Glu Leu Glu Gly Arg Ile Phe Thr Ala Phe Ser Leu Tyr Asp Ala Arg
            965             970             975
Asn Val Ile Lys Asn Gly Asp Phe Asn Asn Gly Leu Ser Cys Trp Asn
            980             985             990
Val Lys Gly His Val Asp Val Glu Glu Gln Asn Asn Gln Arg Ser Val
    995             1000            1005
Leu Val Val Pro Glu Trp Glu Ala Glu Val Ser Gln Glu Val Arg Val
```

|  | 1010 |  |  |  | 1015 |  |  |  | 1020 |  |  |  |  |
|---|---|---|---|---|---|---|---|---|---|---|---|---|---|
| Cys | Pro | Gly | Arg | Gly | Tyr | Ile | Leu | Arg | Val | Thr | Ala | Tyr | Lys | Glu | Gly |
| 1025 |  |  |  |  | 1030 |  |  |  | 1035 |  |  |  |  |  | 1040 |
| Tyr | Gly | Glu | Gly | Cys | Val | Thr | Ile | His | Glu | Ile | Glu | Asn | Asn | Thr | Asp |
|  |  |  |  | 1045 |  |  |  |  | 1050 |  |  |  |  | 1055 |  |
| Glu | Leu | Lys | Phe | Ser | Asn | Cys | Val | Glu | Glu | Glu | Ile | Tyr | Pro | Asn | Asn |
|  |  |  | 1060 |  |  |  |  | 1065 |  |  |  |  | 1070 |  |  |
| Thr | Val | Thr | Cys | Asn | Asp | Tyr | Thr | Val | Asn | Gln | Glu | Glu | Tyr | Gly | Gly |
|  |  | 1075 |  |  |  |  | 1080 |  |  |  |  | 1085 |  |  |  |
| Ala | Tyr | Thr | Ser | Arg | Asn | Arg | Gly | Tyr | Asn | Glu | Ala | Pro | Ser | Val | Pro |
|  | 1090 |  |  |  |  | 1095 |  |  |  |  | 1100 |  |  |  |  |
| Ala | Asp | Tyr | Ala | Ser | Val | Tyr | Glu | Glu | Lys | Ser | Tyr | Thr | Asp | Gly | Arg |
| 1105 |  |  |  |  | 1110 |  |  |  |  | 1115 |  |  |  |  | 1120 |
| Arg | Glu | Asn | Pro | Cys | Glu | Phe | Asn | Arg | Gly | Tyr | Arg | Asp | Tyr | Thr | Pro |
|  |  |  |  | 1125 |  |  |  |  | 1130 |  |  |  |  | 1135 |  |
| Leu | Pro | Val | Gly | Tyr | Val | Thr | Lys | Glu | Leu | Glu | Tyr | Phe | Pro | Glu | Thr |
|  |  |  | 1140 |  |  |  |  | 1145 |  |  |  |  | 1150 |  |  |
| Asp | Lys | Val | Trp | Ile | Glu | Ile | Gly | Glu | Thr | Glu | Gly | Thr | Phe | Ile | Val |
|  |  | 1155 |  |  |  |  | 1160 |  |  |  |  | 1165 |  |  |  |
| Asp | Ser | Val | Glu | Leu | Leu | Leu | Met | Glu | Glu |  |  |  |  |  |  |
|  | 1170 |  |  |  |  | 1175 |  |  |  |  |  |  |  |  |  |

( 2 ) INFORMATION FOR SEQ ID NO: 6:

( i ) SEQUENCE CHARACTERISTICS:
        ( A ) LENGTH: 1176 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 1..1176
        ( D ) OTHER INFORMATION: /note="deduced amino acid sequence
            of the B.t. kurstaki HD1 gene (Schnepf et al.,
            J.B.C. 20, p. 6264, 1985)"

( x i ) SEQUENCE DESCRIPTION: SEQ ID NO: 6:

| Met | Asp | Asn | Asn | Pro | Asn | Ile | Asn | Glu | Cys | Ile | Pro | Tyr | Asn | Cys | Leu |
|---|---|---|---|---|---|---|---|---|---|---|---|---|---|---|---|
| 1 |  |  |  | 5 |  |  |  | 10 |  |  |  |  |  | 15 |  |
| Ser | Asn | Pro | Glu | Val | Glu | Val | Leu | Gly | Gly | Glu | Arg | Ile | Glu | Thr | Gly |
|  |  |  | 20 |  |  |  |  | 25 |  |  |  | 30 |  |  |  |
| Tyr | Thr | Pro | Ile | Asp | Ile | Ser | Leu | Ser | Leu | Thr | Gln | Phe | Leu | Leu | Ser |
|  |  | 35 |  |  |  |  | 40 |  |  |  |  | 45 |  |  |  |
| Glu | Phe | Val | Pro | Gly | Ala | Gly | Phe | Val | Leu | Gly | Leu | Val | Asp | Ile | Ile |
|  | 50 |  |  |  |  | 55 |  |  |  |  | 60 |  |  |  |  |
| Trp | Gly | Ile | Phe | Gly | Pro | Ser | Gln | Trp | Asp | Ala | Phe | Pro | Val | Gln | Ile |
| 65 |  |  |  |  | 70 |  |  |  | 75 |  |  |  |  |  | 80 |
| Glu | Gln | Leu | Ile | Asn | Gln | Arg | Ile | Glu | Glu | Phe | Ala | Arg | Asn | Gln | Ala |
|  |  |  |  | 85 |  |  |  |  | 90 |  |  |  |  | 95 |  |
| Ile | Ser | Arg | Leu | Glu | Gly | Leu | Ser | Asn | Leu | Tyr | Gln | Ile | Tyr | Ala | Glu |
|  |  |  | 100 |  |  |  |  | 105 |  |  |  | 110 |  |  |  |
| Ser | Phe | Arg | Glu | Trp | Glu | Ala | Asp | Pro | Thr | Asn | Pro | Ala | Leu | Arg | Glu |
|  |  | 115 |  |  |  |  | 120 |  |  |  |  | 125 |  |  |  |
| Glu | Met | Arg | Ile | Gln | Phe | Asn | Asp | Met | Asn | Ser | Ala | Leu | Thr | Thr | Ala |
|  | 130 |  |  |  |  | 135 |  |  |  |  | 140 |  |  |  |  |
| Ile | Pro | Leu | Leu | Ala | Val | Gln | Asn | Tyr | Gln | Val | Pro | Leu | Leu | Ser | Val |
| 145 |  |  |  |  | 150 |  |  |  |  | 155 |  |  |  |  | 160 |

```
Tyr Val Gln Ala Ala Asn Leu His Leu Ser Val Leu Arg Asp Val Ser
            165                 170                 175
Val Phe Gly Gln Arg Trp Gly Phe Asp Ala Ala Thr Ile Asn Ser Arg
            180                 185                 190
Tyr Asn Asp Leu Thr Arg Leu Ile Gly Asn Tyr Thr Asp Tyr Ala Val
            195                 200                 205
Arg Trp Tyr Asn Thr Gly Leu Glu Arg Val Trp Gly Pro Asp Ser Arg
    210                 215                 220
Asp Trp Val Arg Tyr Asn Gln Phe Arg Arg Glu Leu Thr Leu Thr Val
225                 230                 235                 240
Leu Asp Ile Val Ala Leu Phe Ser Asn Tyr Asp Ser Arg Arg Tyr Pro
            245                 250                 255
Ile Arg Thr Val Ser Gln Leu Thr Arg Glu Ile Tyr Thr Asn Pro Val
            260                 265                 270
Leu Glu Asn Phe Asp Gly Ser Phe Arg Gly Met Ala Gln Arg Ile Glu
            275                 280                 285
Gln Asn Ile Arg Gln Pro His Leu Met Asp Ile Leu Asn Ser Ile Thr
            290                 295                 300
Ile Tyr Thr Asp Val His Arg Gly Phe Asn Tyr Trp Ser Gly His Gln
305                 310                 315                 320
Ile Thr Ala Ser Pro Val Gly Phe Ser Gly Pro Glu Phe Ala Phe Pro
                325                 330                 335
Leu Phe Gly Asn Ala Gly Asn Ala Ala Pro Pro Val Leu Val Ser Leu
            340                 345                 350
Thr Gly Leu Gly Ile Phe Arg Thr Leu Ser Ser Pro Leu Tyr Arg Arg
            355                 360                 365
Ile Ile Leu Gly Ser Gly Pro Asn Asn Gln Glu Leu Phe Val Leu Asp
    370                 375                 380
Gly Thr Glu Phe Ser Phe Ala Ser Leu Thr Thr Asn Leu Pro Ser Thr
385                 390                 395                 400
Ile Tyr Arg Gln Arg Gly Thr Val Asp Ser Leu Asp Val Ile Pro Pro
                405                 410                 415
Gln Asp Asn Ser Val Pro Pro Arg Ala Gly Phe Ser His Arg Leu Ser
            420                 425                 430
His Val Thr Met Leu Ser Gln Ala Ala Gly Ala Val Tyr Thr Leu Arg
            435                 440                 445
Ala Pro Thr Phe Ser Trp Gln His Arg Ser Ala Glu Phe Asn Asn Ile
    450                 455                 460
Ile Pro Ser Ser Gln Ile Thr Gln Ile Pro Leu Thr Lys Ser Thr Asn
465                 470                 475                 480
Leu Gly Ser Gly Thr Ser Val Val Lys Gly Pro Gly Phe Thr Gly Gly
            485                 490                 495
Asp Ile Leu Arg Arg Thr Ser Pro Gly Gln Ile Ser Thr Leu Arg Val
            500                 505                 510
Asn Ile Thr Ala Pro Leu Ser Gln Arg Tyr Arg Val Arg Ile Arg Tyr
            515                 520                 525
Ala Ser Thr Thr Asn Leu Gln Phe His Thr Ser Ile Asp Gly Arg Pro
    530                 535                 540
Ile Asn Gln Gly Asn Phe Ser Ala Thr Met Ser Ser Gly Ser Asn Leu
545                 550                 555                 560
Gln Ser Gly Ser Phe Arg Thr Val Gly Phe Thr Thr Pro Phe Asn Phe
                565                 570                 575
Ser Asn Gly Ser Ser Val Phe Thr Leu Ser Ala His Val Phe Asn Ser
```

|     |     |     |     |     | 580 |     |     |     |     | 585 |     |     |     |     | 590 |     |     |
|---|---|---|---|---|---|---|---|---|---|---|---|---|---|---|---|---|---|

Gly Asn Glu Val Tyr Ile Asp Arg Ile Glu Phe Val Pro Ala Glu Val
            595                         600                     605

Thr Phe Glu Ala Glu Tyr Asp Leu Glu Arg Ala Gln Lys Ala Val Asn
    610                     615                     620

Glu Leu Phe Thr Ser Ser Asn Gln Ile Gly Leu Lys Thr Asp Val Thr
625                     630                     635                         640

Asp Tyr His Ile Asp Gln Val Ser Asn Leu Val Glu Cys Leu Ser Asp
                645                     650                         655

Glu Phe Cys Leu Asp Glu Lys Gln Glu Leu Ser Glu Lys Val Lys His
            660                     665                     670

Ala Lys Arg Leu Ser Asp Glu Arg Asn Leu Leu Gln Asp Pro Asn Phe
        675                     680                     685

Arg Gly Ile Asn Arg Gln Leu Asp Arg Gly Trp Arg Gly Ser Thr Asp
690                     695                     700

Ile Thr Ile Gln Gly Gly Asp Asp Val Phe Lys Glu Asn Tyr Val Thr
705                 710                     715                         720

Leu Leu Gly Thr Phe Asp Glu Cys Tyr Pro Thr Tyr Leu Tyr Gln Lys
                725                     730                     735

Ile Asp Glu Ser Lys Leu Lys Ala Tyr Thr Arg Tyr Gln Leu Arg Gly
            740                     745                     750

Tyr Ile Glu Asp Ser Gln Asp Leu Glu Ile Tyr Leu Ile Arg Tyr Asn
        755                     760                     765

Ala Lys His Glu Thr Val Asn Val Pro Gly Thr Gly Ser Leu Trp Pro
        770                     775                     780

Leu Ser Ala Gln Ser Pro Ile Gly Lys Cys Gly Glu Pro Asn Arg Cys
785                     790                     795                         800

Ala Pro His Leu Glu Trp Asn Pro Asp Leu Asp Cys Ser Cys Arg Asp
                805                     810                     815

Gly Glu Lys Cys Ala His His Ser His His Phe Ser Leu Asp Ile Asp
            820                     825                     830

Val Gly Cys Thr His Leu Asn Glu Asp Leu Gly Val Trp Val Ile Phe
        835                     840                     845

Lys Ile Lys Thr Gln Asp Gly His Ala Arg Leu Gly Asn Leu Glu Phe
850                     855                     860

Leu Glu Glu Lys Pro Leu Val Gly Glu Ala Leu Ala Arg Val Lys Arg
865                     870                     875                         880

Ala Glu Lys Lys Trp Arg Asp Lys Arg Glu Lys Leu Glu Trp Glu Thr
                885                     890                     895

Asn Ile Val Tyr Lys Glu Ala Lys Glu Ser Val Asp Ala Leu Phe Val
            900                     905                     910

Asn Ser Gln Tyr Asp Gln Leu Gln Ala Asp Thr Asn Ile Ala Met Ile
        915                     920                     925

His Ala Ala Asp Lys Arg Val His Ser Ile Arg Glu Ala Tyr Leu Pro
    930                     935                     940

Glu Leu Ser Val Ile Pro Gly Val Asn Ala Ala Ile Phe Glu Glu Leu
945                     950                     955                         960

Glu Gly Arg Ile Phe Thr Ala Phe Ser Leu Tyr Asp Ala Arg Asn Val
                965                     970                     975

Ile Lys Asn Gly Asp Phe Asn Asn Gly Leu Ser Cys Trp Asn Val Lys
            980                     985                     990

Gly His Val Asp Val Glu Glu Gln Asn Asn Gln Arg Ser Val Leu Val
        995                     1000                    1005

```
Leu Pro Glu Trp Glu Ala Glu Val Ser Gln Glu Val Arg Val Cys Pro
    1010                1015                1020

Gly Arg Gly Tyr Ile Leu Arg Val Thr Ala Tyr Lys Glu Gly Tyr Gly
1025            1030                1035                    1040

Glu Gly Cys Val Thr Ile His Glu Ile Glu Asn Asn Thr Asp Glu Leu
                1045            1050                    1055

Lys Phe Ser Asn Cys Val Glu Glu Ile Tyr Pro Asn Asn Thr Val
            1060            1065                1070

Thr Cys Asn Asp Tyr Thr Val Asn Gln Glu Glu Tyr Gly Gly Ala Tyr
            1075            1080                1085

Thr Ser Arg Asn Arg Gly Tyr Asn Glu Ala Pro Ser Val Pro Ala Asp
            1090            1095            1100

Tyr Ala Ser Val Tyr Glu Glu Lys Ser Tyr Thr Asp Gly Arg Arg Glu
1105            1110                1115                    1120

Asn Pro Cys Glu Phe Asn Arg Gly Tyr Arg Asp Tyr Thr Pro Leu Pro
                1125            1130                    1135

Val Gly Tyr Val Thr Lys Glu Leu Glu Tyr Phe Pro Glu Thr Asp Lys
                1140            1145                1150

Val Trp Ile Glu Ile Gly Glu Thr Glu Gly Thr Phe Ile Val Asp Ser
            1155            1160                1165

Val Glu Leu Leu Leu Met Glu Glu
        1170            1175
```

( 2 ) INFORMATION FOR SEQ ID NO: 7:

( i ) SEQUENCE CHARACTERISTICS:
        ( A ) LENGTH: 934 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 1..934
        ( D ) OTHER INFORMATION: /note="deduced amino acid sequence
            of B.t. sotto (Shibano et al., Gene 34, p. 243,
            1985)"

( x i ) SEQUENCE DESCRIPTION: SEQ ID NO: 7:

Met Asp Asn Asn Pro Asn Ile Asn Glu Cys Ile Pro Tyr Asn Cys Leu
1 5 10 15

Ser Asn Pro Glu Val Glu Val Leu Gly Gly Glu Arg Ile Glu Thr Gly
20 25 30

Tyr Thr Pro Ile Asp Ile Ser Leu Ser Leu Thr Gln Phe Leu Leu Ser
35 40 45

Glu Phe Val Pro Gly Ala Gly Phe Val Leu Gly Leu Val Asp Ile Ile
50 55 60

Trp Gly Ile Phe Gly Pro Ser Gln Trp Asp Ala Phe Leu Val Gln Ile
65 70 75 80

Glu Gln Leu Ile Asn Gln Arg Ile Glu Glu Phe Ala Arg Asn Gln Ala
85 90 95

Ile Ser Arg Leu Glu Gly Leu Ser Asn Leu Tyr Gln Ile Tyr Ala Glu
100 105 110

Ser Phe Arg Glu Trp Glu Ala Asp Pro Thr Asn Pro Ala Leu Arg Glu
115 120 125

Glu Met Arg Ile Gln Phe Asn Asp Met Asn Ser Ala Leu Thr Thr Ala
130 135 140

Ile Pro Leu Phe Ala Val Gln Asn Tyr Gln Val Pro Leu Leu Ser Val

```
145                   150                   155                   160
Tyr  Val  Gln  Ala  Ala  Asn  Leu  His  Leu  Ser  Val  Leu  Arg  Asp  Val  Ser
               165                   170                   175

Val  Phe  Gly  Gln  Arg  Trp  Gly  Phe  Asp  Ala  Ala  Thr  Ile  Asn  Ser  Arg
               180                   185                   190

Tyr  Asn  Asp  Leu  Thr  Arg  Leu  Ile  Gly  Asn  Tyr  Thr  Asp  Tyr  Ala  Val
               195                   200                   205

Arg  Trp  Tyr  Asn  Thr  Gly  Leu  Glu  Arg  Val  Trp  Gly  Pro  Asp  Ser  Arg
     210                   215                   220

Asp  Trp  Val  Arg  Tyr  Asn  Gln  Phe  Arg  Arg  Glu  Leu  Thr  Leu  Thr  Val
225                        230                   235                        240

Leu  Asp  Ile  Val  Ala  Leu  Phe  Ser  Asn  Tyr  Asp  Ser  Arg  Arg  Tyr  Pro
               245                   250                   255

Ile  Arg  Thr  Val  Ser  Gln  Leu  Thr  Arg  Glu  Ile  Tyr  Thr  Asn  Pro  Val
               260                   265                   270

Leu  Glu  Asn  Phe  Asp  Gly  Ser  Phe  Arg  Gly  Met  Ala  Gln  Arg  Ile  Glu
               275                   280                   285

Gln  Asn  Ile  Arg  Gln  Pro  His  Leu  Met  Asp  Ile  Leu  Asn  Arg  Ile  Thr
               290                   295                   300

Ile  Tyr  Thr  Asp  Val  His  Arg  Gly  Phe  Asn  Tyr  Trp  Ser  Gly  His  Gln
305                        310                   315                        320

Ile  Thr  Ala  Ser  Pro  Val  Gly  Phe  Ser  Gly  Pro  Glu  Phe  Ala  Phe  Pro
               325                   330                   335

Leu  Phe  Gly  Asn  Ala  Gly  Asn  Ala  Ala  Pro  Pro  Val  Leu  Val  Ser  Leu
               340                   345                   350

Thr  Gly  Leu  Gly  Ile  Phe  Arg  Thr  Leu  Ser  Ser  Pro  Leu  Tyr  Arg  Arg
               355                   360                   365

Ile  Ile  Leu  Gly  Ser  Gly  Pro  Asn  Asn  Gln  Glu  Leu  Phe  Val  Leu  Asp
               370                   375                   380

Gly  Thr  Glu  Phe  Ser  Phe  Ala  Ser  Leu  Thr  Thr  Asn  Leu  Pro  Ser  Thr
385                        390                   395                        400

Ile  Tyr  Arg  Gln  Arg  Gly  Thr  Val  Asp  Ser  Leu  Asp  Val  Ile  Pro  Pro
                 405                   410                   415

Gln  Asp  Asn  Ser  Val  Pro  Pro  Arg  Ala  Gly  Phe  Ser  His  Arg  Leu  Ser
               420                   425                   430

His  Val  Thr  Met  Leu  Ser  Gln  Ala  Ala  Gly  Ala  Val  Tyr  Thr  Leu  Arg
               435                   440                   445

Ala  Pro  Thr  Phe  Ser  Trp  Gln  His  Arg  Ser  Ala  Glu  Phe  Asn  Asn  Ile
     450                   455                   460

Ile  Pro  Ser  Ser  Gln  Ile  Thr  Gln  Ile  Pro  Leu  Thr  Lys  Ser  Thr  Asn
465                        470                   475                        480

Leu  Gly  Ser  Gly  Thr  Ser  Val  Val  Lys  Gly  Pro  Gly  Phe  Thr  Gly  Gly
               485                   490                   495

Asp  Ile  Leu  Arg  Arg  Thr  Ser  Pro  Gly  Gln  Ile  Ser  Thr  Leu  Arg  Val
               500                   505                   510

Asn  Ile  Thr  Ala  Pro  Leu  Ser  Gln  Arg  Tyr  Arg  Val  Arg  Ile  Arg  Tyr
               515                   520                   525

Ala  Ser  Thr  Thr  Asn  Leu  Gln  Phe  His  Thr  Ser  Ile  Asp  Gly  Arg  Pro
     530                   535                   540

Ile  Asn  Gln  Gly  Asn  Phe  Ser  Ala  Thr  Met  Ser  Ser  Gly  Ser  Asn  Leu
545                        550                   555                        560

Gln  Ser  Gly  Ser  Phe  Arg  Thr  Val  Gly  Phe  Thr  Thr  Pro  Phe  Asn  Phe
               565                   570                   575
```

```
Ser  Asn  Gly  Ser  Ser  Val  Phe  Thr  Leu  Ser  Ala  His  Val  Phe  Asn  Ser
               580                      585                      590

Gly  Asn  Glu  Val  Tyr  Ile  Asp  Arg  Ile  Glu  Phe  Val  Pro  Ala  Glu  Val
          595                      600                      605

Thr  Phe  Glu  Ala  Glu  Tyr  Asp  Leu  Glu  Arg  Ala  Gln  Lys  Ala  Val  Asn
     610                      615                      620

Glu  Leu  Phe  Thr  Ser  Ser  Asn  Gln  Ile  Gly  Leu  Lys  Thr  Asp  Val  Thr
625                      630                      635                      640

Asp  Tyr  His  Ile  Asp  Gln  Val  Ser  Asn  Leu  Val  Glu  Cys  Leu  Ser  Asp
               645                      650                      655

Glu  Phe  Cys  Leu  Asp  Glu  Lys  Gln  Glu  Leu  Ser  Glu  Lys  Val  Lys  His
               660                      665                      670

Ala  Lys  Arg  Leu  Ser  Asp  Glu  Arg  Asn  Leu  Leu  Gln  Asp  Pro  Asn  Phe
          675                      680                      685

Arg  Gly  Ile  Asn  Arg  Gln  Leu  Asp  Arg  Gly  Trp  Arg  Gly  Ser  Thr  Asp
     690                      695                      700

Ile  Thr  Ile  Gln  Gly  Gly  Asp  Asp  Val  Phe  Lys  Glu  Asn  Tyr  Val  Thr
705                      710                      715                      720

Leu  Leu  Gly  Thr  Phe  Asp  Glu  Cys  Tyr  Pro  Thr  Tyr  Leu  Tyr  Gln  Lys
               725                      730                      735

Ile  Asp  Glu  Ser  Lys  Leu  Lys  Ala  Tyr  Thr  Arg  Tyr  Gln  Leu  Arg  Gly
               740                      745                      750

Tyr  Ile  Glu  Asp  Ser  Gln  Asp  Leu  Glu  Ile  Tyr  Leu  Ile  Arg  Tyr  Asn
                    755                      760                      765

Ala  Lys  His  Glu  Thr  Val  Asn  Val  Pro  Gly  Thr  Gly  Ser  Leu  Trp  Pro
     770                      775                      780

Leu  Ser  Ala  Gln  Ser  Pro  Ile  Gly  Lys  Cys  Gly  Glu  Pro  Asn  Arg  Cys
785                      790                      795                      800

Ala  Pro  His  Leu  Glu  Trp  Asn  Pro  Asp  Leu  Asp  Cys  Ser  Cys  Arg  Asp
               805                      810                      815

Gly  Glu  Lys  Cys  Ala  His  His  Ser  His  His  Phe  Ser  Leu  Asp  Ile  Asp
               820                      825                      830

Val  Gly  Cys  Thr  Asp  Leu  Asn  Glu  Asp  Leu  Gly  Val  Trp  Val  Ile  Phe
          835                      840                      845

Lys  Ile  Lys  Thr  Gln  Asp  Gly  His  Ala  Arg  Leu  Gly  Asn  Leu  Glu  Phe
850                      855                      860

Leu  Glu  Glu  Lys  Pro  Leu  Val  Gly  Glu  Ala  Leu  Ala  Arg  Val  Lys  Arg
865                      870                      875                      880

Ala  Glu  Lys  Lys  Trp  Arg  Asp  Lys  Arg  Glu  Lys  Leu  Glu  Trp  Glu  Thr
               885                      890                      895

Asn  Ile  Val  Tyr  Lys  Glu  Ala  Lys  Glu  Ser  Val  Asp  Ala  Leu  Phe  Val
               900                      905                      910

Asn  Ser  Gln  Tyr  Asp  Arg  Leu  Gln  Ala  Asp  Thr  Asn  Ile  Ala  Met  Ile
          915                      920                      925

His  Ala  Ala  Asp  Lys  Arg
          930
```

( 2 ) INFORMATION FOR SEQ ID NO: 8:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
    ( A ) NAME/KEY: misc_feature
    ( B ) LOCATION: 1..19
    ( D ) OTHER INFORMATION: /note="introduced BamHI linker 5' of Bt2 gene in pHD100"

( x i ) SEQUENCE DESCRIPTION: SEQ ID NO: 8:

```
GGGATCCCGG TAACTTATG                                                      19
```

( 2 ) INFORMATION FOR SEQ ID NO: 9:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..20
        ( D ) OTHER INFORMATION: /note="5'end of Bt2 gene in pHD160, pLBKm33 and pLBKm2860"

( x i ) SEQUENCE DESCRIPTION: SEQ ID NO: 9:

```
GGATCCCGTA ACTTATGGAT                                                     20
```

( 2 ) INFORMATION FOR SEQ ID NO: 10:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 18..32

( i x ) FEATURE:
        ( A ) NAME/KEY: misc_feature
        ( B ) LOCATION: 1..32
        ( D ) OTHER INFORMATION: /note="sequences at 5'of the Bt2 gene, including 5 codons"

( x i ) SEQUENCE DESCRIPTION: SEQ ID NO: 10:

```
AGAGATGGAG GTAACTT ATG GAT AAC AAT CCG                                    32
                    Met Asp Asn Asn Pro
                     1               5
```

( 2 ) INFORMATION FOR SEQ ID NO: 11:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 11:

```
Met Asp Asn Asn Pro
 1               5
```

( 2 ) INFORMATION FOR SEQ ID NO: 12:

( i ) SEQUENCE CHARACTERISTICS:
        ( A ) LENGTH: 10 base pairs
        ( B ) TYPE: nucleic acid
        ( C ) STRANDEDNESS: double (D) TOPOLOGY: linear (ii) MOLECULE TYPE: DNA (genomic)

(ix) FEATURE:
                (A) NAME/KEY: misc_feature
                (B) LOCATION: 1..10
                (D) OTHER INFORMATION: /note="BamHI site introduced 5'of
                        Bt2 gene cassettes"

(xi) SEQUENCE DESCRIPTION: SEQ ID NO: 12:

CGGGATCCCG                                                                                          10

(2) INFORMATION FOR SEQ ID NO: 13:

(i) SEQUENCE CHARACTERISTICS:
                (A) LENGTH: 15 base pairs
                (B) TYPE: nucleic acid
                (C) STRANDEDNESS: double
                (D) TOPOLOGY: linear (ii) MOLECULE TYPE: DNA (genomic)

(ix) FEATURE:
                (A) NAME/KEY: misc_feature
                (B) LOCATION: 1..15
                (D) OTHER INFORMATION: /note="sequence at 3'end of Bt2
                        gene"

(xi) SEQUENCE DESCRIPTION: SEQ ID NO: 13:

CACACCACTA CCAGC                                                                                    15

(2) INFORMATION FOR SEQ ID NO: 14:

(i) SEQUENCE CHARACTERISTICS:
                (A) LENGTH: 16 base pairs
                (B) TYPE: nucleic acid
                (C) STRANDEDNESS: double
                (D) TOPOLOGY: linear (ii) MOLECULE TYPE: DNA (genomic)

(ix) FEATURE:
                (A) NAME/KEY: misc_feature
                (B) LOCATION: 1..16
                (D) OTHER INFORMATION: /note="3'end of Bt2 in pHD164,
                        including the stop codon"

(xi) SEQUENCE DESCRIPTION: SEQ ID NO: 14:

TAATATATGC TTTAAA                                                                                   16

(2) INFORMATION FOR SEQ ID NO: 15:

(i) SEQUENCE CHARACTERISTICS:
                (A) LENGTH: 19 base pairs
                (B) TYPE: nucleic acid
                (C) STRANDEDNESS: double
                (D) TOPOLOGY: linear (ii) MOLECULE TYPE: DNA (genomic)

(ix) FEATURE:
                (A) NAME/KEY: misc_feature
                (B) LOCATION: 1..19
                (D) OTHER INFORMATION: /note="3'end of Bt2 gene in pDC3,
                        including stop codon"

(xi) SEQUENCE DESCRIPTION: SEQ ID NO: 15:

TAATATAGCT TTCAGATCT                                                                                19

(2) INFORMATION FOR SEQ ID NO: 16:

( i ) SEQUENCE CHARACTERISTICS:
    ( A ) LENGTH: 49 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..49
    ( D ) OTHER INFORMATION: /note="adaptor sequence for pLK54"

( x i ) SEQUENCE DESCRIPTION: SEQ ID NO: 16:

```
AATTCCCGGG GATCCGTCGA CCTGCAGCCA AGCTTGGTCT AGAGGTCGA                49
```

( 2 ) INFORMATION FOR SEQ ID NO: 17:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..84
        ( D ) OTHER INFORMATION: /note="adaptor sequence for
            plasmid pLK57"

( x i ) SEQUENCE DESCRIPTION: SEQ ID NO: 17:

```
AATTCCCGGG AGAGCTCGAT ATCGCATGCG GTACCTCTAG AAGAAGCTTG GGATCCGTCG    60

ACCTGCAGAT CTGCTAGAGG TCGA                                           84
```

( 2 ) INFORMATION FOR SEQ ID NO: 18:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..42

( i x ) FEATURE:
        ( A ) NAME/KEY: misc_feature
        ( B ) LOCATION: 1..42
        ( D ) OTHER INFORMATION: /note="Bt2 coding sequence
            containing the 3'end sequences of deletion clones
            pLB834 and pLB879"

( x i ) SEQUENCE DESCRIPTION: SEQ ID NO: 18:

```
TAT ATA GAT CGA ATT GAA TTT GTT CCG GCA GAA GTA ACC TTT              42
Tyr Ile Asp Arg Ile Glu Phe Val Pro Ala Glu Val Thr Phe
 1               5                  10
```

( 2 ) INFORMATION FOR SEQ ID NO: 19:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 19:

```
Tyr  Ile  Asp  Arg  Ile  Glu  Phe  Val  Pro  Ala  Glu  Val  Thr  Phe
 1              5                        10
```

( 2 ) INFORMATION FOR SEQ ID NO: 20:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..10
        ( D ) OTHER INFORMATION: /note="5'end of the Bt2 gene in pLBKm13 and pLBKm14"

( x i ) SEQUENCE DESCRIPTION: SEQ ID NO: 20:

```
GGATCCCGAT                                                                                    10
```

( 2 ) INFORMATION FOR SEQ ID NO: 21:

( i ) SEQUENCE CHARACTERISTICS:
        ( A ) LENGTH: 47 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..47
        ( D ) OTHER INFORMATION: /note="5'end of Bt2 gene in pLBKm23 and pLBKm860 (865)"

( x i ) SEQUENCE DESCRIPTION: SEQ ID NO: 21:

```
GGATCCCGTG  GTATCTTAAT  TAAAAGAGAT  GGAGGTAACT  TATGGAT                                       47
```

( 2 ) INFORMATION FOR SEQ ID NO: 22:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..24
        ( D ) OTHER INFORMATION: /note="DNA sequence at Bt2-NPTII fusion in pLBKm13"

( x i ) SEQUENCE DESCRIPTION: SEQ ID NO: 22:

```
GGTACGATCC  GGCCAAGCTT  GGAT                                                                  24
```

( 2 ) INFORMATION FOR SEQ ID NO: 23:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..60

(D) OTHER INFORMATION: /note="Pnos promotor-Bt2 gene
junction in pHD1050, pHD1060, and pGS1110"

(xi) SEQUENCE DESCRIPTION: SEQ ID NO: 23:

CATAAATTCC CCTCGGTATC CAATTAGAGT TCTGATCGAC GGATCCCGTA ACTTATGGAT    60

(2) INFORMATION FOR SEQ ID NO: 24:

(i) SEQUENCE CHARACTERISTICS:
        (A) LENGTH: 71 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..71
        (D) OTHER INFORMATION: /note="Pssu pea-Bt2 junction in
        pHD1076"

(xi) SEQUENCE DESCRIPTION: SEQ ID NO: 24:

TAAAAACATT ATATATAGCA AGTTTTAGCA GAAGCTTGGC TGCAGGTCGA CGGATCCCGT    60

AACTTATGGA T    71

(2) INFORMATION FOR SEQ ID NO: 25:

(i) SEQUENCE CHARACTERISTICS:
        (A) LENGTH: 98 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..98
        (D) OTHER INFORMATION: /note="Tp-Bt2 fusion in pHD1080
        (NNN: stretch of DNA sequences not shown)"

(xi) SEQUENCE DESCRIPTION: SEQ ID NO: 25:

TAAAAACATT ATATATAGCA AGTTTTAGCA GAAGCTTTGC AATTCATACA GAAGTGAGAA    60

AAATGNNNAG AGTAAAGTGC ATGGATCCCG ATAACAAT    98

(2) INFORMATION FOR SEQ ID NO: 26:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..26
        (D) OTHER INFORMATION: /note="PTR2-Bt2 junction in
        pGS1151, pGS1152, pGS1153, pGS1161, pGS1162, and
        pGS1163"

(xi) SEQUENCE DESCRIPTION: SEQ ID NO: 26:

ATACACCAAA ATCGATGGAT CCCGAT    26

(2) INFORMATION FOR SEQ ID NO: 27:

(i) SEQUENCE CHARACTERISTICS:
        (A) LENGTH: 31 base pairs (B) TYPE: nucleic acid
(C) STRANDEDNESS: double
(D) TOPOLOGY: linear (ii) MOLECULE TYPE: DNA (genomic)

(ix) FEATURE:
(A) NAME/KEY: misc_feature
(B) LOCATION: 1..31
(D) OTHER INFORMATION: /note="Pssu 301-Bt2 junction in pGS1171, pGS1181"

(xi) SEQUENCE DESCRIPTION: SEQ ID NO: 27:

```
AAGCAAAATT CTTCTAACCA TGGATCCCGA T                                    31
```

(2) INFORMATION FOR SEQ ID NO: 28:

(i) SEQUENCE CHARACTERISTICS:
(A) LENGTH: 37 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: misc_feature
(B) LOCATION: 1..37
(D) OTHER INFORMATION: /note="P35S1-Bt2 junction in pGS1251, pGS1252, pGS1261, and pGS1262"

(xi) SEQUENCE DESCRIPTION: SEQ ID NO: 28:

```
CTGAAATCAC CAGTCTCGGA TCCCGTAACT TATGGAT                              37
```

(2) INFORMATION FOR SEQ ID NO: 29:

(i) SEQUENCE CHARACTERISTICS:
(A) LENGTH: 39 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: misc_feature
(B) LOCATION: 1..39
(D) OTHER INFORMATION: /note="P35S2-Bt2 junction in pGS1271 and pGS1281"

(xi) SEQUENCE DESCRIPTION: SEQ ID NO: 29:

```
CAGTCTCTCT CTACAAATCG GATCCCGTAA CTTATGGAT                            39
```

(2) INFORMATION FOR SEQ ID NO: 30:

(i) SEQUENCE CHARACTERISTICS:
(A) LENGTH: 979 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: misc_feature
(B) LOCATION: 1..979
(D) OTHER INFORMATION: /note="35S-1 promotor sequence"

(xi) SEQUENCE DESCRIPTION: SEQ ID NO: 30:

```
AGATCTCCTT TGCCCCGGAG ATCACCATGG ACGACTTTCT CTATCTCTAC GATCTAGGAA     60
GAAAGTTCGA CGGAGAAGGT GACGATACCA TGTTCACCAC CGATAATGAG AAGATTAGCC    120
```

```
TCTTCAATTT CAGAAAGAAT GCTGACCCAC AGATGGTTAG AGAGGCCTAC GCGGCAGGTC      180

TCATCAAGAC GATCTACCCG AGTAATAATC TCCAGGAGAT CAAATACCTT CCCAAGAAGG      240

TTAAAGATGC AGTCAAAAGA TTCAGGACTA ACTGCATCAA GAACACAGAG AAAGATATAT      300

TTCTCAAGAT CAGAAGTACT ATTCCAGTAT GGACGATTCA AGGCTTGCTT CATAAACCAA      360

GGCAAGTAAT AGAGATTGGA GTCTCTAAGA AAGTAGTTCC TACTGAATCA AAGGCCATGG      420

AGTCAAAAAT TCAGATCGAG GATCTAACAG AACTCGCCGT GAAGACTGGC GAACAGTTCA      480

TACAGAGTCT TTTACGACTC AATGACAAGA AGAAAATCTT CGTCAACATG GTGGAGCACG      540

ACACTCTCGT CTACTCCAAG AATATCAAAG ATACAGTCTC AGAAGACCAA AGGGCTATTG      600

AGACTTTTCA ACAAAGGGTA ATATCGGGAA ACCTCCTCGG ATTCCATTGC CCAGCTATCT      660

GTCACTTCAT CAAAAGGACA GTAGAAAAGG AAGGTGGCAC CTACAAATGC CATCATTGCG      720

ATAAAGGAAA GGCTATCGTT CAAGATGCCT CTGCCGACAG TGGTCCCAAA GATGGACCCC      780

CACCCACGAG GAGCATCGTG GAAAAGAAG ACGTTCCAAC CACGTCTTCA AAGCAAGTGG       840

ATTGATGTGA TATCTCCACT GACGTAAGGG ATGACGCACA ATCCCACTAT CCTTCGCAAG      900

ACCCTTCCTC TATATAAGGA AGTTCATTTC ATTTGGAGAG GACACGCTGA AATCACCAGT      960

CTCTCTCTAC AAATCTATC                                                  979
```

( 2 ) INFORMATION FOR SEQ ID NO: 31:

( i ) SEQUENCE CHARACTERISTICS:
        ( A ) LENGTH: 978 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..978
        ( D ) OTHER INFORMATION: /note="35S-2 promotor sequence"

( x i ) SEQUENCE DESCRIPTION: SEQ ID NO: 31:

```
AGATCTCCTT TGCCCCGGAG ATCACCATGG ACGACTTTCT CTATCTCTAC GATCTAGGAA       60

GAAAGTTCGA CGGAGAAGGT GACGATACCA TGTTCACCAC CGATAATGAG AAGATTAGCC      120

TCTTCAATTT CAGAAAGAAT GCTGACCCAC AGATGGTTAG AGAGGCCTAC GCGGCAGGTC      180

TCATCAAGAC GATCTACCCG AGTAATAATC TCCAGGAGAT CAAATACCTT CCCAAGAAGG      240

TTAAAGATGC AGTCAAAAGA TTCAGGACTA ACTGCATCAA GAACACAGAG AAAGATATAT      300

TTCTCAAGAT CAGAAGTACT ATTCCAGTAT GGACGATTCA AGGCTTGCTT CATAAACCAA      360

GGCAAGTAAT AGAGATTGGA GTCTCTAAGA AAGTAGTTCC TACTGAATCA AAGGCCATGG      420

AGTCAAAAAT TCAGATCGAG GATCTAACAG AACTCGCCGT GAAGACTGGC GAACAGTTCA      480

TACAGAGTCT TTTACGACTC AATGACAAGA AGAAAATCTT CGTCAACATG GTGGAGCACG      540

ACACTCTCGT CTACTCCAAG AATATCAAAG ATACAGTCTC AGAAGACCAA AGGGCTATTG      600

AGACTTTTCA ACAAAGGGTA ATATCGGGAA ACCTCCTCGG ATTCCATTGC CCAGCTATCT      660

GTCACTTCAT CAAAAGGACA GTAGAAAAGG AAGGTGGCAC CTACAAATGC CATCATTGCG      720

ATAAAGGAAA GGCTATCGTT CAAGATGCCT CTGCCGACAG TGGTCCCAAA GATGGACCCC      780

CACCCACGAG GAGCATCGTG GAAAAGAAG ACGTTCCAAC CACGTCTTCA AAGCAAGTGG       840

ATTGATGTGA TATCTCCACT GACGTAAGGG ATGACGCACA ATCCCACTAT CCTTCGCAAG      900

ACCCTTCCTC TATATAAGGA AGTTCATTTC ATTTGGAGAG GACACGCTGA AATCACCAGT      960
```

CTCTCTCTAC AAATCGAT 978

( 2 ) INFORMATION FOR SEQ ID NO: 32:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..10
        ( D ) OTHER INFORMATION: /note="ClaI site at PTR2'in
            pOP443"

( x i ) SEQUENCE DESCRIPTION: SEQ ID NO: 32:

ATCGATGGAC 10

( 2 ) INFORMATION FOR SEQ ID NO: 33:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..13
        ( D ) OTHER INFORMATION: /note="ClaI-BamHI site at PTR2 in
            pGSH50"

( x i ) SEQUENCE DESCRIPTION: SEQ ID NO: 33:

ATCGATGGAT CCC 13

( 2 ) INFORMATION FOR SEQ ID NO: 34:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..15
        ( D ) OTHER INFORMATION: /note="5'sequence of wild type
            SSU 301 gene, including start codon"

( x i ) SEQUENCE DESCRIPTION: SEQ ID NO: 34:

TCTAACTATG GCTTC 15

( 2 ) INFORMATION FOR SEQ ID NO: 35:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..15
        ( D ) OTHER INFORMATION: /note="5'mutant sequence of SSU 301 gene, including start codon"

(xi) SEQUENCE DESCRIPTION: SEQ ID NO: 35:

TCTAACCATG GCTTC                                                                                      15

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /note="3'sequence of wild type
            SSU 301 gene, including stop codon"

(xi) SEQUENCE DESCRIPTION: SEQ ID NO: 36:

GGCTTCTAAG TTATATTAGG A                                                                               21

(2) INFORMATION FOR SEQ ID NO: 37:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /note="3'mutant sequence of SSU
            301 gene, including stop codon"

(xi) SEQUENCE DESCRIPTION: SEQ ID NO: 37:

GGCTTCTAAG ATCTATTAGG A                                                                               21

(2) INFORMATION FOR SEQ ID NO: 38:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: misc_feature
        (B) LOCATION: 1..12
        (D) OTHER INFORMATION: /note="5'untranslated sequence of
            PTR2', after addition of BamHI linker sequence "

(xi) SEQUENCE DESCRIPTION: SEQ ID NO: 38:

ATCGATGGAT CC                                                                                          12

(2) INFORMATION FOR SEQ ID NO: 39:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: DNA (genomic)

(ix) FEATURE:
 (A) NAME/KEY: misc_feature
 (B) LOCATION: 1..12
 (D) OTHER INFORMATION: /note="sequence around the
  initiation codon of the rbs gene of Petunia"

(xi) SEQUENCE DESCRIPTION: SEQ ID NO: 39:

TAACTATGGC TT  12

(2) INFORMATION FOR SEQ ID NO: 40:

(i) SEQUENCE CHARACTERISTICS:
  (A) LENGTH: 12 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: misc_feature
  (B) LOCATION: 1..12
  (D) OTHER INFORMATION: /note="sequence around the
   initiation codon of the rbs gene of Petunia,
   changed to create a NcoI site"

(xi) SEQUENCE DESCRIPTION: SEQ ID NO: 40:

TAACCATGGC TT  12

(2) INFORMATION FOR SEQ ID NO: 41:

(i) SEQUENCE CHARACTERISTICS:
  (A) LENGTH: 12 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: misc_feature
  (B) LOCATION: 1..12
  (D) OTHER INFORMATION: /note="sequence around TAA stop
   codon of the rbs gene of Petunia"

(xi) SEQUENCE DESCRIPTION: SEQ ID NO: 41:

GGCTTCTAAG TT  12

(2) INFORMATION FOR SEQ ID NO: 42:

(i) SEQUENCE CHARACTERISTICS:
  (A) LENGTH: 15 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: misc_feature
  (B) LOCATION: 1..15
  (D) OTHER INFORMATION: /note="modified sequence around
   TAA stop codon of rbs gene, to create a BglII
   site"

(xi) SEQUENCE DESCRIPTION: SEQ ID NO: 42:

GGCTTCTAAG ATCTT  15

(2) INFORMATION FOR SEQ ID NO: 43:

(i) SEQUENCE CHARACTERISTICS:
  (A) LENGTH: 12 base pairs (B) TYPE: nucleic acid
(C) STRANDEDNESS: double
(D) TOPOLOGY: linear (ii) MOLECULE TYPE: DNA (genomic)

(ix) FEATURE:
(A) NAME/KEY: misc_feature
(B) LOCATION: 1..12
(D) OTHER INFORMATION: /note="stop coding region of ssu 301 gene, including stop codon"

(xi) SEQUENCE DESCRIPTION: SEQ ID NO: 43:

TTCTAAGTTA TA    12

(2) INFORMATION FOR SEQ ID NO: 44:

(i) SEQUENCE CHARACTERISTICS:
(A) LENGTH: 14 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: misc_feature
(B) LOCATION: 1..14
(D) OTHER INFORMATION: /note="stop coding region of ssu 301 gene, modified to create a BglII site"

(xi) SEQUENCE DESCRIPTION: SEQ ID NO: 44:

TTCTAAGATC TATA    14